(12) United States Patent
Yang et al.

(10) Patent No.: US 12,227,499 B2
(45) Date of Patent: *Feb. 18, 2025

(54) FUSED IMIDAZOLE DERIVATIVE, PREPARATION METHOD THEREFOR, AND MEDICAL USE THEREOF

(71) Applicant: Jiangsu Hengrui Pharmaceuticals Co., Ltd., Jiangsu (CN)

(72) Inventors: Fanglong Yang, Shanghai (CN); Ling Zhang, Shanghai (CN); Liangliang Zheng, Shanghai (CN); Feng He, Shanghai (CN); Weikang Tao, Shanghai (CN)

(73) Assignee: Jiangsu Hengrui Pharmaceuticals Co., Ltd., Jiangsu (CN)

( * ) Notice: Subject to any disclaimer, the term of this patent is extended or adjusted under 35 U.S.C. 154(b) by 40 days.

This patent is subject to a terminal disclaimer.

(21) Appl. No.: 18/043,508

(22) PCT Filed: Sep. 1, 2021

(86) PCT No.: PCT/CN2021/115915
§ 371 (c)(1),
(2) Date: Feb. 28, 2023

(87) PCT Pub. No.: WO2022/007979
PCT Pub. Date: Jan. 13, 2022

(65) Prior Publication Data
US 2023/0322756 A1    Oct. 12, 2023

(30) Foreign Application Priority Data

| Sep. 1, 2020 | (CN) | 202010905693.4 |
| Sep. 18, 2020 | (CN) | 202010984336.1 |
| Oct. 20, 2020 | (CN) | 202011124085.6 |
| Nov. 11, 2020 | (CN) | 202011253077.1 |
| Dec. 4, 2020 | (CN) | 202011407911.8 |
| Dec. 31, 2020 | (CN) | 202011627733.X |

(51) Int. Cl.
| *C07D 417/14* | (2006.01) |
| *A61P 1/16* | (2006.01) |
| *C07D 405/14* | (2006.01) |
| *C07D 471/04* | (2006.01) |
| *C07D 495/04* | (2006.01) |

(52) U.S. Cl.
CPC .............. *C07D 417/14* (2013.01); *A61P 1/16* (2018.01); *C07D 405/14* (2013.01); *C07D 471/04* (2013.01); *C07D 495/04* (2013.01)

(58) Field of Classification Search
CPC .. C07D 417/14; C07D 405/14; C07D 471/04; C07D 495/04
USPC .................................................. 514/254.06
See application file for complete search history.

(56) References Cited

U.S. PATENT DOCUMENTS

| 2023/0126875 A1 | 4/2023 | Yang et al. |
| 2023/0295154 A1* | 9/2023 | Meng ................... C07D 405/14 514/303 |
| 2024/0246958 A1 | 7/2024 | Yang et al. |

FOREIGN PATENT DOCUMENTS

| AU | 2022321506 A1 | 8/2022 | |
| WO | 2003099805 A1 | 12/2003 | |
| WO | 2009111700 A2 | 9/2009 | |
| WO | 2010114824 A1 | 10/2010 | |
| WO | 2018056453 A1 | 3/2018 | |
| WO | 2018109607 A1 | 6/2018 | |
| WO | 2019239319 A1 | 12/2019 | |
| WO | 2020103815 A1 | 5/2020 | |
| WO | WO-2021219019 A1 * | 11/2021 | .......... A61K 31/437 |
| WO | WO-2022/007979 A1 | 1/2022 | |
| WO | 2022078380 A1 | 4/2022 | |
| WO | 2022078407 A1 | 4/2022 | |
| WO | 2022199661 A1 | 9/2022 | |
| WO | 2022228490 A1 | 11/2022 | |
| WO | 2023011539 A1 | 2/2023 | |

OTHER PUBLICATIONS

International Search Report issued Nov. 30, 2021 in PCT/CN2021/115915.

* cited by examiner

*Primary Examiner* — Kahsay Habte
(74) *Attorney, Agent, or Firm* — Choate, Hall & Stewart LLP; Charles E. Lyon; Michael A. Shinall

(57) ABSTRACT

Disclosed are fused imidazole derivatives, preparation methods therefor and medical uses thereof. Specifically, the present disclosure relates to a fused imidazole derivative as shown in general formula (IM), a preparation method therefor, a pharmaceutical composition containing the derivative, and the use of same as a therapeutic agent, in particular the use thereof as a GLP-1 receptor agonist, and the use thereof in the preparation of drugs for the treatment and/or prevention of diabetes.

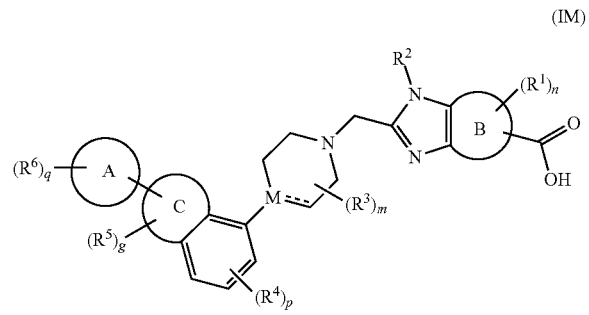

(IM)

18 Claims, No Drawings

FUSED IMIDAZOLE DERIVATIVE, PREPARATION METHOD THEREFOR, AND MEDICAL USE THEREOF

CROSS-REFERENCE TO RELATED APPLICATION

This application is a Section 371 of International Application No. PCT/CN2021/115915 filed Sep. 1, 2021, which was published in the Chinese language Jan. 13, 2022, under International Publication No. WO 2022/007979 A1, which claims priority to Chinese Patent Application No. 202010905693.4 filed Sep. 1, 2020; Chinese Patent Application No. 202010984336.1 filed Sep. 18, 2020; Chinese Patent Application No. 202011124085.6 filed Oct. 20, 2020; Chinese Patent Application No. 202011253077.1 filed Nov. 11, 2020; Chinese Patent Application No. 202011407911.8 filed Dec. 4, 2020; and Chinese Patent Application No. 202011627733.X filed Dec. 31, 2020, the disclosures of which are incorporated herein by reference in their entireties.

TECHNICAL FIELD

The present disclosure belongs to the field of pharmaceutics, and relates to a fused imidazole derivative, a preparation method therefor and pharmaceutical use thereof. In particular, the present disclosure relates to a fused imidazole derivative of general formula (IM), a preparation method therefor, a pharmaceutical composition comprising the derivative, and use of the derivative as a GLP-1 receptor agonist in the field of diabetes treatment.

BACKGROUND

Diabetes is a metabolic disease of multiple etiologies characterized by chronic hyperglycemia accompanied by disturbances in the metabolism of sugars, lipids and proteins due to a deficiency of insulin secretion or its action. Diabetes is a very ancient disease, and is caused by the absolute or relative deficiency of insulin in the human body, so that the concentration of glucose in blood is increased, and then a large amount of sugar is discharged from urine, accompanied by symptoms such as polydipsia, diuresis, polyphagia and emaciation.

Generally, there are two types of diabetes. Patients with type I diabetes, i.e., patients with insulin-dependent diabetes, produce little or no insulin by themselves. Insulin is a hormone used in the body to regulate glucose utilization. Patients with type II diabetes, i.e., patients with non-insulin-dependent diabetes, have the same or higher insulin level in their plasma as or than the non-diabetic population. However, such patients develop resistance to insulin which stimulates glucose and lipid metabolism in cells of major insulin-sensitive tissues, such as muscle, liver and adipose tissues. Even with elevated plasma insulin level, the patients' significant resistance to insulin cannot be overcome.

In addition to insulin resistance resulting from a reduction in the number of insulin receptors, a deficiency of insulin receptors can also lead to insulin resistance and this mechanism has not been fully understood. Insulin responsiveness (insulin resistance) results in failure of insulin to activate the uptake, oxidation and storage of glucose in muscle tissue, failure of effective inhibition of lipolysis in adipose tissue, and failure of effective inhibition of the production and secretion of glucose in the liver.

Glucagon-like peptide-1 (GLP-1) is an incretin hormone secreted from L-cells in the distal intestine.

GLP-1 plays a corresponding role by binding to its ubiquitous specific receptor. Organs in which GLP-1 receptor is now clearly present include islet cells, gastrointestinal, pulmonary, brain, kidney, hypothalamus and cardiovascular systems, and GLP-1 receptor may also be present in liver, adipose tissues and skeletal muscle. GLP-1 not only acts on β cells to promote insulin secretion, but also acts on α cells to inhibit glucagon secretion.

There is generally no significant difference in serum GLP-1 levels in patients with normal glucose tolerance, impaired glucose tolerance, and type II diabetes. However, there is a deficiency of the response of β cells to GLP-1 after eating, and under certain conditions, the response is significantly enhanced after continuous infusion of GLP-1. Since the duration of action of human GLP-1 is very short (t1/2<1.5 minutes via intravenous injection), human GLP-1 is not suitable for clinical treatment of diabetes.

Peptidic GLP-1 receptor agonists (e.g., liraglutide and exenatide) have effects on improving blood glucose level in type II diabetic patients by lowering fasting and postprandial glucose. However, since the peptidic GLP-1 has poor oral bioavailability and is inconvenient to take, small molecule agonists of GLP-1 receptors with good oral bioavailability are highly desirable.

The small molecule agonists of GLP-1 receptors are disclosed in patent applications including WO2009111700A2, WO2010114824A1, WO2018109607A1, WO2019239319A1, WO2018056453A1, and the like.

SUMMARY

The present disclosure is also intended to provide a compound of general formula (IM) or a tautomer, racemate, enantiomer or diastereomer thereof or a mixture thereof, or a pharmaceutically acceptable salt thereof:

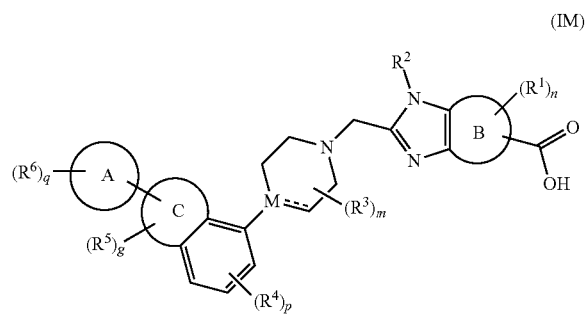

wherein:
ring B is phenyl or 5- or 6-membered heteroaryl;
M is a N atom or a C atom;
$=\!=\!=$ is a single bond or double bond; when M is a N atom, $=\!=\!=$ is a single bond, and when M is a C atom, $=\!=\!=$ is a single bond or double bond;
ring C is 6- to 7-membered heterocycyl, and the 6- to 7-membered heterocyclyl contains 1 to 2 heteroatoms selected from the group consisting of an O atom and a S atom; ring A is aryl or heteroaryl;
$R^1$ are identical or different and are each independently selected from the group consisting of a hydrogen atom, halogen, alkyl, alkenyl, alkynyl, alkoxy, haloalkyl, haloalkoxy, hydroxyalkyl, cyano, amino, nitro, hydroxy, cycloalkyl, heterocyclyl, aryl and heteroaryl;

R² is selected from the group consisting of a hydrogen atom, alkyl, heterocyclylalkyl, cycloalkylalkyl, alkenyl, alkynyl, haloalkyl, hydroxyalkyl, cycloalkyl, heterocyclyl, aryl and heteroaryl, wherein the alkyl, heterocyclylalkyl, cycloalkylalkyl, alkenyl, alkynyl, cycloalkyl, heterocyclyl, aryl and heteroaryl are each independently optionally substituted with one or more substituents selected from the group consisting of halogen, alkyl, alkenyl, alkynyl, alkoxy, haloalkyl, haloalkoxy, cyano, amino, nitro, hydroxy, hydroxyalkyl, cycloalkyl, heterocyclyl, aryl and heteroaryl;

R³ are identical or different and are each independently selected from the group consisting of a hydrogen atom, halogen, alkyl, oxo, alkenyl, alkynyl, alkoxy, haloalkyl, haloalkoxy, hydroxyalkyl, cyano, amino, nitro, hydroxy, cycloalkyl, heterocyclyl, aryl and heteroaryl;

R⁴ are identical or different and are each independently selected from the group consisting of a hydrogen atom, halogen, alkyl, alkenyl, alkynyl, alkoxy, haloalkyl, haloalkoxy, cyano, amino, nitro, hydroxy, hydroxyalkyl, cycloalkyl, heterocyclyl, aryl and heteroaryl;

R⁵ are identical or different and are each independently selected from the group consisting of a hydrogen atom, halogen, alkyl, alkenyl, alkynyl, alkoxy, haloalkyl, haloalkoxy, hydroxyalkyl, cyano, amino, nitro, hydroxy, cycloalkyl, heterocyclyl, aryl and heteroaryl;

R⁶ are identical or different and are each independently selected from the group consisting of a hydrogen atom, halogen, alkyl, alkoxy, cyano, heterocyclylalkyl, cycloalkylalkyl, alkenyl, alkynyl, haloalkyl, haloalkoxy, hydroxyalkyl, cycloalkyl, heterocyclyl, aryl and heteroaryl, wherein the alkyl, heterocyclylalkyl, cycloalkylalkyl, alkenyl, alkynyl, cycloalkyl, heterocyclyl, aryl and heteroaryl are each independently optionally substituted with one or more substituents selected from the group consisting of halogen, alkyl, alkenyl, alkynyl, alkoxy, haloalkyl, haloalkoxy, cyano, amino, nitro, hydroxy, hydroxyalkyl, cycloalkyl, heterocyclyl, aryl and heteroaryl;

n is 0, 1, 2 or 3;
m is 0, 1, 2, 3 or 4;
p is 0, 1, 2 or 3;
g is 0, 1, 2, 3, 4 or 5; and
q is 0, 1, 2, 3 or 4.

In some preferred embodiments of the present disclosure, provided is the compound of general formula (IM) or the tautomer, racemate, enantiomer or diastereomer thereof or the mixture thereof, or the pharmaceutically acceptable salt thereof, wherein:

ring B is phenyl or 5- or 6-membered heteroaryl;
M is a N or a C atom;
⸺ is a single bond or double bond; when M is a N atom, ⸺ is a single bond, and when M is a C atom, ⸺ is a single bond or double bond;
ring C is 6- to 7-membered heterocyclyl, and the 6- to 7-membered heterocyclyl contains 1 to 2 heteroatoms selected from the group consisting of an O atom and a S atom; ring A is aryl or heteroaryl;

R¹ are identical or different and are each independently selected from the group consisting of a hydrogen atom, halogen, alkyl, alkenyl, alkynyl, alkoxy, haloalkyl, haloalkoxy, hydroxyalkyl, cyano, amino, nitro, hydroxy, cycloalkyl, heterocyclyl, aryl and heteroaryl;

R² is selected from the group consisting of a hydrogen atom, alkyl, heterocyclylalkyl, cycloalkylalkyl, alkenyl, alkynyl, haloalkyl, hydroxyalkyl, cycloalkyl, heterocyclyl, aryl and heteroaryl, wherein the alkyl, heterocyclylalkyl, cycloalkylalkyl, alkenyl, alkynyl, cycloalkyl, heterocyclyl, aryl and heteroaryl are each independently optionally substituted with one or more substituents selected from the group consisting of halogen, alkyl, alkenyl, alkynyl, alkoxy, haloalkyl, haloalkoxy, cyano, amino, nitro, hydroxy, hydroxyalkyl, cycloalkyl, heterocyclyl, aryl and heteroaryl;

R³ are identical or different and are each independently selected from the group consisting of a hydrogen atom, halogen, alkyl, oxo, alkenyl, alkynyl, alkoxy, haloalkyl, haloalkoxy, hydroxyalkyl, cyano, amino, nitro, hydroxy, cycloalkyl, heterocyclyl, aryl and heteroaryl;

R⁴ are identical or different and are each independently selected from the group consisting of a hydrogen atom, halogen, alkyl, alkenyl, alkynyl, alkoxy, haloalkyl, haloalkoxy, cyano, amino, nitro, hydroxy, hydroxyalkyl, cycloalkyl, heterocyclyl, aryl and heteroaryl;

R⁵ are identical or different and are each independently selected from the group consisting of a hydrogen atom, halogen, alkyl, alkenyl, alkynyl, alkoxy, haloalkyl, haloalkoxy, hydroxyalkyl, cyano, amino, nitro, hydroxy, cycloalkyl, heterocyclyl, aryl and heteroaryl;

R⁶ are identical or different and are each independently selected from the group consisting of a hydrogen atom, halogen, alkyl, alkoxy, heterocyclylalkyl, cycloalkylalkyl, alkenyl, alkynyl, haloalkyl, haloalkoxy, hydroxyalkyl, cycloalkyl, heterocyclyl, aryl and heteroaryl, wherein the alkyl, heterocyclylalkyl, cycloalkylalkyl, alkenyl, alkynyl, cycloalkyl, heterocyclyl, aryl and heteroaryl are each independently optionally substituted with one or more substituents selected from the group consisting of halogen, alkyl, alkenyl, alkynyl, alkoxy, haloalkyl, haloalkoxy, cyano, amino, nitro, hydroxy, hydroxyalkyl, cycloalkyl, heterocyclyl, aryl and heteroaryl;

n is 0, 1, 2 or 3;
m is 0, 1, 2, 3 or 4;
p is 0, 1, 2 or 3;
g is 0, 1, 2, 3, 4 or 5; and
q is 0, 1, 2, 3 or 4.

In some preferred embodiments of the present disclosure, provided is the compound of general formula (IM) or the tautomer, racemate, enantiomer or diastereomer thereof or the mixture thereof, or the pharmaceutically acceptable salt thereof, which is a compound of general formula (IN) or a tautomer, racemate, enantiomer or diastereomer thereof or a mixture thereof, or a pharmaceutically acceptable salt thereof:

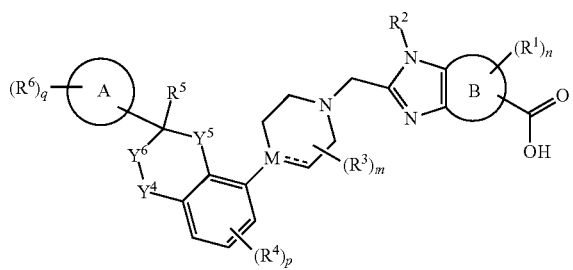

(IN)

wherein:
$Y^5$ is an O atom or a S atom;
$Y^4$ and $Y^6$ are identical or different and are each independently selected from the group consisting of an O atom, a S atom and —$(CR^mR^n)_k$—, provided that $Y^4$ and $Y^6$ are not both heteroatoms;
$R^m$ and $R^n$ are identical or different and are each independently selected from the group consisting of a hydrogen atom, halogen, alkyl, alkenyl, alkynyl, alkoxy, haloalkyl, haloalkoxy, hydroxyalkyl, cyano, amino, nitro, hydroxy, cycloalkyl, heterocyclyl, aryl and heteroaryl;
k is 1 or 2;
ring B, M, ⁃⁃⁃⁃, ring A, $R^1$ to $R^6$, n, m, p and q are as defined in general formula (IM).

In some preferred embodiments of the present disclosure, provided is the compound of general formula (IM) or general formula (IN) or the tautomer, racemate, enantiomer or diastereomer thereof or the mixture thereof, or the pharmaceutically acceptable salt thereof, which is a compound of general formula (INa) or general formula (INb) or a tautomer, racemate, enantiomer or diastereomer thereof or a mixture thereof, or a pharmaceutically acceptable salt thereof:

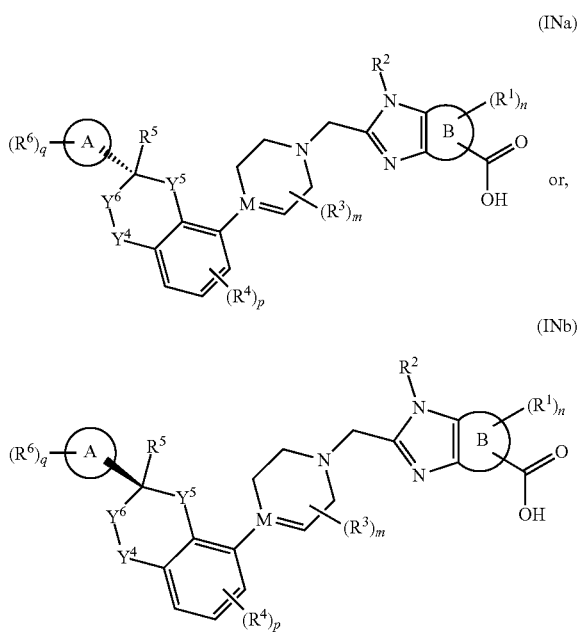

wherein:
$Y^5$ is an O atom or a S atom;
$Y^4$ and $Y^6$ are identical or different and are each independently selected from the group consisting of an O atom, a S atom and —$(CR^mR^n)_k$—, provided that $Y^4$ and $Y^6$ are not both heteroatoms;
$R^m$ and $R^n$ are identical or different and are each independently selected from the group consisting of a hydrogen atom, halogen, alkyl, alkenyl, alkynyl, alkoxy, haloalkyl, haloalkoxy, hydroxyalkyl, cyano, amino, nitro, hydroxy, cycloalkyl, heterocyclyl, aryl and heteroaryl;
k is 1 or 2;
ring B, M, ⁃⁃⁃⁃, ring A, $R^1$ to $R^6$, n, m, p and q are as defined in general formula (IM).

In some preferred embodiments of the present disclosure, provided is the compound of general formula (IM) or the tautomer, racemate, enantiomer or diastereomer thereof or the mixture thereof, or the pharmaceutically acceptable salt thereof, which is a compound of general formula (I) or a tautomer, racemate, enantiomer or diastereomer thereof or a mixture thereof, or a pharmaceutically acceptable salt thereof:

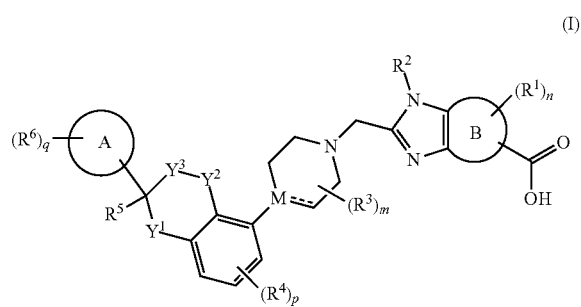

wherein:
$Y^1$ is an O atom or a S atom;
$Y^2$ and $Y^3$ are identical or different and are each independently selected from the group consisting of an O atom, a S atom and —$(CR^mR^n)_k$—, provided that $Y^2$ and $Y^3$ are not both heteroatoms;
$R^m$ and $R^n$ are identical or different and are each independently selected from the group consisting of a hydrogen atom, halogen, alkyl, alkenyl, alkynyl, alkoxy, haloalkyl, haloalkoxy, hydroxyalkyl, cyano, amino, nitro, hydroxy, cycloalkyl, heterocyclyl, aryl and heteroaryl;
k is 1 or 2;
ring B, M, ⁃⁃⁃⁃, ring A, $R^1$ to $R^6$, n, m, p and q are as defined in general formula (IM).

In some preferred embodiments of the present disclosure, provided is the compound of general formula (I) or general formula (IM) or the tautomer, racemate, enantiomer or diastereomer thereof or the mixture thereof, or the pharmaceutically acceptable salt thereof,
wherein:
ring B is phenyl or 5- or 6-membered heteroaryl;
M is a N atom or a C atom;
⁃⁃⁃⁃ is a single bond or double bond; when M is a N atom, ⁃⁃⁃⁃ is a single bond, and when M is a C atom, ⁃⁃⁃⁃ is a single bond or double bond;
$Y^1$ is an O atom or a S atom;
$Y^2$ and $Y^3$ are identical or different and are each independently selected from the group consisting of an O atom, a S atom and —$(CR^mR^n)_k$—, provided that $Y^2$ and $Y^3$ are not both heteroatoms;
ring A is aryl or heteroaryl;
$R^m$ and $R^n$ are identical or different and are each independently selected from the group consisting of a hydrogen atom, halogen, alkyl, alkenyl, alkynyl, alkoxy, haloalkyl, haloalkoxy, hydroxyalkyl, cyano, amino, nitro, hydroxy, cycloalkyl, heterocyclyl, aryl and heteroaryl;
$R^1$ are identical or different and are each independently selected from the group consisting of a hydrogen atom, halogen, alkyl, alkenyl, alkynyl, alkoxy, haloalkyl, haloalkoxy, hydroxyalkyl, cyano, amino, nitro, hydroxy, cycloalkyl, heterocyclyl, aryl and heteroaryl;

$R^2$ is selected from the group consisting of a hydrogen atom, alkyl, heterocyclylalkyl, cycloalkylalkyl, alkenyl, alkynyl, haloalkyl, hydroxyalkyl, cycloalkyl, heterocyclyl, aryl and heteroaryl, wherein the alkyl, heterocyclylalkyl, cycloalkylalkyl, alkenyl, alkynyl, cycloalkyl, heterocyclyl, aryl and heteroaryl are each independently optionally substituted with one or more substituents selected from the group consisting of halogen, alkyl, alkenyl, alkynyl, alkoxy, haloalkyl, haloalkoxy, cyano, amino, nitro, hydroxy, hydroxyalkyl, cycloalkyl, heterocyclyl, aryl and heteroaryl;

$R^3$ are identical or different and are each independently selected from the group consisting of a hydrogen atom, halogen, alkyl, oxo, alkenyl, alkynyl, alkoxy, haloalkyl, haloalkoxy, hydroxyalkyl, cyano, amino, nitro, hydroxy, cycloalkyl, heterocyclyl, aryl and heteroaryl;

$R^4$ are identical or different and are each independently selected from the group consisting of a hydrogen atom, halogen, alkyl, alkenyl, alkynyl, alkoxy, haloalkyl, haloalkoxy, cyano, amino, nitro, hydroxy, hydroxyalkyl, cycloalkyl, heterocyclyl, aryl and heteroaryl;

$R^5$ is selected from the group consisting of a hydrogen atom, halogen, alkyl, alkenyl, alkynyl, alkoxy, haloalkyl, haloalkoxy, hydroxyalkyl, cyano, amino, nitro, hydroxy, cycloalkyl, heterocyclyl, aryl and heteroaryl;

$R^6$ are identical or different and are each independently selected from the group consisting of a hydrogen atom, alkyl, heterocyclylalkyl, cycloalkylalkyl, alkenyl, alkynyl, haloalkyl, hydroxyalkyl, cycloalkyl, heterocyclyl, aryl and heteroaryl, wherein the alkyl, heterocyclylalkyl, cycloalkylalkyl, alkenyl, alkynyl, cycloalkyl, heterocyclyl, aryl and heteroaryl are each independently optionally substituted with one or more substituents selected from the group consisting of halogen, alkyl, alkenyl, alkynyl, alkoxy, haloalkyl, haloalkoxy, cyano, amino, nitro, hydroxy, hydroxyalkyl, cycloalkyl, heterocyclyl, aryl and heteroaryl;

k is 1 or 2;
n is 0, 1, 2 or 3;
m is 0, 1, 2, 3 or 4;
p is 0, 1, 2 or 3; and
q is 0, 1, 2, 3 or 4.

In some preferred embodiments of the present disclosure, provided is the compound of general formula (IM) or general formula (I) or the tautomer, racemate, enantiomer or diastereomer thereof or the mixture thereof, or the pharmaceutically acceptable salt thereof, wherein $R^6$ are identical or different and are each independently selected from the group consisting of a hydrogen atom, halogen, alkyl, alkoxy, heterocyclylalkyl, cycloalkylalkyl, alkenyl, alkynyl, haloalkyl, haloalkoxy, hydroxyalkyl, cycloalkyl, heterocyclyl, aryl and heteroaryl, wherein the alkyl, heterocyclylalkyl, cycloalkylalkyl, alkenyl, alkynyl, cycloalkyl, heterocyclyl, aryl and heteroaryl are each independently optionally substituted with one or more substituents selected from the group consisting of halogen, alkyl, alkenyl, alkynyl, alkoxy, haloalkyl, haloalkoxy, cyano, amino, nitro, hydroxy, hydroxyalkyl, cycloalkyl, heterocyclyl, aryl and heteroaryl.

In some preferred embodiments of the present disclosure, provided is the compound of general formula (IM) or general formula (I) or the tautomer, racemate, enantiomer or diastereomer thereof or the mixture thereof, or the pharmaceutically acceptable salt thereof, which is a compound of general formula (II) or a tautomer, racemate, enantiomer or diastereomer thereof or a mixture thereof, or a pharmaceutically acceptable salt thereof:

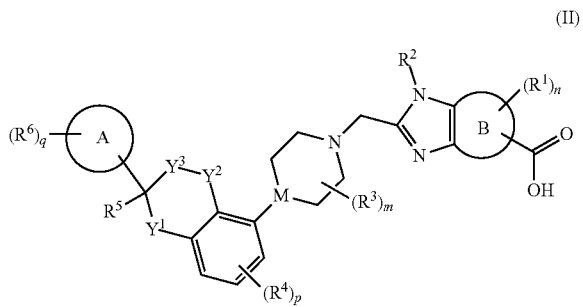

(II)

wherein:
ring B, M, $Y^1$, $Y^2$, $Y^3$, ring A, $R^1$ to $R^6$, n, m, p and q are as defined in general formula (I).

In some preferred embodiments of the present disclosure, provided is the compound of general formula (IM), general formula (I), general formula (II), general formula (IN), general formula (INa) or general formula (INb) or the tautomer, racemate, enantiomer or diastereomer thereof or the mixture thereof, or the pharmaceutically acceptable salt thereof, wherein ring B is selected from the group consisting of phenyl, pyridinyl and thienyl.

In some preferred embodiments of the present disclosure, provided is the compound of general formula (IM), general formula (I), general formula (II), general formula (IN), general formula (INa) or general formula (INb) or the tautomer, racemate, enantiomer or diastereomer thereof or the mixture thereof, or the pharmaceutically acceptable salt thereof, wherein ring B is phenyl or thienyl.

In some preferred embodiments of the present disclosure, provided is the compound of general formula (IM) or general formula (IN) or the tautomer, racemate, enantiomer or diastereomer thereof or the mixture thereof, or the pharmaceutically acceptable salt thereof, which is a compound of general formula (IIG) or a tautomer, racemate, enantiomer or diastereomer thereof or a mixture thereof, or a pharmaceutically acceptable salt thereof:

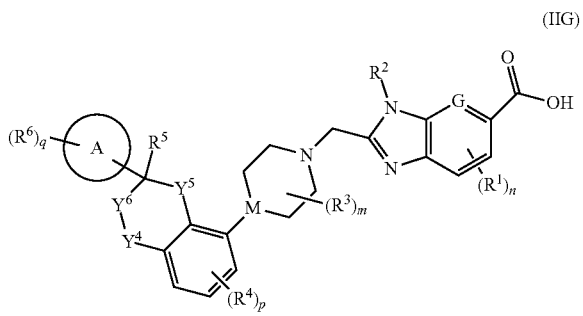

(IIG)

wherein:
G is a C atom or a N atom;
$Y^5$ is an O atom or a S atom;
$Y^4$ and $Y^6$ are identical or different and are each independently selected from the group consisting of an O atom, a S atom and —$(CR^mR^n)_k$—, provided that $Y^4$ and $Y^6$ are not both heteroatoms;
$R^m$ and $R^n$ are identical or different and are each independently selected from the group consisting of a hydrogen atom, halogen, alkyl, alkenyl, alkynyl, alkoxy, haloalkyl, haloalkoxy, hydroxyalkyl, cyano, amino, nitro, hydroxy, cycloalkyl, heterocyclyl, aryl and heteroaryl;

k is 1 or 2;

M, ring A, $R^1$ to $R^6$, n, m, p and q are as defined in general formula (IM).

In some preferred embodiments of the present disclosure, provided is the compound of general formula (IM), general formula (IN) or general formula (IIG) or the tautomer, racemate, enantiomer or diastereomer thereof or the mixture thereof, or the pharmaceutically acceptable salt thereof, which is a compound of general formula (IIGa) or general formula (IIGb) or a tautomer, racemate, enantiomer or diastereomer thereof or a mixture thereof, or a pharmaceutically acceptable salt thereof:

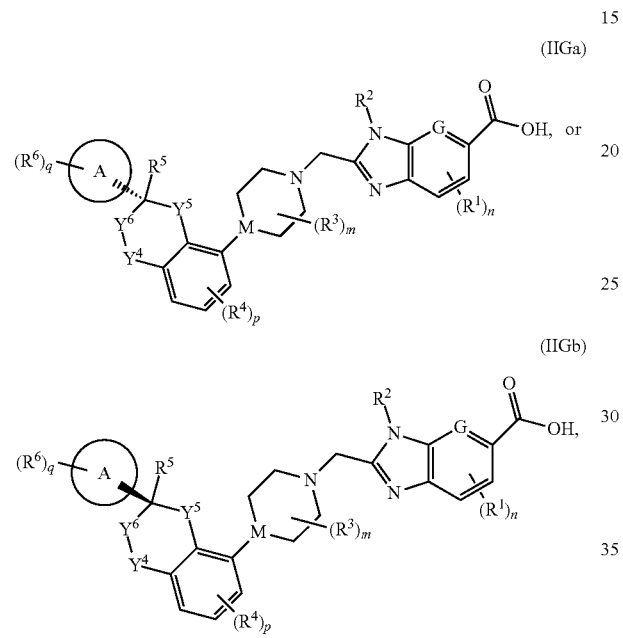

(IIGa)

(IIGb)

wherein:

G is a C atom or a N atom;

$Y^5$ is an O atom or a S atom;

$Y^4$ and $Y^6$ are identical or different and are each independently selected from the group consisting of an O atom, a S atom and —$(CR^mR^n)_k$—, provided that $Y^4$ and $Y^6$ are not both heteroatoms;

$R^m$ and $R^n$ are identical or different and are each independently selected from the group consisting of a hydrogen atom, halogen, alkyl, alkenyl, alkynyl, alkoxy, haloalkyl, haloalkoxy, hydroxyalkyl, cyano, amino, nitro, hydroxy, cycloalkyl, heterocyclyl, aryl and heteroaryl;

k is 1 or 2;

M, ring A, $R^1$ to $R^6$, n, m, p and q are as defined in general formula (IM).

In some preferred embodiments of the present disclosure, provided is the compound of general formula (IM), general formula (IN) or general formula (IIG) or the tautomer, racemate, enantiomer or diastereomer thereof or the mixture thereof, or the pharmaceutically acceptable salt thereof, which is a compound of general formula (IIN) or a tautomer, racemate, enantiomer or diastereomer thereof or a mixture thereof, or a pharmaceutically acceptable salt thereof:

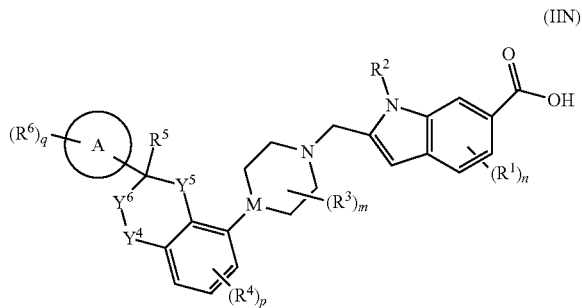

(IIN)

wherein:

$Y^5$ is an O atom or a S atom;

$Y^4$ and $Y^6$ are identical or different and are each independently selected from the group consisting of an O atom, a S atom and —$(CR^mR^n)_k$—, provided that $Y^4$ and $Y^6$ are not both heteroatoms;

$R^m$ and $R^n$ are identical or different and are each independently selected from the group consisting of a hydrogen atom, halogen, alkyl, alkenyl, alkynyl, alkoxy, haloalkyl, haloalkoxy, hydroxyalkyl, cyano, amino, nitro, hydroxy, cycloalkyl, heterocyclyl, aryl and heteroaryl;

k is 1 or 2;

M, ring A, $R^1$ to $R^6$, n, m, p and q are as defined in general formula (IM).

In some preferred embodiments of the present disclosure, provided is the compound of general formula (IM), general formula (IN), general formula (IIG) or general formula (IIN) or the tautomer, racemate, enantiomer or diastereomer thereof or the mixture thereof, or the pharmaceutically acceptable salt thereof, which is a compound of general formula (IINa) or general formula (IINb) or a tautomer, racemate, enantiomer or diastereomer thereof or a mixture thereof, or a pharmaceutically acceptable salt thereof:

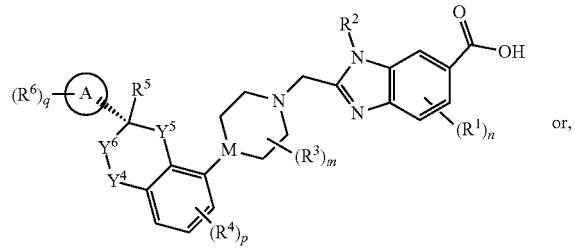

(IINa)

or,

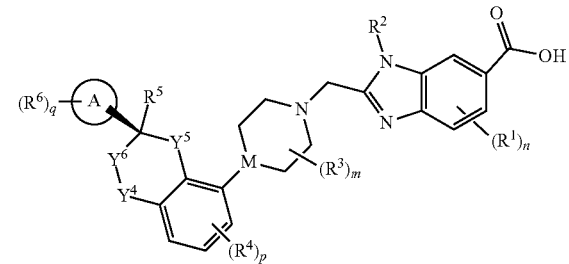

(IINb)

wherein:

Y⁵ is an O atom or a S atom;

Y⁴ and Y⁶ are identical or different and are each independently selected from the group consisting of an O atom, a S atom and —(CR'''R'')$_k$—, provided that Y⁴ and Y⁶ are not both heteroatoms;

R''' and R'' are identical or different and are each independently selected from the group consisting of a hydrogen atom, halogen, alkyl, alkenyl, alkynyl, alkoxy, haloalkyl, haloalkoxy, hydroxyalkyl, cyano, amino, nitro, hydroxy, cycloalkyl, heterocyclyl, aryl and heteroaryl;

k is 1 or 2;

M, ring A, R¹ to R⁶, n, m, p and q are as defined in general formula (IM).

In some preferred embodiments of the present disclosure, provided is the compound of general formula (IN), general formula (INa), general formula (INb), general formula (IIG), general formula (IIGa), general formula (IIGb), general formula (IIN), general formula (IINa) or general formula (IINb) or the tautomer, racemate, enantiomer or diastereomer thereof or the mixture thereof, or the pharmaceutically acceptable salt thereof, wherein Y⁴ and Y⁵ are O atoms, and Y⁶ is —(CR'''R'')$_k$—; or, Y⁵ and Y⁶ are O atoms, and Y⁴ is —(CR'''R'')$_k$—; k is 1 or 2; R''' and R'' are identical or different and are each independently selected from the group consisting of a hydrogen atom, halogen, C$_{1-6}$ alkyl, C$_{2-6}$ alkenyl, C$_{2-6}$ alkynyl, C$_{1-6}$ alkoxy, C$_{1-6}$ haloalkyl, C$_{1-6}$ haloalkoxy, hydroxy C$_{1-6}$ alkyl, cyano, amino, nitro, hydroxy, 3- to 8-membered cycloalkyl, 3- to 8-membered heterocyclyl, 6- to 10-membered aryl and 5- to 10-membered heteroaryl.

In some preferred embodiments of the present disclosure, provided is the compound of general formula (I) or general formula (II) or the tautomer, racemate, enantiomer or diastereomer thereof or the mixture thereof, or the pharmaceutically acceptable salt thereof, wherein Y¹ and Y² are O atoms, and Y³ is —(CR'''R'')$_k$—; or, Y¹ and Y³ are O atoms, and Y² is —(CR'''R'')$_k$—; k is 1 or 2; R''' and R'' are as defined in general formula (I).

In some preferred embodiments of the present disclosure, provided is the compound of general formula (IM), general formula (IN), general formula (IIG) or general formula (IIN) or the tautomer, racemate, enantiomer or diastereomer thereof or the mixture thereof, or the pharmaceutically acceptable salt thereof, which is a compound of general formula (IIIN-1) or general formula (IIIN-2) or a tautomer, racemate, enantiomer or diastereomer thereof or a mixture thereof, or a pharmaceutically acceptable salt thereof:

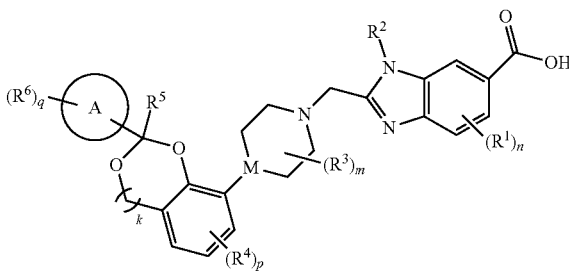

wherein:

k is 1 or 2;

M, ring A, R¹ to R⁶, n, m, p and q are as defined in general formula (IM).

In some preferred embodiments of the present disclosure, provided is the compound of general formula (IM), general formula (I) or general formula (II) or the tautomer, racemate, enantiomer or diastereomer thereof or the mixture thereof, or the pharmaceutically acceptable salt thereof, which is a compound of general formula (III-1) or general formula (III-2) or a tautomer, racemate, enantiomer or diastereomer thereof or a mixture thereof, or a pharmaceutically acceptable salt thereof:

wherein:

k is 1 or 2;

M, ring A, R¹ to R⁶, n, m, p and q are as defined in general formula (IM).

In some preferred embodiments of the present disclosure, provided is the compound of general formula (IM), general formula (I), general formula (IN), general formula (INa) or general formula (INb) or the tautomer, racemate, enantiomer or diastereomer thereof or the mixture thereof, or the pharmaceutically acceptable salt thereof, wherein and $R^3$ is a hydrogen atom or $C_{1-6}$ alkyl; preferably,

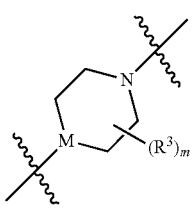

is selected from the group consisting of

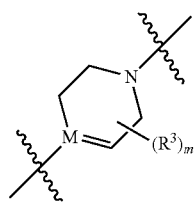

is selected from the group consisting of

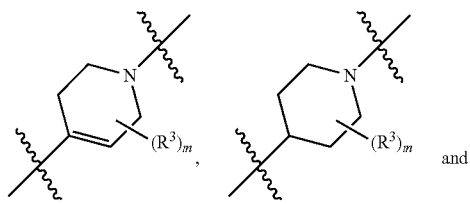 and

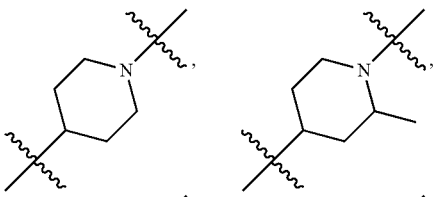

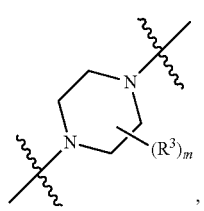

, and $R^3$ and m are as defined in general formula (IM).

In some preferred embodiments of the present disclosure, provided is the compound of general formula (II), general formula (IIG), general formula (IIGa), general formula (IIGb), general formula (IIN), general formula (IINa), general formula (IINb), general formula (IIIN-1), general formula (IIIN-2), general formula (III-1) or general formula (III-2) or the tautomer, racemate, enantiomer or diastereomer thereof or the mixture thereof, or the pharmaceutically acceptable salt thereof, wherein

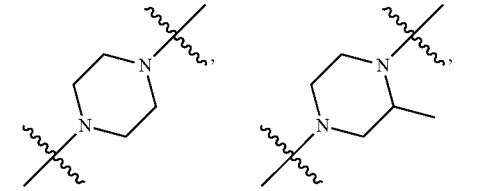

In some preferred embodiments of the present disclosure, provided is the compound of general formula (IM), general formula (I), general formula (II), general formula (IN), general formula (INa), general formula (INb), general formula (IIG), general formula (IIGa), general formula (IIGb), general formula (IIN), general formula (IINa), general formula (IINb), general formula (IIIN-1), general formula (IIIN-2), general formula (III-1) or general formula (III-2) or the tautomer, racemate, enantiomer or diastereomer thereof or the mixture thereof, or the pharmaceutically acceptable salt thereof, wherein

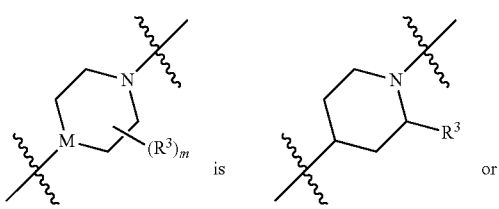 is

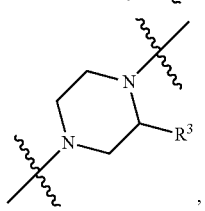

,

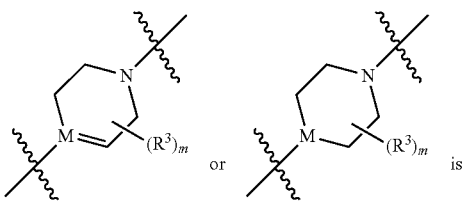 is

-continued

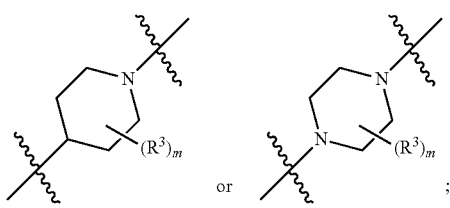

or

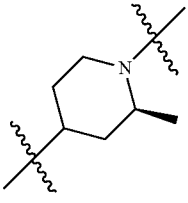

-continued

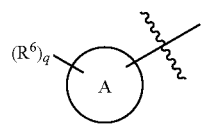

R³ and m are as defined in general formula (IM).

In some preferred embodiments of the present disclosure, provided is the compound of general formula (IM), general formula (I), general formula (II), general formula (IN), general formula (INa), general formula (INb), general formula (IIG), general formula (IIGa), general formula (IIGb), general formula (IIN), general formula (IINa), general formula (IINb), general formula (IIIN-1), general formula (IIIN-2), general formula (III-1) or general formula (III-2) or the tautomer, racemate, enantiomer or diastereomer thereof or the mixture thereof, or the pharmaceutically acceptable salt thereof, wherein

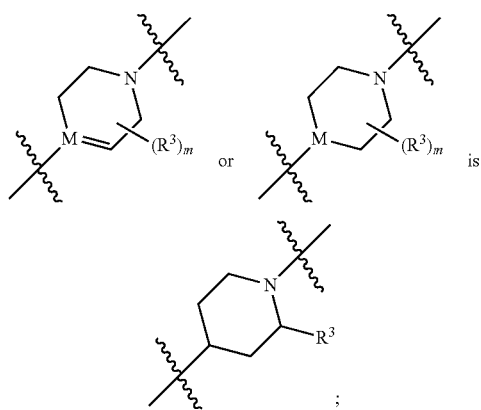

R³ is a hydrogen atom or $C_{1-6}$ alkyl; preferably,

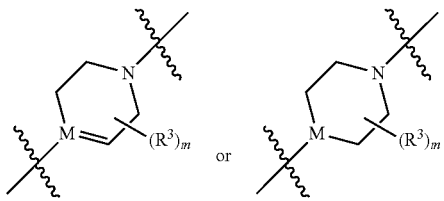

is selected from the group consisting of

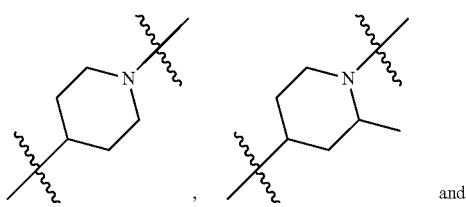

and

In some preferred embodiments of the present disclosure, provided is the compound of general formula (IM), general formula (I), general formula (II), general formula (IN), general formula (INa), general formula (INb), general formula (IIG), general formula (IIGa), general formula (IIGb), general formula (IIN), general formula (IINa), general formula (IINb), general formula (IIIN-1), general formula (IIIN-2), general formula (III-1) or general formula (III-2) or the tautomer, racemate, enantiomer or diastereomer thereof or the mixture thereof, or the pharmaceutically acceptable salt thereof, wherein M is CH.

In some preferred embodiments of the present disclosure, provided is the compound of general formula (IM), general formula (I), general formula (II), general formula (IN), general formula (INa), general formula (INb), general formula (JIG), general formula (IIGa), general formula (IIGb), general formula (IIN), general formula (IINa), general formula (IINb), general formula (IIIN-1), general formula (IIIN-2), general formula (III-1) or general formula (III-2) or the tautomer, racemate, enantiomer or diastereomer thereof or the mixture thereof, or the pharmaceutically acceptable salt thereof, wherein ring A is 6- to 10-membered aryl or 5- to 10-membered heteroaryl; preferably, ring A is selected from the group consisting of phenyl, 5- or 6-membered heteroaryl and

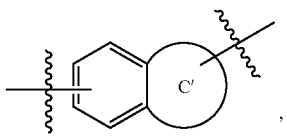

and ring C is 5- or 6-membered heteroaryl; more preferably, ring A is selected from the group consisting of benzothiazolyl, phenyl and pyridinyl.

In some preferred embodiments of the present disclosure, provided is the compound of general formula (IM), general formula (I), general formula (II), general formula (IN), general formula (INa), general formula (INb), general formula (IIG), general formula (IIGa), general formula (IIGb), general formula (IIN), general formula (IINa), general formula (IINb), general formula (IIIN-1), general formula (IIIN-2), general formula (III-1) or general formula (III-2) or the tautomer, racemate, enantiomer or diastereomer thereof or the mixture thereof, or the pharmaceutically acceptable salt thereof, wherein is selected from the group consisting of

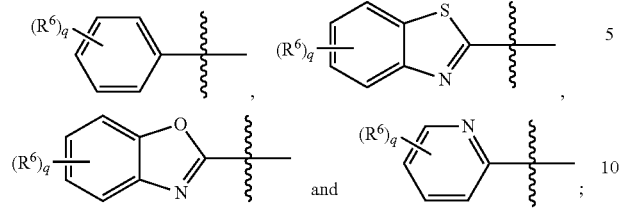

$R^6$ and q are as defined in general formula (IM).

In some preferred embodiments of the present disclosure, provided are the compounds of general formula (IM), general formula (I), general formula (II), general formula (IN), general formula (INa), general formula (INb), general formula (IIG), general formula (IIGa), general formula (IIGb), general formula (IIN), general formula (IINa), general formula (IINb), general formula (IIIN-1), general formula (IIIN-2), general formula (III-1) and general formula (III-2) or the tautomers, racemates, enantiomers or diastereomers thereof or the mixtures thereof, or the pharmaceutically acceptable salts thereof, wherein

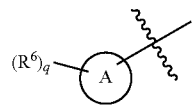

is selected from the group consisting of

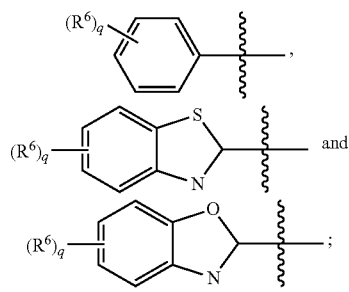

$R^6$ are identical or different and are each independently selected from the group consisting of a hydrogen atom, halogen, alkyl, alkoxy, heterocyclylalkyl, cycloalkylalkyl, alkenyl, alkynyl, haloalkyl, haloalkoxy, hydroxyalkyl, cycloalkyl, heterocyclyl, aryl and heteroaryl, wherein the alkyl, heterocyclylalkyl, cycloalkylalkyl, alkenyl, alkynyl, cycloalkyl, heterocyclyl, aryl and heteroaryl are each independently optionally substituted with one or more substituents selected from the group consisting of halogen, alkyl, alkenyl, alkynyl, alkoxy, haloalkyl, haloalkoxy, cyano, amino, nitro, hydroxy, hydroxyalkyl, cycloalkyl, heterocyclyl, aryl and heteroaryl; q is 0, 1, 2, 3 or 4.

In some preferred embodiments of the present disclosure, provided is the compound of general formula (I) or the tautomer, racemate, enantiomer or diastereomer thereof or the mixture thereof, or the pharmaceutically acceptable salt thereof, wherein

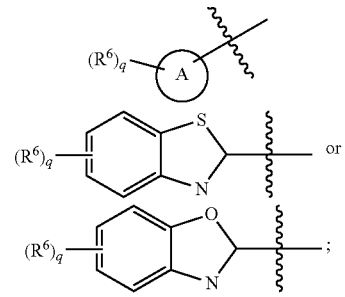

$R^6$ and q are as defined in general formula (I).

In some embodiments of the present disclosure, provided are the compounds of general formula (IM), general formula (I), general formula (II), general formula (IN), general formula (INa), general formula (INb), general formula (IIG), general formula (IIGa), general formula (IIGb), general formula (IIN), general formula (IINa), general formula (IINb), general formula (IIIN-1), general formula (IIIN-2), general formula (III-1) and general formula (III-2) or the tautomers, racemates, enantiomers or diastereomers thereof or the mixtures thereof, or the pharmaceutically acceptable salts thereof, wherein $R^1$ are identical or different and are each independently selected from the group consisting of a hydrogen atom, halogen and $C_{1-6}$ alkyl, preferably a hydrogen atom.

In some embodiments of the present disclosure, provided are the compounds of general formula (IM), general formula (I), general formula (II), general formula (IN), general formula (INa), general formula (INb), general formula (IIG), general formula (IIGa), general formula (IIGb), general formula (IIN), general formula (IINa), general formula (IINb), general formula (IIIN-1), general formula (IIIN-2), general formula (III-1) and general formula (III-2) or the tautomers, racemates, enantiomers or diastereomers thereof or the mixtures thereof, or the pharmaceutically acceptable salts thereof, wherein $R^2$ is $C_{1-6}$ alkyl, wherein the $C_{1-6}$ alkyl is optionally substituted with one or more substituents selected from the group consisting of halogen, hydroxy, $C_{1-6}$ alkoxy, 3- to 6-membered cycloalkyl and 3- to 6-membered heterocyclyl; preferably, $R^2$ is

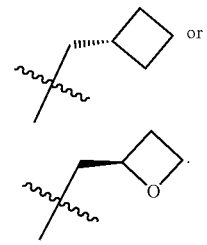

In some embodiments of the present disclosure, provided are the compounds of general formula (IM), general formula (I), general formula (II), general formula (IN), general formula (INa), general formula (INb), general formula (IIG), general formula (IIGa), general formula (IIGb), general formula (IIN), general formula (IINa), general formula (IINb), general formula (IIIN-1), general formula (IIIN-2), general formula (III-1) and general formula (III-2) or the tautomers, racemates, enantiomers or diastereomers thereof or the mixtures thereof, or the pharmaceutically acceptable salts thereof, wherein $R^3$ are identical or different and are each independently selected from the group consisting of a hydrogen atom, halogen, oxo and $C_{1-6}$ alkyl.

In some embodiments of the present disclosure, provided are the compounds of general formula (IM), general formula (I), general formula (II), general formula (IN), general formula (INa), general formula (INb), general formula (IIG), general formula (IIGa), general formula (IIGb), general formula (IIN), general formula (IINa), general formula (IINb), general formula (IIIN-1), general formula (IIIN-2), general formula (III-1) and general formula (III-2) or the tautomers, racemates, enantiomers or diastereomers thereof or the mixtures thereof, or the pharmaceutically acceptable salts thereof, wherein $R^3$ is a hydrogen atom or $C_{1-6}$ alkyl.

In some embodiments of the present disclosure, provided are the compounds of general formula (IM), general formula (I), general formula (II), general formula (IN), general formula (INa), general formula (INb), general formula (IIG), general formula (IIGa), general formula (IIGb), general formula (IIN), general formula (IINa), general formula (IINb), general formula (IIIN-1), general formula (IIIN-2), general formula (III-1) and general formula (III-2) or the tautomers, racemates, enantiomers or diastereomers thereof or the mixtures thereof, or the pharmaceutically acceptable salts thereof, wherein $R^4$ are identical or different and are each independently selected from the group consisting of a hydrogen atom, halogen and $C_{1-6}$ alkyl, preferably a hydrogen atom.

In some embodiments of the present disclosure, provided is the compound of general formula (IM) or the tautomer, racemate, enantiomer or diastereomer thereof or the mixture thereof, or the pharmaceutically acceptable salt thereof, wherein $R^5$ are identical or different and are each independently a hydrogen atom or $C_{1-6}$ alkyl.

In some embodiments of the present disclosure, provided are the compounds of general formula (I), general formula (II), general formula (IN), general formula (INa), general formula (INb), general formula (IIG), general formula (IIGa), general formula (IIGb), general formula (IIN), general formula (IINa), general formula (IINb), general formula (IIIN-1), general formula (IIIN-2), general formula (III-1) and general formula (III-2) or the tautomers, racemates, enantiomers or diastereomers thereof or the mixtures thereof, or the pharmaceutically acceptable salts thereof, wherein $R^5$ is a hydrogen atom or $C_{1-6}$ alkyl.

In some embodiments of the present disclosure, provided are the compounds of general formula (IM), general formula (I), general formula (II), general formula (IN), general formula (INa), general formula (INb), general formula (IIG), general formula (IIGa), general formula (IIGb), general formula (IIN), general formula (IINa), general formula (IINb), general formula (IIIN-1), general formula (IIIN-2), general formula (III-1) and general formula (III-2) or the tautomers, racemates, enantiomers or diastereomers thereof or the mixtures thereof, or the pharmaceutically acceptable salts thereof, wherein $R^6$ are identical or different and are each independently selected from the group consisting of a hydrogen atom, halogen, $C_{1-6}$ alkyl, $C_{1-6}$ alkoxy, cyano, and $C_{1-6}$ haloalkyl, preferably from the group consisting of a hydrogen atom, halogen, $C_{1-6}$ alkyl and cyano.

In some embodiments of the present disclosure, provided are the compounds of general formula (IM), general formula (I), general formula (II), general formula (IN), general formula (INa), general formula (INb), general formula (IIG), general formula (IIGa), general formula (IIGb), general formula (IIN), general formula (IINa), general formula (IINb), general formula (IIIN-1), general formula (IIIN-2), general formula (III-1) and general formula (III-2) or the tautomers, racemates, enantiomers or diastereomers thereof or the mixtures thereof, or the pharmaceutically acceptable salts thereof, wherein $R^6$ are identical or different and are each independently selected from the group consisting of a hydrogen atom, halogen, $C_{1-6}$ alkyl, $C_{1-6}$ alkoxy and $C_{1-6}$ haloalkyl.

In some embodiments of the present disclosure, provided are the compounds of general formula (I), general formula (II), general formula (IN), general formula (INa), general formula (INb), general formula (IIG), general formula (IIGa), general formula (IIGb), general formula (IIN), general formula (IINa), general formula (IINb), general formula (IIIN-1), general formula (IIIN-2), general formula (III-1) and general formula (III-2) or the tautomers, racemates, enantiomers or diastereomers thereof or the mixtures thereof, or the pharmaceutically acceptable salts thereof, wherein k is 1.

In some preferred embodiments of the present disclosure, provided are the compounds of general formula (I), general formula (II), general formula (IN), general formula (INa), general formula (INb), general formula (IIG), general formula (IIGa), general formula (IIGb), general formula (IIN), general formula (IINa) and general formula (IINb) or the tautomers, racemates, enantiomers or diastereomers thereof or the mixtures thereof, or the pharmaceutically acceptable salts thereof, wherein $R^m$ and $R^n$ are identical or different and are each independently selected from the group consisting of a hydrogen atom, halogen and $C_{1-6}$ alkyl, preferably a hydrogen atom and $C_{1-6}$ alkyl.

In some preferred embodiments of the present disclosure, provided is the compound of general formula (IM) or the tautomer, racemate, enantiomer or diastereomer thereof or the mixture thereof, or the pharmaceutically acceptable salt thereof, wherein ring C is 6- to 7-membered heterocyclyl, and the 6- to 7-membered heterocyclyl contains 1 to 2 heteroatoms selected from the group consisting of an O atom and a S atom; M is a nitrogen atom or a carbon atom; ≕ is a single bond or double bond; when M is a N atom, ≕ is a single bond, and when M is a C atom, ≕ is a single bond or double bond; ring B is phenyl or 5- or 6-membered heteroaryl; ring A is 6- to 10-membered aryl or 5- to 10-membered heteroaryl; $R^1$ are identical or different and are each independently selected from the group consisting of a hydrogen atom, halogen and $C_{1-6}$ alkyl; n is 0, 1 or 2; $R^2$ is $C_{1-6}$ alkyl or 3- to 8-membered heterocyclyl $C_{1-6}$ alkyl, wherein the $C_{1-6}$ alkyl is optionally substituted with one or more substituents selected from the group consisting of halogen, hydroxy, $C_{1-6}$ alkoxy, 3- to 6-membered cycloalkyl and 3- to 6-membered heterocyclyl; $R^3$ are identical or different and are each independently selected from the group consisting of a hydrogen atom, halogen, oxo and $C_{1-6}$ alkyl; m is 0 or 1; $R^4$ are identical or different and are each independently selected from the group consisting of a hydrogen atom, halogen and $C_{1-6}$ alkyl; p is 0, 1 or 2; $R^5$ are identical or different and are each independently a hydrogen atom or $C_{1-6}$ alkyl; g is 0, 1 or 2; $R^6$ are identical or different and are each independently selected from the group consisting of a hydrogen atom, halogen, $C_{1-6}$ alkyl, $C_{1-6}$ alkoxy, cyano and $C_{1-6}$ haloalkyl; q is 0, 1, 2 or 3.

In some preferred embodiments of the present disclosure, provided are the compounds of general formula (IN), general formula (INa) and general formula (INb) or the tautomers, racemates, enantiomers or diastereomers thereof or the mixtures thereof, or the pharmaceutically acceptable salts thereof, wherein $Y^4$ and $Y^5$ are O atoms, and $Y^6$ is —$(CR^mR^n)_k$—; or, $Y^5$ and $Y^6$ are O atoms, and $Y^4$ is —$(CR^mR^n)_k$—; k is 1 or 2; $R^m$ and $R^n$ are identical or different and are each independently selected from the group consisting of a hydrogen atom, halogen, $C_{1-6}$ alkyl, $C_{2-6}$ alkenyl, $C_{2-6}$ alkynyl, $C_{1-6}$ alkoxy, $C_{1-6}$ haloalkyl, $C_{1-6}$ haloalkoxy, hydroxy $C_{1-6}$ alkyl, cyano, amino, nitro, hydroxy, 3- to 8-membered cycloalkyl, 3- to 8-membered heterocyclyl, 6- to 10-membered aryl and 5- to 10-membered heteroaryl; M is a nitrogen atom or carbon atom; ring B is phenyl or 5- or 6-membered heteroaryl; ring A is selected from the group consisting of phenyl, 5- or 6-membered heteroaryl and

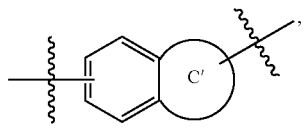

and ring C' is 5- or 6-membered heteroaryl; $R^1$ are identical or different and are each independently selected from the group consisting of a hydrogen atom, halogen and $C_{1-6}$ alkyl; n is 0, 1 or 2; $R^2$ is $C_{1-6}$ alkyl or 3- to 8-membered heterocyclyl $C_{1-6}$ alkyl, wherein the $C_{1-6}$ alkyl is optionally substituted with one or more substituents selected from the group consisting of halogen, hydroxy, $C_{1-6}$ alkoxy, 3- to 6-membered cycloalkyl and 3- to 6-membered heterocyclyl; $R^3$ are identical or different and are each independently selected from the group consisting of a hydrogen atom, halogen, oxo and $C_{1-6}$ alkyl; m is 0 or 1; $R^4$ are identical or different and are each independently selected from the group consisting of a hydrogen atom, halogen and $C_{1-6}$ alkyl; p is 0, 1 or 2; $R^5$ is a hydrogen atom or $C_{1-6}$ alkyl; $R^6$ are identical or different and are each independently selected from the group consisting of a hydrogen atom, halogen, $C_{1-6}$ alkyl, $C_{1-6}$ alkoxy, cyano and $C_{1-6}$ haloalkyl; q is 0, 1, 2 or 3.

In some preferred embodiments of the present disclosure, provided are the compounds of general formula (IIG), general formula (IIGa) and general formula (IIGb) or the tautomers, racemates, enantiomers or diastereomers thereof or the mixtures thereof, or the pharmaceutically acceptable salts thereof, wherein G is a nitrogen atom or carbon atom; $Y^4$ and $Y^5$ are O atoms, and $Y^6$ is —$(CR'''R'')_k$—; or, $Y^5$ and $Y^6$ are O atoms, and $Y^4$ is —$(CR'''R'')_k$—; k is 1 or 2; $R'''$ and $R''$ are both hydrogen atoms; ring A is selected from the group consisting of phenyl, 5- or 6-membered heteroaryl and and ring C' is 5- or 6-membered heteroaryl; $R^1$ are identical or different and are each independently selected from the group consisting of a hydrogen atom, halogen and $C_{1-6}$ alkyl; n is 0, 1 or 2; $R^2$ is $C_{1-6}$ alkyl or 3- to 8-membered heterocyclyl $C_{1-6}$ alkyl, wherein the $C_{1-6}$ alkyl is optionally substituted with one or more substituents selected from the group consisting of halogen, hydroxy, $C_{1-6}$ alkoxy, 3- to 6-membered cycloalkyl and 3- to 6-membered heterocyclyl; $R^3$ are identical or different and are each independently selected from the group consisting of a hydrogen atom, halogen, oxo and $C_{1-6}$ alkyl; m is 0 or 1; $R^4$ are identical or different and are each independently selected from the group consisting of a hydrogen atom, halogen and $C_{1-6}$ alkyl; p is 0, 1 or 2; $R^5$ is a hydrogen atom or $C_{1-6}$ alkyl; $R^6$ are identical or different and are each independently selected from the group consisting of a hydrogen atom, halogen, $C_{1-6}$ alkyl, $C_{1-6}$ alkoxy, cyano and $C_{1-6}$ haloalkyl; q is 0, 1, 2 or 3.

In some preferred embodiments of the present disclosure, provided are the compounds of general formula (IIG), general formula (IIGa) and general formula (IIGb) or the tautomers, racemates, enantiomers or diastereomers thereof or the mixtures thereof, or the pharmaceutically acceptable salts thereof, wherein G is a carbon atom; $Y^4$ and $Y^5$ are O atoms, and $Y^6$ is —$(CR'''R'')_k$—; k is 1; $R'''$ and $R''$ are both hydrogen atoms; ring A is selected from the group consisting of benzothiazolyl, phenyl and pyridinyl; $R^1$ are identical or different and are each independently selected from the group consisting of a hydrogen atom, halogen and $C_{1-6}$ alkyl; n is 0, 1 or 2; $R^2$ is $C_{1-6}$ alkyl or 3- to 8-membered heterocyclyl $C_{1-6}$ alkyl, wherein the $C_{1-6}$ alkyl is optionally substituted with one or more substituents selected from the group consisting of halogen, hydroxy, $C_{1-6}$ alkoxy, 3- to 6-membered cycloalkyl and 3- to 6-membered heterocyclyl; $R^3$ are identical or different and are each independently selected from the group consisting of a hydrogen atom, halogen, oxo and $C_{1-6}$ alkyl; m is 0 or 1; $R^4$ are identical or different and are each independently selected from the group consisting of a hydrogen atom, halogen and $C_{1-6}$ alkyl; p is 0, 1 or 2; $R^5$ is a hydrogen atom or $C_{1-6}$ alkyl; $R^6$ are identical or different and are each independently selected from the group consisting of a hydrogen atom, halogen, $C_{1-6}$ alkyl, $C_{1-6}$ alkoxy, cyano and $C_{1-6}$ haloalkyl; q is 0, 1, 2 or 3.

TABLE A

Typical compounds disclosed herein include, but are not limited to:

| Example No. | Structures and names of compounds |
| --- | --- |
| 1 | 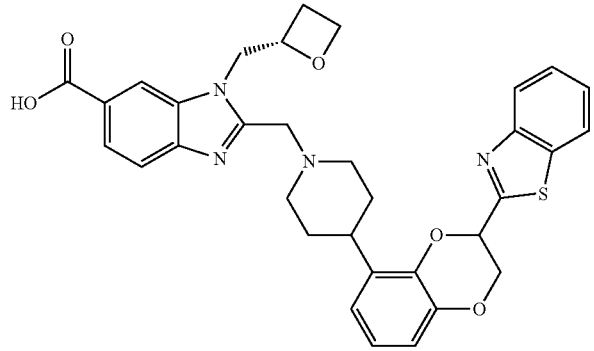<br>1<br>2-((4-(3-(Benzo[d]thiazol-2-yl)-2,3-dihydrobenzo[b][1,4]dioxan-5-yl)piperidin-1-yl)methyl)-1-(((S)-oxetan-2-yl)methyl)-1H-benzo[d]imidazole-6-carboxylic acid (a mixture of diastereomers) 1 |

TABLE A-continued

Typical compounds disclosed herein include, but are not limited to:

| Example No. | Structures and names of compounds |
| --- | --- |
| 1-1 | 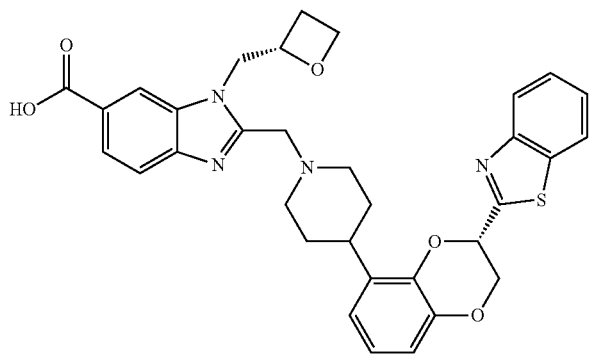<br>1-1<br><br>2-((4-((S)-3-(Benzo[d]thiazol-2-yl)-2,3-dihydrobenzo[b][1,4]dioxan-5-yl)piperidin-1-yl)methyl)-1-(((S)-oxetan-2-yl)methyl)-1H-benzo[d]imidazole-6-carboxylic acid 1-1 |
| 1-2 | 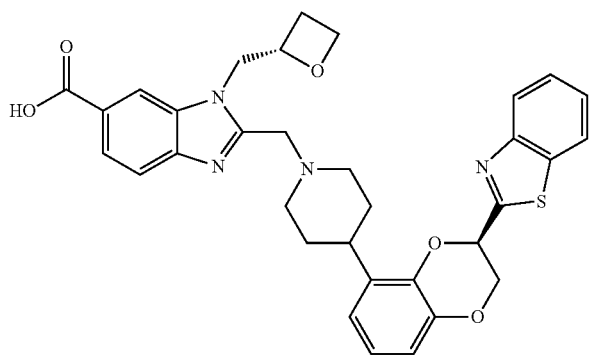<br>1-2<br><br>2-((4-((R)-3-(Benzo[d]thiazol-2-yl)-2,3-dihydrobenzo[b][1,4]dioxan-5-yl)piperidin-1-yl)methyl)-1-(((S)-oxetan-2-yl)methyl)-1H-benzo[d]imidazole-6-carboxylic acid 1-2 |
| 2 | 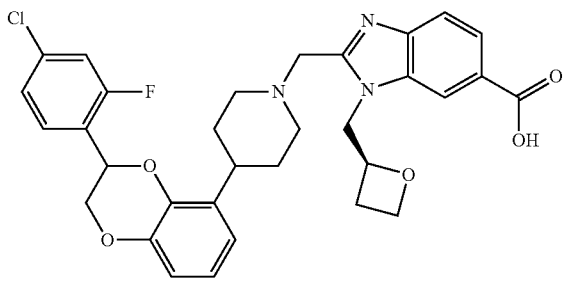<br>2<br><br>2-((4-(3-(4-Chloro-2-fluorophenyl)-2,3-dihydrobenzo[b][1,4]dioxan-5-yl)piperidin-1-yl)methyl)-1-((S)-oxetan-2-ylmethyl)-1H-benzo[d]imidazole-6-carboxylic acid (a mixture of diastereomers) 2 |

TABLE A-continued

Typical compounds disclosed herein include, but are not limited to:

| Example No. | Structures and names of compounds |
|---|---|
| 3 | 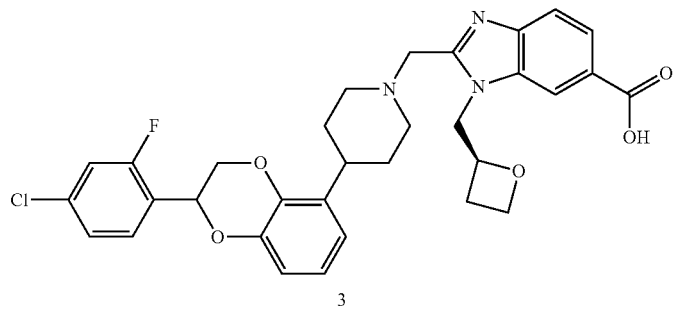 [SMILES: O=C(O)c1ccc2nc(CN3CCC(c4cccc5c4OCC(c4ccc(Cl)cc4F)O5)CC3)n(C[C@@H]3CCO3)c2c1]

2-((4-(2-(4-Chloro-2-fluorophenyl)-2,3-dihydrobenzo[b][1,4]dioxan-5-yl)piperidin-1-yl)methyl)-1-((S)-oxetan-2-ylmethyl)-1H-benzo[d]imidazole-6-carboxylic acid (a mixture of diastereomers) 3

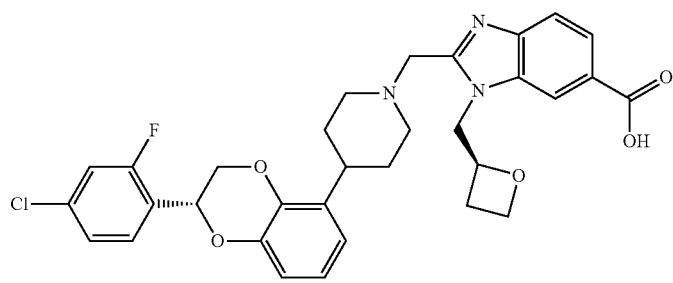 [SMILES: O=C(O)c1ccc2nc(CN3CCC(c4cccc5c4OC[C@@H](c4ccc(Cl)cc4F)O5)CC3)n(C[C@@H]3CCO3)c2c1]

2-((4-((R)-2-(4-Chloro-2-fluorophenyl)-2,3-dihydrobenzo[b][1,4]dioxan-5-yl)piperidin-1-yl)methyl)-1-((S)-oxetan-2-ylmethyl)-1H-benzo[d]imidazole-6-carboxylic acid

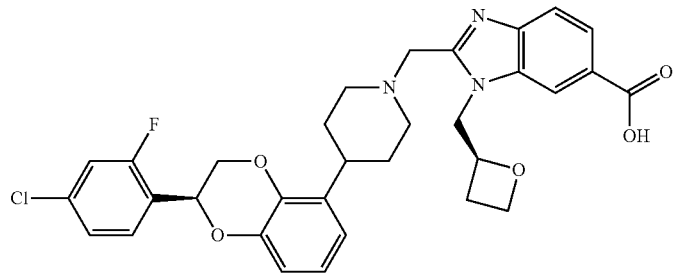 [SMILES: O=C(O)c1ccc2nc(CN3CCC(c4cccc5c4OC[C@H](c4ccc(Cl)cc4F)O5)CC3)n(C[C@@H]3CCO3)c2c1]

2-((4-((S)-2-(4-Chloro-2-fluorophenyl)-2,3-dihydrobenzo[b][1,4]dioxan-5-yl)piperidin-1-yl)methyl)-1-((S)-oxetan-2-ylmethyl)-1H-benzo[d]imidazole-6-carboxylic acid |
| 4 | 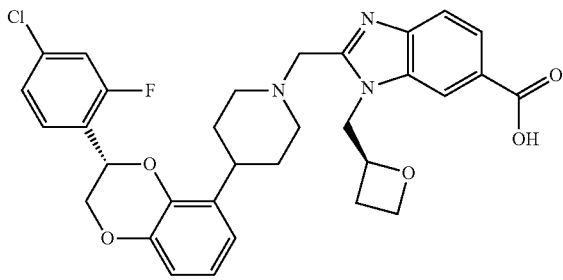

2-((4-((S)-3-(4-Chloro-2-fluorophenyl)-2,3-dihydrobenzo[b][1,4]dioxan-5-yl)piperidin-1-yl)methyl)-1-(((S)-oxetan-2-yl)methyl)-1H-benzo[d]imidazole-6-carboxylic acid 4 |

TABLE A-continued

Typical compounds disclosed herein include, but are not limited to:

| Example No. | Structures and names of compounds |
|---|---|
| | 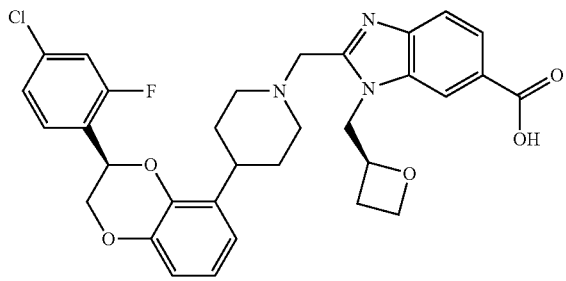<br>2-((4-((R)-3-(4-Chloro-2-fluorophenyl)-2,3-dihydrobenzo[b][1,4]dioxan-5-yl)piperidin-1-yl)methyl)-1-(((S)-oxetan-2-yl)methyl)-1H-benzo[d]imidazole-6-carboxylic acid |
| 5 | 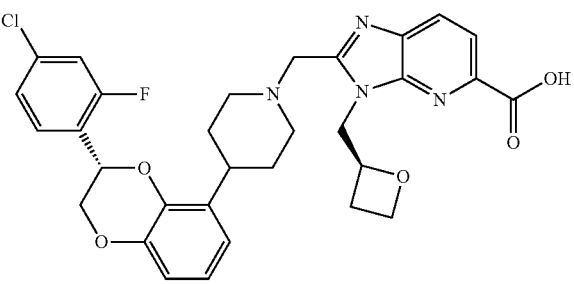<br>5<br>2-((4-((S)-3-(4-Chloro-2-fluorophenyl)-2,3-dihydrobenzo[b][1,4]dioxan-5-yl)piperidin-1-yl)methyl)-3-((S)-oxetan-2-ylmethyl)-3H-imidazo[4,5-b]pyridine-5-carboxylic acid 5 |
| | 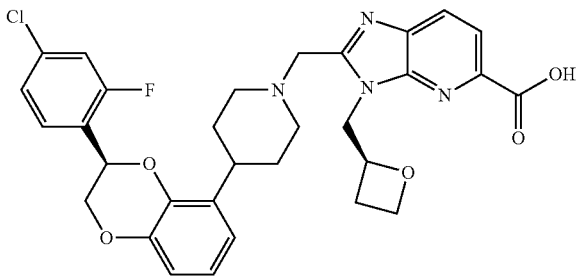 [SMILES: O=C(O)c1ccc2nc(CN3CCC(c4cccc5c4O[C@H](c4ccc(Cl)cc4F)CO5)CC3)n(C[C@@H]3CCO3)c2n1]<br>2-((4-((R)-3-(4-Chloro-2-fluorophenyl)-2,3-dihydrobenzo[b][1,4]dioxan-5-yl)piperidin-1-yl)methyl)-3-((S)-oxetan-2-ylmethyl)-3H-imidazo[4,5-b]pyridine-5-carboxylic acid |
| 6 | 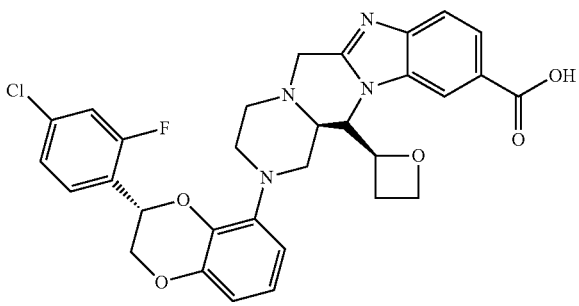<br>6<br>2-(((S)-4-((S)-3-(4-Chloro-2-fluorophenyl)-2,3-dihydrobenzo[b][1,4]dioxan-5-yl)-2-methylpiperazin-1-yl)methyl)-1-(((S)-oxetan-2-yl)methyl)-1H-benzo[d]imidazole-6-carboxylic acid 6 |

TABLE A-continued

Typical compounds disclosed herein include, but are not limited to:

| Example No. | Structures and names of compounds |
|---|---|
| | 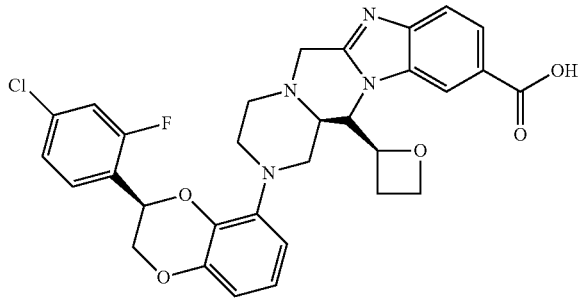<br>2-(((S)-4-((R)-3-(4-Chloro-2-fluorophenyl)-2,3-dihydrobenzo[b][1,4]dioxan-5-yl)-2-methylpiperazin-1-yl)methyl)-1-(((S)-oxetan-2-yl)methyl)-1H-benzo[d]imidazole-6-carboxylic acid |
| 7 | 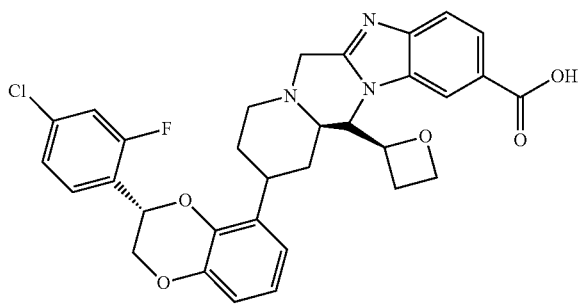<br>2-(((S)-4-((S)-3-(4-Chloro-2-fluorophenyl)-2,3-dihydrobenzo[b][1,4]dioxan-5-yl)-2-methylpiperidin-1-yl)methyl)-1-(((S)-oxetan-2-yl)methyl)-1H-benzo[d]imidazole-6-carboxylic acid 7 |
| | 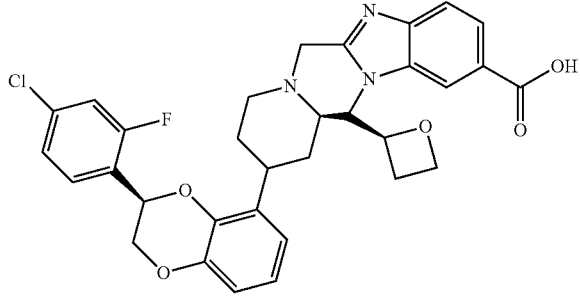<br>2-(((S)-4-((R)-3-(4-Chloro-2-fluorophenyl)-2,3-dihydrobenzo[b][1,4]dioxan-5-yl)-2-methylpiperidin-1-yl)methyl)-1-(((S)-oxetan-2-yl)methyl)-1H-benzo[d]imidazole-6-carboxylic acid |
| | 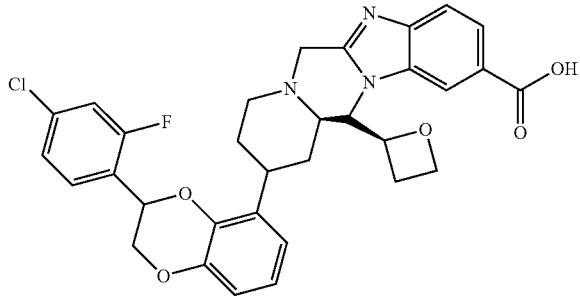<br>2-(((S)-4-(3-(4-Chloro-2-fluorophenyl)-2,3-dihydrobenzo[b][1,4]dioxan-5-yl)-2-methylpiperidin-1-yl)methyl)-1-(((S)-oxetan-2-yl)methyl)-1H-benzo[d]imidazole-6-carboxylic acid (a mixture of diastereomers) |

TABLE A-continued

Typical compounds disclosed herein include, but are not limited to:

| Example No. | Structures and names of compounds |
| --- | --- |

8

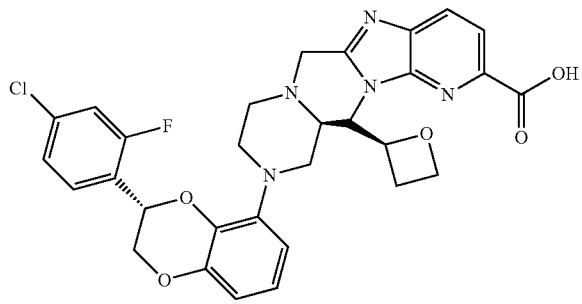

8

2-(((S)-4-((S)-3-(4-Chloro-2-fluorophenyl)-2,3-
dihydrobenzo[b][1,4]dioxan-5-yl)-2-methylpiperazin-1-yl)methyl)-3-
((S)-oxetan-2-ylmethyl)-3H-imidazo[4,5-b]pyridine-5-carboxylic acid

8

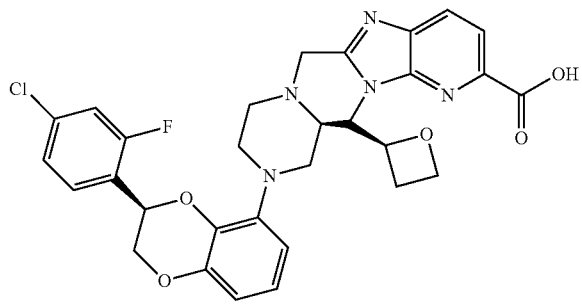

2-(((S)-4-((R)-3-(4-Chloro-2-fluorophenyl)-2,3-
dihydrobenzo[b][1,4]dioxan-5-yl)-2-methylpiperazin-1-yl)methyl)-3-
((S)-oxetan-2-ylmethyl)-3H-imidazo[4,5-b]pyridine-5-carboxylic acid

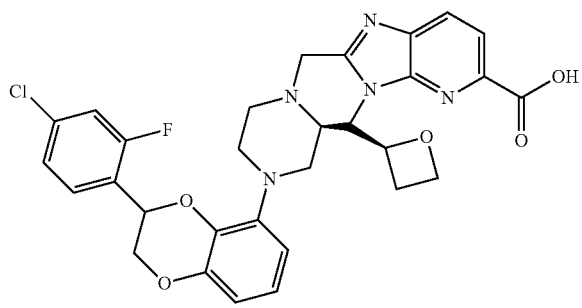

2-(((S)-4-(3-(4-Chloro-2-fluorophenyl)-2,3-
dihydrobenzo[b][1,4]dioxan-5-yl)-2-methylpiperazin-1-yl)methyl)-3-
((S)-oxetan-2-ylmethyl)-3H-imidazo[4,5-b]pyridine-5-carboxylic acid
(a mixture of diastereomers)

TABLE A-continued

Typical compounds disclosed herein include, but are not limited to:

| Example No. | Structures and names of compounds |
|---|---|
| 9 | 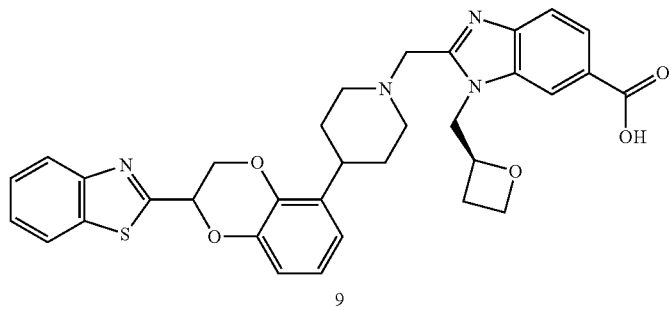 [SMILES: O=C(O)c1ccc2nc(CN3CCC(c4cccc5c4OCC(c4nc6ccccc6s4)O5)CC3)n(C[C@@H]3CCO3)c2c1]

2-((4-(2-(Benzo[d]thiazol-2-yl)-2,3-dihydrobenzo[b][1,4]dioxan-5-yl)piperidin-1-yl)methyl)-1-(((S)-oxetan-2-yl)methyl)-1H-benzo[d]imidazole-6-carboxylic acid (a mixture of diastereomers) 9 |
| 10 | 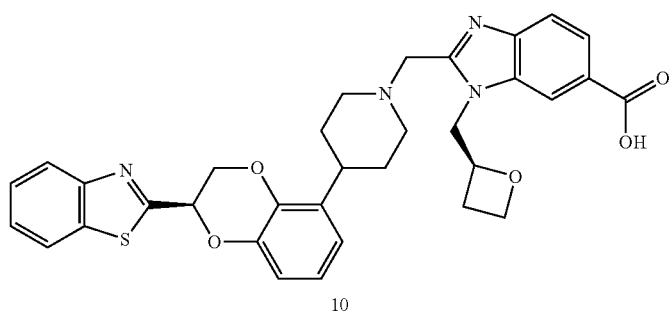 [SMILES: O=C(O)c1ccc2nc(CN3CCC(c4cccc5c4OC[C@H](c4nc6ccccc6s4)O5)CC3)n(C[C@@H]3CCO3)c2c1]

2-((4-((R)-2-(Benzo[d]thiazol-2-yl)-2,3-dihydrobenzo[b][1,4]dioxan-5-yl)piperidin-1-yl)methyl)-1-(((S)-oxetan-2-yl)methyl)-1H-benzo[d]imidazole-6-carboxylic acid 10 |
| 11 | 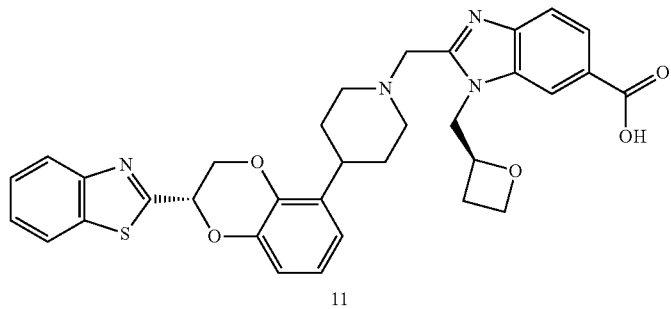

2-((4-((S)-2-(Benzo[d]thiazol-2-yl)-2,3-dihydrobenzo[b][1,4]dioxan-5-yl)piperidin-1-yl)methyl)-1-(((S)-oxetan-2-yl)methyl)-1H-benzo[d]imidazole-6-carboxylic acid 11 |

TABLE A-continued

Typical compounds disclosed herein include, but are not limited to:

| Example No. | Structures and names of compounds |
|---|---|
| 12 | 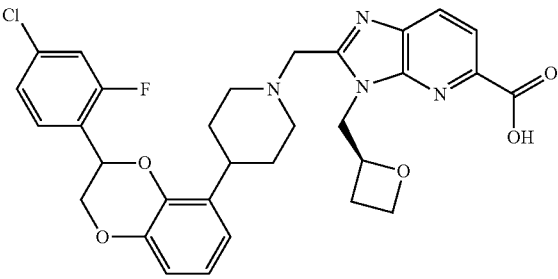

2-((4-(3-(4-Chloro-2-fluorophenyl)-2,3-dihydrobenzo[b][1,4]dioxan-5-yl)piperidin-1-yl)methyl)-3-(((S)-oxetan-2-ylmethyl)-3H-imidazo[4,5-b]pyridine-5-carboxylic acid (a mixture of diastereomers) 12 |
| 13 | 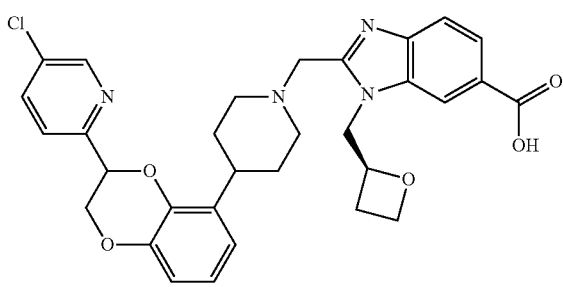 [SMILES: O=C(O)c1ccc2nc(CN3CCC(c4cccc5c4O[C@@H](c4ccc(Cl)cn4)CO5)CC3)n(C[C@@H]3CCO3)c2c1]

2-((4-(3-(5-Chloropyridin-2-yl)-2,3-dihydrobenzo[b][1,4]dioxan-5-yl)piperidin-1-yl)methyl)-1-(((S)-oxetan-2-yl)methyl)-1H-benzo[d]imidazole-6-carboxylic acid (a mixture of diastereomers) 13

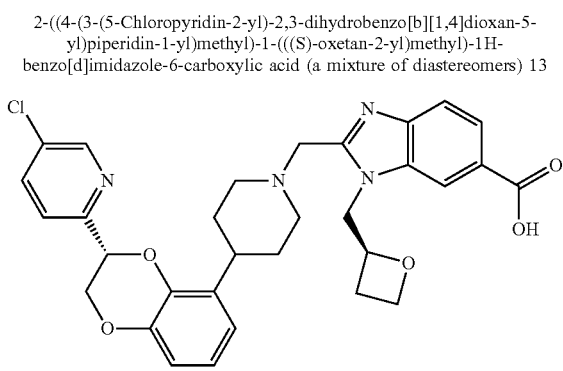

2-((4-((S)-3-(5-Chloropyridin-2-yl)-2,3-dihydrobenzo[b][1,4]dioxan-5-yl)piperidin-1-yl)methyl)-1-(((S)-oxetan-2-yl)methyl)-1H-benzo[d]imidazole-6-carboxylic acid

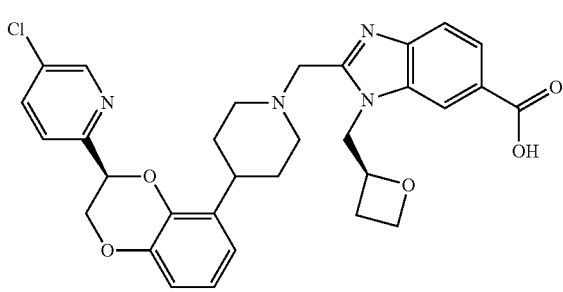 [SMILES: O=C(O)c1ccc2nc(CN3CCC(c4cccc5c4O[C@H](c4ccc(Cl)cn4)CO5)CC3)n(C[C@@H]3CCO3)c2c1]

2-((4-((R)-3-(5-Chloropyridin-2-yl)-2,3-dihydrobenzo[b][1,4]dioxan-5-yl)piperidin-1-yl)methyl)-1-(((S)-oxetan-2-yl)methyl)-1H-benzo[d]imidazole-6-carboxylic acid |

TABLE A-continued

Typical compounds disclosed herein include, but are not limited to:

| Example No. | Structures and names of compounds |
|---|---|
| 14 | 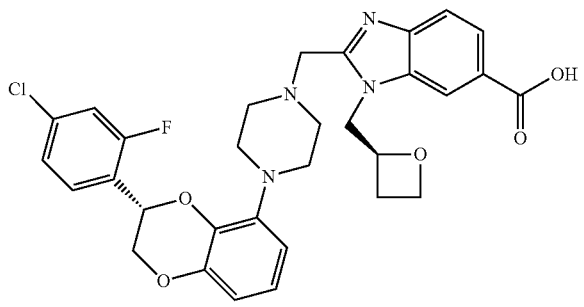

2-((4-(((S)-3-(4-Chloro-2-fluorophenyl)-2,3-dihydrobenzo[b][1,4]dioxan-5-yl)piperazin-1-yl)methyl)-1-(((S)-oxetan-2-yl)methyl)-1H-benzo[d]imidazole-6-carboxylic acid 14

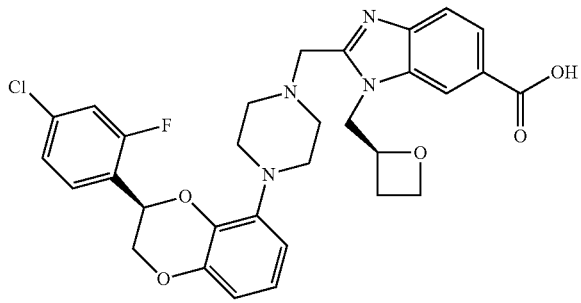 [SMILES: O=C(O)c1ccc2nc(CN3CCN(c4cccc5c4O[C@H](c4ccc(Cl)cc4F)CO5)CC3)n(C[C@@H]3CCO3)c2c1]

2-((4-(((R)-3-(4-Chloro-2-fluorophenyl)-2,3-dihydrobenzo[b][1,4]dioxan-5-yl)piperazin-1-yl)methyl)-1-(((S)-oxetan-2-yl)methyl)-1H-benzo[d]imidazole-6-carboxylic acid

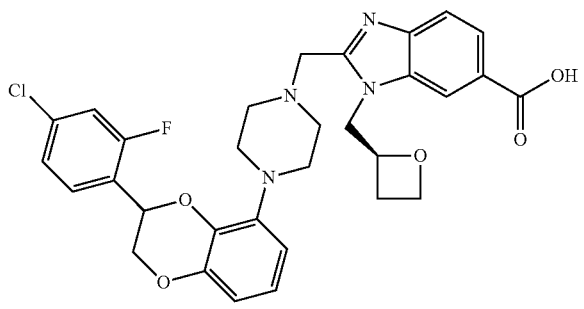 [SMILES: O=C(O)c1ccc2nc(CN3CCN(c4cccc5c4OC(c4ccc(Cl)cc4F)CO5)CC3)n(C[C@@H]3CCO3)c2c1]

2-((4-(3-(4-Chloro-2-fluorophenyl)-2,3-dihydrobenzo[b][1,4]dioxan-5-yl)piperazin-1-yl)methyl)-1-(((S)-oxetan-2-yl)methyl)-1H-benzo[d]imidazole-6-carboxylic acid (a mixture of diastereomers) |

TABLE A-continued

Typical compounds disclosed herein include, but are not limited to:

| Example No. | Structures and names of compounds |
|---|---|
| 15 | 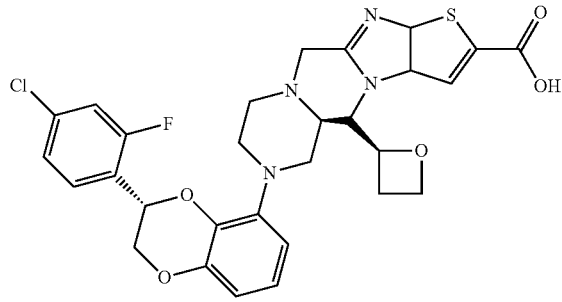

2-(((S)-4-((S)-3-(4-Chloro-2-fluorophenyl)-2,3-dihydrobenzo[b][1,4]dioxan-5-yl)-2-methylpiperazin-1-yl)methyl)-1-((S)-oxetan-2-ylmethyl)-3a,6a-dihydro-1H-thieno[2,3-d]imidazole-5-carboxylic acid 15

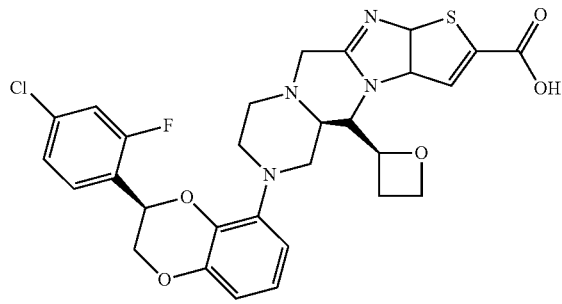

2-(((S)-4-((R)-3-(4-Chloro-2-fluorophenyl)-2,3-dihydrobenzo[b][1,4]dioxan-5-yl)-2-methylpiperazin-1-yl)methyl)-1-((S)-oxetan-2-ylmethyl)-3a,6a-dihydro-1H-thieno[2,3-d]imidazole-5-carboxylic acid

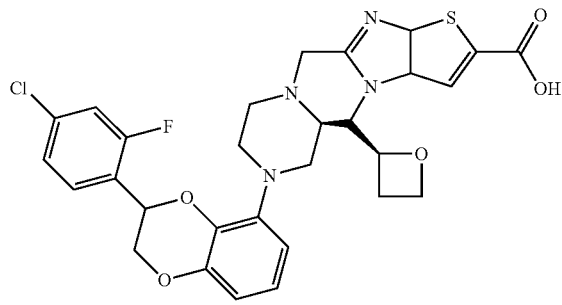

2-(((S)-4-(3-(4-Chloro-2-fluorophenyl)-2,3-dihydrobenzo[b][1,4]dioxan-5-yl)-2-methylpiperazin-1-yl)methyl)-1-((S)-oxetan-2-ylmethyl)-3a,6a-dihydro-1H-thieno[2,3-d]imidazole-5-carboxylic acid (a mixture of diastereomers) |

TABLE A-continued

Typical compounds disclosed herein include, but are not limited to:

| Example No. | Structures and names of compounds |
|---|---|
| 16 | 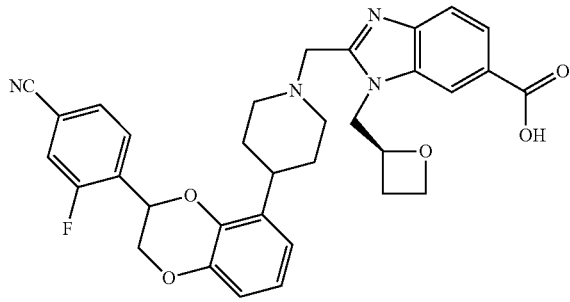 [SMILES: N#Cc1ccc([C@H]2COc3cccc(C4CCN(Cc5nc6ccc(C(=O)O)cc6n5C[C@@H]5CCO5)CC4)c3O2)c(F)c1]<br>2-((4-(3-(4-Cyano-2-fluorophenyl)-2,3-dihydrobenzo[b][1,4]dioxan-5-yl)piperidin-1-yl)methyl)-1-((S)-oxetan-2-ylmethyl)-1H-benzo[d]imidazole-6-carboxylic acid (a mixture of diastereomers) 16<br><br>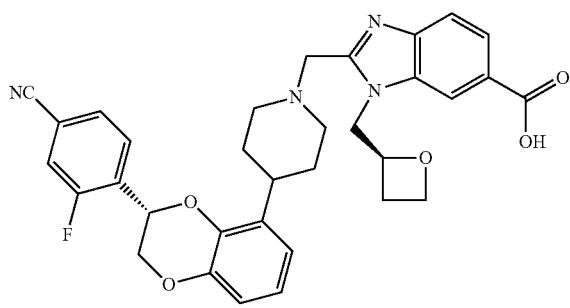<br>2-((4-((S)-3-(4-Cyano-2-fluorophenyl)-2,3-dihydrobenzo[b][1,4]dioxan-5-yl)piperidin-1-yl)methyl)-1-((S)-oxetan-2-ylmethyl)-1H-benzo[d]imidazole-6-carboxylic acid<br><br>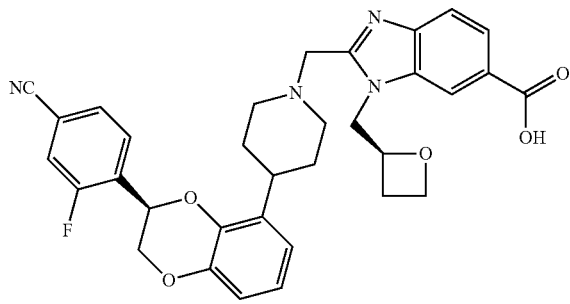 [SMILES: N#Cc1ccc([C@@H]2COc3cccc(C4CCN(Cc5nc6ccc(C(=O)O)cc6n5C[C@@H]5CCO5)CC4)c3O2)c(F)c1]<br>2-((4-((R)-3-(4-Cyano-2-fluorophenyl)-2,3-dihydrobenzo[b][1,4]dioxan-5-yl)piperidin-1-yl)methyl)-1-((S)-oxetan-2-ylmethyl)-1H-benzo[d]imidazole-6-carboxylic acid |
| 17 | 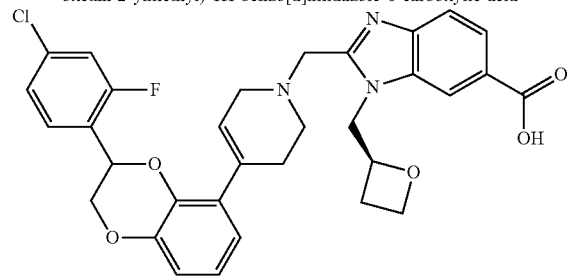<br>17<br>2-((4-(3-(4-Chloro-2-fluorophenyl)-2,3-dihydrobenzo[b][1,4]dioxan-5-yl)-3,6-dihydropyridin-1(2H)-yl)methyl)-1-(((S)-oxacyclohexan-2-yl)methyl)-1H-benzo[d]imidazole-6-carboxylic acid (a mixture of diastereomers) 17 |

TABLE A-continued

Typical compounds disclosed herein include, but are not limited to:

| Example No. | Structures and names of compounds |
| --- | --- |

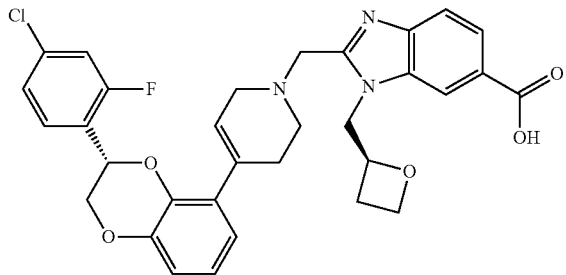 [SMILES: O=C(O)c1ccc2nc(CN3CC=C(c4cccc5c4O[C@@H](c4ccc(Cl)cc4F)CO5)CC3)n(C[C@@H]3CCO3)c2c1]

2-((4-((S)-3-(4-Chloro-2-fluorophenyl)-2,3-
dihydrobenzo[b][1,4]dioxan-5-yl)-3,6-dihydropyridin-1(2H)-
yl)methyl)-1-(((S)-oxacyclohexan-2-yl)methyl)-1H-
benzo[d]imidazole-6-carboxylic acid

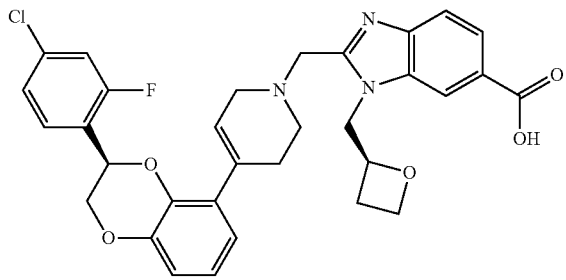 [SMILES: O=C(O)c1ccc2nc(CN3CC=C(c4cccc5c4O[C@H](c4ccc(Cl)cc4F)CO5)CC3)n(C[C@@H]3CCO3)c2c1]

2-((4-((R)-3-(4-Chloro-2-fluorophenyl)-2,3-
dihydrobenzo[b][1,4]dioxan-5-yl)-3,6-dihydropyridin-1(2H)-
yl)methyl)-1-(((S)-oxacyclohexan-2-yl)methyl)-1H-
benzo[d]imidazole-6-carboxylic acid

18

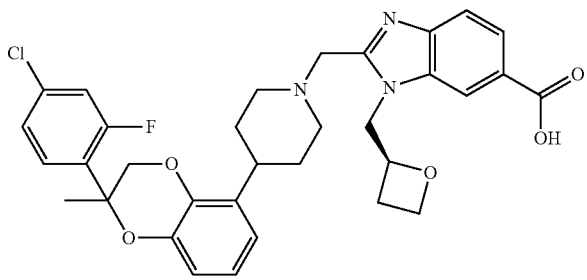

18

2-((4-(2-(4-Chloro-2-fluorophenyl)-2-methyl-2,3-
dihydrobenzo[b][1,4]dioxan-5-yl)piperidin-1-yl)methyl)-1-(((S)-
oxetan-2-yl)methyl)-1H-benzo[d]imidazole-6-carboxylic acid (a
mixture of diastereomers) 18

TABLE A-continued

Typical compounds disclosed herein include, but are not limited to:

| Example No. | Structures and names of compounds |
|---|---|

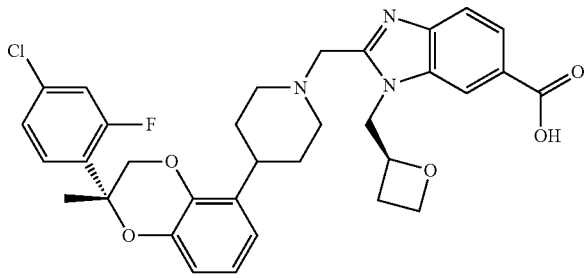 [SMILES: C[C@@]1(c2ccc(Cl)cc2F)COc2c(cccc2C2CCN(Cc3nc4ccc(C(=O)O)cc4n3C[C@@H]3CCO3)CC2)O1]

2-((4-((S)-2-(4-Chloro-2-fluorophenyl)-2-methyl-2,3-dihydrobenzo[b][1,4]dioxan-5-yl)piperidin-1-yl)methyl)-1-(((S)-oxetan-2-yl)methyl)-1H-benzo[d]imidazole-6-carboxylic acid

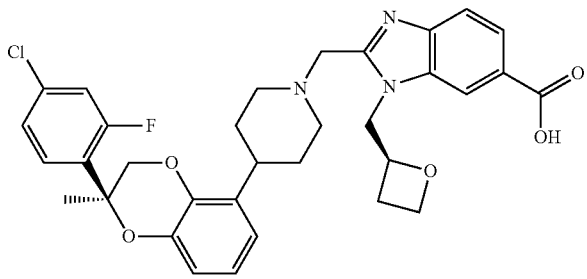 [SMILES: C[C@]1(c2ccc(Cl)cc2F)COc2c(cccc2C2CCN(Cc3nc4ccc(C(=O)O)cc4n3C[C@@H]3CCO3)CC2)O1]

2-((4-((R)-2-(4-Chloro-2-fluorophenyl)-2-methyl-2,3-dihydrobenzo[b][1,4]dioxan-5-yl)piperidin-1-yl)methyl)-1-(((S)-oxetan-2-yl)methyl)-1H-benzo[d]imidazole-6-carboxylic acid

19

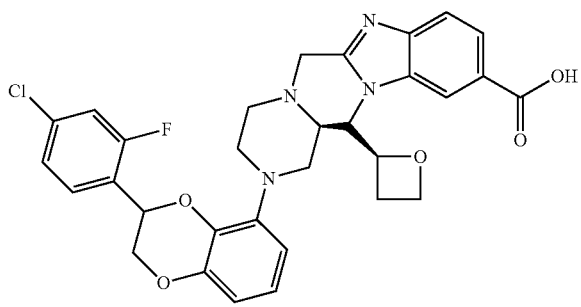

19

2-(((2S)-4-(3-(4-Chloro-2-fluorophenyl)-2,3-dihydrobenzo[b][1,4]dioxan-5-yl)-2-methylpiperazin-1-yl)methyl)-1-(((S)-oxetan-2-yl)methyl)-1H-benzo[d]imidazole-6-carboxylic acid (a mixture of diastereomers) 19

TABLE A-continued

Typical compounds disclosed herein include, but are not limited to:

| Example No. | Structures and names of compounds |
| --- | --- |

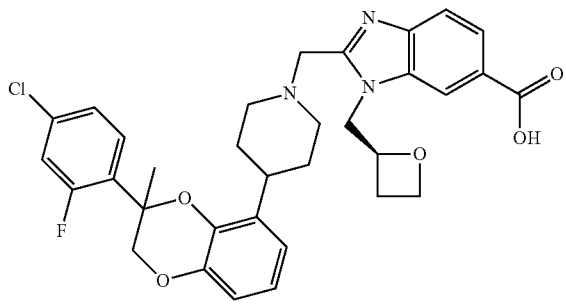

20

2-((4-(3-(4-Chloro-2-fluorophenyl)-3-methyl-2,3-
dihydrobenzo[b][1,4]dioxan-5-yl)piperidin-1-yl)methyl)-1-(((S)-
oxetan-2-yl)methyl)-1H-benzo[d]imidazole-6-carboxylic acid (a
mixture of diastereomers) 20

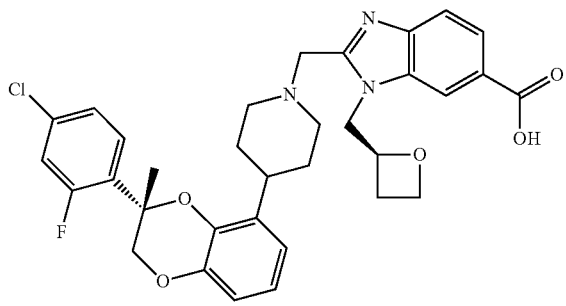 [SMILES: C[C@]1(c2ccc(Cl)cc2F)COc2cccc(C3CCN(Cc4nc5ccc(C(=O)O)cc5n4C[C@@H]4CCO4)CC3)c2O1]

2-((4-((S)-3-(4-Chloro-2-fluorophenyl)-3-methyl-2,3-
dihydrobenzo[b][1,4]dioxan-5-yl)piperidin-1-yl)methyl)-1-(((S)-
oxetan-2-yl)methyl)-1H-benzo[d]imidazole-6-carboxylic acid

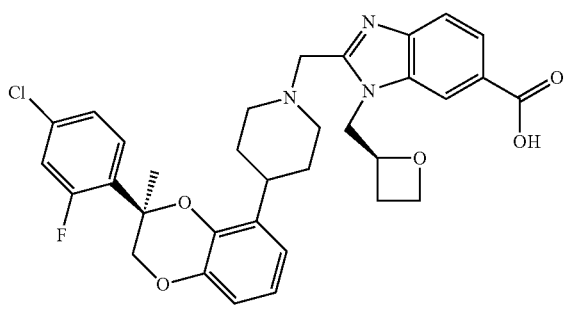 [SMILES: C[C@@]1(c2ccc(Cl)cc2F)COc2cccc(C3CCN(Cc4nc5ccc(C(=O)O)cc5n4C[C@@H]4CCO4)CC3)c2O1]

2-((4-((R)-3-(4-Chloro-2-fluorophenyl)-3-methyl-2,3-
dihydrobenzo[b][1,4]dioxan-5-yl)piperidin-1-yl)methyl)-1-(((S)-
oxetan-2-yl)methyl)-1H-benzo[d]imidazole-6-carboxylic acid or tautomers, racemates, enantiomers or diastereomers thereof or mixtures thereof, or pharmaceutically acceptable salts thereof.

Another aspect of the present disclosure relates to a compound of general formula (IMA) or a tautomer, racemate, enantiomer or diastereomer thereof or a mixture thereof, or a pharmaceutically acceptable salt thereof, (IMA)

wherein:
$R^w$ is $C_{1-6}$ alkyl;

-----, ring B, M ring C, ring A, $R^1$ to $R^6$, n, m, p, g and q are as defined in general formula (IM). It is an intermediate for the preparation of general formula (IM).

Another aspect of the present disclosure relates to a compound of general formula (INA) or a tautomer, racemate, enantiomer or diastereomer thereof or a mixture thereof, or a pharmaceutically acceptable salt thereof, (INA)

wherein:
$R^w$ is $C_{1-6}$ alkyl;

-----, ring B, M, $Y^4$, $Y^5$, $Y^6$ ring A, $R^1$ to $R^6$, n, m, p and q are as defined in general formula (IN). It is an intermediate for the preparation of general formula (IN).

Another aspect of the present disclosure relates to a compound of general formula (INaA) or general formula (INbA) or a tautomer, racemate, enantiomer or diastereomer thereof or a mixture thereof, or a pharmaceutically acceptable salt thereof,

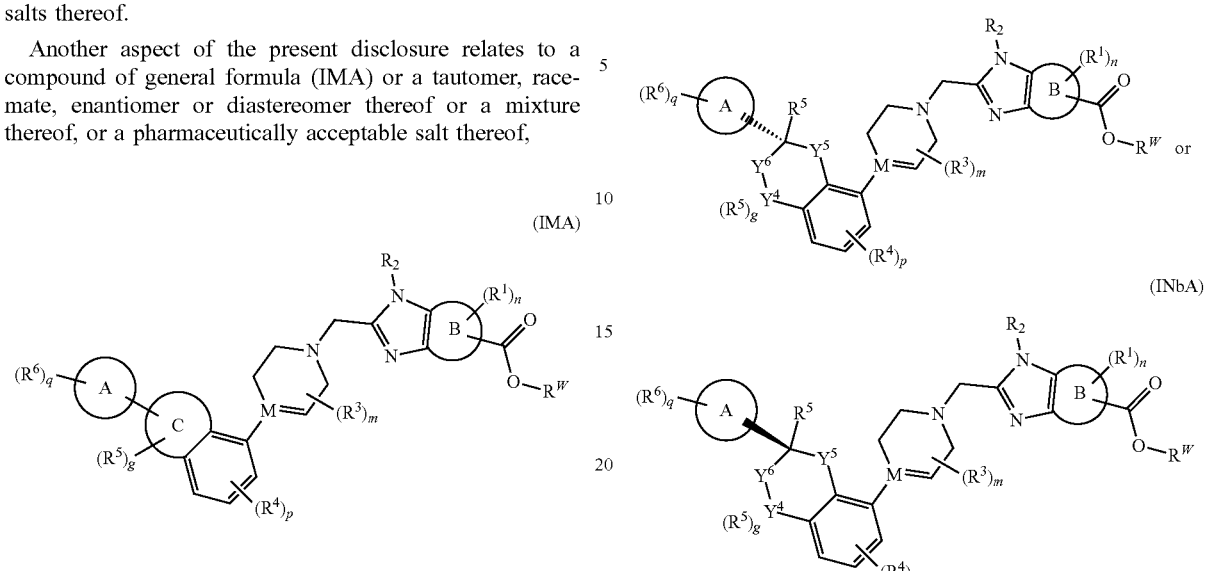

(INaA)

(INbA)

wherein:
$R^w$ is $C_{1-6}$ alkyl;

-----, ring B, M, $Y^4$, $Y^5$, $Y^6$, ring A, $R^1$ to $R^6$, n, m, p and q are as defined in general formula (IN). It is an intermediate for the preparation of general formula (INa) or general formula (INb).

Another aspect of the present disclosure relates to a compound of general formula (IIGA) or a tautomer, racemate, enantiomer or diastereomer thereof or a mixture thereof, or a pharmaceutically acceptable salt thereof,

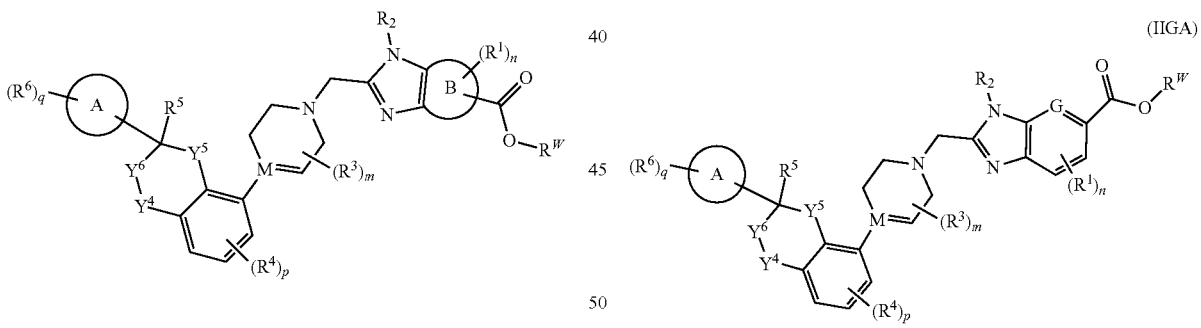

(IIGA)

wherein:
$R^w$ is $C_{1-6}$ alkyl;
G, M, $Y^4$, $Y^5$, $Y^6$, ring A, $R^1$ to $R^6$, n, m, p and q are as defined in general formula (IIG).

It is an intermediate for the preparation of general formula (IIG).

Another aspect of the present disclosure relates to a compound of general formula (IINA) or a tautomer, racemate, enantiomer or diastereomer thereof or a mixture thereof, or a pharmaceutically acceptable salt thereof,

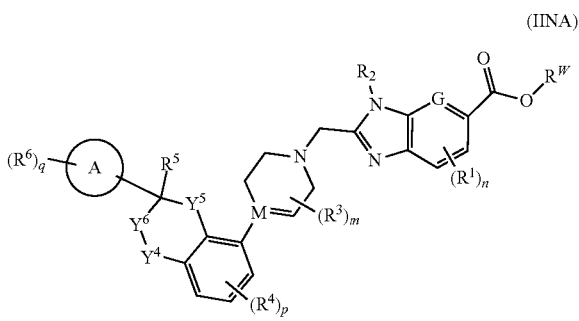

(IINA)

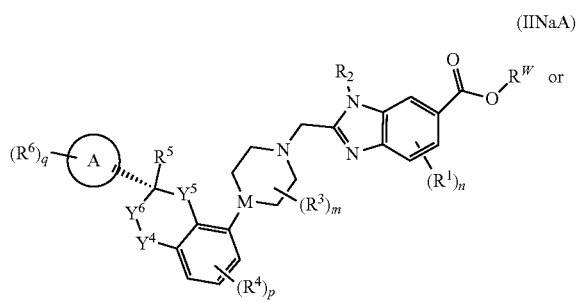

(IINaA) or wherein:
$R^w$ is $C_{1-6}$ alkyl;
M, $Y^4$, $Y^5$, $Y^6$, ring A, $R^1$ to $R^6$, n, m, p and q are as defined in general formula (IIN). It is an intermediate for the preparation of general formula (IIN).

Another aspect of the present disclosure relates to a compound of general formula (IIGaA) or general formula (IIGbA) or a tautomer, racemate, enantiomer or diastereomer thereof or a mixture thereof, or a pharmaceutically acceptable salt thereof,

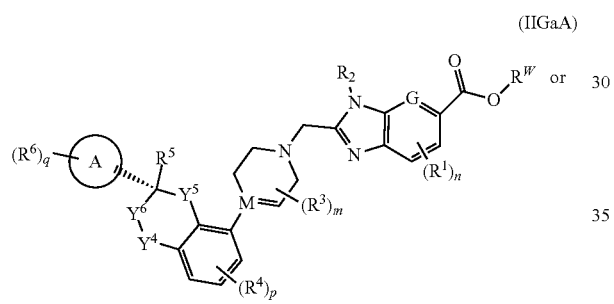

(IIGaA) or

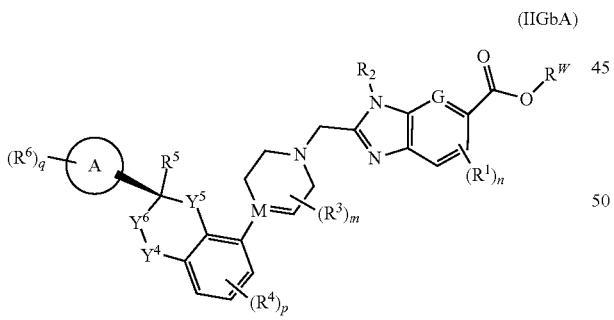

(IIGbA)

wherein:
$R^w$ is $C_{1-6}$ alkyl;
G, M, $Y^4$, $Y^5$, $Y^6$, ring A, $R^1$ to $R^6$, n, m, p and q are as defined in general formula (IIGa) or general formula (IIGb). It is an intermediate for the preparation of general formula (IIGa) or general formula (IIGb).

Another aspect of the present disclosure relates to a compound of general formula (IINaA) or general formula (IINbA) or a tautomer, racemate, enantiomer or diastereomer thereof or a mixture thereof, or a pharmaceutically acceptable salt thereof, (IINbA)

wherein:
$R^w$ is $C_{1-6}$alkyl;
M, $Y^4$, $Y^5$, $Y^6$, ring A, $R^1$ to $R^6$, n, m, p and q are as defined in general formula (IINa) or general formula (IINb). It is an intermediate for the preparation of general formula (IINa) or general formula (IINb).

Another aspect of the present disclosure relates to a compound of general formula (IIINA-1) or a tautomer, racemate, enantiomer or diastereomer thereof or a mixture thereof, or a pharmaceutically acceptable salt thereof,

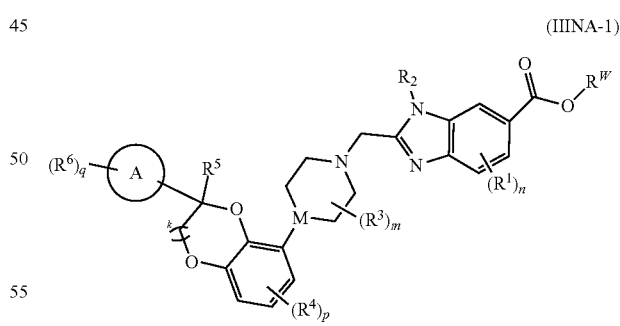

(IIINA-1)

wherein:
$R^w$ is $C_{1-6}$ alkyl;
M, ring A, $R^1$ to $R^6$, k, n, m, p and q are as defined in general formula (IIIN-1). It is an intermediate for the preparation of general formula (IIIN-1).

Another aspect of the present disclosure relates to a compound of general formula (IIINA-2) or a tautomer, racemate, enantiomer or diastereomer thereof or a mixture thereof, or a pharmaceutically acceptable salt thereof, (INA)

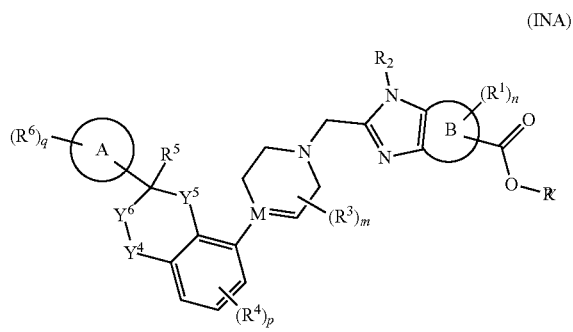

wherein:

$R^w$ is $C_{1-6}$ alkyl;

M, ring A, $R^1$ to $R^6$, k, n, m, p and q are as defined in general formula (IIIN-2). It is an intermediate for the preparation of general formula (IIIN-2).

Another aspect of the present disclosure relates to a compound of general formula (IA) or a tautomer, racemate, enantiomer or diastereomer thereof or a mixture thereof, or a pharmaceutically acceptable salt thereof, (IA)

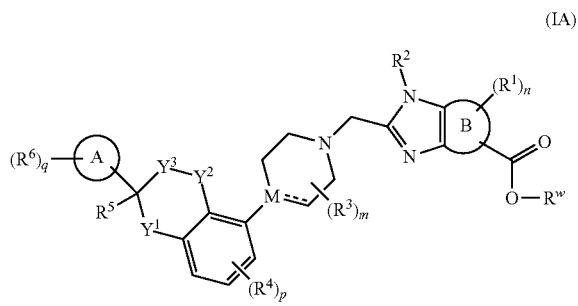

wherein:

$R^w$ is $C_{1-6}$ alkyl;

- - - - - ring B, M, $Y^1$, $Y^2$, $Y^3$, ring A, $R^1$ to $R^6$, n, m, p and q are as defined in general formula (I). It is an intermediate for the preparation of general formula (I).

Another aspect of the present disclosure relates to a compound of general formula (IIA) or a tautomer, racemate, enantiomer or diastereomer thereof or a mixture thereof, or a pharmaceutically acceptable salt thereof, (IIA)

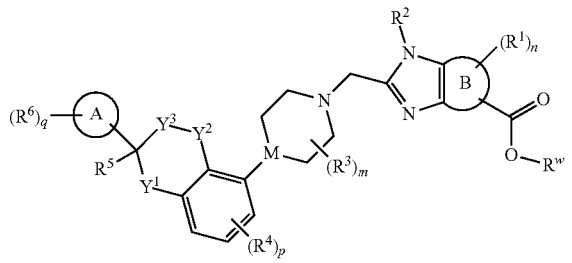

wherein:

$R^w$ is $C_{1-6}$ alkyl;

ring B, M, $Y^1$, $Y^2$, $Y^3$, ring A, $R^1$ to $R^6$, n, m, p and q are as defined in general formula (IA). It is an intermediate for the preparation of general formula (II).

Another aspect of the present disclosure relates to a compound of general formula (III-1A) or general formula (III-2A) or a tautomer, racemate, enantiomer or diastereomer thereof or a mixture thereof, or a pharmaceutically acceptable salt thereof, (III-1A)

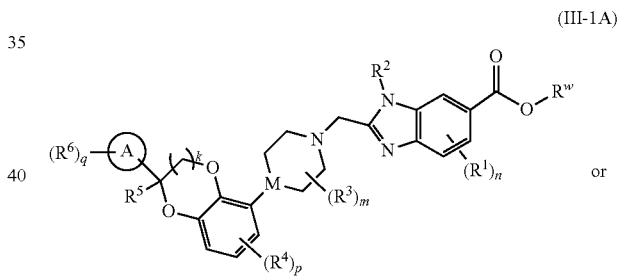

or (III-2A)

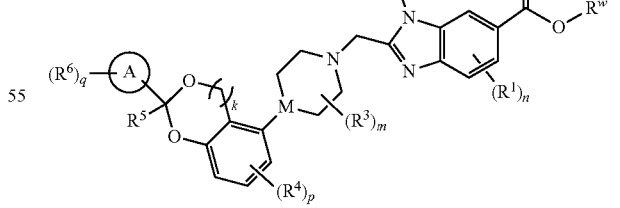

wherein:

$R^w$ is $C_{1-6}$ alkyl;

M, ring A, $R^1$ to $R^6$, k, n, m, p and q are as defined in general formula (IA). It is an intermediate for the preparation of general formula (III-1) or general formula (III-2).

TABLE B

Typical intermediate compounds of the present disclosure include, but are not limited to:

| Example No. | Structures and names of compounds |
| --- | --- |
| 1n | 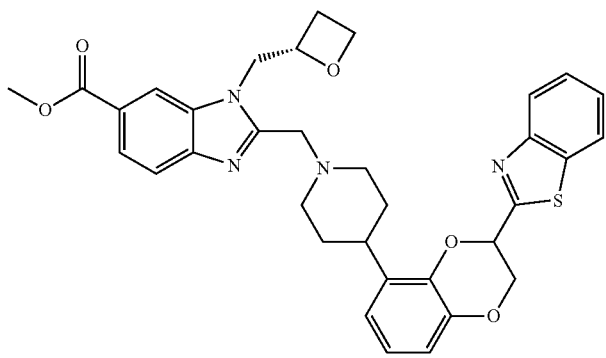

1n

Methyl 2-((4-(3-(benzo[d]thiazol-2-yl)-2,3-dihydrobenzo[b][1,4]dioxan-5-yl)piperidin-1-yl)methyl)-1-(((S)-oxetan-2-yl)methyl)-1H-benzo[d]imidazole-6-carboxylate (a mixture of diastereomers) 1n

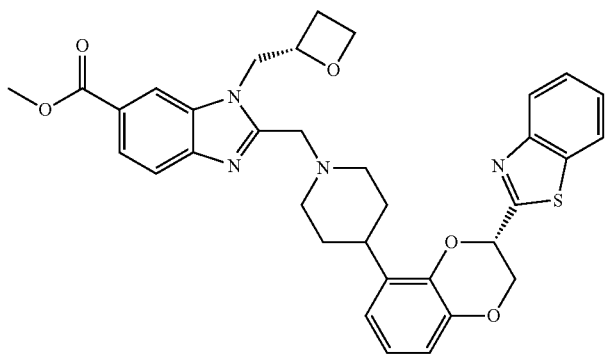 [SMILES: COC(=O)c1ccc2nc(CN3CCC(c4cccc5c4O[C@H](c4nc6ccccc6s4)CO5)CC3)n(C[C@@H]3CCO3)c2c1]

Methyl 2-((4-((S)-3-(benzo[d]thiazol-2-yl)-2,3-dihydrobenzo[b][1,4]dioxan-5-yl)piperidin-1-yl)methyl)-1-(((S)-oxetan-2-yl)methyl)-1H-benzo[d]imidazole-6-carboxylate

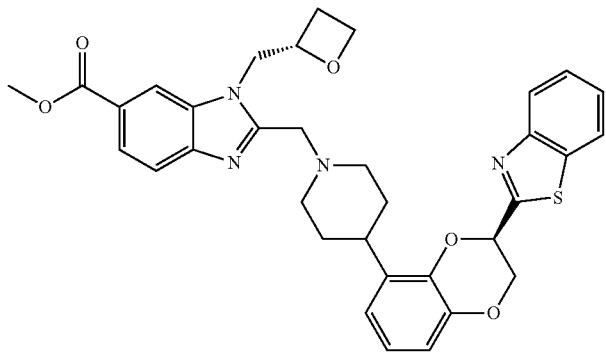 [SMILES: COC(=O)c1ccc2nc(CN3CCC(c4cccc5c4O[C@@H](c4nc6ccccc6s4)CO5)CC3)n(C[C@@H]3CCO3)c2c1]

Methyl 2-((4-((R)-3-(benzo[d]thiazol-2-yl)-2,3-dihydrobenzo[b][1,4]dioxan-5-yl)piperidin-1-yl)methyl)-1-(((S)-oxetan-2-yl)methyl)-1H-benzo[d]imidazole-6-carboxylate |

TABLE B-continued

Typical intermediate compounds of the present disclosure include, but are not limited to:

| Example No. | Structures and names of compounds |
|---|---|
| 2j | 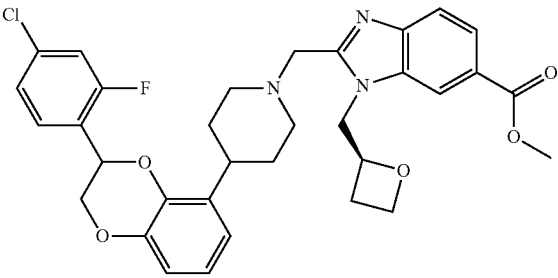 2j <br> Methyl 2-((4-(3-(4-chloro-2-fluorophenyl)-2,3-dihydrobenzo[b][1,4]dioxan-5-yl)piperidin-1-yl)methyl)-1-((S)-oxetan-2-ylmethyl)-1H-benzo[d]imidazole-6-carboxylate (a mixture of diastereomers) 2j |
| | 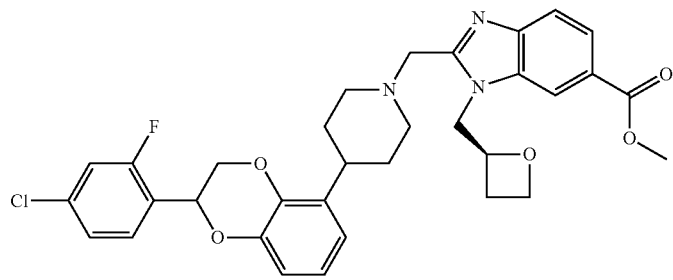 [SMILES: COC(=O)c1ccc2nc(CN3CCC(c4cccc5c4OCC(c4ccc(Cl)cc4F)O5)CC3)n(C[C@@H]3CCO3)c2c1] <br> Methyl 2-((4-(2-(4-chloro-2-fluorophenyl)-2,3-dihydrobenzo[b][1,4]dioxan-5-yl)piperidin-1-yl)methyl)-1-((S)-oxetan-2-ylmethyl)-1H-benzo[d]imidazole-6-carboxylate (a mixture of diastereomers) |
| | 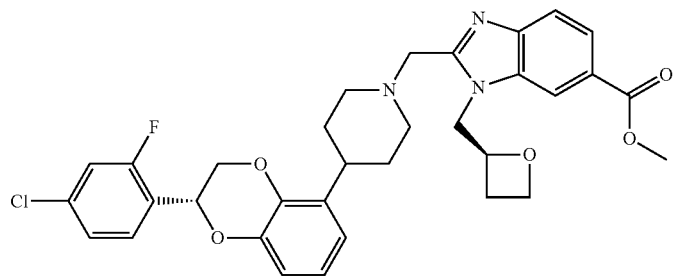 [SMILES: COC(=O)c1ccc2nc(CN3CCC(c4cccc5c4OC[C@@H](c4ccc(Cl)cc4F)O5)CC3)n(C[C@@H]3CCO3)c2c1] <br> Methyl 2-((4-((R)-2-(4-chloro-2-fluorophenyl)-2,3-dihydrobenzo[b][1,4]dioxan-5-yl)piperidin-1-yl)methyl)-1-((S)-oxetan-2-ylmethyl)-1H-benzo[d]imidazole-6-carboxylate |
| | 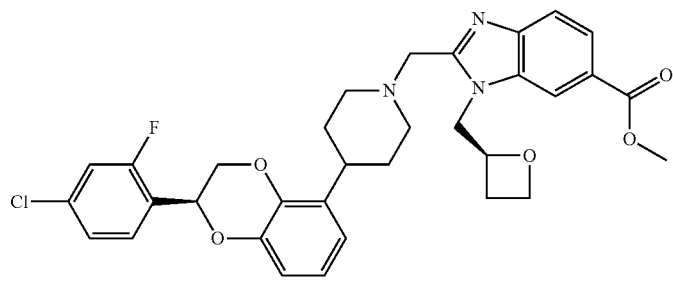 <br> Methyl 2-((4-((S)-2-(4-chloro-2-fluorophenyl)-2,3-dihydrobenzo[b][1,4]dioxan-5-yl)piperidin-1-yl)methyl)-1-((S)-oxetan-2-ylmethyl)-1H-benzo[d]imidazole-6-carboxylate |

TABLE B-continued

Typical intermediate compounds of the present disclosure include, but are not limited to:

| Example No. | Structures and names of compounds |
|---|---|
| 4a | 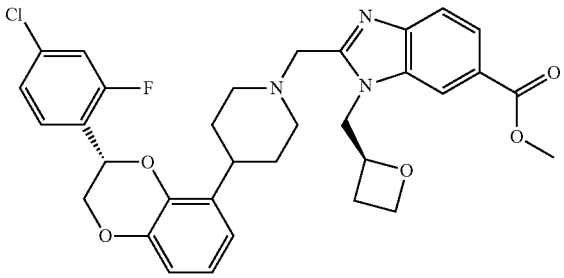<br>4a<br><br>Methyl 2-((4-((S)-3-(4-chloro-2-fluorophenyl)-2,3-dihydrobenzo[b][1,4]dioxan-5-yl)piperidin-1-yl)methyl)-1-(((S)-oxetan-2-yl)methyl)-1H-benzo[d]imidazole-6-carboxylate 4a |
| 4b | 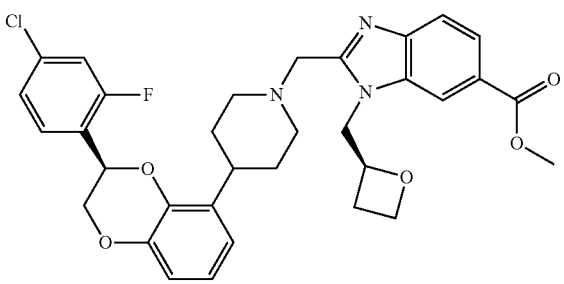<br>4b<br><br>Methyl 2-((4-((R)-3-(4-chloro-2-fluorophenyl)-2,3-dihydrobenzo[b][1,4]dioxan-5-yl)piperidin-1-yl)methyl)-1-(((S)-oxetan-2-yl)methyl)-1H-benzo[d]imidazole-6-carboxylate 4b |
| 5f | 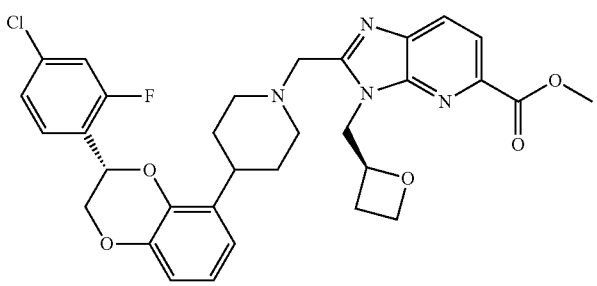<br>5f<br><br>Methyl 2-((4-((S)-3-(4-chloro-2-fluorophenyl)-2,3-dihydrobenzo[b][1,4]dioxan-5-yl)piperidin-1-yl)methyl)-3-((S)-oxetan-2-ylmethyl)-3H-imidazo[4,5-b]pyridine-5-carboxylate 5f |
| | 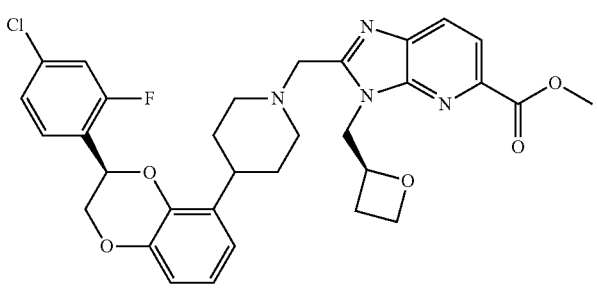 [SMILES: COC(=O)c1ccc2nc(CN3CCC(c4cccc5c4O[C@H](c4ccc(Cl)cc4F)CO5)CC3)n(C[C@@H]3CCO3)c2n1]<br><br>Methyl 2-((4-((R)-3-(4-chloro-2-fluorophenyl)-2,3-dihydrobenzo[b][1,4]dioxan-5-yl)piperidin-1-yl)methyl)-3-((S)-oxetan-2-ylmethyl)-3H-imidazo[4,5-b]pyridine-5-carboxylate |

TABLE B-continued

Typical intermediate compounds of the present disclosure include, but are not limited to:

| Example No. | Structures and names of compounds |
| --- | --- |

6d

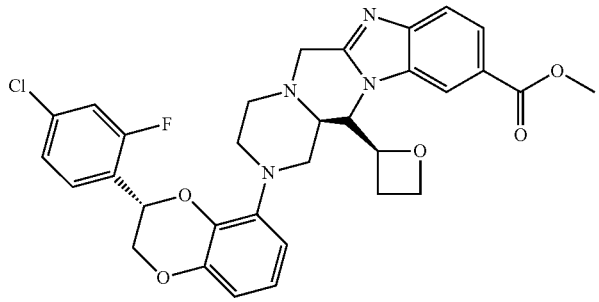

6d

Methyl 2-(((S)-4-((S)-3-(4-chloro-2-fluorophenyl)-2,3-dihydrobenzo[b][1,4]dioxan-5-yl)-2-methylpiperazin-1-yl)methyl)-1-(((S)-oxetan-2-yl)methyl)-1H-benzo[d]imidazole-6-carboxylate 6d

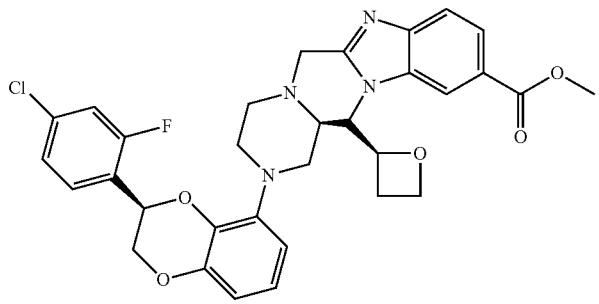

Methyl 2-(((S)-4-((R)-3-(4-chloro-2-fluorophenyl)-2,3-dihydrobenzo[b][1,4]dioxan-5-yl)-2-methylpiperazin-1-yl)methyl)-1-(((S)-oxetan-2-yl)methyl)-1H-benzo[d]imidazole-6-carboxylate 7g

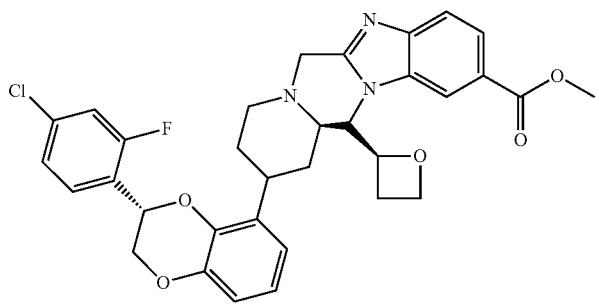

7g

Methyl 2-(((2S)-4-((S)-3-(4-chloro-2-fluorophenyl)-2,3-dihydrobenzo[b][1,4]dioxan-5-yl)-2-methylpiperidin-1-yl)methyl)-1-(((S)-oxetan-2-yl)methyl)-1H-benzo[d]imidazole-6-carboxylate 7g TABLE B-continued Typical intermediate compounds of the present disclosure include, but are not limited to:

| Example No. | Structures and names of compounds |
| --- | --- |

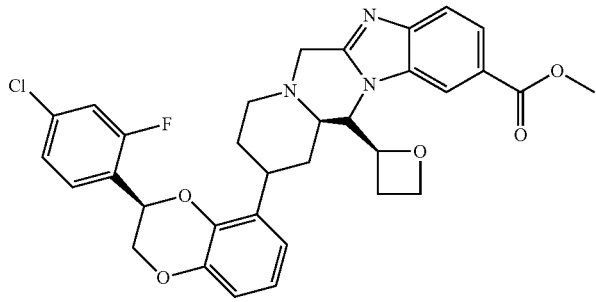

Methyl 2-(((2S)-4-((R)-3-(4-chloro-2-fluorophenyl)-2,3-dihydrobenzo[b][1,4]dioxan-5-yl)-2-methylpiperidin-1-yl)methyl)-1-(((S)-oxetan-2-yl)methyl)-1H-benzo[d]imidazole-6-carboxylate

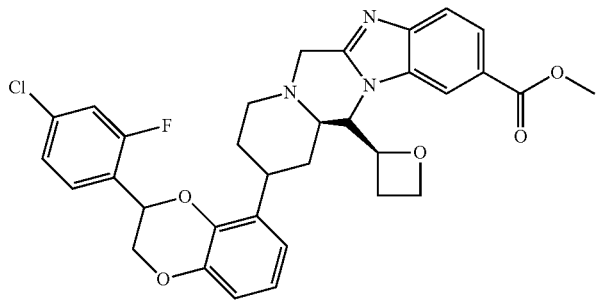

Methyl 2-(((2S)-4-(3-(4-chloro-2-fluorophenyl)-2,3-dihydrobenzo[b][1,4]dioxan-5-yl)-2-methylpiperidin-1-yl)methyl)-1-(((S)-oxetan-2-yl)methyl)-1H-benzo[d]imidazole-6-carboxylate (a mixture of diastereomers)

8a

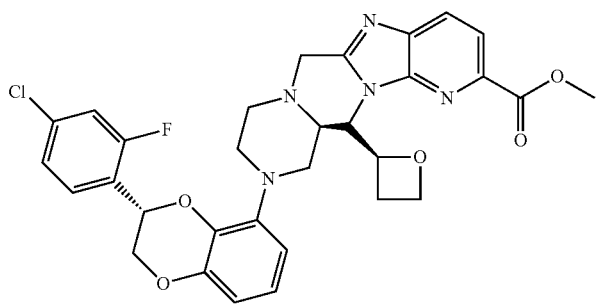

8a

Methyl 2-(((S)-4-((S)-3-(4-chloro-2-fluorophenyl)-2,3-dihydrobenzo[b][1,4]dioxan-5-yl)-2-methylpiperazin-1-yl)methyl)-3-((S)-oxetan-2-ylmethyl)-3H-imidazo[4,5-b]pyridine-5-carboxylate 8a

TABLE B-continued

Typical intermediate compounds of the present disclosure include, but are not limited to:

| Example No. | Structures and names of compounds |
|---|---|

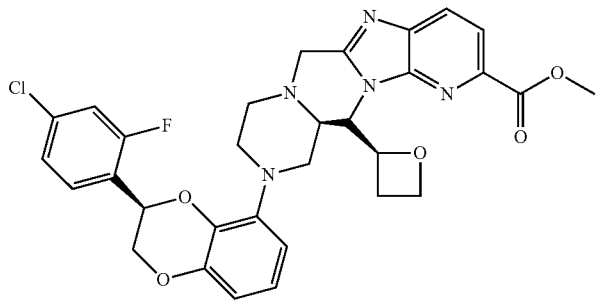

Methyl 2-(((S)-4-((R)-3-(4-chloro-2-fluorophenyl)-2,3-dihydrobenzo[b][1,4]dioxan-5-yl)-2-methylpiperazin-1-yl)methyl)-3-((S)-oxetan-2-ylmethyl)-3H-imidazo[4,5-b]pyridine-5-carboxylate

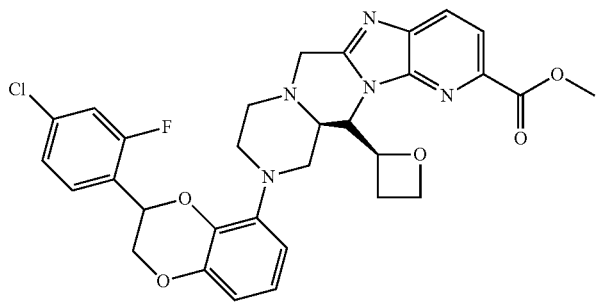

Methyl 2-(((S)-4-(3-(4-chloro-2-fluorophenyl)-2,3-dihydrobenzo[b][1,4]dioxan-5-yl)-2-methylpiperazin-1-yl)methyl)-3-((S)-oxetan-2-ylmethyl)-3H-imidazo[4,5-b]pyridine-5-carboxylate (a mixture of diastereomers)

9i

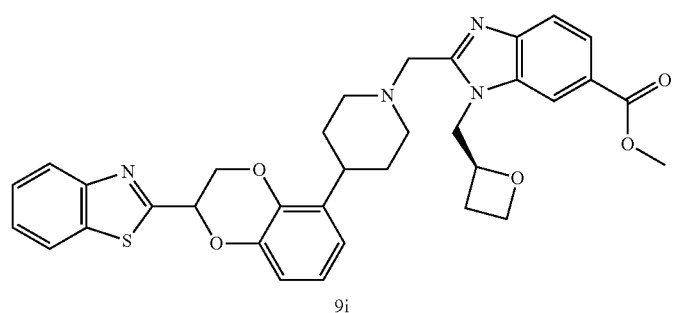

9i

Methyl 2-((4-(2-(benzo[d]thiazol-2-yl)-2,3-dihydrobenzo[b][1,4]dioxan-5-yl)piperidin-1-yl)methyl)-1-(((S)-oxetan-2-yl)methyl)-1H-benzo[d]imidazole-6-carboxylate (a mixture of diastereomers) 9i TABLE B-continued Typical intermediate compounds of the present disclosure include, but are not limited to:

| Example No. | Structures and names of compounds |
| --- | --- |
| 10a | 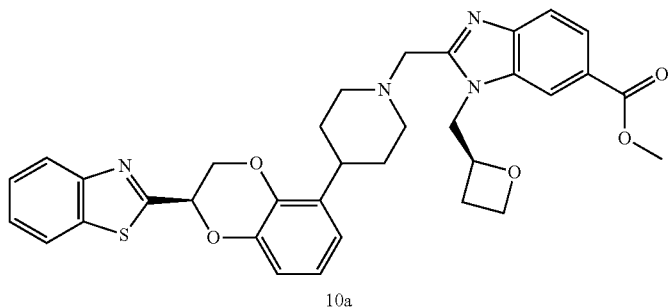

Methyl 2-((4-((R)-2-(benzo[d]thiazol-2-yl)-2,3-dihydrobenzo[b][1,4]dioxan-5-yl)piperidin-1-yl)methyl)-1-(((S)-oxetan-2-yl)methyl)-1H-benzo[d]imidazole-6-carboxylate 10a |
| 10b | 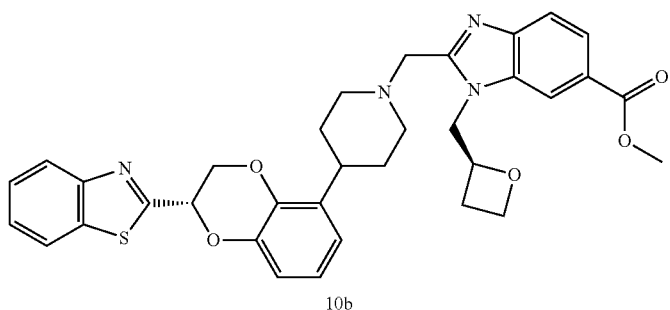 [SMILES: COC(=O)c1ccc2nc(CN3CCC(c4cccc5c4OCC(c4nc6ccccc6s4)O5)CC3)n(C[C@@H]3CCO3)c2c1]

Methyl 2-((4-((S)-2-(benzo[d]thiazol-2-yl)-2,3-dihydrobenzo[b][1,4]dioxan-5-yl)piperidin-1-yl)methyl)-1-(((S)-oxetan-2-yl)methyl)-1H-benzo[d]imidazole-6-carboxylate 10b |
| 12a | 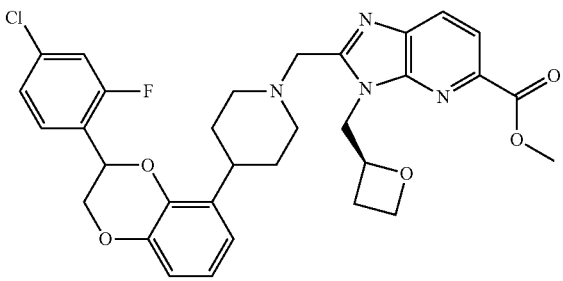

Methyl 2-((4-(3-(4-chloro-2-fluorophenyl)-2,3-dihydrobenzo[b][1,4]dioxan-5-yl)piperidin-1-yl)methyl)-3-((S)-oxetan-2-ylmethyl)-3H-imidazo[4,5-b]pyridine-5-carboxylate (a mixture of diastereomers) 12a |

TABLE B-continued

Typical intermediate compounds of the present disclosure include, but are not limited to:

| Example No. | Structures and names of compounds |
| --- | --- |
| 13i | 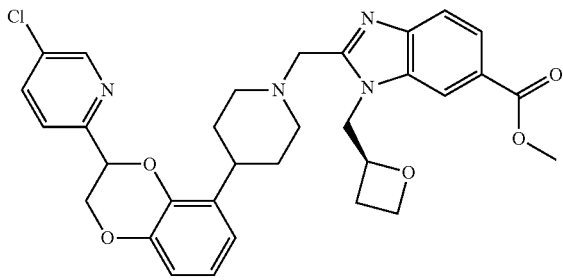

Methyl 2-((4-(3-(5-chloropyridin-2-yl)-2,3-dihydrobenzo[b][1,4]dioxan-5-yl)piperidin-1-yl)methyl)-1-(((S)-oxetan-2-yl)methyl)-1H-benzo[d]imidazole-6-carboxylate (a mixture of diastereomers) 13i

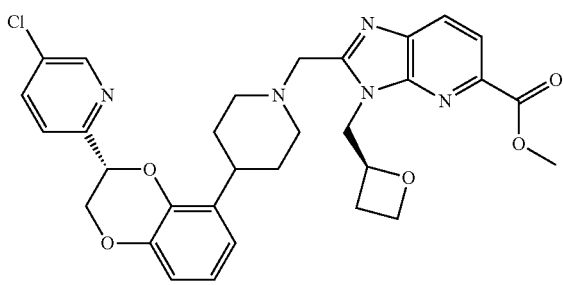 [SMILES: COC(=O)c1ccc2nc(CN3CCC(c4cccc5c4O[C@@H](c4ccc(Cl)cn4)CO5)CC3)n(C[C@@H]3CCO3)c2n1]

Methyl 2-((4-((S)-3-(5-chloropyridin-2-yl)-2,3-dihydrobenzo[b][1,4]dioxan-5-yl)piperidin-1-yl)methyl)-1-(((S)-oxetan-2-yl)methyl)-1H-benzo[d]imidazole-6-carboxylate

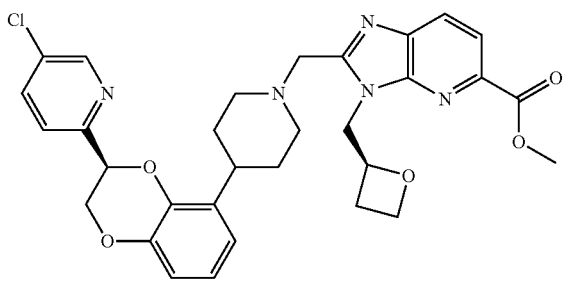 [SMILES: COC(=O)c1ccc2nc(CN3CCC(c4cccc5c4O[C@H](c4ccc(Cl)cn4)CO5)CC3)n(C[C@@H]3CCO3)c2n1]

Methyl 2-((4-((R)-3-(5-chloropyridin-2-yl)-2,3-dihydrobenzo[b][1,4]dioxan-5-yl)piperidin-1-yl)methyl)-1-(((S)-oxetan-2-yl)methyl)-1H-benzo[d]imidazole-6-carboxylate |
| 14l | 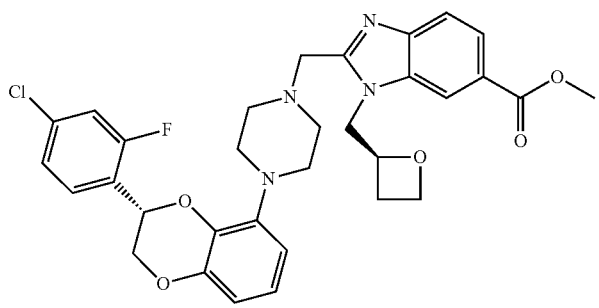

Methyl 2-((4-((S)-3-(4-chloro-2-fluorophenyl)-2,3-dihydrobenzo[b][1,4]dioxan-5-yl)piperazin-1-yl)methyl)-1-(((S)-oxetan-2-yl)methyl)-1H-benzo[d]imidazole-6-carboxylate 14l |

TABLE B-continued

Typical intermediate compounds of the present disclosure include, but are not limited to:

| Example No. | Structures and names of compounds |
|---|---|

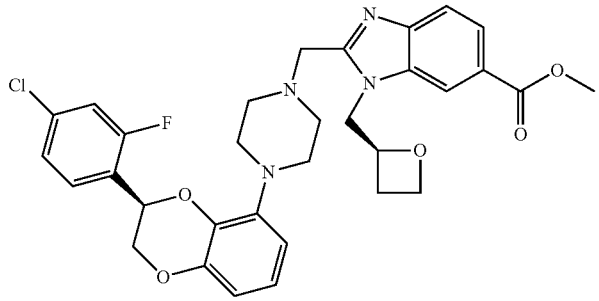 [SMILES: COC(=O)c1ccc2nc(CN3CCN(c4cccc5c4O[C@H](c4ccc(Cl)cc4F)CO5)CC3)n(C[C@@H]3CCO3)c2c1]

Methyl 2-((4-((R)-3-(4-chloro-2-fluorophenyl)-2,3-dihydrobenzo[b][1,4]dioxan-5-yl)piperazin-1-yl)methyl)-1-(((S)-oxetan-2-yl)methyl)-1H-benzo[d]imidazole-6-carboxylate

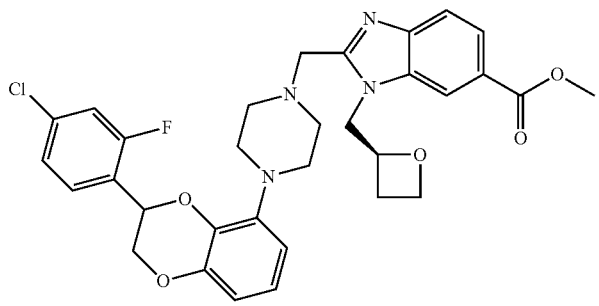 [SMILES: COC(=O)c1ccc2nc(CN3CCN(c4cccc5c4OC(c4ccc(Cl)cc4F)CO5)CC3)n(C[C@@H]3CCO3)c2c1]

Methyl 2-((4-(3-(4-chloro-2-fluorophenyl)-2,3-dihydrobenzo[b][1,4]dioxan-5-yl)piperazin-1-yl)methyl)-1-(((S)-oxetan-2-yl)methyl)-1H-benzo[d]imidazole-6-carboxylate (a mixture of diastereomers)

15f

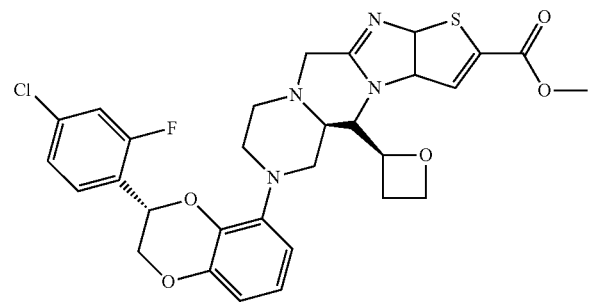

15f

Methyl 2-(((S)-4-((S)-3-(4-chloro-2-fluorophenyl)-2,3-dihydrobenzo[b][1,4]dioxan-5-yl)-2-methylpiperazin-1-yl)methyl)-1-((S)-oxetan-2-ylmethyl)-3a,6a-dihydro-1H-thieno[2,3-d]imidazole-5-carboxylate 15f TABLE B-continued Typical intermediate compounds of the present disclosure include, but are not limited to:

| Example No. | Structures and names of compounds |
|---|---|

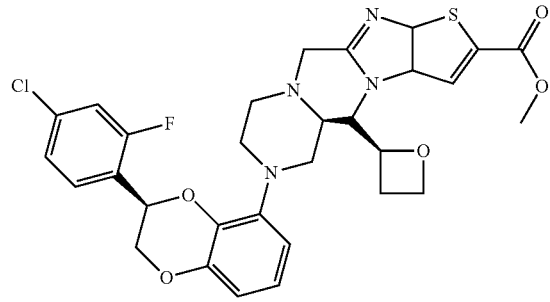

Methyl 2-(((S)-4-((R)-3-(4-chloro-2-fluorophenyl)-2,3-
dihydrobenzo[b][1,4]dioxan-5-yl)-2-methylpiperazin-1-yl)methyl)-1-
((S)-oxetan-2-ylmethyl)-3a,6a-dihydro-1H-thieno[2,3-d]imidazole-5-
carboxylate

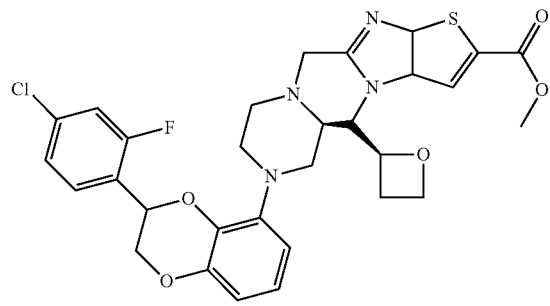

Methyl 2-(((S)-4-(3-(4-chloro-2-fluorophenyl)-2,3-
dihydrobenzo[b][1,4]dioxan-5-yl)-2-methylpiperazin-1-yl)methyl)-1-
((S)-oxetan-2-ylmethyl)-3a,6a-dihydro-1H-thieno[2,3-d]imidazole-5-
carboxylate (a mixture of diastereomers)

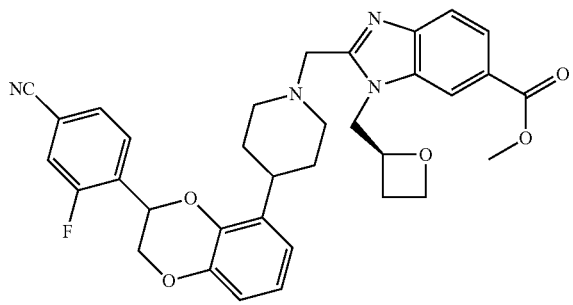

Methyl 2-((4-(3-(4-cyano-2-fluorophenyl)-2,3-
dihydrobenzo[b][1,4]dioxan-5-yl)piperidin-1-yl)methyl)-1-((S)-oxetan-
2-ylmethyl)-1H-benzo[d]imidazole-6-carboxylate (a mixture of
diastereomers)

TABLE B-continued

Typical intermediate compounds of the present disclosure include, but are not limited to:

| Example No. | Structures and names of compounds |
| --- | --- |

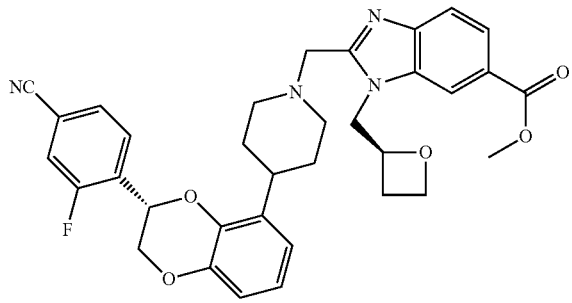 [SMILES: COC(=O)c1ccc2nc(CN3CCC(c4cccc5c4O[C@@H](c4ccc(C#N)cc4F)CO5)CC3)n(C[C@@H]3CCO3)c2c1]

Methyl 2-((4-((S)-3-(4-cyano-2-fluorophenyl)-2,3-dihydrobenzo[b][1,4]dioxan-5-yl)piperidin-1-yl)methyl)-1-((S)-oxetan-2-ylmethyl)-1H-benzo[d]imidazole-6-carboxylate

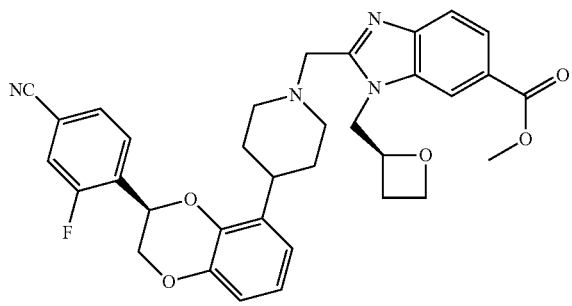 [SMILES: COC(=O)c1ccc2nc(CN3CCC(c4cccc5c4O[C@H](c4ccc(C#N)cc4F)CO5)CC3)n(C[C@@H]3CCO3)c2c1]

Methyl 2-((4-((R)-3-(4-cyano-2-fluorophenyl)-2,3-dihydrobenzo[b][1,4]dioxan-5-yl)piperidin-1-yl)methyl)-1-((S)-oxetan-2-ylmethyl)-1H-benzo[d]imidazole-6-carboxylate 17b

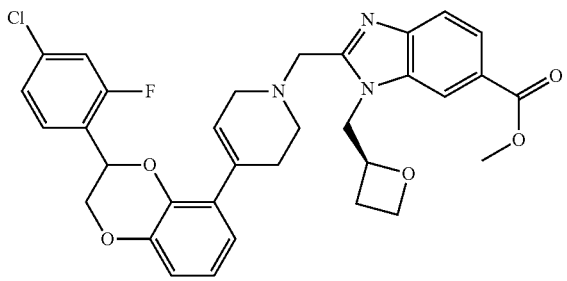

17b

Methyl 2-((4-(3-(4-chloro-2-fluorophenyl)-2,3-dihydrobenzo[b][1,4]dioxan-5-yl)-3,6-dihydropyridin-1(2H)-yl)methyl)-1-(((S)-oxetan-2-yl)methyl)-1H-benzo[d]imidazole-6-carboxylate (a mixture of diastereomers) 17b TABLE B-continued Typical intermediate compounds of the present disclosure include, but are not limited to:

| Example No. | Structures and names of compounds |
|---|---|
| | 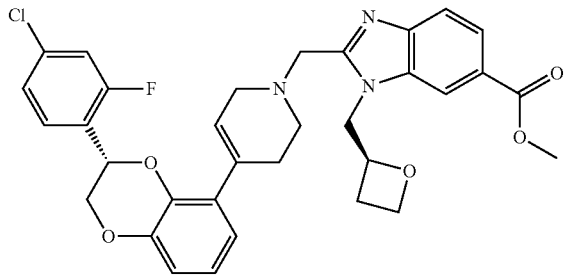 [SMILES: COC(=O)c1ccc2nc(CN3CC=C(c4cccc5c4O[C@@H](c4ccc(Cl)cc4F)CO5)CC3)n(C[C@@H]3CCO3)c2c1]
Methyl 2-((4-((S)-3-(4-chloro-2-fluorophenyl)-2,3-dihydrobenzo[b][1,4]dioxan-5-yl)-3,6-dihydropyridin-1(2H)-yl)methyl)-1-(((S)-oxacyclohexan-2-yl)methyl)-1H-benzo[d]imidazole-6-carboxylate |
| | 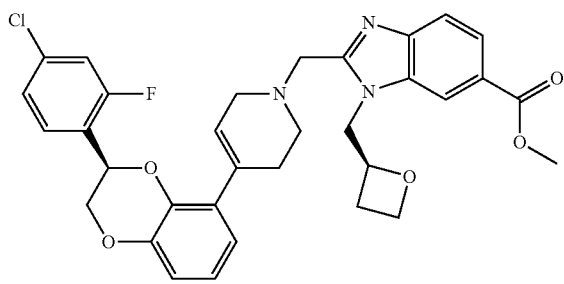 [SMILES: COC(=O)c1ccc2nc(CN3CC=C(c4cccc5c4O[C@H](c4ccc(Cl)cc4F)CO5)CC3)n(C[C@@H]3CCO3)c2c1]
Methyl 2-((4-((R)-3-(4-chloro-2-fluorophenyl)-2,3-dihydrobenzo[b][1,4]dioxan-5-yl)-3,6-dihydropyridin-1(2H)-yl)methyl)-1-(((S)-oxacyclohexan-2-yl)methyl)-1H-benzo[d]imidazole-6-carboxylate |
| 18i | 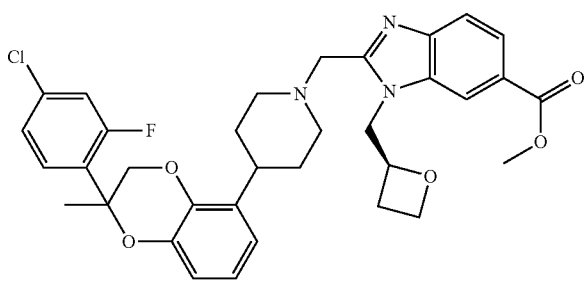
18i
Methyl 2-((4-(2-(4-chloro-2-fluorophenyl)-2-methyl-2,3-dihydrobenzo[b][1,4]dioxan-5-yl)piperidin-1-yl)methyl)-1-(((S)-oxetan-2-yl)methyl)-1H-benzo[d]imidazole-6-carboxylate (a mixture of diastereomers) 18i |
| | 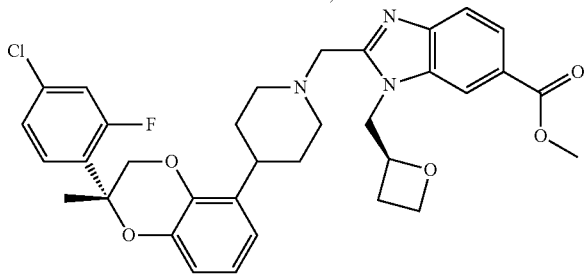
Methyl 2-((4-((S)-2-(4-chloro-2-fluorophenyl)-2-methyl-2,3-dihydrobenzo[b][1,4]dioxan-5-yl)piperidin-1-yl)methyl)-1-(((S)-oxetan-2-yl)methyl)-1H-benzo[d]imidazole-6-carboxylate |

TABLE B-continued

Typical intermediate compounds of the present disclosure include, but are not limited to:

| Example No. | Structures and names of compounds |
| --- | --- |
| | 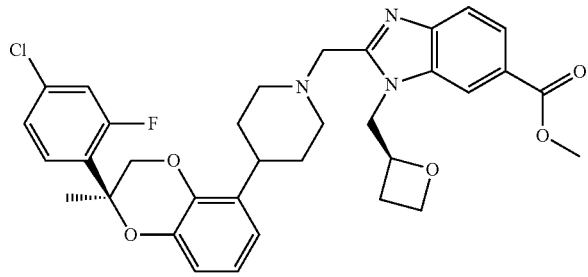 [SMILES: COC(=O)c1ccc2nc(CN3CCC(c4cccc5c4OC[C@](C)(c4ccc(Cl)cc4F)O5)CC3)n(C[C@@H]3CCO3)c2c1]<br>Methyl 2-((4-((R)-2-(4-chloro-2-fluorophenyl)-2-methyl-2,3-dihydrobenzo[b][1,4]dioxan-5-yl)piperidin-1-yl)methyl)-1-(((S)-oxetan-2-yl)methyl)-1H-benzo[d]imidazole-6-carboxylate |
| 19c | 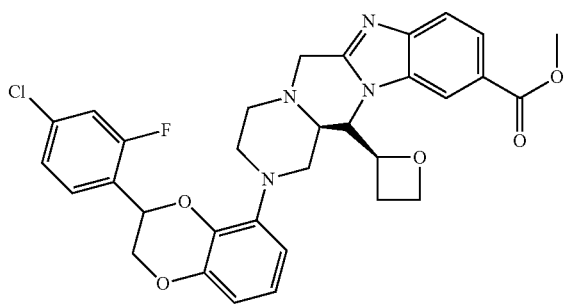<br>19c<br>Methyl 2-(((2S)-4-(3-(4-chloro-2-fluorophenyl)-2,3-dihydrobenzo[b][1,4]dioxan-5-yl)-2-methylpiperazin-1-yl)methyl)-1-(((S)-oxetan-2-yl)methyl)-1H-benzo[d]imidazole-6-carboxylate (a mixture of diastereomers) 19c |
| | 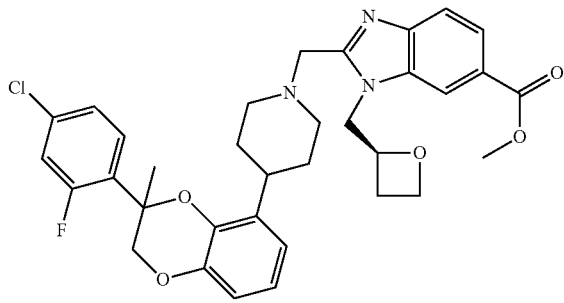 [SMILES: COC(=O)c1ccc2nc(CN3CCC(c4cccc5c4OC(C)(c4ccc(Cl)cc4F)CO5)CC3)n(C[C@@H]3CCO3)c2c1]<br>Methyl 2-((4-(3-(4-chloro-2-fluorophenyl)-3-methyl-2,3-dihydrobenzo[b][1,4]dioxan-5-yl)piperidin-1-yl)methyl)-1-(((S)-oxetan-2-yl)methyl)-1H-benzo[d]imidazole-6-carboxylate (a mixture of diastereomers) |

TABLE B-continued

Typical intermediate compounds of the present disclosure include, but are not limited to:

| Example No. | Structures and names of compounds |
|---|---|
| | 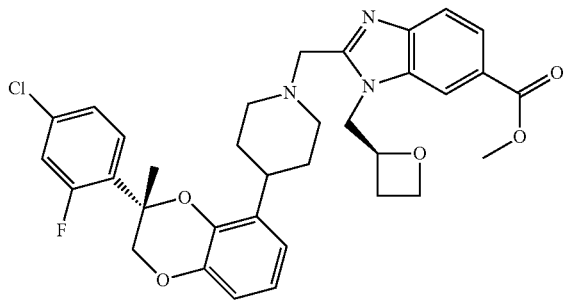 [SMILES: COC(=O)c1ccc2nc(CN3CCC(c4cccc5c4O[C@@](C)(c4ccc(Cl)cc4F)CO5)CC3)n(C[C@@H]3CCO3)c2c1]
Methyl 2-((4-((S)-3-(4-chloro-2-fluorophenyl)-3-methyl-2,3-dihydrobenzo[b][1,4]dioxan-5-yl)piperidin-1-yl)methyl)-1-(((S)-oxetan-2-yl)methyl)-1H-benzo[d]imidazole-6-carboxylate |
| | 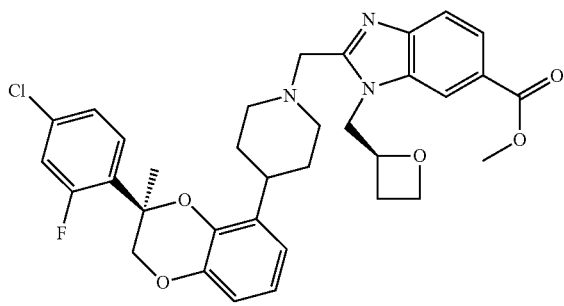 [SMILES: COC(=O)c1ccc2nc(CN3CCC(c4cccc5c4O[C@](C)(c4ccc(Cl)cc4F)CO5)CC3)n(C[C@@H]3CCO3)c2c1]
Methyl 2-((4-((R)-3-(4-chloro-2-fluorophenyl)-3-methyl-2,3-dihydrobenzo[b][1,4]dioxan-5-yl)piperidin-1-yl)methyl)-1-(((S)-oxetan-2-yl)methyl)-1H-benzo[d]imidazole-6-carboxylate | or tautomers, racemates, enantiomers or diastereomers thereof or mixtures thereof, or pharmaceutically acceptable salts thereof.

Another aspect of the present disclosure relates to a method for preparing a compound of general formula (IM) or a tautomer, racemate, enantiomer or diastereomer thereof or a mixture thereof, or a pharmaceutically acceptable salt thereof, which comprises the following step:

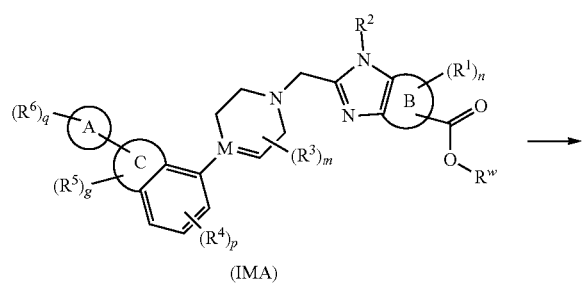

(IMA)

→

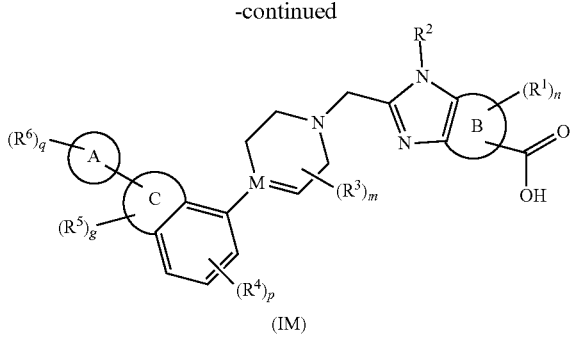

(IM)

conducting a hydrolysis reaction of a compound of general formula (IMA) to obtain the compound of general formula (IM), wherein:

$R^w$ is $C_{1-6}$ alkyl;

⸺, ring B, M, ring C, ring A, $R^1$ to $R^6$, n, m, p, g and q are as defined in general formula (IM).

Another aspect of the present disclosure relates to a method for preparing a compound of general formula (IN) or a tautomer, racemate, enantiomer or diastereomer thereof or a mixture thereof, or a pharmaceutically acceptable salt thereof, which comprises the following step:

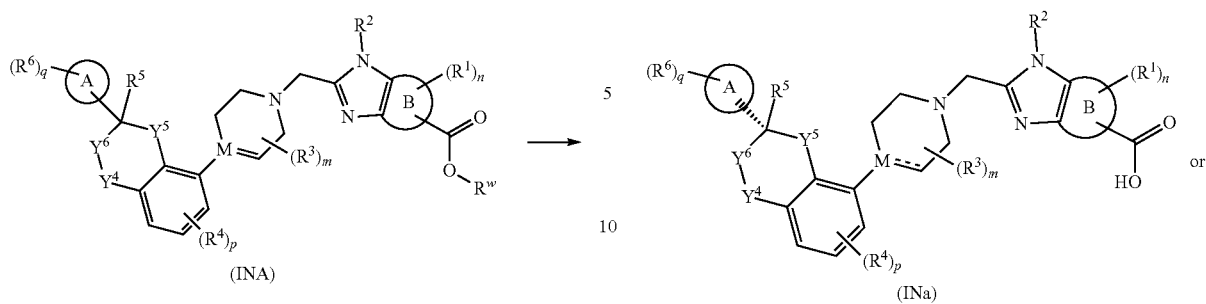

(INA) → (INa)

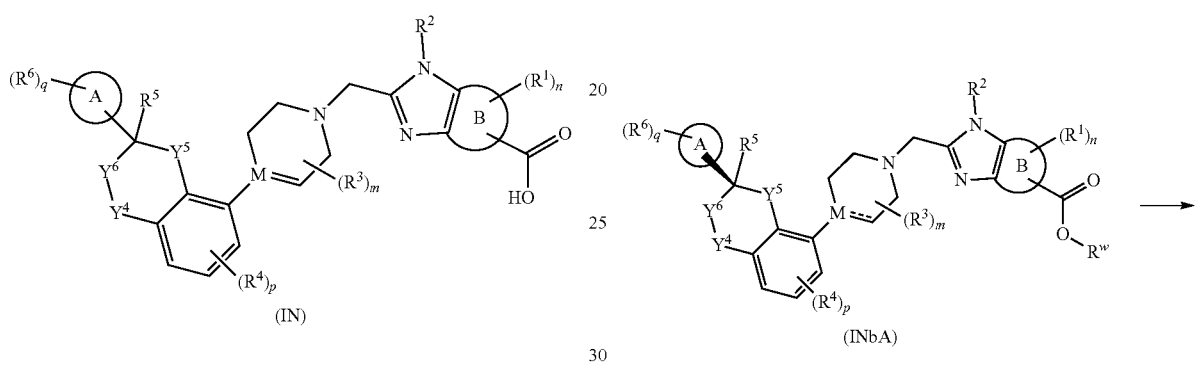

(IN)

conducting a hydrolysis reaction of a compound of general formula (INA) to obtain the compound of general formula (IN), wherein:

R^w is $C_{1-6}$ alkyl;

-----, ring B, M, $Y^4$, $Y^5$, $Y^6$, ring A, $R^1$ to $R^6$, n, m, p and q are as defined in general formula (IN).

Another aspect of the present disclosure relates to a method for preparing a compound of general formula (INa) or general formula (INb) or a tautomer, racemate, enantiomer or diastereomer thereof or a mixture thereof, or a pharmaceutically acceptable salt thereof, which comprises the following step:

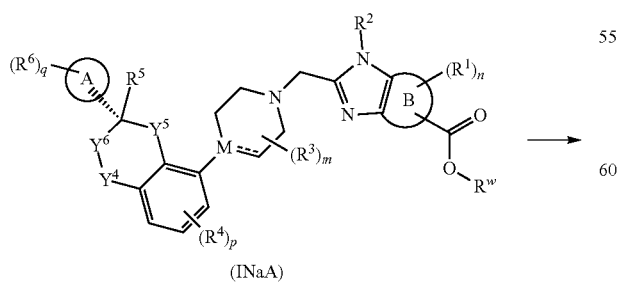

(INaA) →

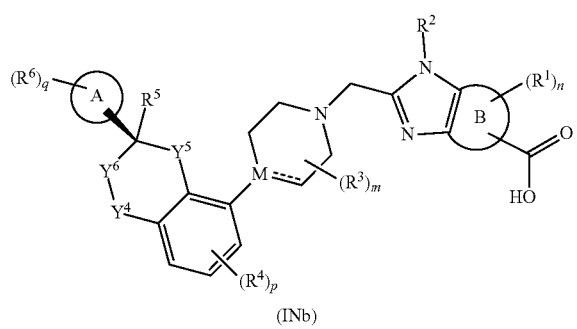

(INbA) →

(INb)

conducting a hydrolysis reaction of a compound of general formula (INaA) to obtain the compound of general formula (INa), or conducting a hydrolysis reaction of a compound of general formula (INbA) to obtain the compound of general formula (INb), wherein:

R^w is $C_{1-6}$ alkyl;

-----, ring B, M, $Y^4$, $Y^5$, $Y^6$, ring A, $R^1$ to $R^6$, n, m, p and q are as defined in general formula (INa) or general formula (INb).

Another aspect of the present disclosure relates to a method for preparing a compound of general formula (INa) or general formula (INb) or a tautomer, racemate, enantiomer or diastereomer thereof or a mixture thereof, or a pharmaceutically acceptable salt thereof, which comprises the following step:

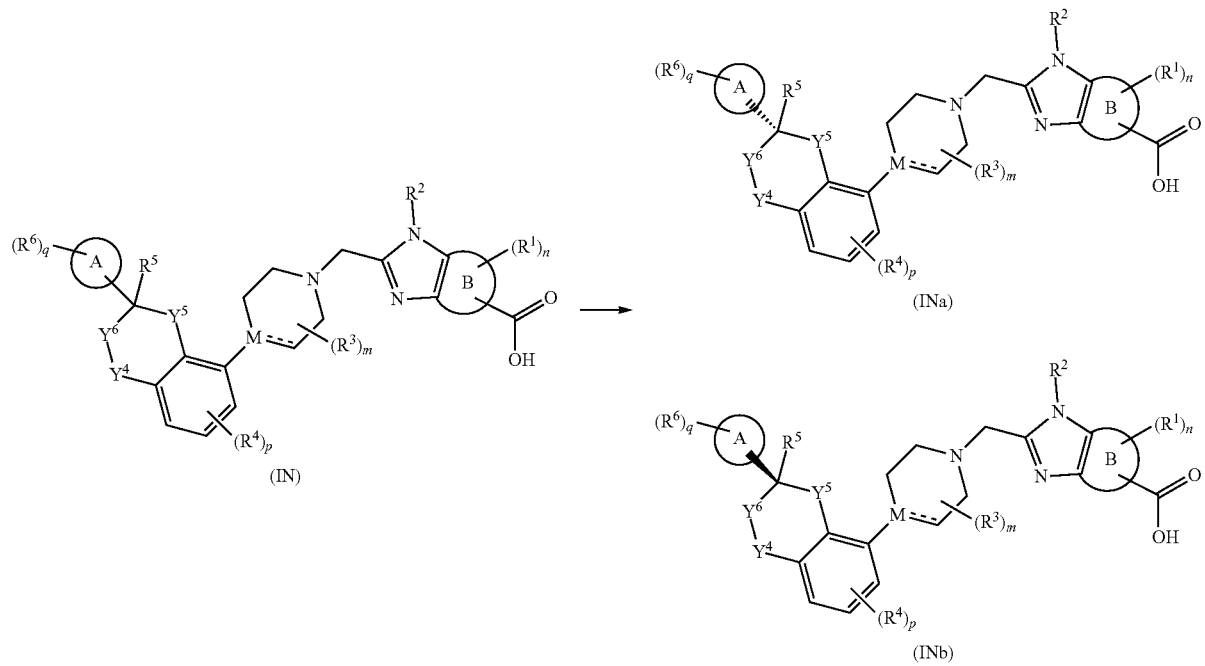

performing chiral resolution of a compound of general formula (IN) to obtain a compound of general formula (INa) and a compound of general formula (Nb);
wherein:
⁓⁓⁓, ring B, M, Y⁴, Y⁵, Y⁶, ring A, R¹ to R⁶, n, m, p and q are as defined in general formula (INa) or general formula (Nb).

Another aspect of the present disclosure relates to a method for preparing a compound of general formula (IIG) or a tautomer, racemate, enantiomer or diastereomer thereof or a mixture thereof, or a pharmaceutically acceptable salt thereof, which comprises the following step:

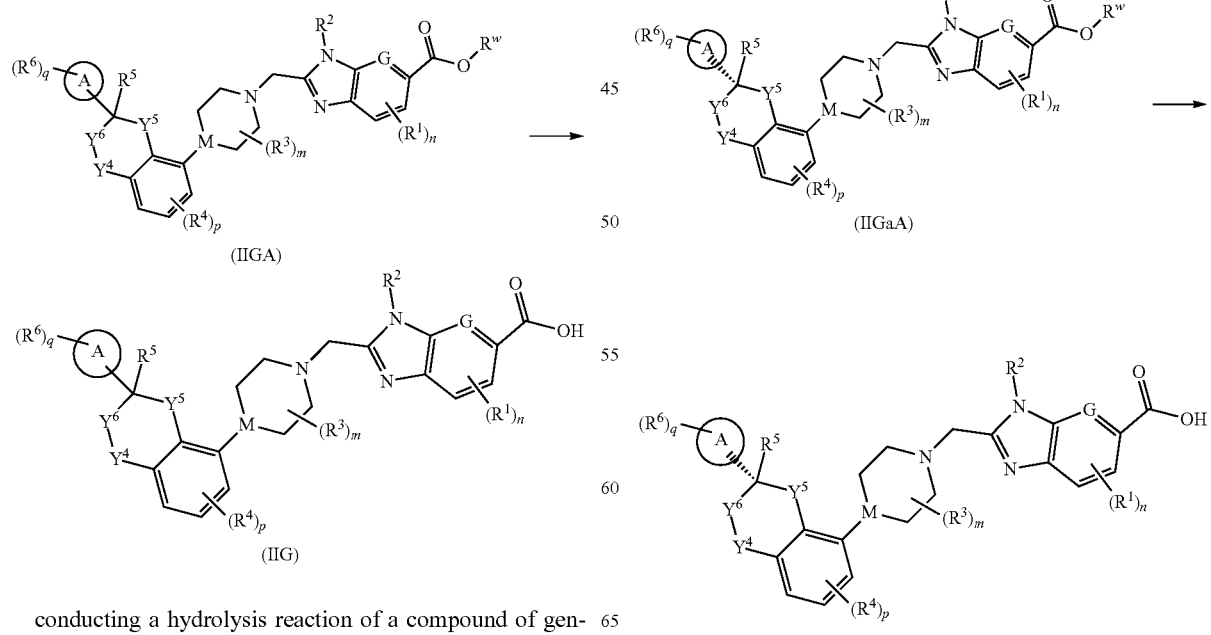

conducting a hydrolysis reaction of a compound of general formula (IIGA) to obtain the compound of general formula (IIG), wherein:
$R^w$ is $C_{1-6}$ alkyl;
G, M, Y⁴, Y⁵, Y⁶, ring A, R¹ to R⁶, n, m, p and q are as defined in general formula (IIG).

Another aspect of the present disclosure relates to a method for preparing a compound of general formula (IIGa) or general formula (IIGb) or a tautomer, racemate, enantiomer or diastereomer thereof or a mixture thereof, or a pharmaceutically acceptable salt thereof, which comprises the following step:

-continued

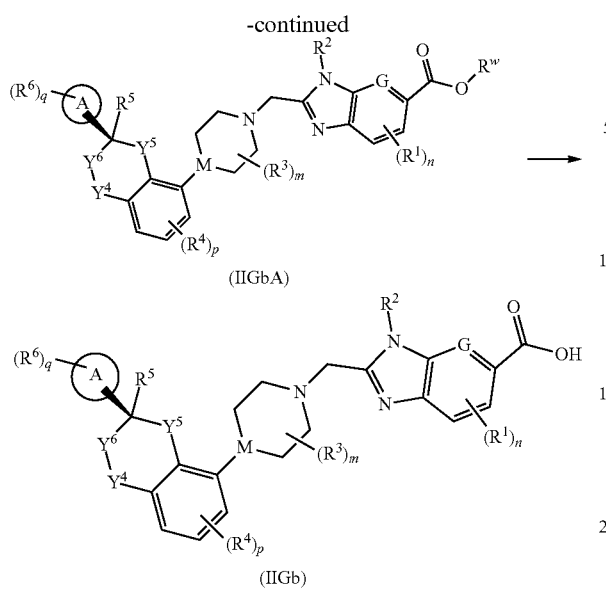

(IIGbA)

(IIGb)

conducting a hydrolysis reaction of a compound of general formula (IIGaA) to obtain the compound of general formula (IIGa), or conducting a hydrolysis reaction of a compound of general formula (IIGbA) to obtain the compound of general formula (IIGb), wherein:
$R^w$ is $C_{1-6}$ alkyl;
G, M, $Y^4$, $Y^5$, $Y^6$, ring A, $R^1$ to $R^6$, n, m, p and q are as defined in general formula (IIGa) or general formula (IIGb).

Another aspect of the present disclosure relates to a method for preparing a compound of general formula (IIGa) or general formula (IIGb) or a tautomer, racemate, enantiomer or diastereomer thereof or a mixture thereof, or a pharmaceutically acceptable salt thereof, which comprises the following step:

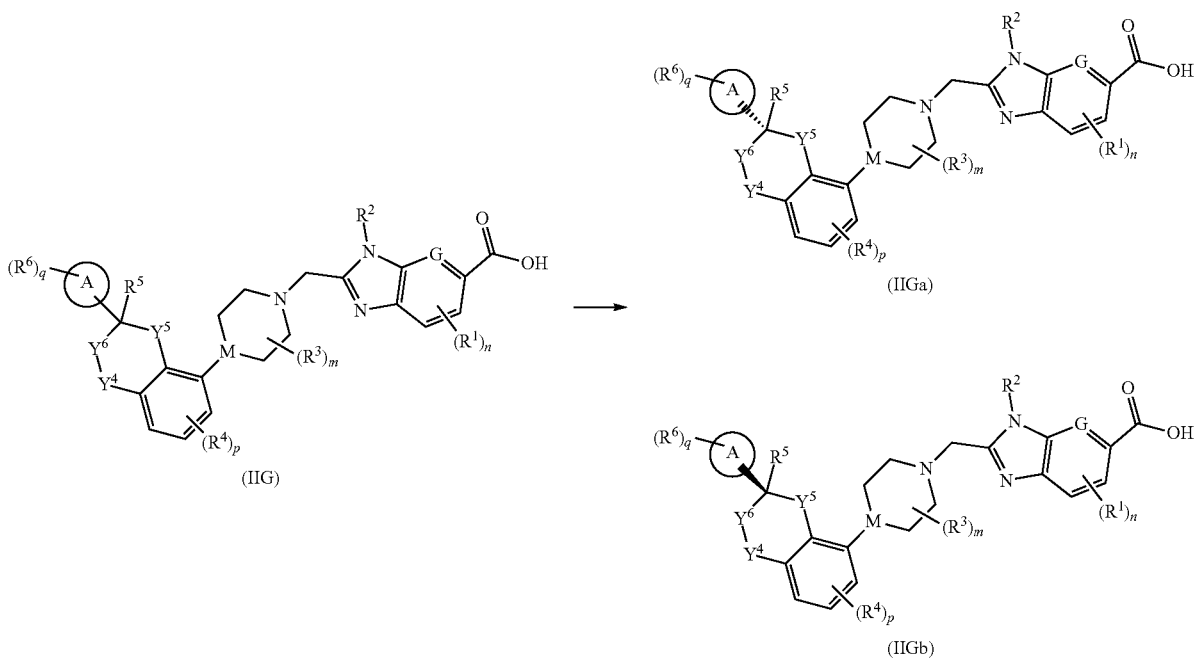

(IIG)

(IIGa)

(IIGb)

performing chiral resolution of a compound of general formula (IIG) to obtain a compound of general formula (IIGa) and a compound of general formula (IIGb), wherein: G, M, $Y^4$, $Y^5$, $Y^6$, ring A, $R^1$ to $R^6$, n, m, p and q are as defined in general formula (IIGa) or general formula (IIGb).

Another aspect of the present disclosure relates to a method for preparing a compound of general formula (IIN) or a tautomer, racemate, enantiomer or diastereomer thereof or a mixture thereof, or a pharmaceutically acceptable salt thereof, which comprises the following step:

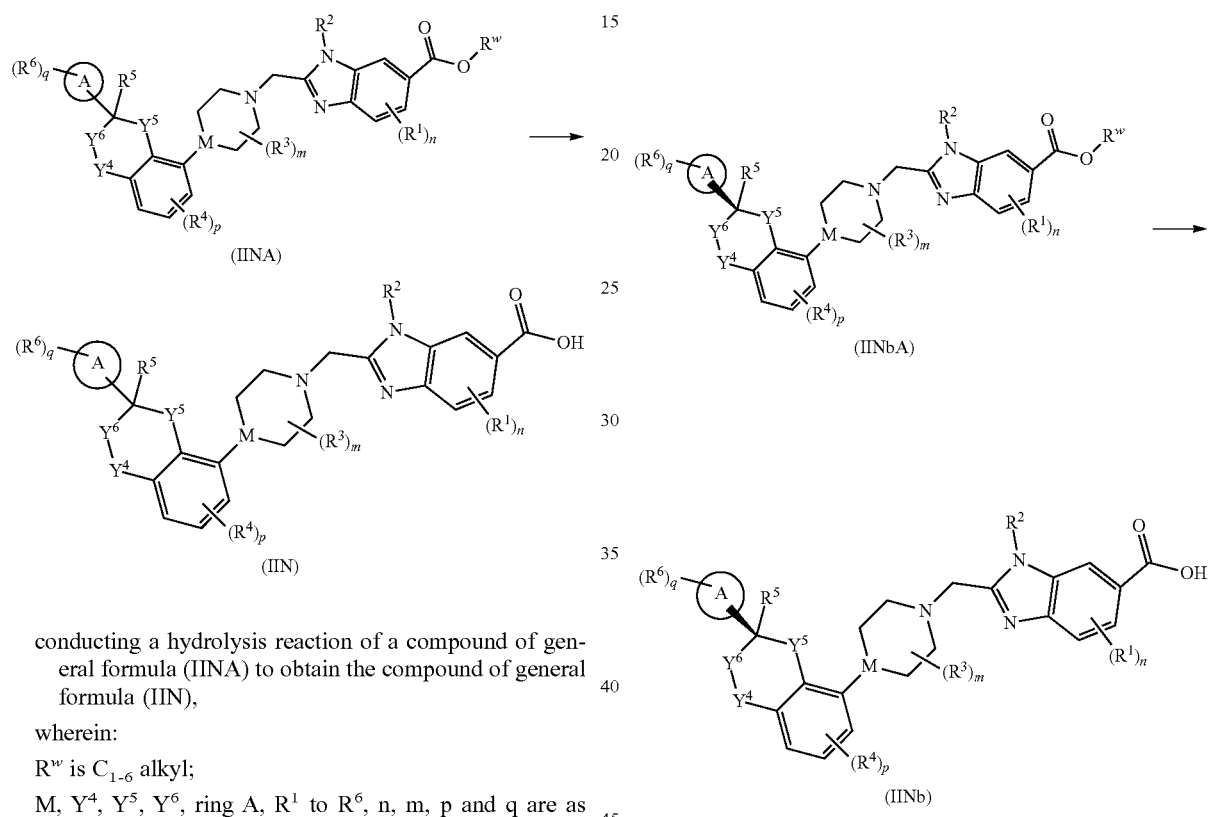

conducting a hydrolysis reaction of a compound of general formula (IINA) to obtain the compound of general formula (IIN), wherein:

$R^w$ is $C_{1-6}$ alkyl;

M, $Y^4$, $Y^5$, $Y^6$, ring A, $R^1$ to $R^6$, n, m, p and q are as defined in general formula (IIN).

Another aspect of the present disclosure relates to a method for preparing a compound of general formula (IINa) or general formula (IINb) or a tautomer, racemate, enantiomer or diastereomer thereof or a mixture thereof, or a pharmaceutically acceptable salt thereof, which comprises the following step:

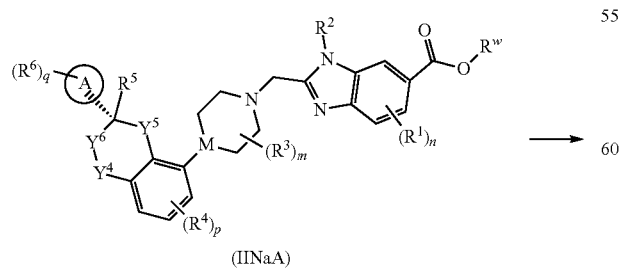

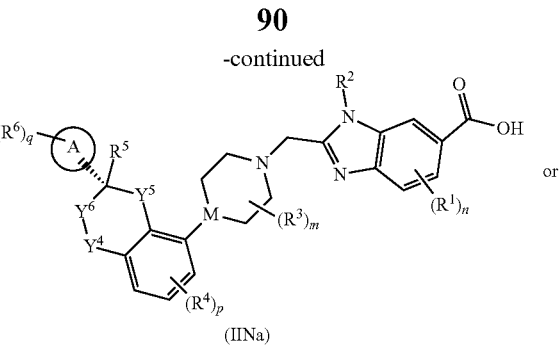

conducting a hydrolysis reaction of a compound of general formula (IINaA) to obtain the compound of general formula (IINa), or conducting a hydrolysis reaction of a compound of general formula (IINbA) to obtain the compound of general formula (IINb), wherein:

$R^w$ is $C_{1-6}$ alkyl;

M, $Y^4$, $Y^5$, $Y^6$, ring A, $R^1$ to $R^6$, n, m, p and q are as defined in general formula (IINa) or general formula (IINb).

Another aspect of the present disclosure relates to a method for preparing a compound of general formula (IINa) or general formula (IINb) or a tautomer, racemate, enantiomer or diastereomer thereof or a mixture thereof, or a pharmaceutically acceptable salt thereof, which comprises the following step:

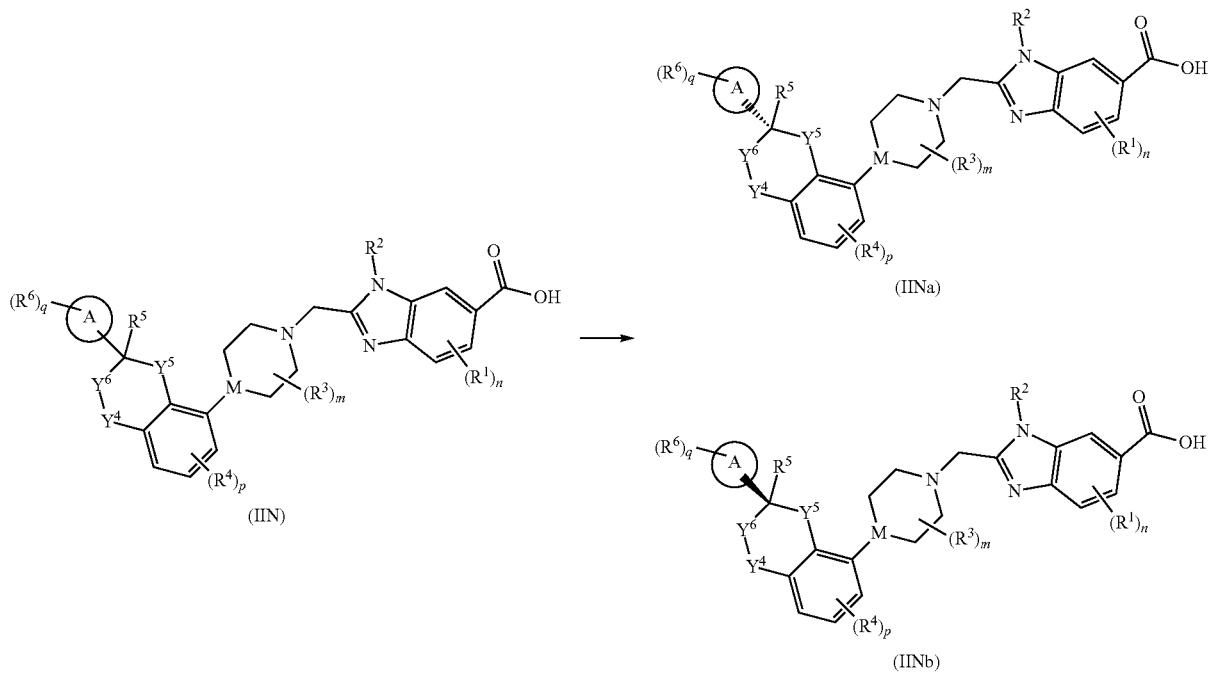

(IIN)

(IINa)

(IINb)

performing chiral resolution of a compound of general formula (IIN) to obtain a compound of general formula (IINa) and a compound of general formula (IINb), wherein: M, $Y^4$, $Y^5$, $Y^6$, ring A, $R^1$ to $R^6$, n, m, p and q are as defined in general formula (IINa) or general formula (IINb).

Another aspect of the present disclosure relates to a method for preparing a compound of general formula (IIIN-1) or general formula (IIIN-2) or a tautomer, racemate, enantiomer or diastereomer thereof or a mixture thereof, or a pharmaceutically acceptable salt thereof, which comprises the following step:

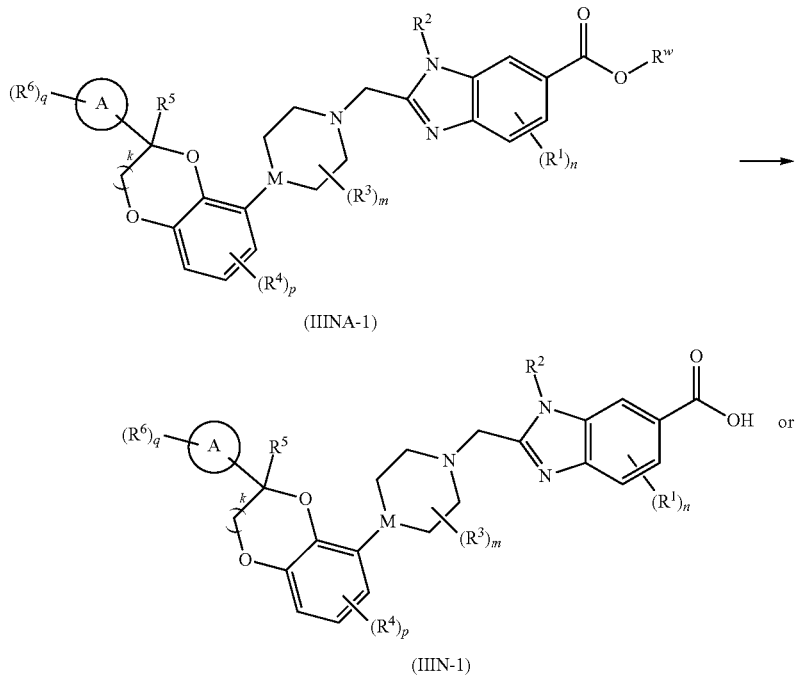

(IIINA-1)

(IIIN-1)

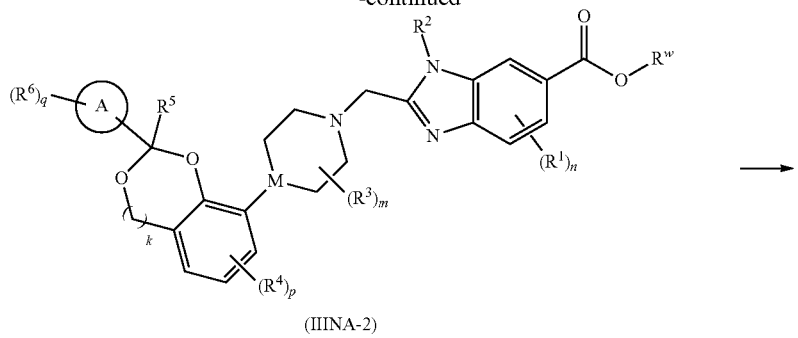

(IIINA-2)

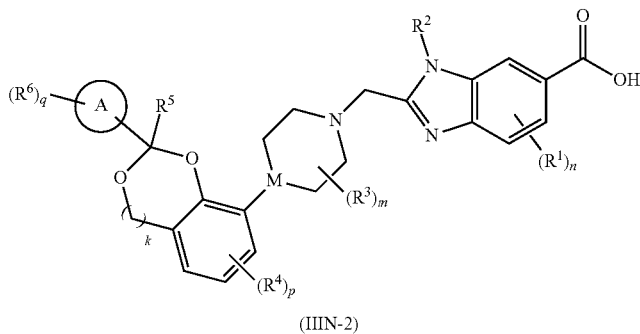

(IIIN-2)

conducting a hydrolysis reaction of a compound of general formula (IIINA-1) to obtain the compound of general formula (IIIN-1), or conducting a hydrolysis reaction of a compound of general formula (IIINA-2) to obtain the compound of general formula (IIIN-2), wherein:

$R^w$ is $C_{1-6}$ alkyl;

M, ring A, $R^1$ to $R^6$, k, n, m, p and q are as defined in general formula (IIIN-1) or general formula (IIIN-2).

Another aspect of the present disclosure relates to a method for preparing a compound of general formula (I) or a tautomer, racemate, enantiomer or diastereomer thereof or a mixture thereof, or a pharmaceutically acceptable salt thereof, which comprises the following step:

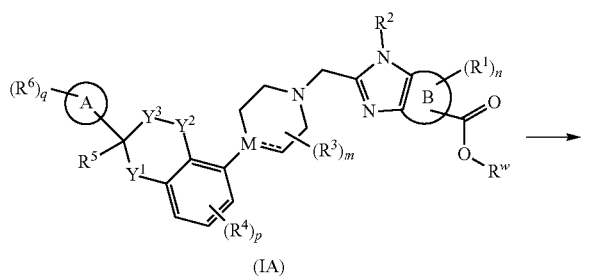

(IA)

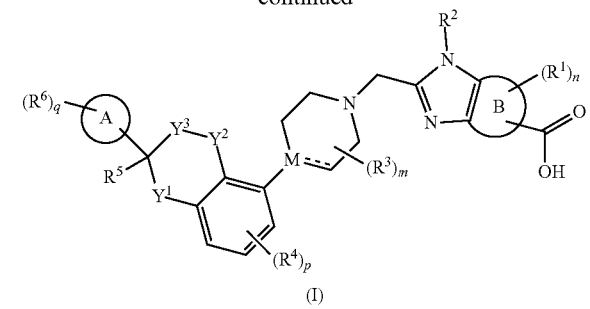

(I)

conducting a hydrolysis reaction of a compound of general formula (IA) to obtain the compound of general formula (I), wherein:

$R^w$ is $C_{1-6}$ alkyl;

═══ ring B, M, $Y^1$, $Y^2$, $Y^3$, ring A, $R^1$ to $R^6$, n, m, p and q are as defined in general formula (I).

Another aspect of the present disclosure relates to a method for preparing a compound of general formula (II) or a tautomer, racemate, enantiomer or diastereomer thereof or a mixture thereof, or a pharmaceutically acceptable salt thereof, which comprises the following step:

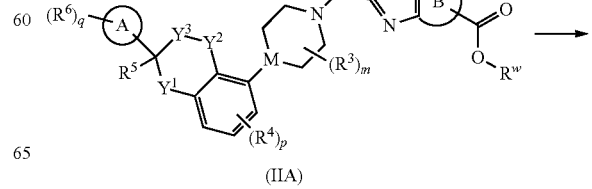

(IIA)

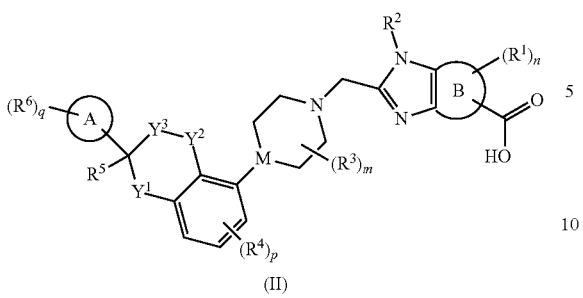

(II)

conducting a hydrolysis reaction of a compound of general formula (IIA) to obtain the compound of general formula (II), wherein:

$R^w$ is $C_{1-6}$ alkyl;

ring B, M, $Y^1$, $Y^2$, $Y^3$, ring A, $R^1$ to $R^6$, n, m, p and q are as defined in general formula (II).

Another aspect of the present disclosure relates to a method for preparing a compound of general formula (III-1) or general formula (III-2) or a tautomer, racemate, enantiomer or diastereomer thereof or a mixture thereof, or a pharmaceutically acceptable salt thereof, which comprises the following step:

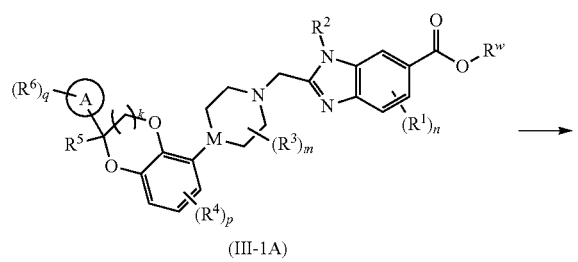

(III-1A)

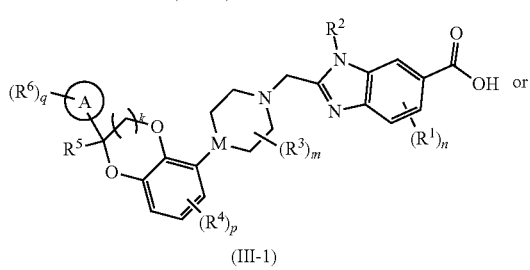

(III-1)

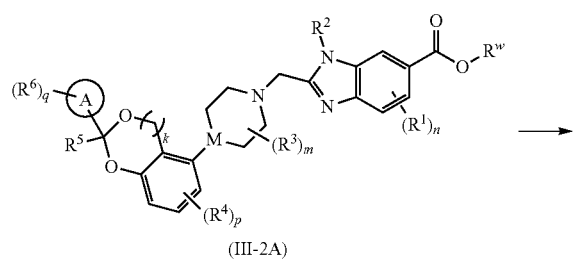

(III-2A)

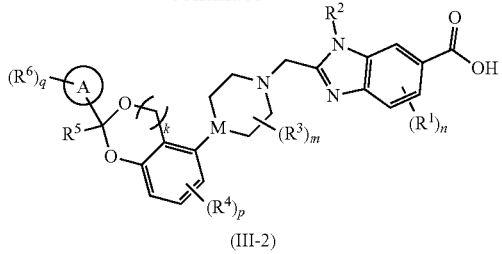

(III-2)

conducting a hydrolysis reaction of a compound of general formula (III-1A) to obtain the compound of general formula (III-1), or conducting a hydrolysis reaction of a compound of general formula (III-2A) to obtain the compound of general formula (III-2), wherein:

$R^w$ is $C_{1-6}$ alkyl;

M, ring A, $R^1$ to $R^6$, k, n, m, p and q are as defined in general formula (III-1) or general formula (III-2).

Another aspect of the present disclosure relates to a pharmaceutical composition, which comprises the compounds of general formula (IM), general formula (I), general formula (II), general formula (IN), general formula (INa), general formula (INb), general formula (IIG), general formula (IIGa), general formula (IIGb), general formula (IIN), general formula (IINa), general formula (IINb), general formula (IIIN-1), general formula (IIIN-2), general formula (III-1) and general formula (III-2) or the tautomers, racemates, enantiomers or diastereomers thereof or the mixtures thereof, or the pharmaceutically acceptable salts thereof disclosed herein, and one or more pharmaceutically acceptable carriers, diluents or excipients.

The present disclosure further relates to use of the compounds of general formula (IM), general formula (I), general formula (II), general formula (IN), general formula (INa), general formula (INb), general formula (IIN), general formula (IIG), general formula (IIGa), general formula (IIGb), general formula (IINa), general formula (IINb), general formula (IIIN-1), general formula (IIIN-2), general formula (III-1) and general formula (III-2) or the tautomers, racemates, enantiomers or diastereomers thereof or the mixtures thereof, or the pharmaceutically acceptable salts thereof, or the pharmaceutical composition comprising the same in manufacturing medicaments for agonizing a GLP-1 receptor.

The present disclosure further relates to use of the compounds of general formula (IM), general formula (I), general formula (II), general formula (IN), general formula (INa), general formula (INb), general formula (IIG), general formula (IIGa), general formula (IIGb), general formula (IIN), general formula (IINa), general formula (IINb), general formula (IIIN-1), general formula (IIIN-2), general formula (III-1) and general formula (III-2) or the tautomers, racemates, enantiomers or diastereomers thereof or the mixtures thereof, or the pharmaceutically acceptable salts thereof, or the pharmaceutical composition comprising the same in manufacturing medicaments for treating and/or preventing type I diabetes, type II diabetes, malnutrition-related diabetes, diabetes complications, obesity, hyperglycemia, glucose intolerance, cardiovascular diseases, hyperlipidemia, cerebral infarction, strokes, nonalcoholic steatohepatitis (NASH), Parkinson's disease, dementia, insulin resistance and hepatic insulin resistance, preferably in manufacturing medicaments for treating and/or preventing type I diabetes, type II diabetes, obesity, diabetes complications, nonalcoholic steatohepatitis and cardiovascular diseases.

The present disclosure further relates to use of the compounds of general formula (IM), general formula (I), general formula (II), general formula (IN), general formula (INa), general formula (INb), general formula (IIG), general formula (IIGa), general formula (IIGb), general formula (IIN), general formula (IINa), general formula (IINb), general formula (IIIN-1), general formula (IIIN-2), general formula (III-1) and general formula (III-2) or the tautomers, racemates, enantiomers or diastereomers thereof or the mixtures thereof, or the pharmaceutically acceptable salts thereof, or the pharmaceutical composition comprising the same in manufacturing medicaments for treating and/or preventing idiopathic type I diabetes, latent autoimmune diabetes in adults (LADA), maturity-onset diabetes of the young (MODY), gestational diabetes, nonalcoholic fatty liver disease (NAFLD), atherosclerosis, hypertension and coronary heart disease.

The present disclosure also relates to a method for agonizing a GLP-1 receptor, which comprises administering to a patient in need a therapeutically effective amount of the compounds of general formula (IM), general formula (I), general formula (II), general formula (IN), general formula (INa), general formula (INb), general formula (IIG), general formula (IIGa), general formula (IIGb), general formula (IIN), general formula (IINa), general formula (IINb), general formula (IIIN-1), general formula (IIIN-2), general formula (III-1) and general formula (III-2) or the tautomers, racemates, enantiomers or diastereomers thereof or the mixtures thereof, or the pharmaceutically acceptable salts thereof, or the pharmaceutical composition comprising the same.

The present disclosure also relates to a method for treating and/or preventing type I diabetes, type II diabetes, malnutrition-related diabetes, diabetes complications, obesity, hyperglycemia, glucose intolerance, cardiovascular diseases, hyperlipidemia, cerebral infarction, strokes, nonalcoholic fatty liver disease (NAFLD), Parkinson's disease, dementia, insulin resistance and liver insulin resistance, preferably type I diabetes, type II diabetes, obesity, diabetes complications, nonalcoholic fatty liver disease and cardiovascular diseases, which comprises administering to a patient in need a therapeutically effective amount of the compounds of general formula (IM), general formula (I), general formula (II), general formula (IN), general formula (INa), general formula (INb), general formula (IIG), general formula (IIGa), general formula (IIGb), general formula (IIN), general formula (IINa), general formula (IINb), general formula (IIIN-1), general formula (IIIN-2), general formula (III-1) and general formula (III-2) or the tautomers, racemates, enantiomers or diastereomers thereof or the mixtures thereof, or the pharmaceutically acceptable salts thereof, or the pharmaceutical composition comprising the same.

The present disclosure also relates to a method for treating and/or preventing idiopathic type I diabetes, latent autoimmune diabetes in adults (LADA), maturity-onset diabetes of the young (MODY), gestational diabetes, nonalcoholic fatty liver disease (NAFLD), atherosclerosis, hypertension and coronary heart disease, which comprises administering to a patient in need a therapeutically effective amount of the compounds of general formula (IM), general formula (I), general formula (II), general formula (IN), general formula (INa), general formula (INb), general formula (IIG), general formula (IIGa), general formula (IIGb), general formula (IIN), general formula (IINa), general formula (IINb), general formula (IIIN-1), general formula (IIIN-2), general formula (III-1) and general formula (III-2) or the tautomers, racemates, enantiomers or diastereomers thereof or the mixtures thereof, or the pharmaceutically acceptable salts thereof, or the pharmaceutical composition comprising the same.

The present disclosure further relates to compounds of general formula (IM), general formula (I), general formula (II), general formula (IN), general formula (INa), general formula (INb), general formula (IIN), general formula (IIG), general formula (IIGa), general formula (IIGb), general formula (IINa), general formula (IINb), general formula (IIIN-1), general formula (IIIN-2), general formula (III-1) and general formula (III-2) or tautomers, racemates, enantiomers or diastereomers thereof or mixtures thereof, or pharmaceutically acceptable salts thereof, or pharmaceutical compositions comprising the same, which are used as medicaments.

The present disclosure also relates to compounds of general formula (IM), general formula (I), general formula (II), general formula (IN), general formula (INa), general formula (INb), general formula (IIN), general formula (IIG), general formula (IIGa), general formula (IIGb), general formula (IINa), general formula (IINb), general formula (IIIN-1), general formula (IIIN-2), general formula (III-1) and general formula (III-2) or tautomers, racemates, enantiomers or diastereomers thereof or mixtures thereof, or pharmaceutically acceptable salts thereof, or pharmaceutical compositions comprising the same, which are used as GLP-1 receptor agonists.

The present disclosure further relates to compounds of general formula (IM), general formula (I), general formula (II), general formula (IN), general formula (INa), general formula (INb), general formula (IIN), general formula (IIG), general formula (IIGa), general formula (IIGb), general formula (IINa), general formula (IINb), general formula (IIIN-1), general formula (IIIN-2), general formula (III-1) and general formula (III-2) or tautomers, racemates, enantiomers or diastereomers thereof or mixtures thereof, or pharmaceutically acceptable salts thereof, or pharmaceutical compositions comprising the same, which are used for treating and/or preventing type I diabetes, type II diabetes, malnutrition-related diabetes, diabetes complications, obesity, hyperglycemia, glucose intolerance, cardiovascular diseases, hyperlipidemia, cerebral infarction, strokes, nonalcoholic fatty liver disease (NAFLD), Parkinson's disease, dementia, insulin resistance and hepatic insulin resistance, preferably for treating and/or preventing diseases selected from the group consisting of type I diabetes, type II diabetes, obesity, diabetes complications, nonalcoholic fatty liver disease and cardiovascular diseases.

The present disclosure further relates to compounds of general formula (IM), general formula (I), general formula (II), general formula (IN), general formula (INa), general formula (INb), general formula (IIN), general formula (IIG), general formula (IIGa), general formula (IIGb), general formula (IINa), general formula (IINb), general formula (IIIN-1), general formula (IIIN-2), general formula (III-1) and general formula (III-2) or tautomers, racemates, enantiomers or diastereomers thereof or mixtures thereof, or pharmaceutically acceptable salts thereof, or pharmaceutical compositions comprising the same, which are used for treating and/or preventing idiopathic type I diabetes, latent autoimmune diabetes in adults (LADA), maturity-onset diabetes of the young (MODY), gestational diabetes, nonalcoholic fatty liver disease (NAFLD), atherosclerosis, hypertension and coronary heart disease.

"Diabetic complications" are complications arising from diabetes or hyperglycemia, and may be acute or chronic complexes. The term "acute complex" includes ketoacidosis and infectious diseases (e.g., skin infection, soft tissue infection, biliary system infection, respiratory system infection and urinary tract infection), and "chronic complex" includes, for example, microangiopathy (e.g., nephropathy and retinopathy), neuropathy (e.g., sensory neuropathy, motor neuropathy and autonomic neuropathy) and gangrene. The major diabetic complexes include diabetic retinopathy, diabetic nephropathy and diabetic neuropathy.

"Coronary heart disease" includes myocardial infarction and angina pectoris.

"Dementia" includes, for example, Alzheimer's disease, (early-onset dementia) EOD, vascular dementia and diabetic dementia.

The active compound may be formulated into a form suitable for administration by any suitable route, and one or more pharmaceutically acceptable carriers are used to formulate the composition of the present disclosure by conventional methods. Thus, the active compound of the present disclosure may be formulated into a variety of dosage forms for oral administration, administration by injection (e.g., intravenous, intramuscular or subcutaneous), or administration by inhalation or insufflation. The compound of the present disclosure may also be formulated into a sustained-release dosage form, such as tablets, hard or soft capsules, aqueous or oily suspensions, emulsions, injections, dispersible powders or granules, suppositories, lozenges or syrups.

As a general guide, the active compound is preferably in a form of a unit dose, or in a form of a single dose that can be self-administered by a patient. The unit dose of the compound or composition of the present disclosure may be in a tablet, capsule, cachet, vial, powder, granule, lozenge, suppository, regenerating powder or liquid formulation. A suitable unit dose may be 0.1-1000 mg.

The pharmaceutical composition of the present disclosure may comprise, in addition to the active compound, one or more auxiliary materials selected from the group consisting of a filler (diluent), a binder, a wetting agent, a disintegrant, an excipient, and the like. Depending on the method of administration, the composition may comprise 0.1 wt. % to 99 wt. % of the active compound.

The tablet comprises the active ingredient and a non-toxic pharmaceutically acceptable excipient that is used for mixing and is suitable for the preparation of the tablet. Such an excipient may be an inert excipient, a granulating agent, a disintegrant, a binder and a lubricant. Such a tablet may be uncoated or may be coated by known techniques for masking the taste of the drug or delaying the disintegration and absorption of the drug in the gastrointestinal tract and thus enabling sustained release of the drug over a longer period.

An oral formulation in a soft gelatin capsule where the active ingredient is mixed with an inert solid diluent or with a water-soluble carrier or oil vehicle may also be provided.

An aqueous suspension comprises the active substance and an excipient that is used for mixing and is suitable for the preparation of the aqueous suspension. Such an excipient is a suspending agent, a dispersant or a wetting agent. The aqueous suspension may also comprise one or more preservatives, one or more colorants, one or more corrigents and one or more sweeteners.

An oil suspension may be formulated by suspending the active ingredient in a vegetable oil, or in a mineral oil. The oil suspension may comprise a thickening agent. The sweeteners and corrigents described above may be added to provide a palatable formulation. Antioxidants may also be added to preserve the compositions.

The pharmaceutical composition of the present disclosure may also be in the form of an oil-in-water emulsion. The oil phase may be a vegetable oil or a mineral oil, or a mixture thereof. Suitable emulsifiers may be naturally occurring phospholipids, and the emulsion may also comprise a sweetener, a corrigent, a preservative and an antioxidant. Such a formulation may also comprise a palliative, a preservative, a colorant and an antioxidant. The pharmaceutical composition of the present disclosure may be in the form of a sterile injectable aqueous solution. Acceptable vehicles or solvents that can be used include water, Ringer's solution and isotonic sodium chloride solution. A sterile injectable formulation may be a sterile injectable oil-in-water microemulsion in which an active ingredient is dissolved in an oil phase. The injection or microemulsion can be locally injected into the bloodstream of a patient in large quantities. Alternatively, it may be desirable to administer the solution and microemulsion in such a way as to maintain a constant circulating concentration of the compound of the present disclosure. To maintain such a constant concentration, a continuous intravenous delivery device may be used. An example of such a device is a Deltec CADD-PLUS™ 5400 intravenous injection pump.

The pharmaceutical composition of the present disclosure may be in the form of a sterile injectable aqueous or oil suspension for intramuscular and subcutaneous administration. The suspension can be prepared according to the prior art using those suitable dispersants or wetting agents and suspending agents as described above. The sterile injectable formulation may also be a sterile injection or suspension prepared in a parenterally acceptable non-toxic diluent or solvent. In addition, a sterile fixed oil may be conventionally used as a solvent or a suspending medium. For this purpose, any blend fixed oil may be used. In addition, fatty acids may also be used to prepare injections.

The compound of the present disclosure may be administered in the form of a suppository for rectal administration. Such a pharmaceutical composition can be prepared by mixing a drug with a suitable non-irritating excipient which is a solid at ambient temperature but a liquid in the rectum and therefore will melt in the rectum to release the drug.

The compound of the present disclosure can be administered in the form of dispersible powders and granules that are formulated into aqueous suspensions by adding water. Such a pharmaceutical composition can be prepared by mixing the active ingredient with a dispersant or a wetting agent, a suspending agent, or one or more preservatives.

As is well known to those skilled in the art, the dose of the drug administered depends on a variety of factors, including but not limited to, the activity of the particular compound used, the age of the patient, the body weight of the patient, the health condition of the patient, the behavior of the patient, the diet of the patient, the time of administration, the route of administration, the rate of excretion, the combination of drugs, the severity of the disease, and the like. In addition, the optimal treatment regimen, such as the mode of administration, the daily dose of the compound or the type of pharmaceutically acceptable salts, can be verified according to conventional treatment regimens.

Description of the Terms

Unless otherwise stated, the terms used in the specification and claims have the following meanings.

The term "alkyl" refers to a saturated aliphatic hydrocarbon group which is a linear or branched group containing 1 to 20 carbon atoms, preferably alkyl having 1 to 12 (e.g., 1, 2, 3, 4, 5, 6, 7, 8, 9, 10, 11 and 12) carbon atoms (i.e., $C_{1-12}$ alkyl), and more preferably alkyl having 1 to 6 carbon atoms (i.e., $C_{1-6}$ alkyl). Non-limiting examples of alkyl include methyl, ethyl, n-propyl, isopropyl, n-butyl, isobutyl, tert-butyl, sec-butyl, n-pentyl, 1,1-dimethylpropyl, 1,2-dimethylpropyl, 2,2-dimethylpropyl, 1-ethylpropyl, 2-methylbutyl, 3-methylbutyl, n-hexyl, 1-ethyl-2-methylpropyl, 1,1,2-trimethylpropyl, 1,1-dimethylbutyl, 1,2-dimethylbutyl, 2,2-dimethylbutyl, 1,3-dimethylbutyl, 2-ethylbutyl, 2-methylpentyl, 3-methylpentyl, 4-methylpentyl, 2,3-dimethylbutyl, n-heptyl, 2-methylhexyl, 3-methylhexyl, 4-methylhexyl, 5-methylhexyl, 2,3-dimethylpentyl, 2,4-dimethylpentyl, 2,2-dimethylpentyl, 3,3-dimethylpentyl, 2-ethylpentyl, 3-ethylpentyl, n-octyl, 2,3-dimethylhexyl, 2,4-dimethylhexyl, 2,5-dimethylhexyl, 2,2-dimethylhexyl, 3,3-dimethylhexyl, 4,4-dimethylhexyl, 2-ethylhexyl, 3-ethylhexyl, 4-ethylhexyl, 2-methyl-2-ethylpentyl, 2-methyl-3-ethylpentyl, n-nonyl, 2-methyl-2-ethylhexyl, 2-methyl-3-ethylhexyl, 2,2-diethylpentyl, n-decyl, 3,3-diethylhexyl, 2,2-diethylhexyl, and various side-chain isomers thereof, and the like. Most preferably, the alkyl is a lower alkyl having 1 to 6 carbon atoms, and non-limiting examples include methyl, ethyl, n-propyl, isopropyl, n-butyl, isobutyl, tert-butyl, sec-butyl, n-pentyl, 1,1-dimethylpropyl, 1,2-dimethylpropyl, 2,2-dimethylpropyl, 1-ethylpropyl, 2-methylbutyl, 3-methylbutyl, n-hexyl, 1-ethyl-2-methylpropyl, 1,1,2-trimethylpropyl, 1,1-dimethylbutyl, 1,2-dimethylbutyl, 2,2-dimethylbutyl, 1,3-dimethylbutyl, 2-ethylbutyl, 2-methylpentyl, 3-methylpentyl, 4-methylpentyl, 2,3-dimethylbutyl, and the like. The alkyl may be substituted or unsubstituted. When substituted, it may be substituted at any accessible connection site, wherein the substituent is preferably one or more substituents independently and optionally selected from the group consisting of a D atom, halogen, alkoxy, haloalkyl, haloalkoxy, cycloalkyloxy, heterocyclyloxy, hydroxy, hydroxyalkyl, oxo, cyano, amino, nitro, cycloalkyl, heterocyclyl, aryl and heteroaryl.

The term "alkylene" refers to a saturated linear or branched aliphatic hydrocarbon group, which is a residue derived from the parent alkane by removal of two hydrogen atoms from the same carbon atom or two different carbon atoms. It is a linear or branched group containing 1 to 20 carbon atoms, preferably alkylene containing 1 to 12 (e.g., 1, 2, 3, 4, 5, 6, 7, 8, 9, 10, 11 and 12) carbon atoms (i.e., $C_{1-12}$ alkylene), and more preferably alkylene containing 1 to 6 carbon atoms. Non-limiting examples of alkylene include, but are not limited to, methylene (—CH$_2$—), 1,1-ethylene (—CH(CH$_3$)—), 1,2-ethylene (—CH$_2$CH$_2$—), 1,1-propylene (—CH(CH$_2$CH$_3$)—), 1,2-propylene (—CH$_2$CH(CH$_3$)—), 1,3-propylene (—CH$_2$CH$_2$CH$_2$—), 1,4-butylene (—CH$_2$CH$_2$CH$_2$CH$_2$—), and the like. The alkylene may be substituted or unsubstituted. When substituted, it may be substituted at any accessible connection site, wherein the substituent is preferably one or more substituents selected from the group consisting of alkenyl, alkynyl, alkoxy, haloalkoxy, cycloalkyloxy, heterocyclyloxy, alkylthio, alkylamino, halogen, mercapto, hydroxy, nitro, cyano, cycloalkyl, heterocyclyl, aryl, heteroaryl, cycloalkoxy, heterocycloalkoxy, cycloalkylthio, heterocycloalkylthio and oxo.

The term "alkoxy" refers to —O-(alkyl), wherein the alkyl is as defined above. Non-limiting examples of alkoxy include methoxy, ethoxy, propoxy and butoxy. The alkoxy may be optionally substituted or unsubstituted. When substituted, the substituent is preferably one or more groups independently selected from the group consisting of a D atom, halogen, alkyl, alkoxy, haloalkyl, haloalkoxy, cycloalkyloxy, heterocyclyloxy, hydroxy, hydroxyalkyl, cyano, amino, nitro, cycloalkyl, heterocyclyl, aryl and heteroaryl.

The term "alkenyl" refers to an alkyl compound containing at least one carbon-carbon double bond in the molecule, wherein the alkyl is as defined above. The alkenyl preferably has 2 to 12 (e.g., 2, 3, 4, 5, 6, 7, 8, 9, 10, 11 and 12) carbon atoms (i.e., $C_{2-12}$ alkenyl), and more preferably has 2 to 6 carbon atoms (i.e., $C_{2-6}$ alkenyl). The alkenyl may be substituted or unsubstituted. When substituted, the substituent is preferably one or more groups independently selected from the group consisting of alkoxy, halogen, haloalkyl, haloalkoxy, cycloalkyloxy, heterocyclyloxy, hydroxy, hydroxyalkyl, oxo, cyano, amino, nitro, cycloalkyl, heterocyclyl, aryl and heteroaryl.

The term "alkynyl" refers to an alkyl compound containing at least one carbon-carbon triple bond in the molecule, wherein the alkyl is as defined above. The alkynyl preferably has 2 to 12 (e.g., 2, 3, 4, 5, 6, 7, 8, 9, 10, 11 and 12) carbon atoms (i.e., $C_{2-12}$ alkynyl), and more preferably has 2 to 6 carbon atoms (i.e., $C_{2-6}$ alkynyl). Alkynyl may be substituted or unsubstituted. When substituted, the substituent is preferably one or more groups independently selected from the group consisting of alkoxy, halogen, haloalkyl, haloalkoxy, cycloalkyloxy, heterocyclyloxy, hydroxy, hydroxyalkyl, cyano, amino, nitro, cycloalkyl, heterocyclyl, aryl and heteroaryl.

The term "cycloalkyl" refers to a saturated or partially unsaturated monocyclic or polycyclic hydrocarbon substituent. The cycloalkyl ring contains 3 to 20 carbon atoms, preferably 3 to 12 (e.g., 3, 4, 5, 6, 7, 8, 9, 10, 11 and 12) carbon atoms (i.e., 3- to 12-membered cycloalkyl), preferably 3 to 8 (e.g., 3, 4, 5, 6, 7 and 8) carbon atoms (i.e., 3- to 8-membered cycloalkyl), and more preferably 3 to 6 carbon atoms (i.e., 3- to 6-membered cycloalkyl). Non-limiting examples of monocyclic cycloalkyl include cyclopropyl, cyclobutyl, cyclopentyl, cyclopentenyl, cyclohexyl, cyclohexenyl, cyclohexadienyl, cycloheptyl, cycloheptatrienyl, cyclooctyl, and the like. Polycyclic cycloalkyl includes spiro cycloalkyl, fused cycloalkyl, and bridged cycloalkyl.

The term "spiro cycloalkyl" refers to a 5- to 20-membered polycyclic group in which monocyclic rings share one carbon atom (referred to as the spiro atom), wherein the spiro cycloalkyl may contain one or more double bonds. The spiro cycloalkyl is preferably 6- to 14-membered, and more preferably 7- to 10-membered (e.g., 7-membered, 8-membered, 9-membered or 10-membered). According to the number of the spiro atoms shared among the rings, the spiro cycloalkyl may be monospiro cycloalkyl or polyspiro cycloalkyl (e.g., bispiro cycloalkyl), preferably monospiro cycloalkyl and bispiro cycloalkyl, and more preferably 3-membered/5-membered, 3-membered/6-membered, 4-membered/4-membered, 4-membered/5-membered, 4-membered/6-membered, 5-membered/5-membered or 5-membered/6-membered monospiro cycloalkyl. Non-limiting examples of spiro cycloalkyl include:

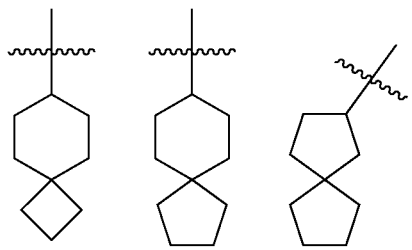

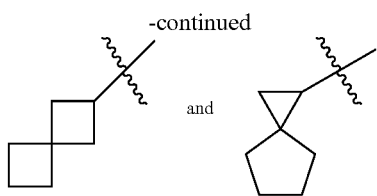

The term "fused cycloalkyl" refers to a 5- to 20-membered carbon polycyclic group in which each ring shares a pair of adjacent carbon atoms with the other rings in the system, wherein one or more of the rings may contain one or more double bonds. The fused cycloalkyl is preferably 6- to 14-membered, and more preferably 7- to 10-membered (e.g., 7-membered, 8-membered, 9-membered or 10-membered). According to the number of the formed rings, the fused cycloalkyl may be bicyclic, tricyclic, tetracyclic or polycyclic cycloalkyl, preferably bicyclic or tricyclic cycloalkyl, and more preferably 3-membered/4-membered, 3-membered/5-membered, 3-membered/6-membered, 4-membered/4-membered, 4-membered/5-membered, 4-membered/6-membered, 5-membered/4-membered, 5-membered/5-membered, 5-membered/6-membered, 6-membered/3-membered, 6-membered/4-membered, 6-membered/5-membered and 6-membered/6-membered bicyclic cycloalkyl. Non-limiting examples of fused cycloalkyl include:

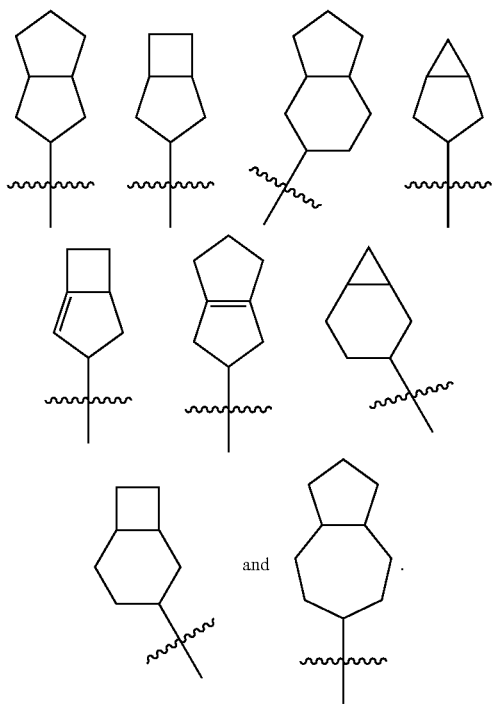

The term "bridged cycloalkyl" refers to a 5- to 20-membered carbon polycyclic group in which any two rings share two carbon atoms that are not directly connected to each other, wherein the bridged cycloalkyl may contain one or more double bonds. The bridged cycloalkyl is preferably 6- to 14-membered, and more preferably 7- to 10-membered (e.g., 7-membered, 8-membered, 9-membered or 10-membered). According to the number of the formed rings, the bridged cycloalkyl may be bicyclic, tricyclic, tetracyclic or polycyclic, preferably bicyclic, tricyclic or tetracyclic, and more preferably bicyclic or tricyclic. Non-limiting examples of bridged cycloalkyl include:

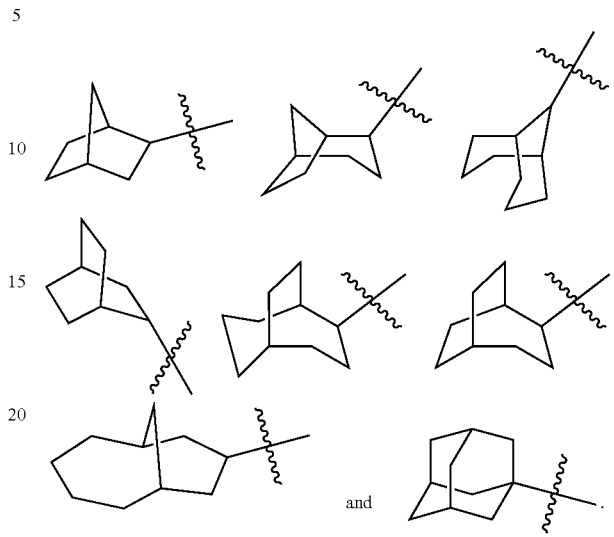

The cycloalkyl ring includes those in which the cycloalkyl described above (including monocyclic, spiro, fused and bridged rings) is fused to an aryl, heteroaryl or heterocycloalkyl ring, wherein the ring connected to the parent structure is cycloalkyl. Non-limiting examples include

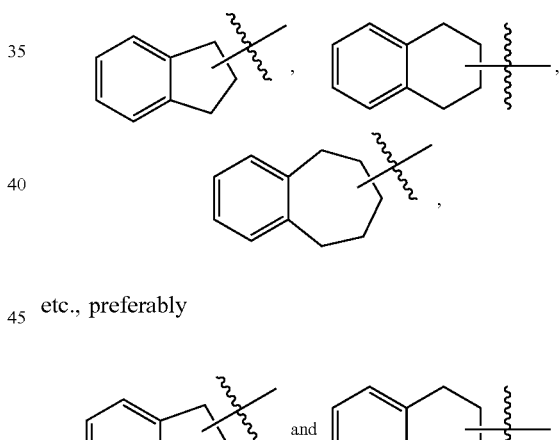

etc., preferably

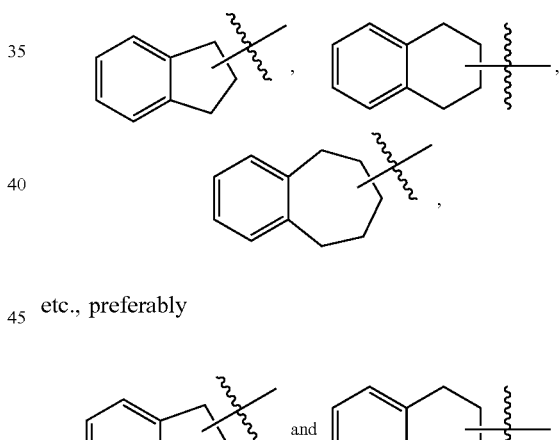

The cycloalkyl may be substituted or unsubstituted. When substituted, it may be substituted at any accessible connection site, wherein the substituent is preferably one or more substituents independently and optionally selected from the group consisting of halogen, alkyl, alkoxy, haloalkyl, haloalkoxy, cycloalkyloxy, heterocyclyloxy, hydroxy, hydroxyalkyl, cyano, amino, nitro, cycloalkyl, heterocyclyl, aryl and heteroaryl.

The term "heterocyclyl" refers to a saturated or partially unsaturated monocyclic or polycyclic substituent containing 3 to 20 ring atoms, wherein one or more of the ring atoms is a heteroatom selected from the group consisting of nitrogen, oxygen and sulfur, the sulfur optionally being substituted with oxo (i.e., form sulfoxide or sulfone), but excluding a cyclic portion of —O—O—, —O—S— or —S—S—; and the remaining ring atoms are carbon. Preferably, the heterocyclyl contains 3 to 12 (e.g., 3, 4, 5, 6, 7, 8, 9, 10, 11 and 12) ring atoms (i.e., 3- to 12-membered heterocyclyl), of which 1-4 (e.g., 1, 2, 3 and 4) are heteroatoms; more preferably, the heterocyclyl contains 3 to 8 ring atoms (e.g., 3, 4, 5, 6, 7 and 8), of which 1-3 (e.g., 1, 2 and 3) are heteroatoms (i.e., 3- to 8-membered heterocyclyl); more preferably, the heterocyclyl contains 3 to 6 ring atoms (i.e., 3- to 6-membered heterocyclyl), of which 1-3 are heteroatoms; most preferably, the heterocyclyl contains 5 or 6 ring atoms (i.e., 5- or 6-membered heterocyclyl), of which 1-3 are heteroatoms. Non-limiting examples of monocyclic heterocyclyl include oxetanyl, pyrrolidinyl, tetrahydropyranyl, 1,2,3,6-tetrahydropyridinyl, piperidinyl, piperazinyl, morpholinyl, thiomorpholinyl, homopiperazinyl, and the like. Polycyclic heterocyclyl includes spiro heterocyclyl, fused heterocyclyl, and bridged heterocyclyl.

The term "spiro heterocyclyl" refers to a 5- to 20-membered polycyclic heterocyclyl group in which monocyclic rings share one atom (referred to as the spiro atom), wherein one or more of the ring atoms is a heteroatom selected from the group consisting of nitrogen, oxygen and sulfur, the sulfur optionally being substituted with oxo (i.e., form sulfoxide or sulfone); and the remaining ring atoms are carbon. The spiro heterocyclyl may contain one or more double bonds. The spiro heterocyclyl is preferably 6- to 14-membered, and more preferably 7- to 10-membered (e.g., 7-membered, 8-membered, 9-membered or 10-membered). According to the number of spiro atoms shared among the rings, the spiro heterocyclyl may be monospiro heterocyclyl, bispiro heterocyclyl or polyspiro heterocyclyl, preferably monospiro heterocyclyl and bispiro heterocyclyl, and more preferably 3-membered/5-membered, 3-membered/6-membered, 4-membered/4-membered, 4-membered/5-membered, 4-membered/6-membered, 5-membered/5-membered or 5-membered/6-membered monospiro heterocyclyl. Non-limiting examples of spiro heterocyclyl include:

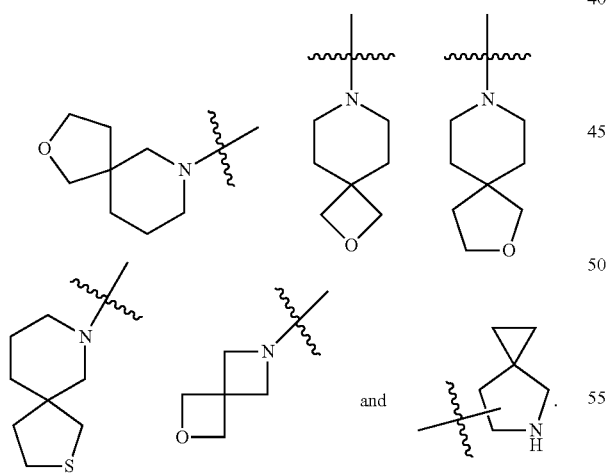

The term "fused heterocyclyl" refers to a 5- to 20-membered polycyclic heterocyclyl group in which each ring shares a pair of adjacent atoms with the other rings in the system, wherein one or more of the rings may contain one or more double bonds, wherein one or more of the ring atoms is a heteroatom selected from the group consisting of nitrogen, oxygen and sulfur, the sulfur optionally being substituted with oxo (i.e., form sulfoxide or sulfone); and the remaining ring atoms are carbon. The fused heterocyclyl is preferably 6- to 14-membered, and more preferably 7- to 10-membered (e.g., 7-membered, 8-membered, 9-membered or 10-membered). According to the number of the formed rings, the fused heterocyclyl may be bicyclic, tricyclic, tetracyclic or polycyclic fused heterocyclyl, preferably bicyclic or tricyclic fused heterocyclyl, and more preferably 3-membered/4-membered, 3-membered/5-membered, 3-membered/6-membered, 4-membered/4-membered, 4-membered/5-membered, 4-membered/6-membered, 5-membered/4-membered, 5-membered/5-membered, 5-membered/6-membered, 6-membered/3-membered, 6-membered/4-membered, 6-membered/5-membered and 6-membered/6-membered bicyclic fused heterocyclyl. Non-limiting examples of fused heterocyclyl include:

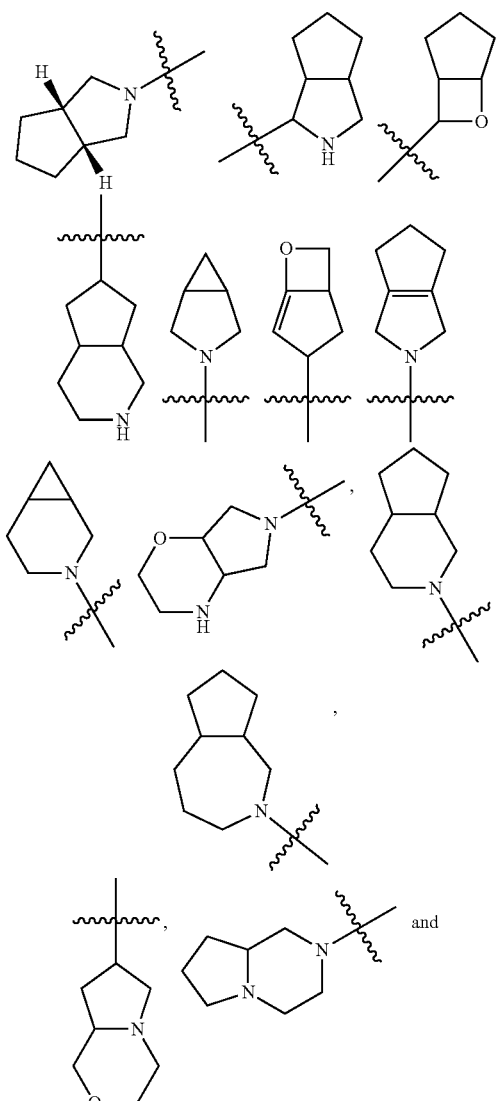

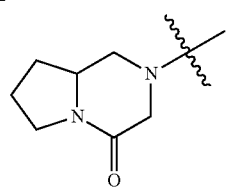

The term "bridged heterocyclyl" refers to a 5- to 14-membered polycyclic heterocyclyl group in which any two rings share two atoms that are not directly connected, wherein the bridged heterocyclyl may contain one or more double bonds, wherein one or more of the ring atoms is a heteroatom selected from the group consisting of nitrogen, oxygen and sulfur, the sulfur optionally being substituted with oxo (i.e., form sulfoxide or sulfone); and the remaining ring atoms are carbon. The bridged heterocyclyl is preferably 6- to 14-membered, and more preferably 7- to 10-membered (e.g., 7-membered, 8-membered, 9-membered or 10-membered). According to the number of the formed rings, the bridged heterocyclyl may be bicyclic, tricyclic, tetracyclic or polycyclic, preferably bicyclic, tricyclic or tetracyclic, and more preferably bicyclic or tricyclic. Non-limiting examples of bridged heterocyclyl include:

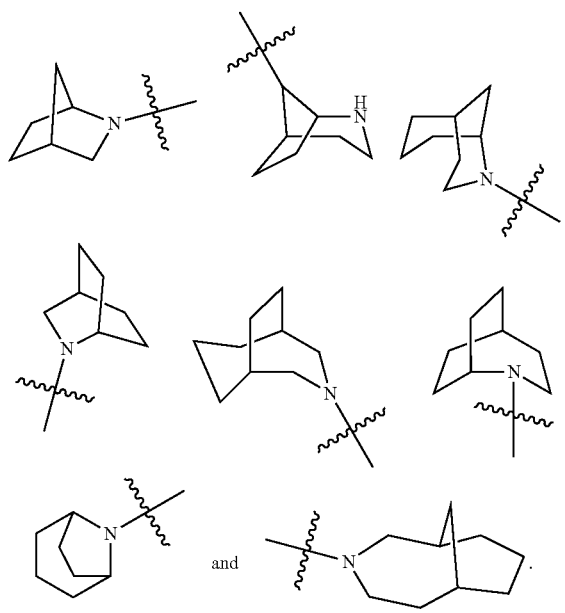

The heterocyclyl ring includes those in which the heterocyclyl described above (including monocyclic, spiro heterocyclic, fused heterocyclic and bridged heterocyclic rings) is fused to an aryl, heteroaryl or cycloalkyl ring, wherein the ring connected to the parent structure is heterocyclyl. Non-limiting examples include:

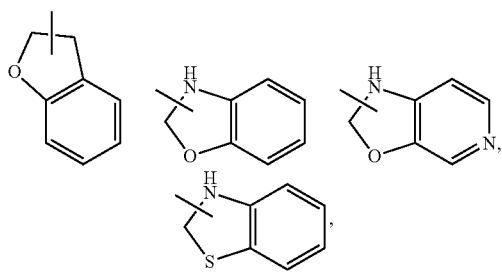

etc.

The heterocyclyl may be substituted or unsubstituted. When substituted, it may be substituted at any accessible connection site, wherein the substituent is preferably one or more substituents independently and optionally selected from the group consisting of a hydrogen atom, halogen, alkyl, alkoxy, haloalkyl, haloalkoxy, cycloalkyloxy, heterocyclyloxy, hydroxy, hydroxyalkyl, cyano, amino, nitro, cycloalkyl, heterocyclyl, aryl and heteroaryl.

The term "aryl" refers to a 6- to 14-membered, preferably 6- to 10-membered carbon monocyclic or fused polycyclic (in which the rings share a pair of adjacent carbon atoms) group having a conjugated 7-electron system, such as phenyl and naphthyl. The aryl ring includes those in which the aryl ring described above is fused to a heteroaryl, heterocyclyl or cycloalkyl ring, wherein the ring connected to the parent structure is an aryl ring. Non-limiting examples include:

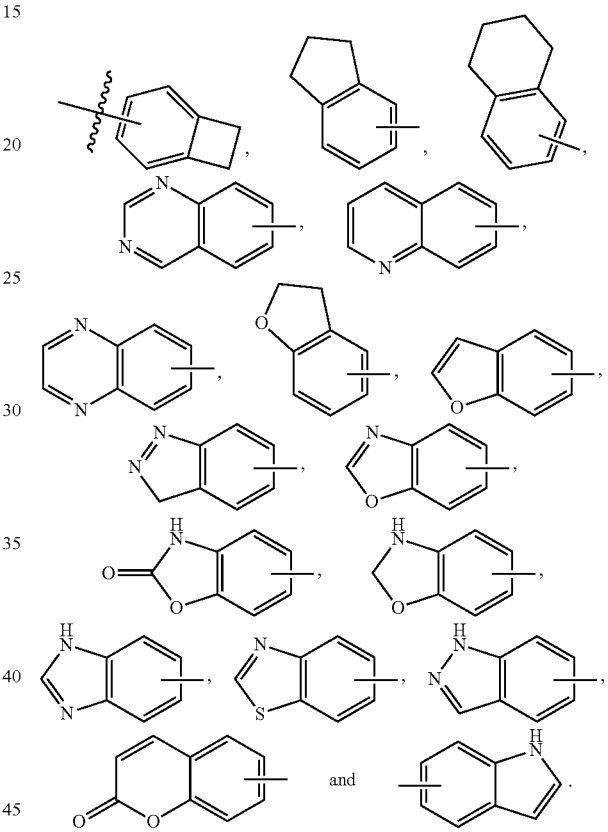

The aryl may be substituted or unsubstituted. When substituted, it may be substituted at any accessible connection site, wherein the substituent is preferably one or more substituents independently and optionally selected from the group consisting of a hydrogen atom, halogen, alkyl, alkoxy, haloalkyl, haloalkoxy, cycloalkyloxy, heterocyclyloxy, hydroxy, hydroxyalkyl, cyano, amino, nitro, cycloalkyl, heterocyclyl, aryl and heteroaryl.

The term "heteroaryl" refers to a heteroaromatic system containing 1 to 4 (e.g., 1, 2, 3 or 4) heteroatoms and 5 to 14 ring atoms, wherein the heteroatoms are selected from the group consisting of oxygen, sulfur and nitrogen. The heteroaryl is preferably 5- to 10-membered (e.g., 5-membered, 6-membered, 7-membered, 8-membered, 9-membered or 10-membered) and more preferably 5-membered or 6-membered (i.e., 5-membered or 6-membered heteroaryl), e.g., furyl, thienyl, pyridinyl, pyrrolyl, N-alkylpyrrolyl, pyrimidinyl, pyrazinyl, pyridazinyl, imidazolyl, pyrazolyl, triazolyl and tetrazolyl. The heteroaryl ring includes those in which the heteroaryl ring described above is fused to an aryl, heterocyclyl or cycloalkyl ring, wherein the ring connected to the parent structure is a heteroaryl ring. Non-limiting examples include:

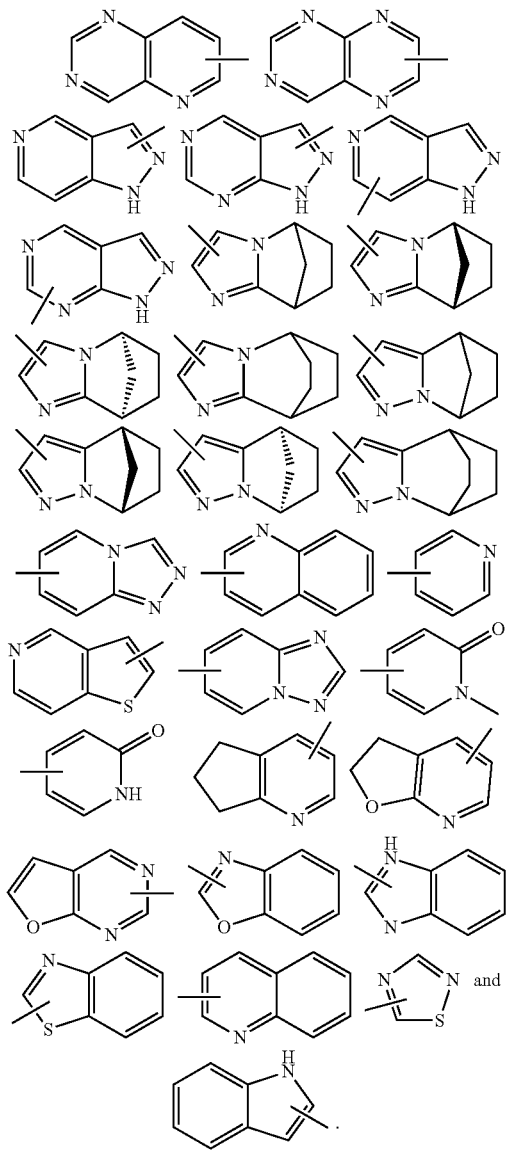

The heteroaryl may be substituted or unsubstituted. When substituted, it may be substituted at any accessible connection site, wherein the substituent is preferably one or more substituents independently and optionally selected from the group consisting of a hydrogen atom, halogen, alkyl, alkoxy, haloalkyl, haloalkoxy, cycloalkyloxy, heterocyclyloxy, hydroxy, hydroxyalkyl, cyano, amino, nitro, cycloalkyl, heterocyclyl, aryl and heteroaryl.

The cycloalkyl, heterocyclyl, aryl and heteroaryl described above have 1 residue derived from the parent ring by removal of one hydrogen atom from a ring atom, or 2 residues derived from the parent ring by removal of two hydrogen atoms from the same ring atom or two different ring atoms, i.e., "divalent cycloalkyl", "divalent heterocyclyl", "arylene", or "heteroarylene".

In the chemical structure of the compound of the present disclosure, a bond "" represents an unspecified configuration, namely if chiral isomers exist in the chemical structure, the bond "" may be "" or "", or contains both the configurations of "" and "".

The compounds of the present disclosure may exist in specific geometric or stereoisomeric forms. The present disclosure contemplates all such compounds, including cis and trans isomers, (−)- and (+)-enantiomers, (R)- and (S)-enantiomers, diastereomers, (D)-isomer, (L)-isomer, and racemic mixtures and other mixtures thereof, such as enantiomerically or diastereomerically enriched mixtures, all of which are within the scope of the present disclosure. Additional asymmetric carbon atoms may be present in substituents such as an alkyl group. All such isomers and mixtures thereof are included within the scope of the present disclosure. Optically active (R)- and (S)-enantiomers, and D- and L-isomers can be prepared by chiral synthesis, chiral reagents or other conventional techniques. If one enantiomer of a certain compound of the present disclosure is desired, it may be prepared by asymmetric synthesis or derivatization with a chiral auxiliary, wherein the resulting mixture of diastereomers is separated and the auxiliary group is cleaved to provide the pure desired enantiomer. Alternatively, when the molecule contains a basic functional group (e.g., amino) or an acidic functional group (e.g., carboxyl), salts of diastereomers are formed with an appropriate optically active acid or base, followed by resolution of diastereomers by conventional methods known in the art, and the pure enantiomers are obtained by recovery. Furthermore, separation of enantiomers and diastereomers is typically accomplished by chromatography.

The term "amino protecting group" refers to a group that can be easily removed and is intended to protect an amino group from being changed when a reaction is conducted elsewhere in the molecule. Non-limiting examples include (trimethylsilyl)ethoxymethyl, tetrahydropyranyl (THP), tert-butoxycarbonyl (Boc), acetyl, benzyl, allyl, p-methoxybenzyl, and the like. These groups may be optionally substituted with 1-3 substituents selected from the group consisting of halogen, alkoxy and nitro. The amino protecting groups are preferably (trimethylsilyl)ethoxymethyl and tert-butoxycarbonyl.

The term "hydroxy protecting group" is a suitable group known in the art for protecting hydroxy. See the hydroxy protecting groups in the literature ("*Protective Groups in Organic Synthesis*", 5$^{th}$ Ed. T. W. Greene & P. G. M. Wuts). By way of example, preferably, the hydroxy protecting group may be ($C_{1-10}$ alkyl or aryl)$_3$silyl, e.g., triethylsilyl, triisopropylsilyl, tert-butyldimethylsilyl, tert-butyldiphenylsilyl or the like; $C_{1-10}$ alkyl or substituted alkyl, preferably alkoxy or aryl-substituted alkyl, more preferably $C_{1-6}$ alkoxy-substituted $C_{1-6}$ alkyl or phenyl-substituted $C_{1-6}$ alkyl, and most preferably $C_{1-4}$ alkoxy-substituted $C_{1-4}$ alkyl, e.g., methyl, tert-butyl, allyl, benzyl, methoxymethyl (MOM), ethoxyethyl, or the like; ($C_{1-10}$ alkyl or aryl)acyl, e.g., formyl, acetyl, benzoyl, p-nitrobenzoyl or the like; ($C_{1-6}$ alkyl or 6-membered to 10-membered aryl)sulfonyl; or ($C_{1-6}$ alkoxy or 6-membered to 10-membered aryloxy)carbonyl. The hydroxy protecting group is preferably p-nitrobenzoyl.

The term "heterocyclylalkyl" refers to alkyl substituted with one or more heterocyclyl groups, wherein the heterocyclyl and alkyl are as defined above.

The term "heteroarylalkyl" refers to alkyl substituted with one or more heteroaryl groups, wherein the heteroaryl and alkyl are as defined above.

The term "cycloalkylalkyl" refers to alkyl substituted with one or more cycloalkyl groups, wherein the cycloalkyl and alkyl are as defined above.

The term "cycloalkyloxy" refers to cycloalkyl-O—, wherein the cycloalkyl is as defined above.

The term "heterocyclyloxy" refers to heterocyclyl-O—, wherein the heterocyclyl is as defined above.

The term "alkylthio" refers to alkyl-S—, wherein the alkyl is as defined above.

The term "haloalkyl" refers to alkyl substituted with one or more halogens, wherein the alkyl is as defined above.

The term "haloalkoxy" refers to alkoxy substituted with one or more halogens, wherein the alkoxy is as defined above.

The term "deuterated alkyl" refers to alkyl substituted with one or more deuterium atoms, wherein the alkyl is as defined above.

The term "hydroxyalkyl" refers to alkyl substituted with one or more hydroxy groups, wherein the alkyl is as defined above.

The term "halogen" refers to fluorine, chlorine, bromine or iodine.

The term "hydroxy" refers to —OH.

The term "mercapto" refers to —SH.

The term "amino" refers to —NH$_2$.

The term "cyano" refers to —CN.

The term "nitro" refers to —NO$_2$.

The term "oxo" refers to "=O".

The term "carbonyl" refers to C=O.

The term "carboxyl" refers to —C(O)OH.

The term "carboxylate group" refers to —C(O)O(alkyl), —C(O)O(cycloalkyl), (alkyl)C(O)O— or (cycloalkyl)C(O)O—, wherein the alkyl and cycloalkyl are as defined above.

The compounds disclosed herein include isotopic derivatives thereof. The term "isotopic derivative" refers to compounds that differ in structure only by having one or more enriched isotopic atoms. For example, compounds with the structure disclosed herein having "deuterium" or "tritium" in place of hydrogen, or $^{18}$F-fluorine labeling ($^{18}$F isotope) in place of fluorine, or $^{11}$C-, $^{13}$C- or $^{14}$C-enriched carbon ($^{11}$C-, $^{13}$C- or $^{14}$C-carbon labeling; $^{11}$C-, $^{13}$C- or $^{14}$C-isotope) in place of a carbon atom are within the scope of the present disclosure. Such a compound can be used as an analytical tool or a probe in, for example, a biological assay, or may be used as a tracer for in vivo diagnostic imaging of disease, or as a tracer in a pharmacodynamic, pharmacokinetic or receptor study. The deuterated forms of the compound of formula (I) mean that each available hydrogen atom connected to a carbon atom may be independently replaced with a deuterium atom. Those skilled in the art are able to synthesize the deuterated forms of the compound of general formula (I) with reference to the relevant literature. Commercially available deuterated starting materials can be used in preparing the deuterated forms of the compound of formula (I), or they can be synthesized using conventional techniques with deuterated reagents including, but not limited to, deuterated borane, tri-deuterated borane in tetrahydrofuran, deuterated lithium aluminum hydride, deuterated iodoethane, deuterated iodomethane, and the like. Deuterides can generally retain comparable activity to non-deuterated compounds and can achieve better metabolic stability when deuterated at certain specific sites, thereby achieving certain therapeutic advantages.

The term "optional" or "optionally" means that the event or circumstance subsequently described may, but not necessarily, occur, and that the description includes instances where the event or circumstance occurs or does not occur.

For example, the expression "a heterocyclyl group optionally substituted with alkyl" means that the alkyl may be, but not necessarily, present, and includes instances where the heterocyclyl group is or is not substituted with the alkyl.

"Substituted" means that one or more, preferably 1-5, more preferably 1-3 hydrogen atoms in the group are independently substituted with a corresponding number of substituents. Those skilled in the art are able to determine (experimentally or theoretically) possible or impossible substitution without undue efforts. For example, it may be unstable when an amino or hydroxy group having a free hydrogen is bound to a carbon atom having an unsaturated (e.g., olefinic) bond.

The term "pharmaceutical composition" refers to a mixture containing one or more of the compounds described herein or a physiologically/pharmaceutically acceptable salt or pro-drug thereof, and other chemical components, and other components, for example, physiologically/pharmaceutically acceptable carriers and excipients. The pharmaceutical composition is intended to promote the administration to an organism, so as to facilitate the absorption of the active ingredient, thereby exerting biological activities.

The term "pharmaceutically acceptable salt" refers to the salts of the compound of the present disclosure, which are safe and effective for use in the body of a mammal and possess the requisite biological activities. The salts may be prepared separately during the final separation and purification of the compound, or by reacting an appropriate group with an appropriate base or acid. Bases commonly used to form pharmaceutically acceptable salts include inorganic bases such as sodium hydroxide and potassium hydroxide, and organic bases such as ammonia. Acids commonly used to form pharmaceutically acceptable salts include inorganic acids and organic acids.

For drugs or pharmacological active agents, the term "therapeutically effective amount" refers to an amount of a medicament or an agent that is sufficient to provide the desired effect but is non-toxic. The determination of the effective amount varies from person to person. It depends on the age and general condition of a subject, as well as the particular active substance used. The appropriate effective amount in a case may be determined by those skilled in the art in the light of routine tests.

The term "pharmaceutically acceptable" used herein means that those compounds, materials, compositions and/or dosage forms that are, within the scope of reasonable medical judgment, suitable for use in contact with the tissues of patients without excessive toxicity, irritation, allergic reaction, or other problems or complications, and are commensurate with a reasonable benefit/risk ratio and effective for the intended use.

As used herein, the singular forms "a", "an" and "the" include plural references and vice versa, unless otherwise clearly defined in the context.

When the term "about" is applied to parameters such as pH, concentration and temperature, it means that the parameter may vary by +10%, and sometimes more preferably within ±5%. As will be appreciated by those skilled in the art, when the parameters are not critical, the numbers are generally given for illustrative purposes only and are not intended to be limiting.

Synthesis Method of Compounds of the Present Disclosure

To achieve the purpose of the present disclosure, the following technical schemes are adopted in the present disclosure:

Scheme 1

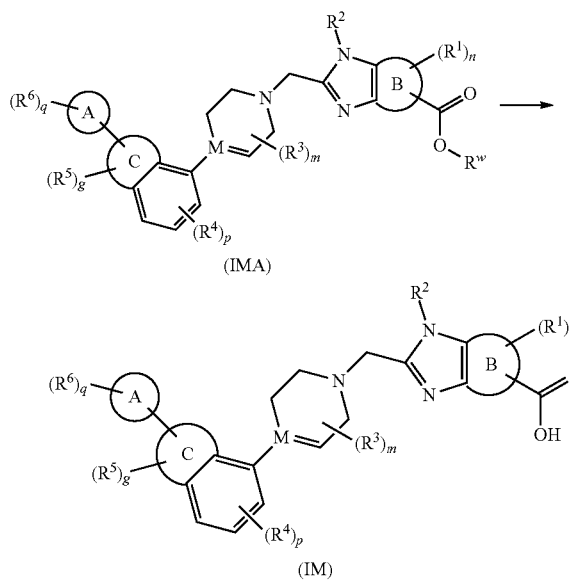

A method for preparing the compound of general formula (IM) or the tautomer, racemate, enantiomer or diastereomer thereof or the mixture thereof, or the pharmaceutically acceptable salt thereof disclosed herein, comprising the following step:

conducting a hydrolysis reaction of a compound of general formula (IMA) in the presence of a basic reagent to obtain the compound of general formula (IM), wherein:

$R^w$ is $C_{1-6}$ alkyl;

-----, ring B, M, ring C, ring A, $R^1$ to $R^6$, n, m, p, g and q are as defined in general formula (IM).

Scheme 2

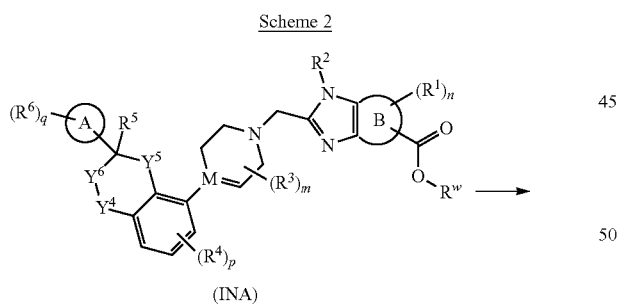

(INA)

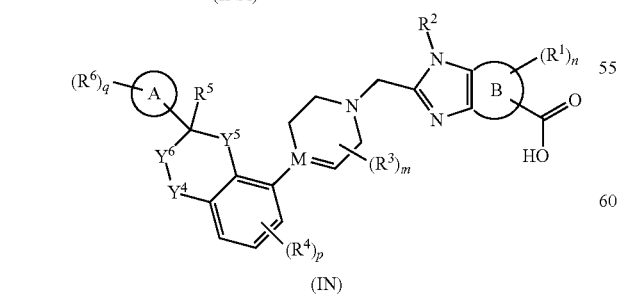

(IN)

A method for preparing the compound of general formula (IN) or the tautomer, racemate, enantiomer or diastereomer thereof or the mixture thereof, or the pharmaceutically acceptable salt thereof disclosed herein, comprising the following step:

conducting a hydrolysis reaction of a compound of general formula (INA) in the presence of a basic reagent to obtain the compound of general formula (IN), wherein:

$R^w$ is $C_{1-6}$ alkyl;

-----, ring B, M, $Y^4$, $Y^5$, $Y^6$, ring A, $R^1$ to $R^6$, n, m, p and q are as defined in general formula (IN).

Scheme 3

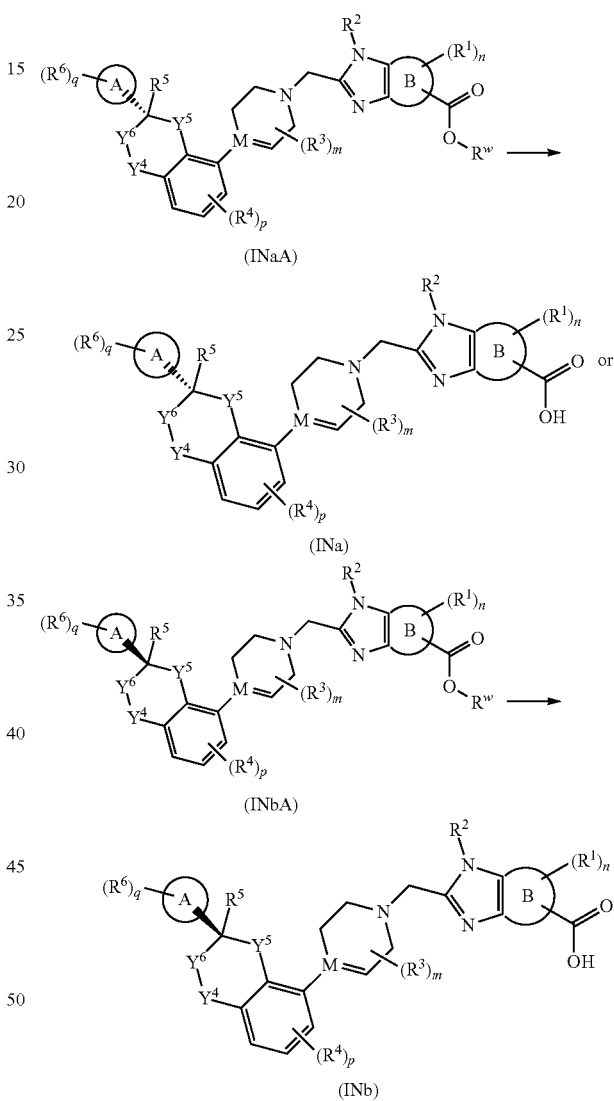

A method for preparing the compound of general formula (INb) or the tautomer, racemate, enantiomer or diastereomer thereof or the mixture thereof, or the pharmaceutically acceptable salt thereof disclosed herein, comprising the following step:

conducting a hydrolysis reaction of a compound of general formula (INaA) in the presence of a basic reagent to obtain the compound of general formula (INa), or conducting a hydrolysis reaction of a compound of general formula (INbA) in the presence of a basic reagent to obtain the compound of general formula (INb), wherein:

$R^w$ is $C_{1-6}$ alkyl;

╌╌╌, ring B, M, $Y^4$, $Y^5$, $Y^6$, ring A, $R^1$ to $R^6$, n, m, p and q are as defined in general formula (INa) or general formula (INb).

Scheme 4

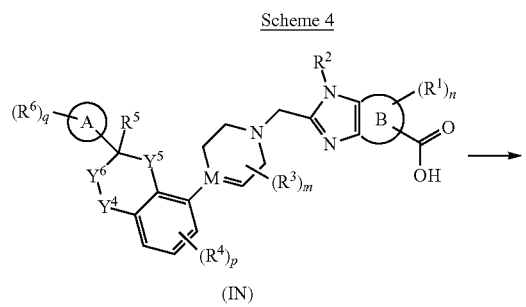

(IN)

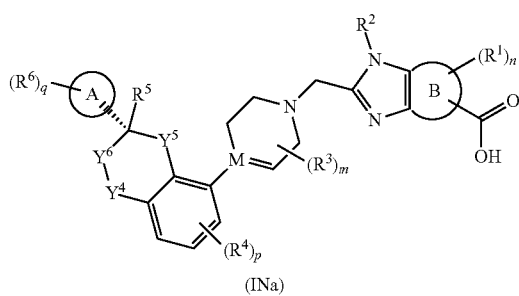

(INa)

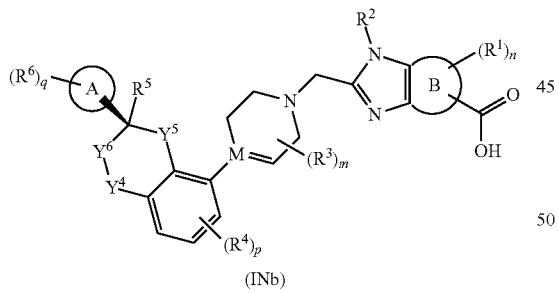

(INb)

A method for preparing the compound of general formula (INa) or general formula (INb) or the tautomer, racemate, enantiomer or diastereomer thereof or the mixture thereof, or the pharmaceutically acceptable salt thereof disclosed herein, comprising the following step:

performing chiral resolution of a compound of general formula (IN) to obtain a compound of general formula (INa) and a compound of general formula (INb);

wherein:

╌╌╌, ring B, M, $Y^4$, $Y^5$, $Y^6$, ring A, $R^1$ to $R^6$, n, m, p and q are as defined in general formula (INa) or general formula (INb).

Scheme 5

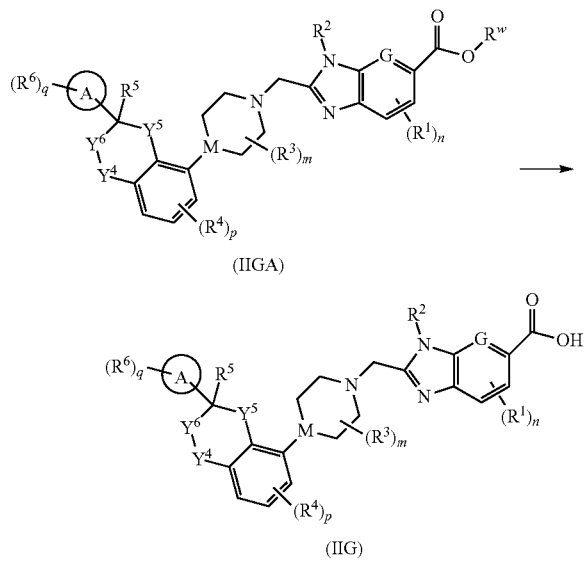

(IIGA)

(IIG)

A method for preparing the compound of general formula (IIG) or the tautomer, racemate, enantiomer or diastereomer thereof or the mixture thereof, or the pharmaceutically acceptable salt thereof disclosed herein, comprising the following step:

conducting a hydrolysis reaction of a compound of general formula (IIGA) in the presence of a basic reagent to obtain the compound of general formula (IIG), wherein:

$R^w$ is $C_{1-6}$ alkyl;

G, M, $Y^4$, $Y^5$, $Y^6$, ring A, $R^1$ to $R^6$, n, m, p and q are as defined in general formula (IIG).

Scheme 6

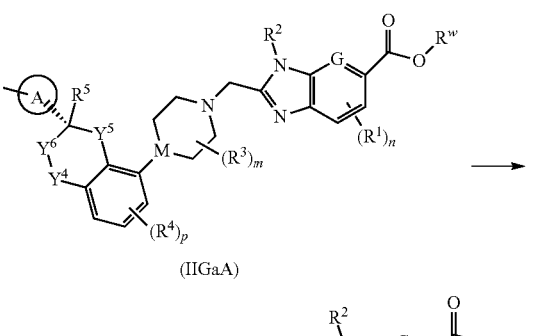

(IIGaA)

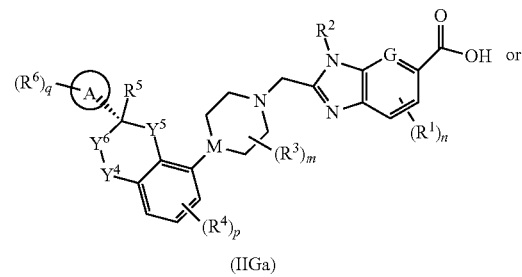

(IIGa)

-continued

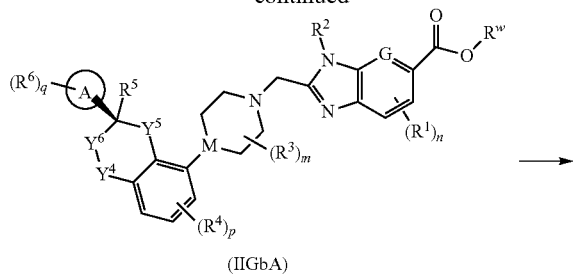

(IIGbA)

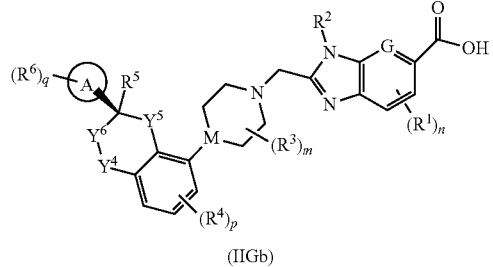

(IIGb)

A method for preparing the compound of general formula (IIGa) or general formula (IIGb) or the tautomer, racemate, enantiomer or diastereomer thereof or the mixture thereof, or the pharmaceutically acceptable salt thereof disclosed herein, comprising the following step:

conducting a hydrolysis reaction of a compound of general formula (IIGaA) in the presence of a basic reagent to obtain the compound of general formula (IIGa), or conducting a hydrolysis reaction of a compound of general formula (IIGbA) in the presence of a basic reagent to obtain the compound of general formula (IIGb), wherein:

$R^w$ is $C_{1-6}$ alkyl;

G, M, $Y^4$, $Y^5$, $Y^6$, ring A, $R^1$ to $R^6$, n, m, p and q are as defined in general formula (IIGa) or general formula (IIGb).

Scheme 7

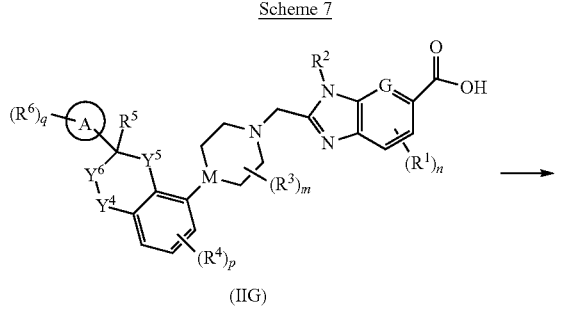

(IIG)

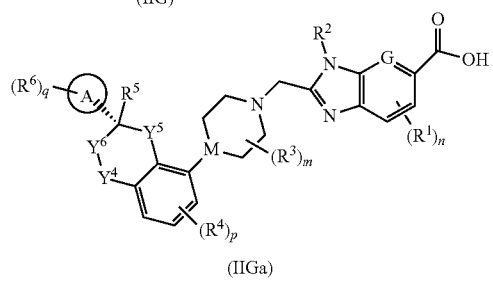

(IIGa)

-continued

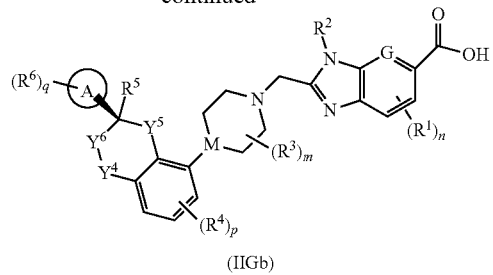

(IIGb)

A method for preparing the compound of general formula (IIGa) or general formula (IIGb) or the tautomer, racemate, enantiomer or diastereomer thereof or the mixture thereof, or the pharmaceutically acceptable salt thereof disclosed herein, comprising the following step:

performing chiral resolution of a compound of general formula (IIG) to obtain a compound of general formula (IIGa) and a compound of general formula (IIGb), wherein: G, M, $Y^4$, $Y^5$, $Y^6$, ring A, $R^1$ to $R^6$, n, m, p and q are as defined in general formula (IIGa) or general formula (IIGb).

Scheme 8

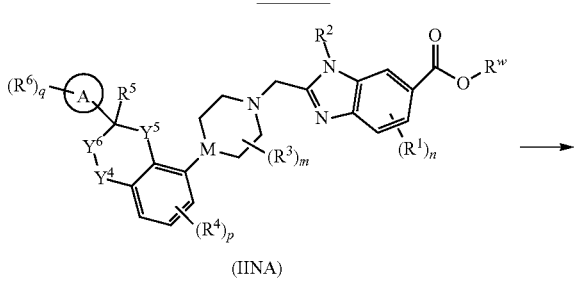

(IINA)

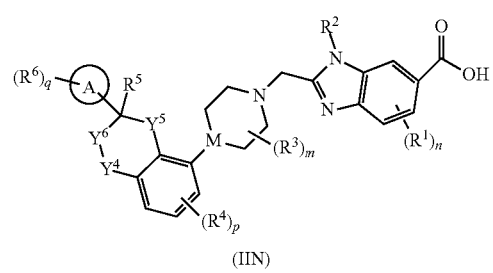

(IIN)

A method for preparing the compound of general formula (IIN) or the tautomer, racemate, enantiomer or diastereomer thereof or the mixture thereof, or the pharmaceutically acceptable salt thereof disclosed herein, comprising the following step:

conducting a hydrolysis reaction of a compound of general formula (IINA) in the presence of a basic reagent to obtain the compound of general formula (IIN), wherein:

$R^w$ is $C_{1-6}$ alkyl;

M, $Y^4$, $Y^5$, $Y^6$, ring A, $R^1$ to $R^6$, n, m, p and q are as defined in general formula (IIN).

Scheme 9

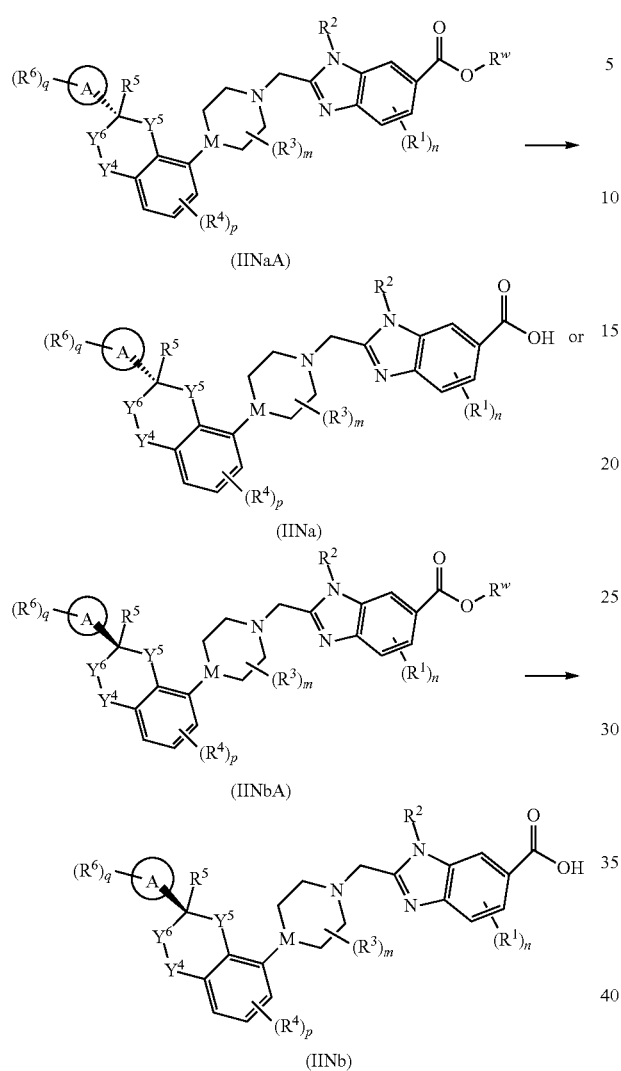

A method for preparing the compound of general formula (IINa) or general formula (IINb) or the tautomer, racemate, enantiomer or diastereomer thereof or the mixture thereof, or the pharmaceutically acceptable salt thereof disclosed herein, comprising the following step:

conducting a hydrolysis reaction of a compound of general formula (IINaA) in the presence of a basic reagent to obtain the compound of general formula (IINa), or conducting a hydrolysis reaction of a compound of general formula (IINbA) in the presence of a basic reagent to obtain the compound of general formula (IINb), wherein:

$R^w$ is $C_{1-6}$ alkyl;

M, $Y^4$, $Y^5$, $Y^6$, ring A, $R^1$ to $R^6$, n, m, p and q are as defined in general formula (IINa) or general formula (IINb).

Scheme 10

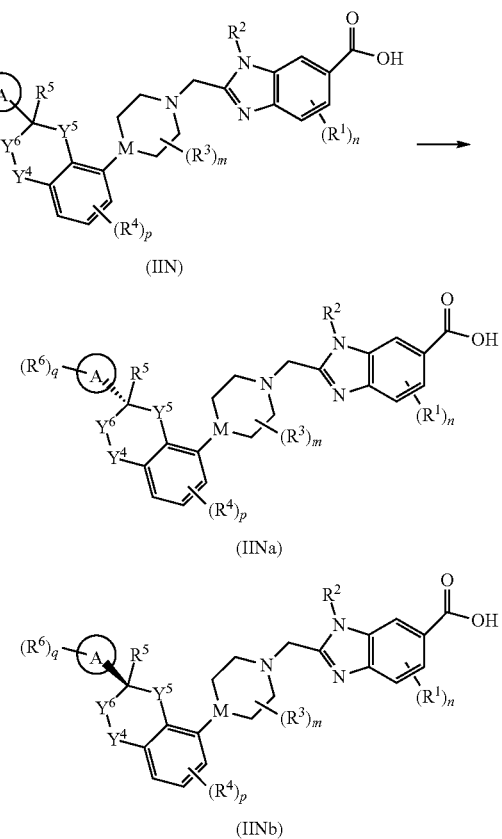

A method for preparing the compound of general formula (IINa) or general formula (IINb) or the tautomer, racemate, enantiomer or diastereomer thereof or the mixture thereof, or the pharmaceutically acceptable salt thereof disclosed herein, comprising the following step:

performing chiral resolution of a compound of general formula (IIN) to obtain a compound of general formula (IINa) and a compound of general formula (IINb), wherein: M, $Y^4$, $Y^5$, $Y^6$, ring A, $R^1$ to $R^6$, n, m, p and q are as defined in general formula (IINa) or general formula (IINb).

Scheme 11

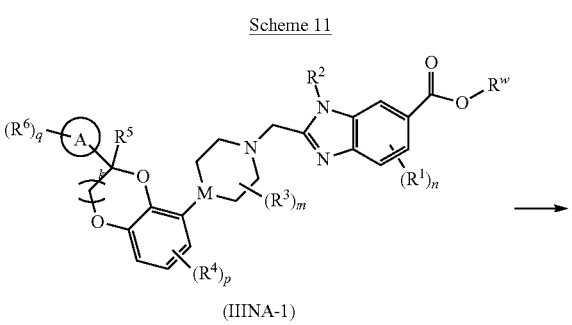

(IIINA-1)

-continued

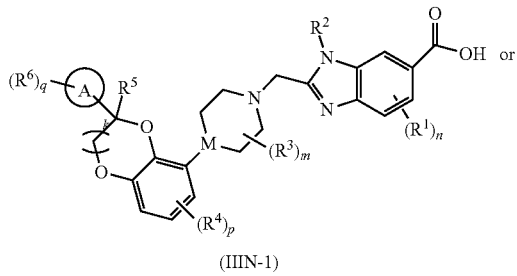

(IIIN-1)

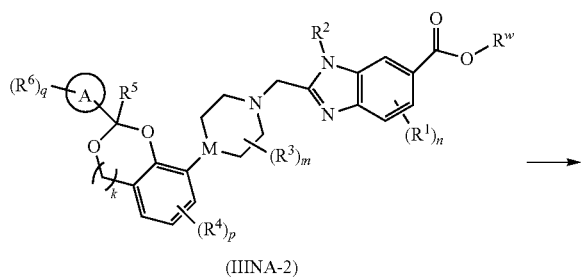

(IIINA-2)

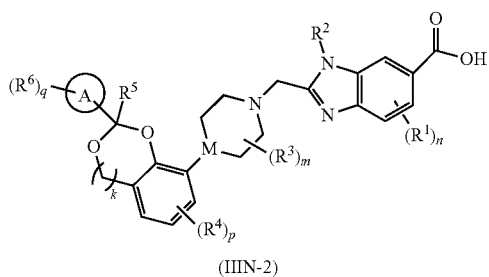

(IIIN-2)

A method for preparing the compound of general formula (IIIN-1) or general formula (IIIN-2) or the tautomer, racemate, enantiomer or diastereomer thereof or the mixture thereof, or the pharmaceutically acceptable salt thereof disclosed herein, comprising the following step:

conducting a hydrolysis reaction of a compound of general formula (IIINA-1) in the presence of a basic reagent to obtain the compound of general formula (IIIN-1), or conducting a hydrolysis reaction of a compound of general formula (IIINA-2) in the presence of a basic reagent to obtain the compound of general formula (IIIN-2), wherein:

$R^w$ is $C_{1-6}$ alkyl;

M, ring A, $R^1$ to $R^6$, k, n, m, p and q are as defined in general formula (IIIN-1) or general formula (IIIN-2).

Scheme 12

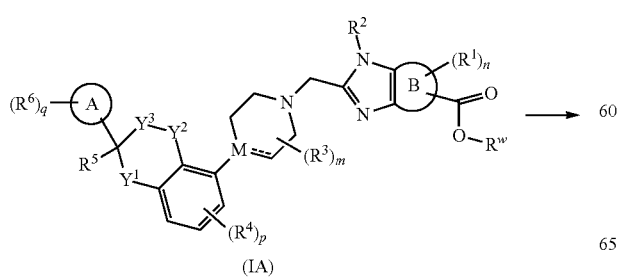

(IA)

-continued

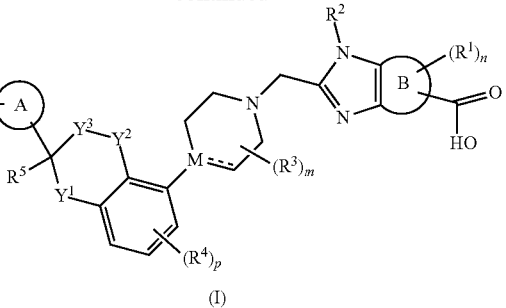

(I)

A method for preparing the compound of general formula (I) or the tautomer, racemate, enantiomer or diastereomer thereof or the mixture thereof, or the pharmaceutically acceptable salt thereof disclosed herein, comprising the following step:

conducting a hydrolysis reaction of a compound of general formula (IA) in the presence of a basic reagent to obtain the compound of general formula (I), wherein:

$R^w$ is $C_{1-6}$ alkyl;

$=\!=\!=$, ring B, M, $Y^1$, $Y^2$, $Y^3$, ring A, $R^1$ to $R^6$, n, m, p and q are as defined in general formula (I).

Scheme 13

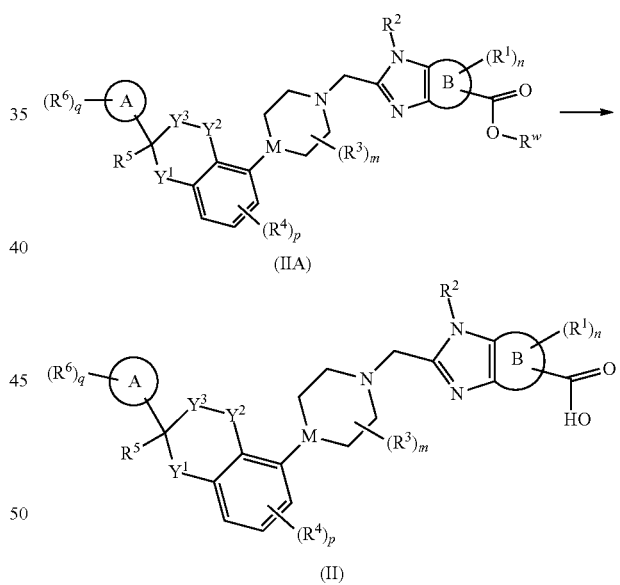

A method for preparing the compound of general formula (II) or the tautomer, racemate, enantiomer or diastereomer thereof or the mixture thereof, or the pharmaceutically acceptable salt thereof disclosed herein, comprising the following step:

conducting a hydrolysis reaction of a compound of general formula (IIA) in the presence of a basic reagent to obtain the compound of general formula (II), wherein:

$R^w$ is $C_{1-6}$ alkyl;

ring B, M, $Y^1$, $Y^2$, $Y^3$, ring A, $R^1$ to $R^6$, n, m, p and q are as defined in general formula (II).

Scheme 14

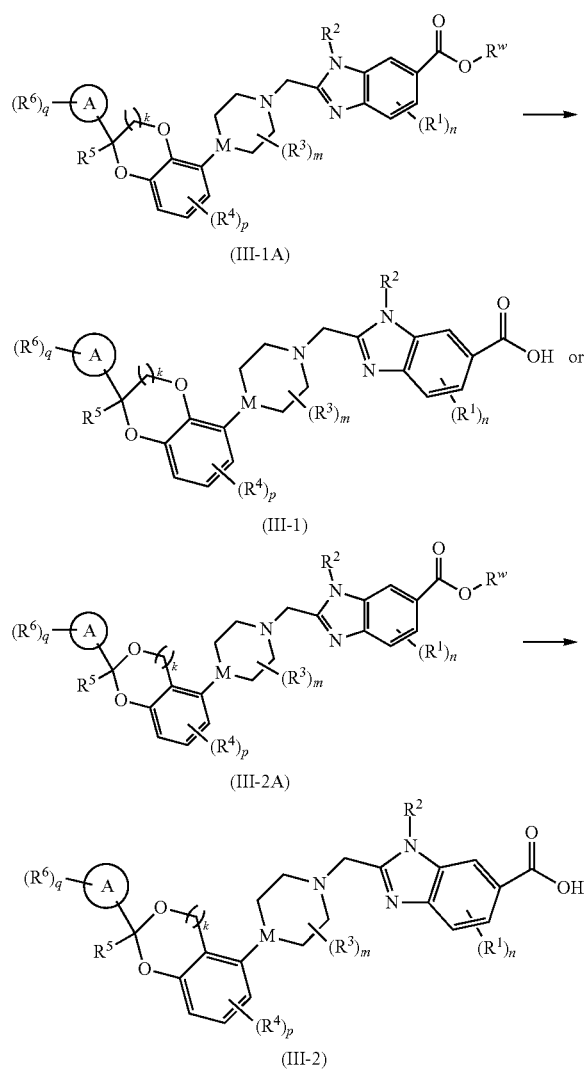

(III-1A)

(III-1)

(III-2A)

(III-2)

A method for preparing the compound of general formula (III-1) or general formula (III-2) or the tautomer, racemate, enantiomer or diastereomer thereof or the mixture thereof, or the pharmaceutically acceptable salt thereof disclosed herein, comprising the following step:

conducting a hydrolysis reaction of a compound of general formula (III-1A) in the presence of a basic reagent to obtain the compound of general formula (III-1), or conducting a hydrolysis reaction of a compound of general formula (III-2A) in the presence of a basic reagent to obtain the compound of general formula (III-2), wherein:

$R^w$ is $C_{1-6}$ alkyl;

M, ring A, $R^1$ to $R^6$, k, n, m, p and q are as defined in general formula (II-1) or general formula (III-2).

The basic reagents in the above synthesis schemes include organic bases and inorganic bases, wherein the organic bases include, but are not limited to, triethylamine, N,N-diisopropylethylamine, n-butyllithium, lithium diisopropylamide, sodium acetate, potassium acetate, sodium tert-butoxide and potassium tert-butoxide, and the inorganic bases include, but are not limited to, sodium hydride, potassium phosphate, sodium carbonate, potassium carbonate, cesium carbonate, sodium hydroxide, lithium hydroxide monohydrate, lithium hydroxide and potassium hydroxide; lithium hydroxide or lithium hydroxide monohydrate is preferred.

The reactions in the above synthesis schemes are preferably conducted in solvents, which include, but are not limited to, ethylene glycol dimethyl ether, acetic acid, methanol, ethanol, acetonitrile, n-butanol, toluene, tetrahydrofuran, dichloromethane, petroleum ether, ethyl acetate, n-hexane, dimethyl sulfoxide, 1,4-dioxane, water, N,N-dimethylformamide, and mixtures thereof.

DETAILED DESCRIPTION

The present disclosure is further described below with reference to examples below, which are not intended to limit the scope of the present disclosure.

Abbreviations

1. "Ts" stands for p-toluenesulfonyl;
2. "Tf" stands for trifluoromethanesulfonyl.

EXAMPLES

The structures of the compounds were determined by nuclear magnetic resonance (NMR) spectroscopy and/or mass spectrometry (MS). NMR shifts (δ) are given in a unit of $10^{-6}$ (ppm). NMR spectra were measured using a Bruker AVANCE-400 nuclear magnetic resonance instrument, with deuterated dimethyl sulfoxide (DMSO-$d_6$), deuterated chloroform (CDCl$_3$) and deuterated methanol (CD$_3$OD) as solvents and tetramethylsilane (TMS) as an internal standard.

MS analysis was performed using a FINNIGAN LCQAd (ESI) mass spectrometer (manufacturer: Thermo, model: Finnigan LCQ advantage MAX).

High performance liquid chromatography (HPLC) analysis was performed using Agilent HPLC 1200DAD, Agilent HPLC 1200VWD and Waters HPLC e2695-2489 high performance liquid chromatographs.

Chiral HPLC analysis was performed using an Agilent 1260 DAD high performance liquid chromatograph.

Preparative HPLC was performed using Waters 2767, Waters 2767-SQ Detecor2, Shimadzu LC-20AP and Gilson-281 preparative chromatographs.

Preparative chiral chromatography was performed using a Shimadzu LC-20AP preparative chromatograph.

The CombiFlash preparative flash chromatograph used was CombiFlash Rf200 (TELEDYNE ISCO).

Yantai Huanghai HSGF254 or Qingdao GF254 silica gel plates, 0.15-0.2 mm layer thickness, were adopted for thin-layer chromatography (TLC) analysis and 0.4-0.5 mm layer thickness for TLC separation and purification.

Silica gel column chromatography generally used 200- to 300-mesh silica gel (Huanghai, Yantai) as the carrier.

The mean inhibition of kinase and the IC$_{50}$ value were determined using a NovoStar microplate reader (BMG, Germany).

Known starting materials described herein may be synthesized using or according to methods known in the art, or may be purchased from ABCR GmbH & Co. KG, Acros Organics, Aldrich Chemical Company, Accela ChemBio Inc., Chembee Chemicals, and other companies.

In the examples, the reactions can be performed in an argon atmosphere or a nitrogen atmosphere unless otherwise specified.

The argon atmosphere or nitrogen atmosphere means that the reaction flask is connected to a balloon containing about 1 L of argon or nitrogen.

The hydrogen atmosphere means that the reaction flask is connected to a balloon containing about 1 L of hydrogen.

Parr 3916EKX hydrogenator, Qinglan QL-500 hydrogenator or HC2-SS hydrogenator was used in the pressurized hydrogenation reactions.

Hydrogenation reactions generally involve 3 cycles of vacuumization and hydrogen purging.

A CEM Discover-S 908860 microwave reactor was used in microwave reactions.

In the examples, a solution refers to an aqueous solution unless otherwise specified.

In the examples, reactions were conducted at room temperature, i.e., 20° C. to 30° C., unless otherwise specified.

The monitoring of the reaction progress in the examples was conducted by thin-layer chromatography (TLC). The developing solvent for reactions, the eluent system for column chromatography purification and the developing solvent system for thin-layer chromatography included: A: dichloromethane/methanol system, B: n-hexane/ethyl acetate system, C: n-hexane/dichloromethane system, and D: ethyl acetate/dichloromethane/n-hexane. The volume ratio of the solvents was adjusted according to the polarity of the compound, or by adding a small amount of basic or acidic reagents such as triethylamine and acetic acid.

Example 1

2-((4-(3-(Benzo[d]thiazol-2-yl)-2,3-dihydrobenzo[b][1,4]dioxan-5-yl)piperidin-1-yl)methyl)-1-(((S)-oxetan-2-yl)methyl)-1H-benzo[d]imidazole-6-carboxylic acid (A Mixture of Diastereomers) 1

2-((4-((S)-3-(Benzo[d]thiazol-2-yl)-2,3-dihydrobenzo[b][1,4]dioxan-5-yl)piperidin-1-yl)methyl)-1-(((S)-oxetan-2-yl)methyl)-1H-benzo[d]imidazole-6-carboxylic acid 1-1

2-((4-((R)-3-(Benzo[d]thiazol-2-yl)-2,3-dihydrobenzo[b][1,4]dioxan-5-yl)piperidin-1-yl)methyl)-1-(((S)-oxetan-2-yl)methyl)-1H-benzo[d]imidazole-6-carboxylic acid 1-2

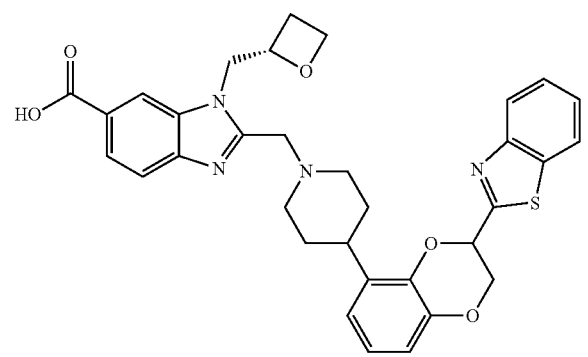

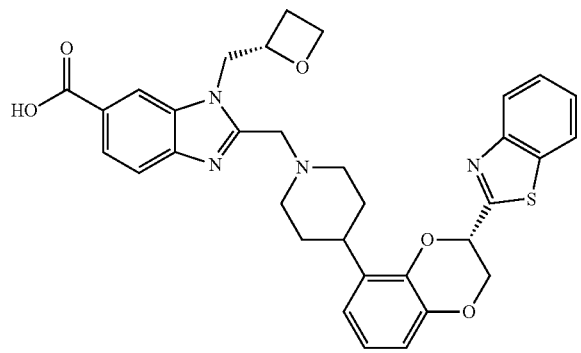

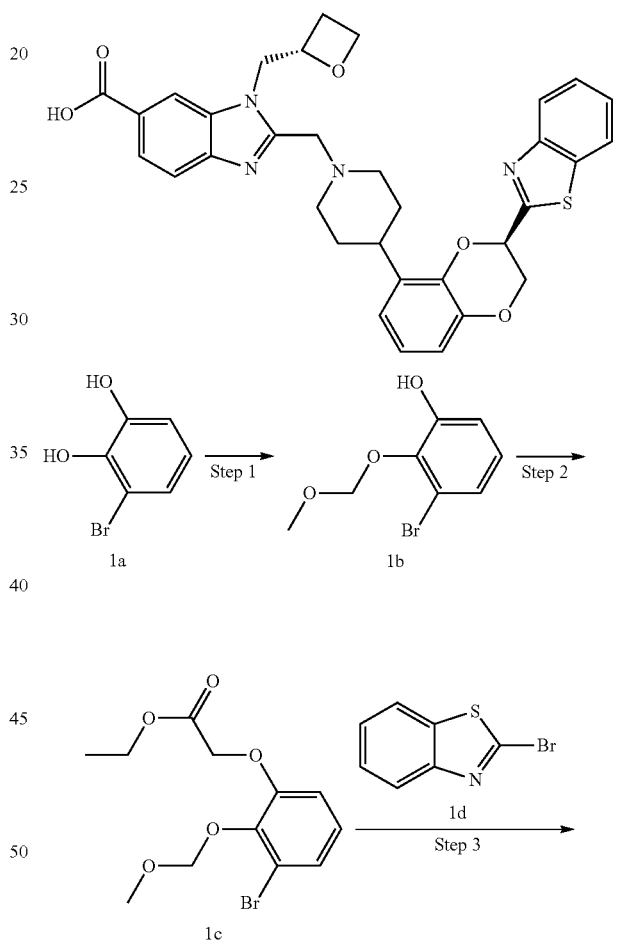

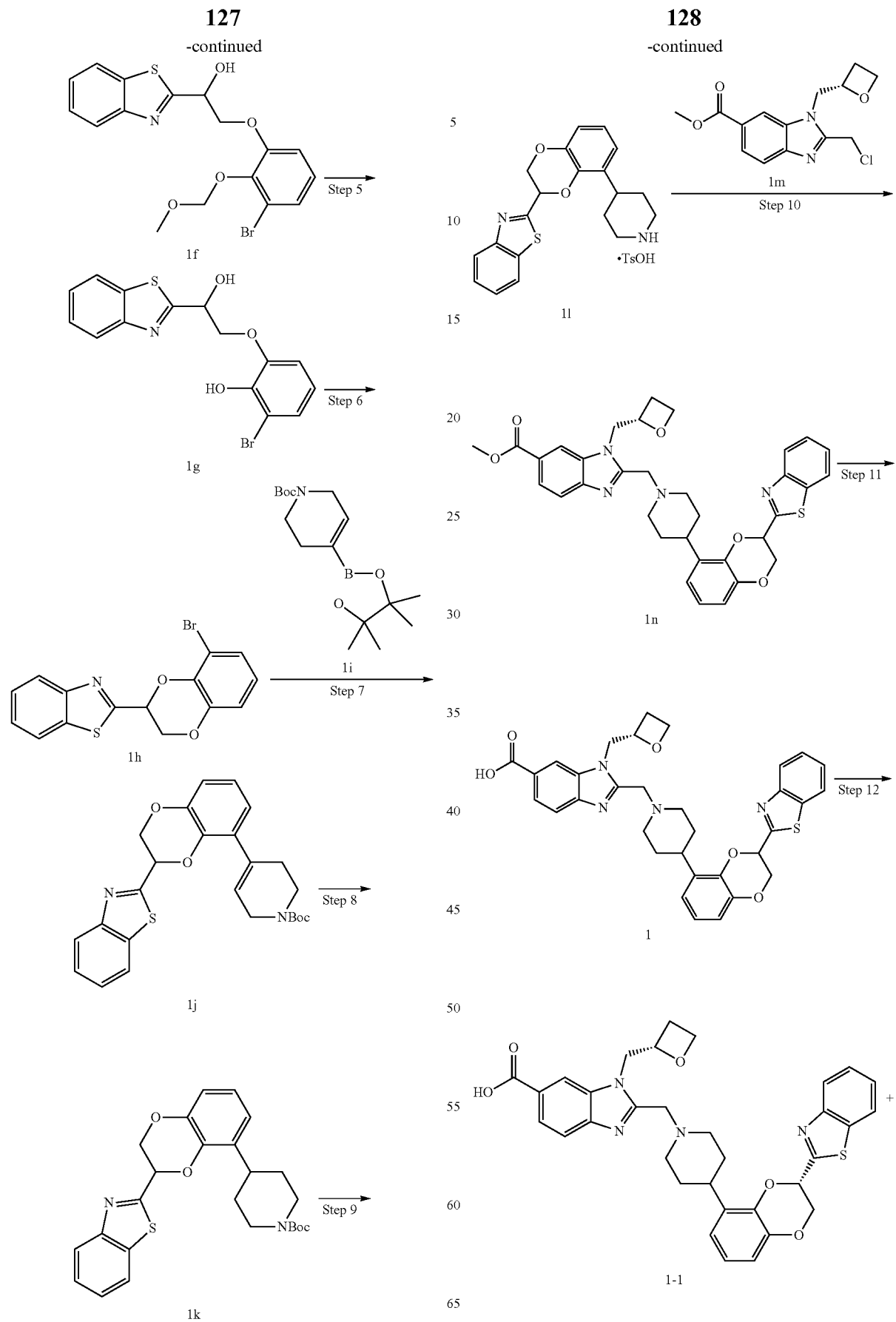

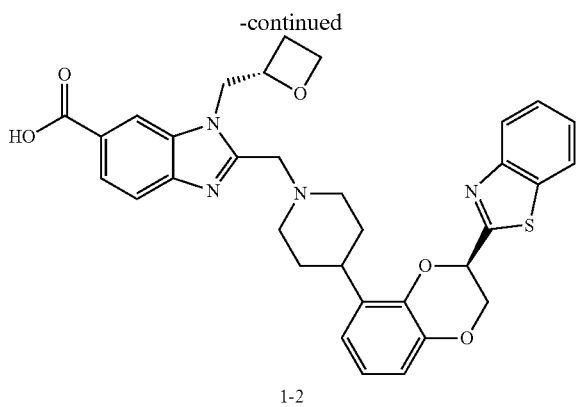

1-2

Step 1

3-Bromo-2-(methoxymethoxy)phenol 1b

The compound 3-bromobenzene-1,2-diol 1a (49.8 g, 263.48 mmol, Accela ChemBio (Shanghai) Inc.) was dissolved in 600 mL of dichloromethane. N,N-diisopropylethylamine (51.0 g, 394.60 mmol, 65.21 mL) was added with stirring. Bromomethyl methyl ether (30.0 g, 240.0 mmol, 19.59 mL, Adamas Reagent Co., Ltd.) was added dropwise under ice bath conditions. The mixture was stirred at room temperature for 2 h and washed with 200 mL of water. The organic phase was dried over anhydrous sodium sulfate and concentrated. The resulting residue was purified by silica gel column chromatography with eluent system B to give the title compound 1b (26.65 g, yield: 43.39%).

MS m/z (ESI): 232.0 [M−1]

Step 2

Ethyl 2-(3-bromo-2-(methoxymethoxy)phenoxy)acetate 1c

Compound 1b (3.02 g, 12.95 mmol) was dissolved in 10 mL of dimethyl sulfoxide. Ethyl bromoacetate (2.16 g, 12.93 mmol, Accela ChemBio (Shanghai) Inc.) and potassium carbonate (1.79 g, 12.95 mmol, Accela ChemBio Inc.) were added. The mixture was heated to 95° C. and reacted for 21 h. Water (20 mL) was added, and the mixture was stirred, extracted with ethyl acetate (20 mL×3), washed with saturated brine (20 mL), dried over anhydrous sodium sulfate and concentrated under reduced pressure to remove the solvent to give the title compound 1c (3.5 g, yield: 84.63%).

Step 3

1-(Benzo[d]thiazol-2-yl)-2-(3-bromo-2-(methoxymethoxy)phenoxy)ethan-1-one 1c

Compound 1c (957 mg, 2.99 mmol) was dissolved in 10 mL of tetrahydrofuran. The solution was cooled to −78° C. under nitrogen. n-Butyllithium (384 mg, 5.99 mmol, Adamas Reagent Co., Ltd.) was added dropwise. The reaction continued for 1.5 h. 2-Bromobenzothiazole 1d (1.20 g, 5.60 mmol, Accela ChemBio (Shanghai) Inc.) was added to the reaction flask. After 1 h of reaction, the reaction mixture was quenched with 10 mL of saturated ammonium chloride solution, extracted with 60 mL of ethyl acetate and washed with saturated brine (20 mL). The organic layer was dried over anhydrous sodium sulfate and concentrated under reduced pressure. The resulting residue was purified by silica gel column chromatography with eluent system B to give the title product 1e (1.20 g, yield: 98.02%).

MS m/z (ESI): 409.0 [M+1].

Step 4

1-(Benzo[d]thiazol-2-yl)-2-(3-bromo-2-(methoxymethoxy)phenoxy)ethan-1-ol 1f

Compound 1e (600 mg, 1.46 mmol) was dissolved in 20 mL of ethanol. Sodium borohydride (55.84 mg, 1.46 mmol, Accela ChemBio (Shanghai) Inc.) was added under ice bath conditions. The mixture was stirred for 10 min. Water (20 mL) was added, and the mixture was stirred, extracted with ethyl acetate (20 mL×3), washed with saturated brine (20 mL), dried over anhydrous sodium sulfate and concentrated under reduced pressure to remove the solvent to give the title compound 1f (570 mg, yield: 94.53%).

Step 5

2-(2-(Benzo[d]thiazol-2-yl)-2-hydroxyethoxy)-6-bromophenol 1g

Compound 1f (570 mg, 1.39 mmol) was dissolved in 80 mL of dichloromethane. 20 mL of a solution of hydrogen chloride in dioxane (4 mmol/mL) was added under ice bath conditions. The mixture was stirred for half an hour. The organic phase was concentrated. The residue was triturated with 15 mL of a mixed solution of n-hexane and ethyl acetate (V:V=5:1). The mixture was filtered to give the title compound 1g (503 mg, yield: 98.95%).

Step 6

2-(8-Bromo-2,3-dihydrobenzo[b][1,4]dioxan-2-yl)benzo[d]thiazole 1h

Compound 1g (350 mg, 0.95 mmol) was dissolved in 25 mL of tetrahydrofuran. Triphenylphosphine (375 mg, 1.43 mmol, Sinopharm Chemical Reagent Co., Ltd.) was added. Diisopropyl azodicarboxylate (289 mg, 1.43 mmol, Accela ChemBio (Shanghai) Inc.) was added dropwise under ice bath conditions. The reaction continued for 1 h. The reaction mixture was concentrated under reduced pressure. The resulting residue was purified by silica gel column chromatography with eluent system B to give the title compound 1h (248 mg, yield: 74.52%).

MS m/z (ESI): 349.0 [M+1].

Step 7 tert-Butyl 4-(3-(benzo[d]thiazol-2-yl)-2,3-dihydrobenzo[b][1,4]dioxan-5-yl)-3,6-dihydropiperidine-1(2H)-carboxylate 1j Compound 1h (220 mg, 0.63 mmol) was dissolved in 1,4-dioxane (20 mL). 3,6-Dihydro-2H-pyridine-1-tert-butoxycarbonyl-1-boronic acid pinacol ester 1i (215 mg, 0.69 mmol), sodium carbonate (134 mg, 1.26 mmol), tetrakis(triphenylphosphine)palladium (73 mg, 63 μmol) and water (4 mL) were added. The mixture was heated to 90° C., stirred for 4 h under nitrogen, cooled to room temperature, concentrated and then purified by silica gel column chromatography with eluent system B to give the title compound 1j (230 mg, yield: 80.79%).

MS m/z (ESI): 451.1 [M+1].

Step 8 tert-Butyl 4-(3-(benzo[d]thiazol-2-yl)-2,3-dihydrobenzo[b][1,4]dioxan-5-yl)piperidine-1-carboxylate 1k Compound 1j (230 mg, 0.51 mmol) was dissolved in ethyl acetate (20 mL). 10% palladium on carbon (138 mg, 0.30 mmol) was added. Hydrogenation was performed at room temperature for 3 h under one atmosphere of hydrogen. The mixture was filtered. The filtrate was concentrated to give the crude title compound 1k (230 mg). The product was directly used in the next step without being purified.

MS m/z (ESI): 453.0 [M+1].

Step 9

2-(8-(Piperidin-4-yl)-2,3-dihydrobenzo[b][1,4]dioxan-2-yl)benzo[d]thiazole 4-methylbenzenesulfonate 1l Compound 1k (220 mg, 0.48 mmol) was dissolved in 10 mL of dichloromethane. 2 mL of trifluoroacetic acid was added. The mixture was stirred at room temperature for 10 min and concentrated under reduced pressure to give the crude title compound 1l [M+1].

Step 10

Methyl 2-((4-(3-(benzo[d]thiazol-2-yl)-2,3-dihydrobenzo[b][1,4]dioxan-5-yl)piperidin-1-yl)methyl)-1-(((S)-oxetan-2-yl)methyl)-1H-benzo[d]imidazole-6-carboxylate (A Mixture of Diastereomers) 1n Compound 1l (170 mg, 0.48 mmol) was dissolved in 20 mL of acetonitrile. The compound methyl (S)-2-(chloromethyl)-1-(oxetan-2-ylmethyl)-1H-benzo[d]imidazole-6-carboxylate 1m (143 mg, 0.48 mmol, prepared using the method for intermediate 23 disclosed on page 69 of the specification in patent application WO2018109607A1) was added. Potassium carbonate (670 mg, 4.8 mmol) was added. The mixture was heated to 50° C. and stirred for 5 h. The reaction mixture was cooled to room temperature and concentrated under reduced pressure. The resulting residue was purified by silica gel column chromatography with eluent system B to give the title mixture of diastereomers 1n (220 mg, yield: 74.24%).

MS m/z (ESI): 611.2 [M+1].

Step 11

2-((4-(-3-(Benzo[d]thiazol-2-yl)-2,3-dihydrobenzo[b][1,4]dioxan-5-yl)piperidin-1-yl)methyl)-1-(((S)-oxetan-2-yl)methyl)-1H-benzo[d]imidazole-6-carboxylic acid (A Mixture of Diastereomers) 1

Compound 1n (20 mg, 0.032 mmol) was dissolved in 5 mL of a mixed solvent of acetonitrile and tetrahydrofuran (V:V=1:1). Lithium hydroxide monohydrate (5.5 mg, 0.13 mmol) and 1 mL of water were added at room temperature. The mixture was reacted at 40° C. for 16 h, cooled to room temperature, adjusted to pH 6-7 with 5% aqueous citric acid solution and extracted with ethyl acetate (20 mL×2). The organic layers were combined, concentrated and purified by silica gel column chromatography with eluent system A to give the title mixture of diastereomers 1 as a crude product (20 mg).

Step 12

2-((4-((S)-3-(Benzo[d]thiazol-2-yl)-2,3-dihydrobenzo[b][1,4]dioxan-5-yl)piperidin-1-yl)methyl)-1-(((S)-oxetan-2-yl)methyl)-1H-benzo[d]imidazole-6-carboxylic acid 1-1

2-((4-((R)-3-(Benzo[d]thiazol-2-yl)-2,3-dihydrobenzo[b][1,4]dioxan-5-yl)piperidin-1-yl)methyl)-1-(((S)-oxetan-2-yl)methyl)-1H-benzo[d]imidazole-6-carboxylic acid 1-2

Compound 1 (20 mg, 0.032 mmol) was resolved using a preparative chiral column and concentrated under reduced pressure to give the title compound 1-1 (6 mg, yield: 30.70%) and the title compound 1-2 (6 mg, yield: 30.70%).

Compound 1-1:

Chiral HPLC analysis: retention time 3.859 min, chiral purity: 99% (column: (resolution conditions: CHIRALPAK IE 150×4.6 mm, 5 μm; mobile phase hexane/EtOH (0.1% DEA+0.1 TFA)=20/80 (V/V))

MS m/z (ESI): 597.2 [M+1].

$^1$H NMR (500 MHz, DMSO-$d_6$) δ 12.46 (s, 1H), 8.25 (s, 1H), 8.18 (d, 1H), 8.06 (d, 1H), 7.81 (d, 1H), 7.61 (d, 1H), 7.54-7.58 (m, 1H), 7.46-7.49 (m, 1H), 6.85-6.87 (m, 2H), 6.75-6.76 (m, 1H), 5.31-5.34 (m, 1H), 5.08-5.13 (m, 1H), 4.78-4.83 (m, 1H), 4.64-4.68 (m, 2H), 4.47-4.53 (m, 2H), 4.36-4.39 (m, 1H), 3.96-3.98 (m, 1H), 3.80-3.83 (m, 1H), 2.93-3.07 (m, 3H), 2.68-2.71 (m, 1H), 2.20-2.35 (m, 2H), 1.92-1.98 (m, 2H), 1.65-1.80 (m, 2H).

Compound 1-2:

Chiral HPLC analysis: retention time 2.999 min, chiral purity: 99% (column: (separation conditions: CHIRALPAK IE 150×4.6 mm, 5 μm; mobile phase hexane/EtOH (0.1% DEA+0.1 TFA)=20/80 (V/V))

MS m/z (ESI): 597.2 [M+1].

$^1$H NMR (500 MHz, DMSO-$d_6$) δ 12.46 (s, 1H), 8.25 (s, 1H), 8.18 (d, 1H), 8.06 (d, 1H), 7.81 (d, 1H), 7.61 (d, 1H), 7.54-7.59 (m, 1H), 7.46-7.48 (m, 1H), 6.85-6.87 (m, 2H), 6.75-6.76 (m, 1H), 5.31-5.35 (m, 1H), 5.08-5.14 (m, 1H), 4.78-4.83 (m, 1H), 4.64-4.68 (m, 2H), 4.47-4.53 (m, 2H), 4.36-4.39 (m, 1H), 3.96-3.98 (m, 1H), 3.80-3.83 (m, 1H), 2.93-3.07 (m, 3H), 2.68-2.71 (m, 1H), 2.20-2.34 (m, 2H), 1.92-1.98 (m, 2H), 1.65-1.80 (m, 2H).

Example 2
2-((4-(3-(4-Chloro-2-fluorophenyl)-2,3-dihydrobenzo[b][1,4]dioxan-5-yl)piperidin-1-yl)methyl)-1-((S)-oxetan-2-ylmethyl)-1H-benzo[d]imidazole-6-carboxylic acid (A Mixture of Diastereomers) 2
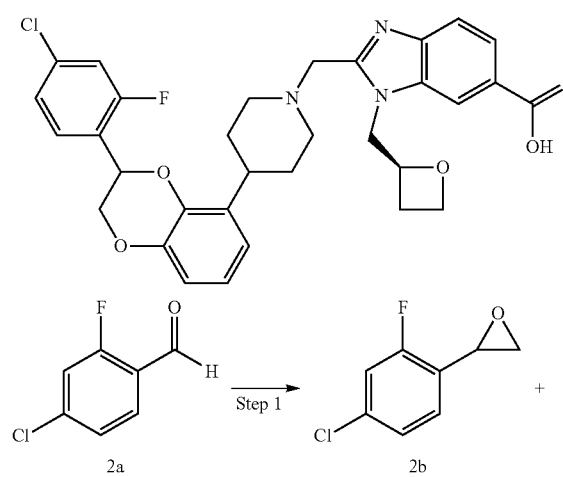
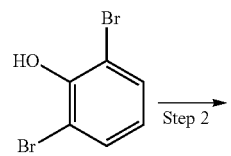
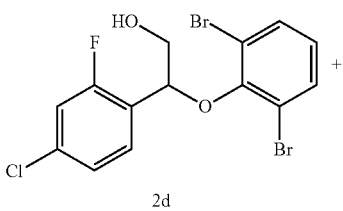
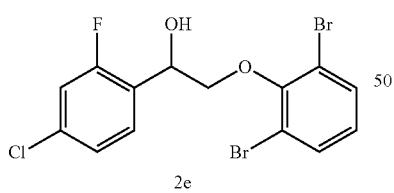
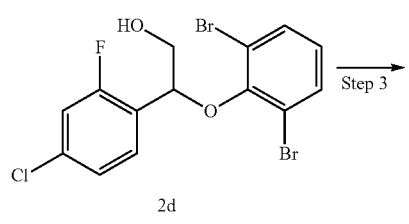
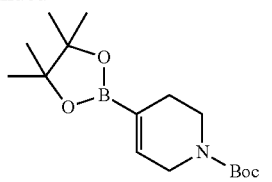
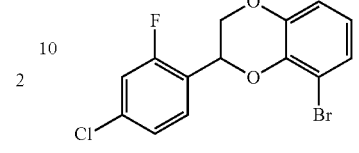
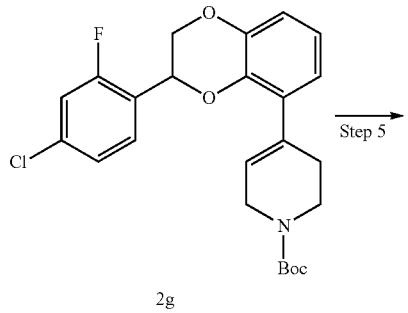
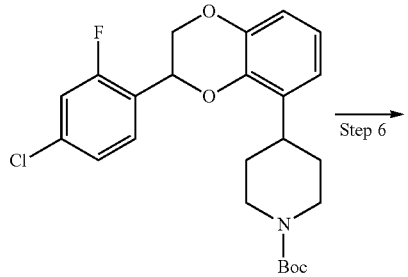
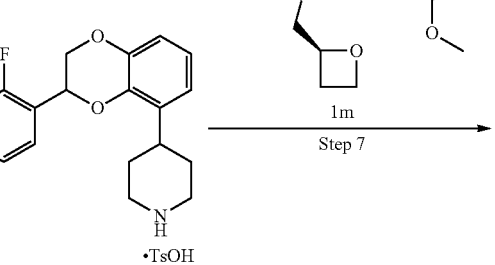
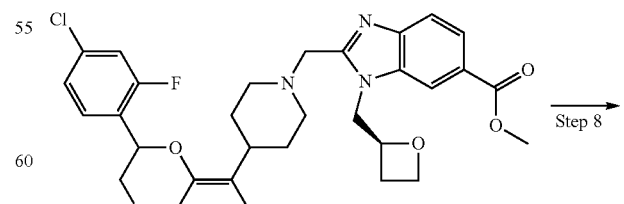

-continued

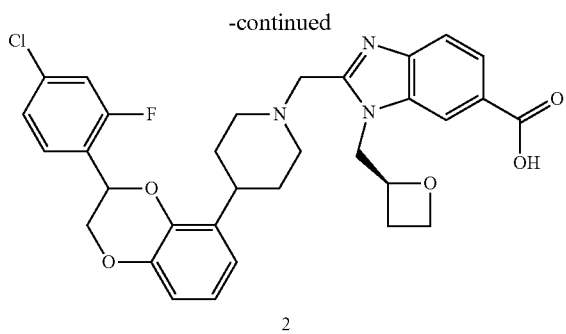

2

Step 1

2-(4-Chloro-2-fluorophenyl)oxirane 2b

Potassium tert-butoxide (1.70 g, 15.14 mmol, Accela ChemBio (Shanghai) Inc.) was added to tetrahydrofuran (30 mL). Trimethylsulfonium iodide (3.09 g, 15.14 mmol, Adamas Reagent Co., Ltd.) was added under ice bath conditions. The mixture was stirred for 5 min. 4-Chloro-2-fluorobenzaldehyde 2a (2.0 g, 12.61 mmol, Accela ChemBio (Shanghai) Inc.) was added. The mixture was filtered, diluted with ethyl acetate (80 mL), washed with saturated aqueous ammonium chloride solution (30 mL×2), washed with saturated brine (30 mL×2), dried over anhydrous sodium sulfate and concentrated under reduced pressure to remove the solvent. The resulting residue was purified by silica gel column chromatography with eluent system B to give the title compound 2b (650 mg, yield: 29.9%).

$^1$H NMR (500 MHz, CDCl$_3$) δ 7.05-7.13 (m, 3H), 4.01-4.15 (m, 1H), 3.17 (dd, 1H), 3.75 (dd, 1H).

Step 2

2-(4-Chloro-2-fluorophenyl)-2-(2,6-dibromophenoxy)ethanol 2d

1-(4-Chloro-2-fluorophenyl)-2-(2,6-dibromophenoxy)ethanol 2e

After compound 2b (520 mg, 3.01 mmol) and 2,6-dibromophenol 2c (759 mg, 3.01 mmol, TCI (Shanghai) Co., Ltd.) were mixed, sodium methoxide (16 mg, 0.30 mmol, Adamas Reagent Co., Ltd.) was added. The mixture was stirred at 130° C. for 2 h. After cooling, the resulting residue was purified by silica gel column chromatography with eluent system B to give the title compound 2d (210 mg, yield: 16.4%) and compound 2e (140 mg, yield: 10.9%).

2d MS m/z (ESI): 422.9 [M−1].

2d $^1$H NMR (500 MHz, DMSO-d$_6$) δ 7.69 (t, 1H), 7.63 (d, 2H), 7.40 (dd, 1H), 7.35 (dd, 1H), 7.00 (t, 1H), 5.59 (t, 1H), 5.02 (t, 1H), 3.98-4.03 (m, 1H), 3.81-3.90 (m, 1H).

2e $^1$H NMR (500 MHz, DMSO-d$_6$) δ 7.64 (d, 2H), 7.62 (t, 1H), 7.39 (dd, 1H), 7.32 (dd, 1H), 7.02 (t, 1H), 5.82-6.01 (m, 1H), 5.28 (t, 1H), 4.07-4.12 (m, 1H), 3.95-4.00 (m, 1H).

Step 3

8-Bromo-2-(4-chloro-2-fluorophenyl)-2,3-dihydrobenzo[b][1,4]dioxane 2f

Compound 2d (595 mg, 1.40 mmol) was dissolved in anhydrous toluene (8 mL). S-1,1'-Bi-2-naphthol (159 mg, 0.55 mmol, Accela ChemBio (Shanghai) Inc.), cuprous iodide (52 mg, 0.27 mmol, Sinopharm Chemical Reagent Co., Ltd.) and cesium carbonate (912 mg, 2.80 mmol, Accela ChemBio (Shanghai) Inc.) were successively added. The mixture was heated at reflux and stirred for 18 h, cooled and concentrated under reduced pressure to remove the solvent. The resulting residue was purified by silica gel column chromatography with eluent system B to give the title compound 2f (380 mg, yield: 78.9%).

MS m/z (ESI): 343.1 [M−1].

$^1$H NMR (500 MHz, DMSO-d$_6$) δ 7.57 (dd, 1H), 7.54 (t, 1H), 7.43 (dd, 1H), 7.19 (dd, 1H), 6.98 (dd, 1H), 6.85 (t, 1H), 5.58 (dd, 1H), 4.51 (dd, 1H), 4.20 (dd, 1H).

Step 4 tert-Butyl 4-(3-(4-chloro-2-fluorophenyl)-2,3-dihydrobenzo[b][1,4]dioxan-5-yl)-5,6-dihydropyridine-1(2H)-carboxylate 2g Compound 2f (354 mg, 1.03 mmol) and compound 1i (350 mg, 1.13 mmol, Accela ChemBio (Shanghai) Inc.) were dissolved in 24 mL of a mixed solution of 1,4-dioxane and water (V/V=5:1). Sodium carbonate (218 mg, 2.06 mmol), tetrakis(triphenylphosphine)palladium (119 mg, 1.03 mmol) were added. The mixture was stirred at 90° C. for 4 h under nitrogen, cooled to room temperature, filtered and concentrated under reduced pressure to remove the solvent. The resulting residue was purified by silica gel column chromatography with eluent system B to give the title compound 2g (410 mg, yield: 89.2%).

MS m/z (ESI): 390.1 [M−55].

$^1$H NMR (500 MHz, CDCl$_3$) δ 7.39 (t, 1H), 7.19-7.23 (m, 1H), 7.15 (dd, 1H), 6.83-6.89 (m, 2H), 6.77-6.81 (m, 1H), 5.76-5.91 (m, 1H), 5.32-5.46 (m, 1H), 5.41 (dd, 1H), 3.99-4.08 (m, 2H), 3.97 (dd, 1H), 3.43-3.69 (m, 2H), 2.40-2.63 (m, 2H), 1.47 (s, 9H).

Step 5 tert-Butyl 4-(3-(4-chloro-2-fluorophenyl)-2,3-dihydrobenzo[b][1,4]dioxan-5-yl)piperidine-1-carboxylate 2h Compound 2g (220 mg, 0.49 mmol) was dissolved in ethyl acetate (10 mL) and 1,2-dichlorobenzene (0.5 mL, TCI (Shanghai) Co., Ltd.). 10% palladium on carbon (50 mg, 0.47 mmol) was added. Hydrogenation was performed at room temperature for 1 h under one atmosphere of hydrogen. The mixture was filtered and concentrated under reduced pressure to remove the solvent. The resulting residue was purified by silica gel column chromatography with eluent system B to give the title compound 2h (178 mg, yield: 80.5%).

MS m/z (ESI): 392.1[M−55].

$^1$H NMR (500 MHz, CDCl$_3$) δ 7.40 (t, 1H), 7.21-7.24 (m, 1H), 7.16 (dd, 1H), 6.82-6.88 (m, 1H), 6.76-6.81 (m, 2H), 5.35-5.45 (m, 1H), 4.40 (dd, 1H), 4.09-4.33 (m, 2H), 3.96 (dd, 1H), 2.99-3.11 (m, 1H), 2.67-2.90 (m, 2H), 1.72-1.91 (m, 2H), 1.58-1.69 (m, 2H), 1.46 (s, 9H).

Step 6

4-(3-(4-Chloro-2-fluorophenyl)-2,3-dihydrobenzo[b][1,4]dioxan-5-yl)piperidine 4-methylbenzenesulfonate 2i Compound 2h (178 mg, 0.40 mmol) was dissolved in ethyl acetate (5 mL). p-Toluenesulfonic acid monohydrate (189 mg, 0.99 mmol) was added. The mixture was stirred at 60° C. for 2 h. The mixture was cooled to room temperature and concentrated under reduced pressure to give the crude title product 2i (206 mg). The product was directly used in the next step without being purified.

MS m/z (ESI): 348.1 [M+1].

Step 7

Methyl 2-((4-(3-(4-chloro-2-fluorophenyl)-2,3-dihydrobenzo[b][1,4]dioxan-5-yl)piperidin-1-yl)methyl)-1-((S)-oxetan-2-ylmethyl)-1H-benzo[d]imidazole-6-carboxylate (A Mixture of Diastereomers) 2j Compound 1m (175 mg, 0.59 mmol) and 2i (206 mg, 0.59 mmol) were dissolved in acetonitrile (10 mL). Potassium carbonate (410 mg, 2.97 mmol) was added. The mixture was stirred at 60° C. for 3 h, filtered and concentrated under reduced pressure to remove the solvent. The resulting residue was purified by silica gel column chromatography with eluent system B to give the title mixture of diastereomers 2j (207 mg, yield: 57.7%).

MS m/z (ESI): 606.2 [M+1].

Step 8

2-((4-(3-(4-Chloro-2-fluorophenyl)-2,3-dihydrobenzo[b][1,4]dioxan-5-yl)piperidin-1-yl)methyl)-1-((S)-oxetan-2-ylmethyl)-1H-benzo[d]imidazole-6-carboxylic acid (A Mixture of Diastereomers) 2

Compound 2j (206 mg, 0.34 mmol) was dissolved in 18 mL of a mixed solution of acetonitrile and water (V/V=5:1). Lithium hydroxide monohydrate (71 mg, 1.69 mmol) was added. The mixture was stirred at 40° C. for 18 h, cooled to room temperature, adjusted to pH 5-6 with aqueous citric acid solution (1 M), extracted with ethyl acetate (30 mL×3), dried over anhydrous sodium sulfate and concentrated under reduced pressure. The resulting residue was purified by preparative high performance liquid chromatography (column: Boston Phlex C18 150×30 mm, 5 μm; mobile phase 1: water (containing 10 mmol/L ammonium bicarbonate); mobile phase 2: acetonitrile; 15 min of gradient elution: 30% to 50%, flow rate: 30 mL/min) to give the title mixture of diastereomers 2 (120 mg, yield: 59.6%).

MS m/z (ESI): 592.1 [M+1].

$^1$H NMR (500 MHz, DMSO-d$_6$) δ 12.42-12.97 (brs, 1H), 8.20-8.28 (m, 1H), 7.74-7.83 (m, 1H), 7.61 (d, 1H), 7.55-7.58 (m, 1H), 7.48-7.54 (m, 1H), 7.38-7.44 (m, 1H), 6.70-6.90 (m, 3H), 5.40-7.49 (m, 1H), 5.01-5.13 (m, 1H), 4.72-4.84 (m, 1H), 4.59-4.67 (m, 1H), 4.39-4.51 (m, 2H), 4.31-4.38 (m, 1H), 4.04-4.13 (m, 1H), 3.86-3.95 (m, 1H), 3.71-3.79 (m, 1H), 2.91-3.01 (m, 1H), 2.77-2.88 (m, 2H), 2.61-2.72 (m, 1H), 2.33-2.44 (m, 1H), 2.07-2.25 (m, 2H), 1.73-1.81 (m, 1H), 1.63-1.73 (m, 2H), 1.54-1.63 (m, 1H).

Example 3

2-((4-(2-(4-Chloro-2-fluorophenyl)-2,3-dihydrobenzo[b][1,4]dioxan-5-yl)piperidin-1-yl)methyl)-1-((S)-oxetan-2-ylmethyl)-1H-benzo[d]imidazole-6-carboxylic acid (A Mixture of Diastereomers) 3

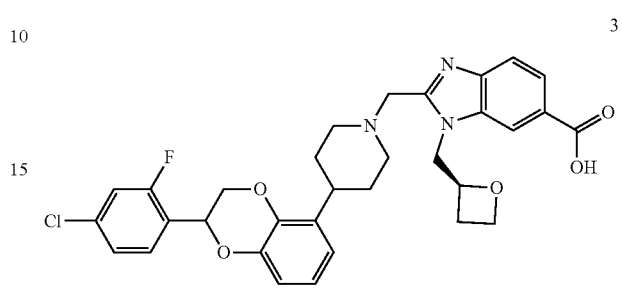

The title mixture of diastereomers 3 (7 mg, yield: 23.9%) was prepared by using the synthesis scheme of Example 2 and replacing 2d, the starting material of step 3, with 1-(4-chloro-2-fluorophenyl)-2-(2,6-dibromophenoxy)ethanol 2e.

MS m/z (ESI): 592.2 [M+1].

$^1$H NMR (500 MHz, DMSO-d$_6$) δ 12.56-12.77 (brs, 1H), 8.23-8.31 (m, 1H), 7.75-7.83 (m, 1H), 7.59-7.67 (m, 1H), 7.44-7.58 (m, 2H), 7.34-7.42 (m, 1H), 6.70-6.95 (m, 3H), 5.38-7.47 (m, 1H), 5.05-5.14 (m, 1H), 4.75-4.86 (m, 1H), 4.62-4.70 (m, 1H), 4.45-4.60 (m, 2H), 4.33-4.42 (m, 1H), 4.09-4.18 (m, 1H), 3.88-3.98 (m, 1H), 3.73-3.83 (m, 1H), 2.96-3.05 (m, 1H), 2.78-2.93 (m, 2H), 2.66-2.77 (m, 1H), 2.41-2.45 (m, 1H), 2.13-2.29 (m, 2H), 1.51-1.81 (m, 4H).

Example 4

2-((4-((S)-3-(4-Chloro-2-fluorophenyl)-2,3-dihydrobenzo[b][1,4]dioxan-5-yl)piperidin-1-yl)methyl)-1-(((S)-oxetan-2-yl)methyl)-1H-benzo[d]imidazole-6-carboxylic acid 4

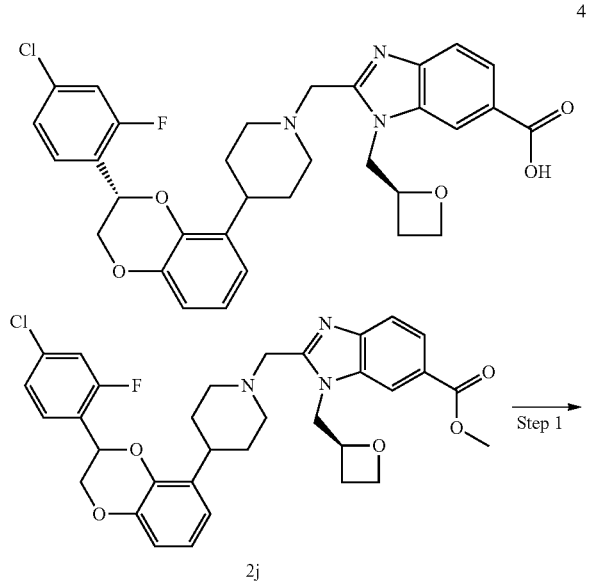

-continued

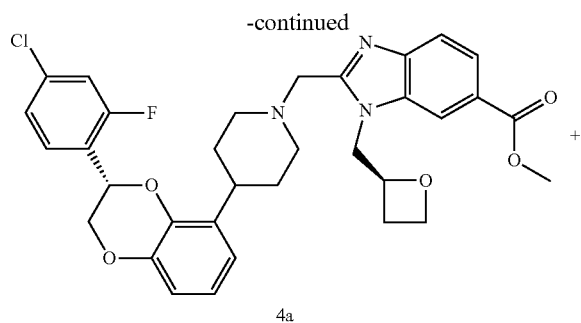
4a

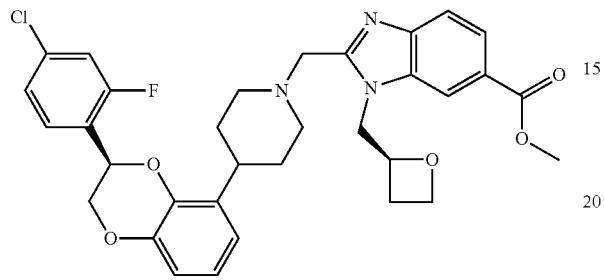
4b

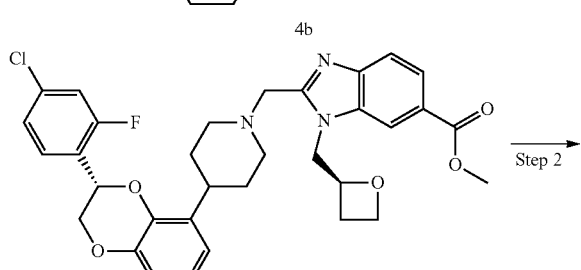
4a

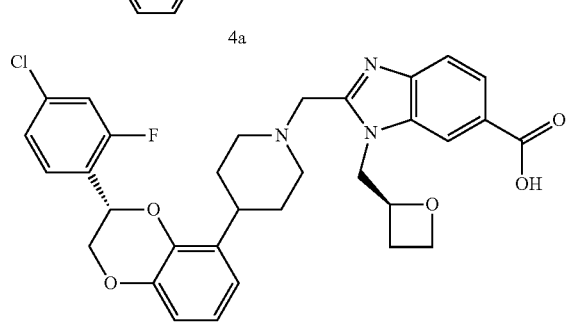
4

Step 1

Methyl 2-((4-((R)-3-(4-chloro-2-fluorophenyl)-2,3-dihydrobenzo[b][1,4]dioxan-5-yl)piperidin-1-yl)methyl)-1-(((S)-oxetan-2-yl)methyl)-1H-benzo[d]imidazole-6-carboxylate 4a Methyl 2-((4-((R)-3-(4-chloro-2-fluorophenyl)-2,3-dihydrobenzo[b][1,4]dioxan-5-yl)piperidin-1-yl)methyl)-1-(((S)-oxetan-2-yl)methyl)-1H-benzo[d]imidazole-6-carboxylate 4b Compound 2j (830 mg, 1.37 mmol) was resolved by preparative chiral chromatography (resolution conditions: CHIRALPAK IG 250×20 mm, 5 μm (with column protection); mobile phase: hexane/EtOH (0.1% DEA)=70/30 (V/V), flow rate: 20 mL/min). The corresponding fractions were collected and concentrated under reduced pressure to give the title products (415 mg, yield: 47.6%) and (340 mg, yield: 39%).

Single-configuration compound 4a (415 mg, yield: 47.6%) (shorter retention time):
MS m/z (ESI): 606.0 [M+1].
Preparative chiral chromatography: retention time 13.653 min.

Single-configuration compound 4b (340 mg, yield: 39%) (longer retention time):
MS m/z (ESI): 606.0 [M+1].
Preparative chiral chromatography: retention time 16.422 min.

Step 2

2-((4-((S)-3-(4-Chloro-2-fluorophenyl)-2,3-dihydrobenzo[b][1,4]dioxan-5-yl)piperidin-1-yl)methyl)-1-(((S)-oxetan-2-yl)methyl)-1H-benzo[d]imidazole-6-carboxylic acid 4

4a (415 mg, 0.68 mmol) was dissolved in 36 mL of a mixed solvent of acetonitrile and water (V:V=6:1). Lithium hydroxide monohydrate (145 mg, 3.46 mmol) was added. The mixture was stirred at 40° C. for 18 h. The reaction mixture was cooled to room temperature, adjusted to pH 5-6 with aqueous citric acid solution (1 M) and extracted with ethyl acetate (30 mL×3). The organic phase was concentrated under reduced pressure and then purified by high performance liquid chromatography (Gilson281, column: Boston Phlex C18 150×30 mm, 5 μm; mobile phase 1: water (containing 10 mmol/L ammonium bicarbonate); mobile phase 2: acetonitrile; 15 min of gradient elution: 30% to 50%, flow rate: 30 mL/min) to give the title product 4 (310 mg, yield: 76.46%).

MS m/z (ESI): 592.2 [M+1].
$^1$H NMR (500 MHz, DMSO-$d_6$) δ 12.42-12.97 (brs, 1H), 8.20-8.28 (m, 1H), 7.74-7.83 (m, 1H), 7.61 (d, 1H), 7.55-7.58 (m, 1H), 7.48-7.54 (m, 1H), 7.38-7.44 (m, 1H), 6.70-6.90 (m, 3H), 5.40-7.49 (m, 1H), 5.01-5.13 (m, 1H), 4.72-4.84 (m, 1H), 4.59-4.67 (m, 1H), 4.39-4.51 (m, 2H), 4.31-4.38 (m, 1H), 4.04-4.13 (m, 1H), 3.86-3.95 (m, 1H), 3.71-3.79 (m, 1H), 2.91-3.01 (m, 1H), 2.77-2.88 (m, 2H), 2.61-2.72 (m, 1H), 2.33-2.44 (m, 1H), 2.07-2.25 (m, 2H), 1.73-1.81 (m, 1H), 1.63-1.73 (m, 2H), 1.54-1.63 (m, 1H).

Example 5

2-((4-((S)-3-(4-Chloro-2-fluorophenyl)-2,3-dihydrobenzo[b][1,4]dioxan-5-yl)piperidin-1-yl)methyl)-3-((S)-oxetan-2-ylmethyl)-3H-imidazo[4,5-b]pyridine-5-carboxylic acid 5

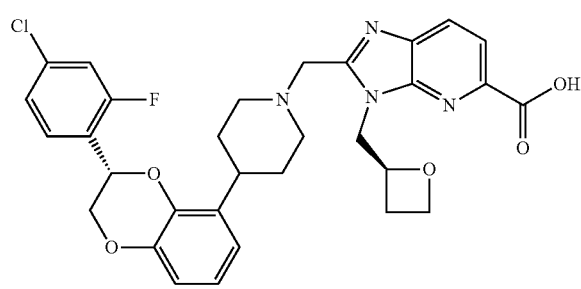
5

-continued

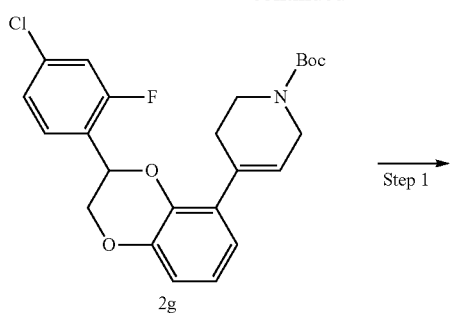

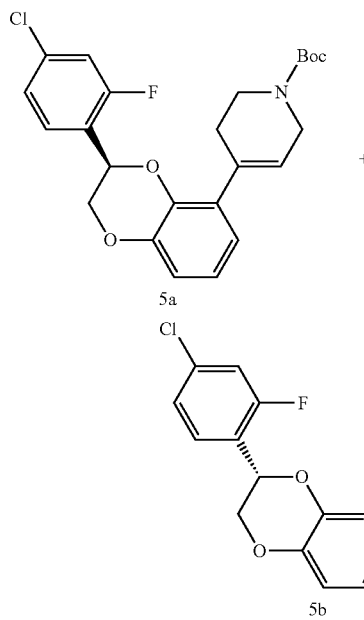

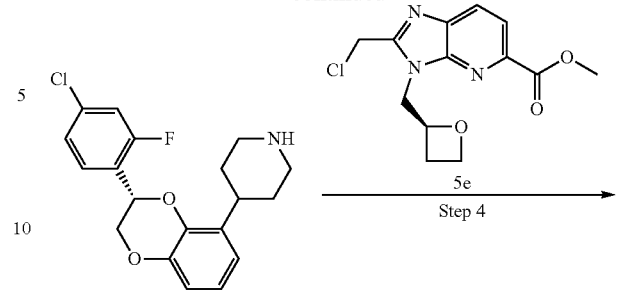

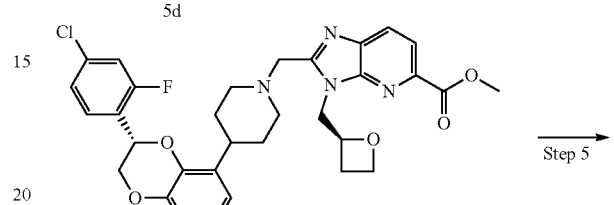

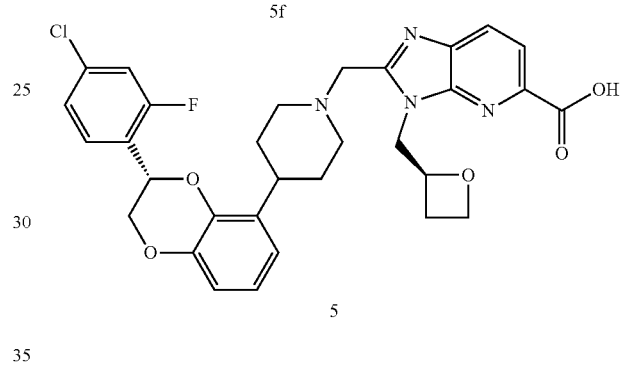

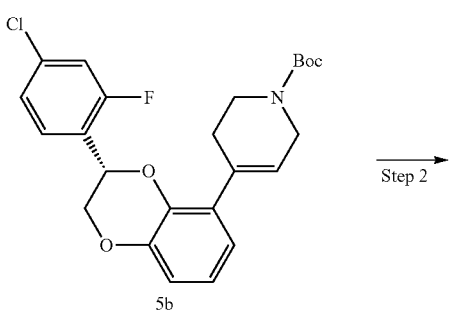

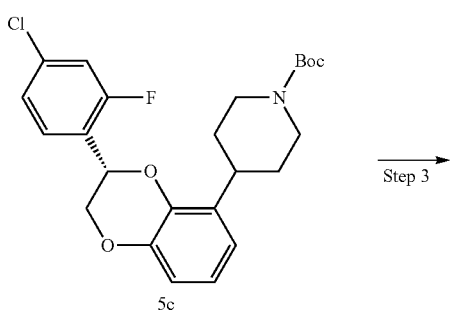

Step 1 tert-Butyl (R)-4-(3-(4-chloro-2-fluorophenyl)-2,3-dihydrobenzo[b][1,4]dioxan-5-yl)-5,6-dihydropyridine-1(2H)-carboxylate 5a tert-Butyl (S)-4-(3-(4-chloro-2-fluorophenyl)-2,3-dihydrobenzo[b][1,4]dioxan-5-yl)-5,6-dihydropyridine-1(2H)-carboxylate 5b Compound 2g (3.50 g, 7.85 mmol) was resolved by preparative chiral chromatography (resolution conditions: DAICEL CHIRALPAK®AD chiral preparative column, 250×25 mm, 10 μm; mobile phase: Supercritical $CO_2$:ETOH (+0.1% DEA)=85:15 (V/V), flow rate: 70 mL/min). The corresponding fractions were collected and concentrated under reduced pressure to give the title products (1.62 g, yield: 46.2%) and (1.65 g, yield: 47.1%).

Single-configuration compound 5a (1.62 g, yield: 46.2%) (shorter retention time):

MS m/z (ESI): 389.9 [M−55].

Chiral HPLC analysis: retention time 2.072 min, chiral purity: 98.76% (column: DAICEL CHIRALPAK®AD-3 100×3 mm, 3 μm; mobile phase: Supercritical $CO_2$:ETOH (+0.1% DEA)=95:5 to 60:40 (V/V).

Single-configuration compound 5b (1.65 g, yield: 47.1%) (longer retention time):

MS m/z (ESI): 389.9 [M−55].

Chiral HPLC analysis: retention time 2.348 min, chiral purity: 98.44% (column: DAICEL CHIRALPAK®AD-3

Step 2 tert-Butyl (S)-4-(3-(4-chloro-2-fluorophenyl)-2,3-dihydrobenzo[b][1,4]dioxan-5-yl)piperidine-1-carboxylate 5c 5b (600 mg, 1.35 mmol) was dissolved in 13.2 mL of a mixed solution of ethyl acetate and 1,2-dichlorobenzene (V:V=10:1). Palladium/carbon (300 mg, 10%) was added. The system was purged three times with hydrogen. The mixture was stirred at room temperature for 1 h and filtered through celite. The filtrate was concentrated under reduced pressure and then purified by silica gel column chromatography with eluent system B to give the title compound 5c (530 mg, yield: 87.9%).

MS m/z (ESI): 392.0 [M−55].

$^1$H NMR (500 MHz, CDCl$_3$) δ 7.43 (t, 1H), 7.25 (dd, 1H), 7.18 (dd, 1H), 6.89 (t, 1H), 6.85-6.80 (m, 2H), 5.44 (dd, 1H), 4.43 (dd, 1H), 4.24 (brs, 2H), 3.99 (dd, 1H), 3.11-3.05 (m, 1H), 2.81 (brs, 2H), 1.88 (d, 1H), 1.80 (d, 1H), 1.67-1.62 (m, 2H), 1.49 (s, 9H).

Step 3

(S)-4-(3-(4-Chloro-2-fluorophenyl)-2,3-dihydrobenzo[b][1,4]dioxan-5-yl)piperidine 5d Compound 5c (530 mg, 1.18 mmol) was dissolved in dichloromethane (10 mL). Trifluoroacetic acid (1 mL) was added at 0° C. The reaction mixture was stirred at 0° C. to room temperature for 2 h. The reaction mixture was concentrated. Saturated sodium bicarbonate solution (30 mL) was added to the reaction mixture. The mixture was extracted with ethyl acetate (30 mL×3). The organic phases were combined, washed with saturated sodium chloride solution (30 mL), dried over anhydrous sodium sulfate and filtered. The filtrate was concentrated under reduced pressure to give the crude title compound 5d (411 mg). The product was directly used in the next step without being purified.

Step 4

Methyl 2-((4-((S)-3-(4-chloro-2-fluorophenyl)-2,3-dihydrobenzo[b][1,4]dioxan-5-yl)piperidin-1-yl)methyl)-3-((S)-oxetan-2-ylmethyl)-3H-imidazo[4,5-b]pyridine-5-carboxylate 5f Compound 5d (411 mg, 1.18 mmol) and the compound methyl (S)-2-(chloromethyl)-3-(oxetan-2-ylmethyl)-3H-imidazo[4,5-b]pyridine-5-carbonate 5e (350 mg, 1.18 mmol, prepared using the method for intermediate 27 disclosed on page 72 of the specification in patent application WO2018109607A1) are dissolved in acetonitrile (40 mL). Potassium carbonate (441 mg, 3.19 mmol) was added. The reaction mixture was heated to 70° C. and stirred for 3 h. After concentration under reduced pressure, the residue was purified by silica gel column chromatography with eluent system A to give the title compound 5f (710 mg, yield: 98.9%).

MS m/z (ESI): 607.2 [M+1].

Step 5

2-((4-((S)-3-(4-Chloro-2-fluorophenyl)-2,3-dihydrobenzo[b][1,4]dioxan-5-yl)piperidin-1-yl)methyl)-3-((S)-oxetan-2-ylmethyl)-3H-imidazo[4,5-b]pyridine-5-carboxylic acid 5

Compound 5f (710 mg, 1.17 mmol) was dissolved in 54 mL of a mixed solvent of acetonitrile, tetrahydrofuran and water (V:V:V=5:3:1). Lithium hydroxide monohydrate (246 mg, 5.86 mmol) was added. The reaction mixture was stirred at 40° C. for 1 h. The reaction mixture was cooled to room temperature, adjusted to pH 5-6 with aqueous citric acid solution (1 M) and extracted with ethyl acetate (30 mL×3). The organic phases were combined, concentrated under reduced pressure and then purified by high performance liquid chromatography (Waters-2545, column: SharpSil-T, 30×50 mm, 5 μm; mobile phase A: water (containing 10 mmol/L ammonium bicarbonate); mobile phase B: acetonitrile; 15 min of gradient elution: 36% to 49%, flow rate: 30 mL/min) to give the title product 5 (620 mg, yield: 89.4%).

MS m/z (ESI): 593.1 [M+1].

$^1$H NMR (500 MHz, DMSO-d$_6$) δ 7.96 (d, 1H), 7.89 (d, 1H), 7.57 (dd, 1H), 7.53 (t, 1H), 7.43 (dd, 1H), 6.86-6.78 (m, 3H), 5.47 (dd, 1H), 5.17-5.12 (m, 1H), 4.81 (dd, 1H), 4.67 (dd, 1H), 4.50-4.42 (m, 2H), 4.37-4.33 (m, 1H), 4.10 (dd, 1H), 3.96 (d, 1H), 3.84 (d, 1H), 2.96 (d, 1H), 2.91-2.82 (m, 2H), 2.70-2.63 (m, 1H), 2.49-2.43 (m, 1H), 2.23-2.16 (m, 2H), 1.79-1.70 (m, 3H), 1.65-1.56 (m, 1H).

Example 6

2-(((S)-4-((S)-3-(4-Chloro-2-fluorophenyl)-2,3-dihydrobenzo[b][1,4]dioxan-5-yl)-2-methylpiperazin-1-yl)methyl)-1-(((S)-oxetan-2-yl)methyl)-1H-benzo[d]imidazole-6-carboxylic acid 6

-continued

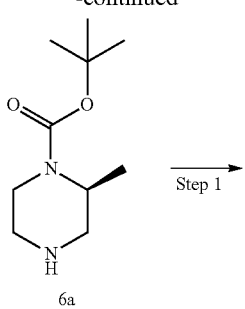
6a

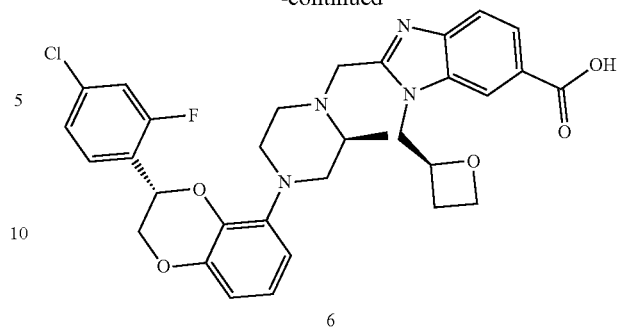
6

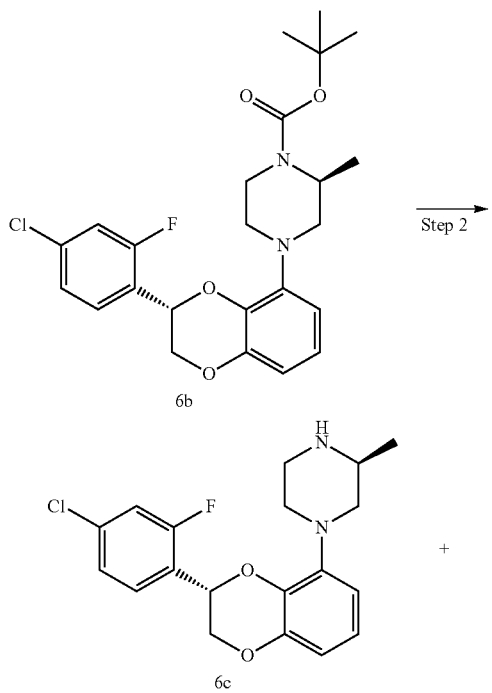

Step 1 tert-Butyl (S)-4-((S)-3-(4-chloro-2-fluorophenyl)-2,3-dihydrobenzo[b][1,4]dioxan-5-yl)-2-methylpiperazine-1-carboxylate 6b Compound 2f (260 mg, 0.76 mmol) and tert-butyl (S)-2-methylpiperazine-1-carboxylate 6a (152 mg, 0.76 mmol, Accela ChemBio Inc.) were dissolved in 10 mL of 1,4-dioxane. Methanesulfonato(2-dicyclohexylphosphino-2″,6″-diisopropoxy-1,1″-biphenyl)(2″-amino-1,1″-biphenyl-2-yl)palladium(II) (27 mg, 0.03 mmol, Bide Pharmatech Ltd.) and cesium carbonate (493 mg, 1.51 mmol, Accela ChemBio Inc.) were added. The mixture was heated to 90° C. and stirred for 10 h under nitrogen atmosphere. The reaction mixture was cooled to room temperature and filtered. The organic phase was concentrated under reduced pressure and then purified by high performance liquid chromatography (column: Boston Phlex Prep C18 150×30 mm, 5 μm; mobile phase 1: water (containing 10 mmol/L ammonium bicarbonate); mobile phase 2: acetonitrile; 15 min of gradient elution: 75% to 95%, flow rate: 30 mL/min) to give the title product 6b (10 mg, yield: 3%).

MS m/z (ESI): 463.1 [M+1].

Step 2

(S)-1-((S)-3-(4-chloro-2-fluorophenyl)-2,3-dihydrobenzo[b][1,4]dioxan-5-yl)-3-methylpiperazine 6c Compound 6b (8 mg, 0.017 mmol) was dissolved in 5 mL of dichloromethane. 0.5 mL of trifluoroacetic acid was added at 0° C. The mixture was stirred at that temperature for another 2 h. The reaction mixture was warmed to room temperature and concentrated under reduced pressure to give the title product 6c (8 mg, yield: 97.1%).

MS m/z (ESI): 363.1 [M+1].

Step 3

Methyl 2-(((S)-4-((S)-3-(4-Chloro-2-fluorophenyl)-2,3-dihydrobenzo[b][1,4]dioxan-5-yl)-2-methylpiperazin-1-yl)methyl)-1-(((S)-oxetan-2-yl)methyl)-1H-benzo[d]imidazole-6-carboxylate 6d Compound 6c (8 mg, 0.022 mmol) and compound 1m (7 mg, 0.023 mmol) were dissolved in 3 mL of acetonitrile. Potassium carbonate (20 mg, 0.145 mmol, Accela ChemBio Inc.) was added at room temperature. The mixture was heated to 70° C. and reacted for 3 h. The reaction mixture was cooled to room temperature and concentrated under

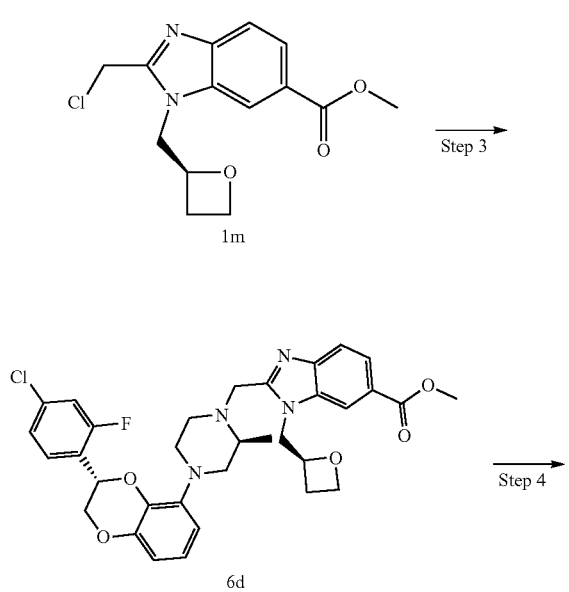

reduced pressure. The resulting residue was purified by silica gel column chromatography with eluent system A to give the title product 6d (13 mg, yield: 94.9%).

MS m/z (ESI): 621.2 [M+1].

Step 4

2-(((S)-4-((S)-3-(4-Chloro-2-fluorophenyl)-2,3-dihydrobenzo[b][1,4]dioxan-5-yl)-2-methylpiperazin-1-yl)methyl)-1-(((S)-oxetan-2-yl)methyl)-1H-benzo[d]imidazole-6-carboxylic acid 6

Compound 6d (13 mg, 0.021 mmol) was dissolved in 3 mL of acetonitrile. 0.6 mL of water and lithium hydroxide monohydrate (8 mg, 0.19 mmol, Accela ChemBio Inc.) were added. The mixture was heated to 40° C. and reacted for 6 h. The reaction mixture was cooled, then adjusted to pH 5-6 with citric acid (2.5 M) and concentrated under reduced pressure. The resulting residue was purified by high performance liquid chromatography (column: SharpSil-T Prep C18 50×30 mm, 5 μm; mobile phase 1: water (containing 10 mmol/L ammonium bicarbonate); mobile phase 2: acetonitrile; 17 min of gradient elution: 30% to 47%, flow rate: 30 mL/min) to give the title product 6 (10 mg, yield: 78.7%).

MS m/z (ESI): 607.2 [M+1].

$^1$H NMR (500 MHz, DMSO-$d_6$) δ 8.19 (s, 1H), 7.78-7.80 (dd, 1H), 7.55-7.60 (m, 3H), 7.42-7.45 (dd, 1H), 6.76-6.80 (t, 1H), 6.58-6.60 (dd, 1H), 6.48-6.51 (dd, 1H), 5.41-5.43 (dd, 1H), 5.13-5.18 (m, 1H), 4.67-4.77 (m, 2H), 4.44-4.49 (m, 2H), 4.32-4.35 (d, 1H), 4.25-4.29 (m, 1H), 4.07-4.11 (dd, 1H), 3.59-3.62 (d, 1H), 3.32-3.34 (d, 1H), 3.02-3.05 (d, 1H), 2.78-2.82 (m, 1H), 2.64-2.69 (m, 3H), 2.35-2.41 (m, 3H), 1.09-1.10 (d, 3H).

Example 7

2-(((S)-4-((S)-3-(4-Chloro-2-fluorophenyl)-2,3-dihydrobenzo[b][1,4]dioxan-5-yl)-2-methylpiperidin-1-yl)methyl)-1-(((S)-oxetan-2-yl)methyl)-1H-benzo[d]imidazole-6-carboxylic acid 7

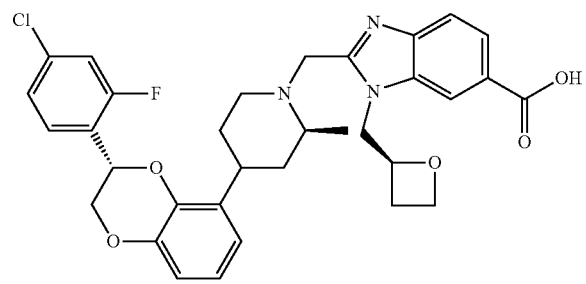

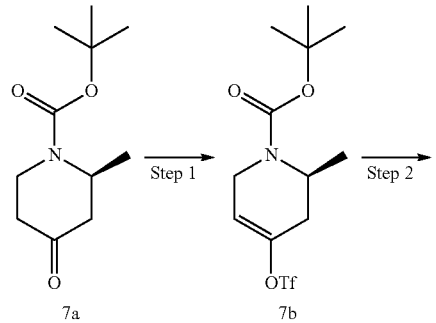

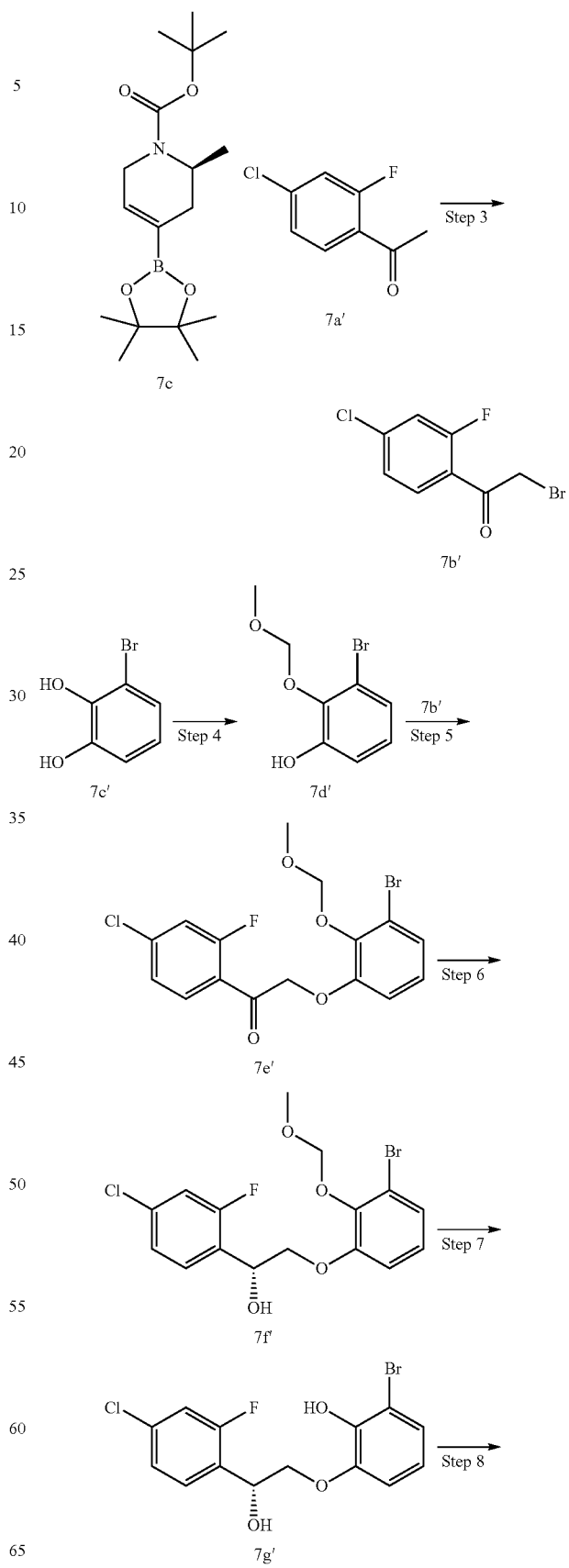

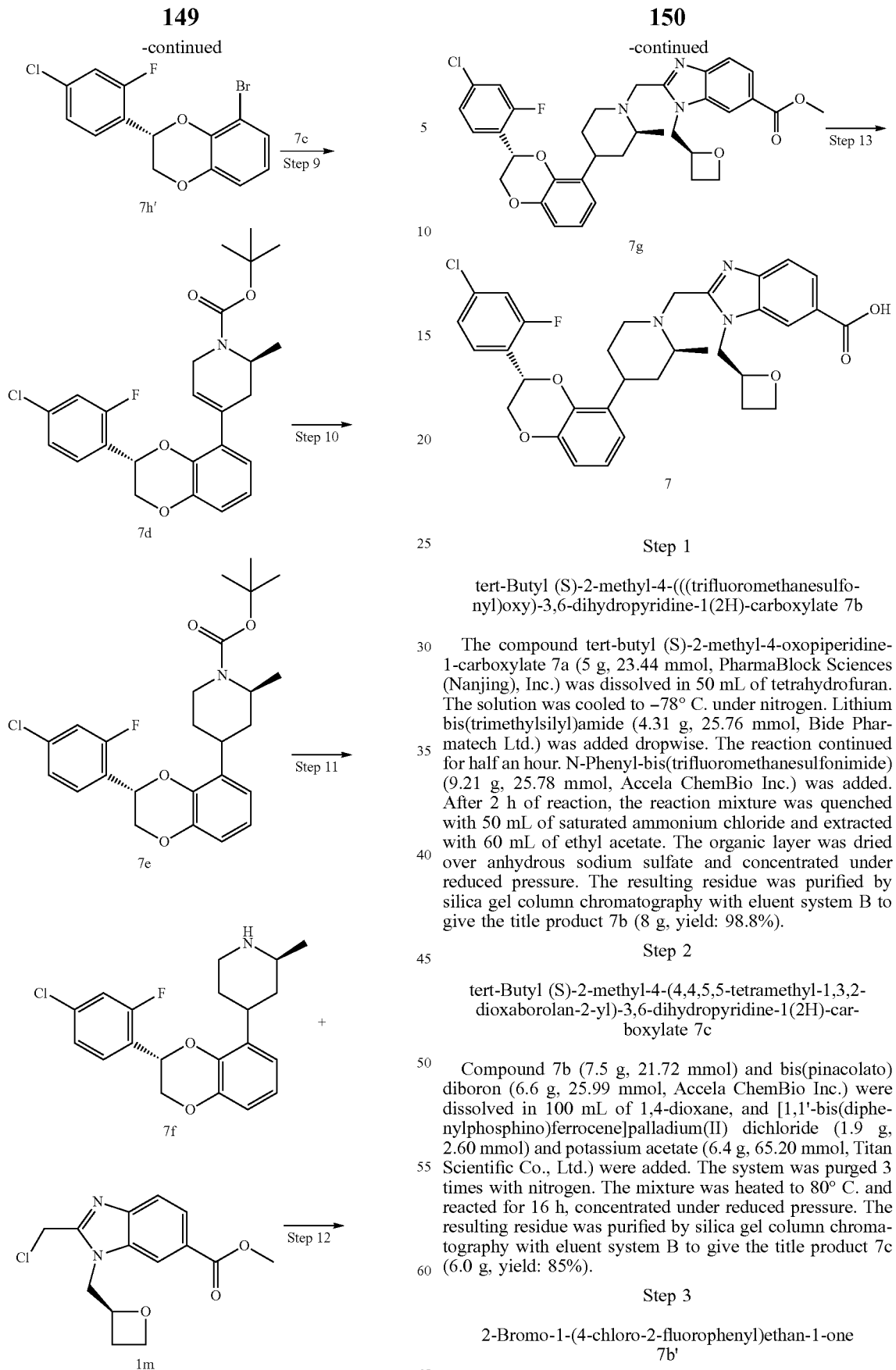

Step 1 tert-Butyl (S)-2-methyl-4-(((trifluoromethanesulfonyl)oxy)-3,6-dihydropyridine-1(2H)-carboxylate 7b The compound tert-butyl (S)-2-methyl-4-oxopiperidine-1-carboxylate 7a (5 g, 23.44 mmol, PharmaBlock Sciences (Nanjing), Inc.) was dissolved in 50 mL of tetrahydrofuran. The solution was cooled to −78° C. under nitrogen. Lithium bis(trimethylsilyl)amide (4.31 g, 25.76 mmol, Bide Pharmatech Ltd.) was added dropwise. The reaction continued for half an hour. N-Phenyl-bis(trifluoromethanesulfonimide) (9.21 g, 25.78 mmol, Accela ChemBio Inc.) was added. After 2 h of reaction, the reaction mixture was quenched with 50 mL of saturated ammonium chloride and extracted with 60 mL of ethyl acetate. The organic layer was dried over anhydrous sodium sulfate and concentrated under reduced pressure. The resulting residue was purified by silica gel column chromatography with eluent system B to give the title product 7b (8 g, yield: 98.8%).

Step 2 tert-Butyl (S)-2-methyl-4-(4,4,5,5-tetramethyl-1,3,2-dioxaborolan-2-yl)-3,6-dihydropyridine-1(2H)-carboxylate 7c Compound 7b (7.5 g, 21.72 mmol) and bis(pinacolato)diboron (6.6 g, 25.99 mmol, Accela ChemBio Inc.) were dissolved in 100 mL of 1,4-dioxane, and [1,1'-bis(diphenylphosphino)ferrocene]palladium(II) dichloride (1.9 g, 2.60 mmol) and potassium acetate (6.4 g, 65.20 mmol, Titan Scientific Co., Ltd.) were added. The system was purged 3 times with nitrogen. The mixture was heated to 80° C. and reacted for 16 h, concentrated under reduced pressure. The resulting residue was purified by silica gel column chromatography with eluent system B to give the title product 7c (6.0 g, yield: 85%).

Step 3

2-Bromo-1-(4-chloro-2-fluorophenyl)ethan-1-one 7b'

The compound 1-(4-chloro-2-fluorophenyl)ethan-1-one 7a' (46.51 g, 269 mmol, Accela ChemBio Inc.) was dissolved in 400 mL of tetrahydrofuran, and 10 mL of a suspension of pyridinium tribromide (88 g, 275 mmol, Accela ChemBio Inc.) in tetrahydrofuran was added to the above system. The mixture was reacted at room temperature for 2 h. The reaction mixture was cooled to room temperature and filtered. The filtrate was diluted with 50 mL of ethyl acetate and washed with 50 mL of water. The organic layer was dried over anhydrous sodium sulfate, filtered and then concentrated to dryness by rotary evaporation. The resulting solid was triturated with 11 mL of a mixed solution of ethyl acetate and n-hexane (V:V=1:10). The mixture was filtered. The filter cake was dried under reduced pressure to give the title product 7b' (64.6 g, yield: 95%).

Step 4

3-Bromo-2-(methoxymethoxy)phenol 7d'

3-Bromobenzene-1,2-diol 7c' (50 g, 264 mmol, Bide Pharmatech Ltd.) was dissolved in 1000 mL of dichloromethane. Bromomethoxymethane (33 g, 264 mmol, Shanghai Titan Scientific Co., Ltd.) was added at 0° C. The mixture was stirred at that temperature for another 2 h and washed with 200 mL of water. The organic phase was dried and concentrated to dryness by rotary evaporation. The resulting residue was purified by silica gel column chromatography with eluent system B to give the title product 7d' (25 g, yield: 40.5%).

MS m/z (ESI): 233.0 [M+1].

Step 5

2-(3-Bromo-2-(methoxymethoxy)phenoxy)-1-(4-chloro-2-fluorophenyl)ethan-1-one 7e'

Compound 7d' (37.5 g, 103 mmol) and compound 7b' (30.5 g, 103 mmol) were dissolved in 200 mL of acetonitrile. Potassium carbonate (28.5 g, 206 mmol, Accela ChemBio Inc.) was added at room temperature. The mixture was warmed to room temperature, reacted for 2 h and concentrated under reduced pressure. The resulting residue was purified by silica gel column chromatography with eluent system B to give the title product 7e' (36 g, yield: 86.6%).

Step 6

(R)-2-(3-Bromo-2-(methoxymethoxy)phenoxy)-1-(4-chloro-2-fluorophenyl)ethan-1-one 7f'

Compound 7e' (5 g, 12.4 mmol) was dissolved in 60 mL of tetrahydrofuran. Borane dimethyl sulfide complex (1.23 mg, 16.2 mmol, Shanghai Titan Scientific Co., Ltd.) was added under nitrogen atmosphere. The mixture was heated to 40° C. Diphenyl-[(2R)-pyrrolin-2-yl]methanol was added in batches. The mixture was reacted at 45° C. for 3 h. The reaction mixture was quenched with 5 mL of methanol and extracted with 50 mL of water and 60 mL of ethyl acetate. The organic phase was dried over anhydrous sodium sulfate, filtered and concentrated under reduced pressure to give the title product 7f' (5 g, yield: 99.5%).

Step 7

(R)-2-Bromo-6-(2-(4-bromo-2-fluorophenyl)-2-hydroxyethoxy)phenol 7g'

Compound 7f' (5 g, 12.3 mmol) was dissolved in 100 mL of a mixed solution of dichloromethane and dioxane hydrochloride (V:V=4:1). The mixture was heated to 35° C. and reacted for 2 h. Diphenyl-[(2R)-pyrrolin-2-yl]methanol was added in batches. The mixture was reacted at 35° C. for 2 h, concentrated under reduced pressure and exacted with 50 mL of water and 60 mL of ethyl acetate. The organic phase was dried over anhydrous sodium sulfate, filtered and concentrated under reduced pressure to give the title product 7g' (4 g, yield: 89.7%).

MS m/z (ESI): 358.9 [M−1].

Step 8

(S)-8-Bromo-2-(4-chloro-2-fluorophenyl)-2,3-dihydrobenzo[b][1,4]dioxane 7h'

Compound 7g' (4 g, 11.1 mmol) was dissolved in 60 mL of tetrahydrofuran. Triphenylphosphine (4.35 g, 16.6 mmol, Sinopharm Chemical Reagent Co., Ltd.) was added under nitrogen atmosphere. Diisopropyl azodicarboxylate (3.36 g, 16.6 mmol, Accela ChemBio Inc.) was added dropwise under ice bath conditions. The mixture was reacted at that temperature for 0.5 h, concentrated under reduced pressure and extracted with 50 mL of water and 60 mL of ethyl acetate. The organic phase was dried, filtered and then concentrated under reduced pressure. The resulting residue was purified by silica gel column chromatography with eluent system B to give the title product 7h' (2.5 g, yield: 65.8%).

MS m/z (ESI): 342.9 [M+1].

Step 9 tert-Butyl (S)-4-((S)-3-(4-chloro-2-fluorophenyl)-2,3-dihydrobenzo[b][1,4]dioxan-5-yl)-2-methyl-3,6-dihydropyridine-1(2H)-carboxylate 7d 7h' (2.0 g, 5.82 mmol) and compound 7c (2.8 g, 8.66 mmol) were dissolved in 36 mL of a mixed solution of 1,4-dioxane and water (V:V=5:1). Sodium carbonate (1.23 g, 11.6 mmol) and tetrakis(triphenylphosphine)palladium (670 mg, 0.58 mmol, Titan Scientific Co., Ltd.) were added. The mixture was stirred at 90° C. for 12 h under nitrogen, cooled to room temperature, filtered and concentrated under reduced pressure to remove the solvent. The resulting residue was purified by silica gel column chromatography with eluent system B to give the title compound 7d (1.2 g, yield: 44.8%).

MS m/z (ESI): 404.1 [M−55].

Step 10 tert-Butyl (2S)-4-((S)-3-(4-chloro-2-fluorophenyl)-2,3-dihydrobenzo[b][1,4]dioxan-5-yl)-2-methylpiperidine-1-carboxylate 7e 7d (1.2 g, 2.61 mmol) was dissolved in 22 mL of a mixed solution of ethyl acetate and 1,2-dichlorobenzene (V:V=10:1). 10% palladium on carbon (240 mg, 0.52 mmol) was added. The system was purged 3 times with hydrogen, and the mixture was stirred at room temperature for 1 h under hydrogen and filtered. The filtrate was concentrated under reduced pressure to remove the solvent to give the title compound 7e (1.2 g, yield: 99.56%).

MS m/z (ESI): 406.1 [M−55].

Step 11

(2S)-4-((S)-3-(4-chloro-2-fluorophenyl)-2,3-dihydrobenzo[b][1,4]dioxan-5-yl)-2-methylpiperidine 7f 7e (1.2 g, 2.59 mmol) was dissolved in 20 mL of dichloromethane. The solution was cooled to 0° C. 2 mL of trifluoroacetic acid was added. The mixture was warmed to room temperature, stirred for 1 h and concentrated under reduced pressure to remove the solvent to give the title compound 7f (940 mg, yield: 99.95%).

MS m/z (ESI): 362.1 [M+1].

Step 12

Methyl 2-(((2S)-4-((S)-3-(4-chloro-2-fluorophenyl)-2,3-dihydrobenzo[b][1,4]dioxan-5-yl)-2-methylpiperidin-1-yl)methyl)-1-(((S)-oxetan-2-yl)methyl)-1H-benzo[d]imidazole-6-carboxylate 7g Compound 1m (780 mg, 2.65 mmol) and compound 7f (940 mg, 2.60 mmol) were dissolved in 30 mL of acetonitrile. Potassium carbonate (3.0 g, 21.71 mmol) was added. The mixture was stirred at 60° C. for 12 h, cooled to room temperature and concentrated under reduced pressure. The resulting residue was purified by silica gel column chromatography with eluent system A to give the title compound 7g (700 mg, yield: 43.5%).

MS m/z (ESI): 620.2 [M+1].

Step 13

2-(((S)-4-((S)-3-(4-Chloro-2-fluorophenyl)-2,3-dihydrobenzo[b][1,4]dioxan-5-yl)-2-methylpiperidin-1-yl)methyl)-1-(((S)-oxetan-2-yl)methyl)-1H-benzo[d]imidazole-6-carboxylic acid 7

Compound 7g (700 mg, 1.13 mmol) was dissolved in 20 mL of acetonitrile. 4 mL of water and lithium hydroxide monohydrate (300 mg, 7.15 mmol, Accela ChemBio Inc.) were added. The mixture was heated to 40° C. and reacted for 6 h. After cooling, 2.5 M citric acid was added to adjust the pH to 5-6, and a white solid precipitated. The mixture was filtered. The filter cake was washed with water and dried to give the title product 7 (550 mg, yield: 80.39%).

MS m/z (ESI): 606.2 [M+1].

$^1$H NMR (500 MHz, DMSO-d$_6$) δ 12.73 (brs, 1H), 8.27 (s, 1H), 7.79-7.81 (dd, 1H), 7.64-7.65 (d, 1H), 7.55-7.59 (m, 2H), 7.42-7.44 (dd, 1H), 6.79-6.87 (m, 3H), 5.47-5.49 (dd, 1H), 4.80-4.84 (m, 1H), 4.61-4.64 (dd, 2H), 4.39-4.53 (m, 3H), 4.06-4.12 (m, 2H), 3.86 (brs, 1H), 3.20-3.23 (m, 2H), 2.57-2.74 (m, 3H), 2.40-2.47 (m, 1H), 1.86-1.91 (m, 1H), 1.60-1.72 (m, 3H), 1.09-1.10 (d, 3H).

Example 8

2-(((S)-4-((S)-3-(4-Chloro-2-fluorophenyl)-2,3-dihydrobenzo[b][1,4]dioxan-5-yl)-2-methylpiperazin-1-yl)methyl)-3-((S)-oxetan-2-ylmethyl)-3H-imidazo[4,5-b]pyridine-5-carboxylic acid 8

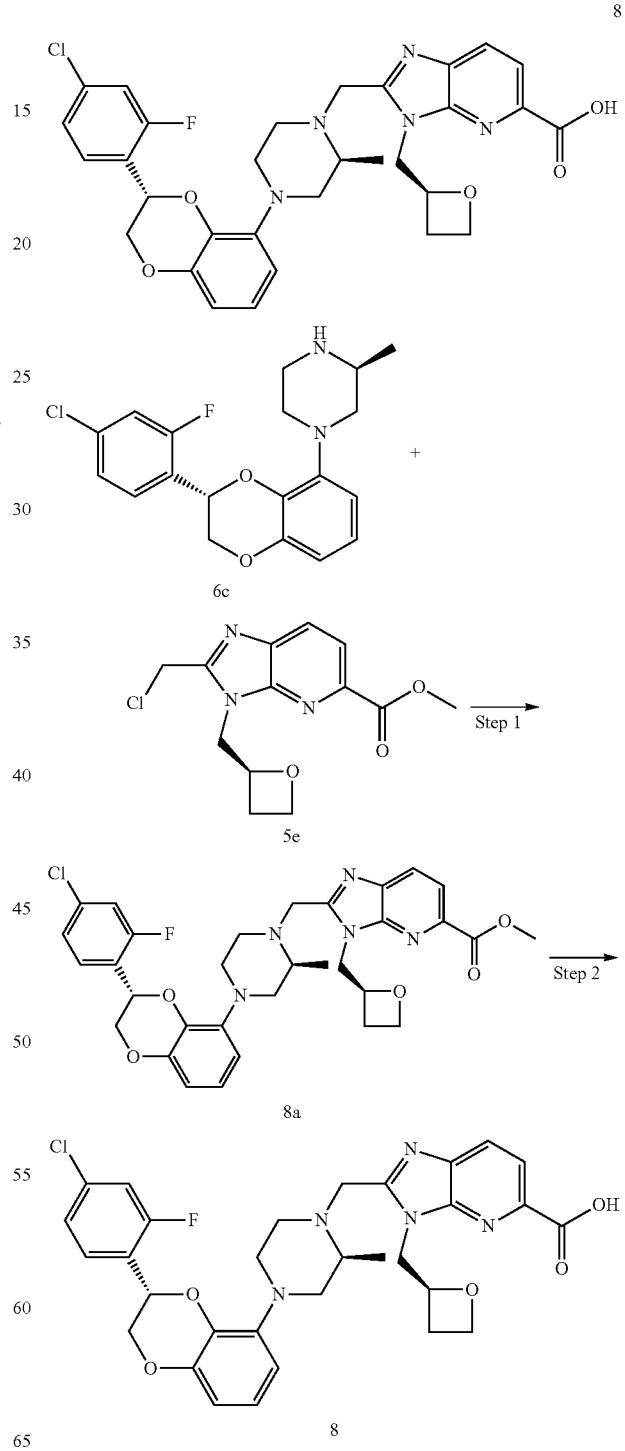

Step 1

Methyl 2-(((S)-4-((S)-3-(4-chloro-2-fluorophenyl)-2,3-dihydrobenzo[b][1,4]dioxan-5-yl)-2-methylpiperazin-1-yl)methyl)-3-((S)-oxetan-2-ylmethyl)-3H-imidazo[4,5-b]pyridine-5-carboxylate 8a The trifluoroacetate salt of compound 6c (70 mg, 0.19 mmol) and compound 5e (57 mg, 0.19 mmol) were dissolved in 5 mL of acetonitrile. Potassium carbonate (134 mg, 0.97 mmol, Accela ChemBio (Shanghai) Inc.) and tetrabutylammonium iodide (10 mg, 0.03 mmol) were added at room temperature. The mixture was heated to 50° C. and reacted for 16 h. The reaction mixture was cooled to room temperature and concentrated under reduced pressure. The resulting residue was purified by silica gel column chromatography with eluent system A to give the title product 8a (103 mg, yield: 85.8%).

MS m/z (ESI): 622.2 [M+1].

Step 2

2-(((S)-4-((S)-3-(4-Chloro-2-fluorophenyl)-2,3-dihydrobenzo[b][1,4]dioxan-5-yl)-2-methylpiperazin-1-yl)methyl)-3-((S)-oxetan-2-ylmethyl)-3H-imidazo[4,5-b]pyridine-5-carboxylic acid 8

Compound 8a (103 mg, 0.165 mmol) was dissolved in 5 mL of acetonitrile. 0.6 mL of water and lithium hydroxide monohydrate (35 mg, 0.83 mmol, Accela ChemBio (Shanghai) Inc.) were added. The mixture was heated to 40° C. and reacted for 16 h. The reaction mixture was cooled, then adjusted to pH 5-6 with citric acid (0.5 M), concentrated under reduced pressure and purified by high performance liquid chromatography (column: SharpSil-T Prep C18 50×30 mm, 5 μm; mobile phase: water (containing 10 mmol/L ammonium bicarbonate), mobile phase: acetonitrile; 12 min of gradient elution: 33% to 45%, flow rate: 30 mL/min) to give the title product 8 (70 mg, yield: 69.5%).

MS m/z (ESI): 608.2 [M+1].

$^1$H NMR (500 MHz, DMSO-$d_6$) δ 7.99 (d, 1H), 7.91 (d, 1H), 7.60-7.56 (m, 2H), 7.45 (d, 1H), 6.78 (t, 1H), 6.59 (d, 1H) 6.49 (d, 1H), 5.42 (dd, 1H), 5.23-5.18 (m, 1H), 4.80-4.71 (m, 2H), 4.49-4.41 (m, 3H), 4.19-4.14 (m, 1H), 4.08 (d, 1H), 3.60 (d, 1H), 3.38 (d, 1H), 3.05 (d, 1H), 2.78 (t, 1H), 2.67-2.59 (m, 3H), 2.56-2.53 (m, 1H), 2.44-2.30 (m, 2H), 1.11 (d, 3H).

Example 9

2-((4-(2-(Benzo[d]thiazol-2-yl)-2,3-dihydrobenzo[b][1,4]dioxan-5-yl)piperidin-1-yl)methyl)-1-(((S)-oxetan-2-yl)methyl)-1H-benzo[d]imidazole-6-carboxylic acid (A Mixture of Diastereomers) 9

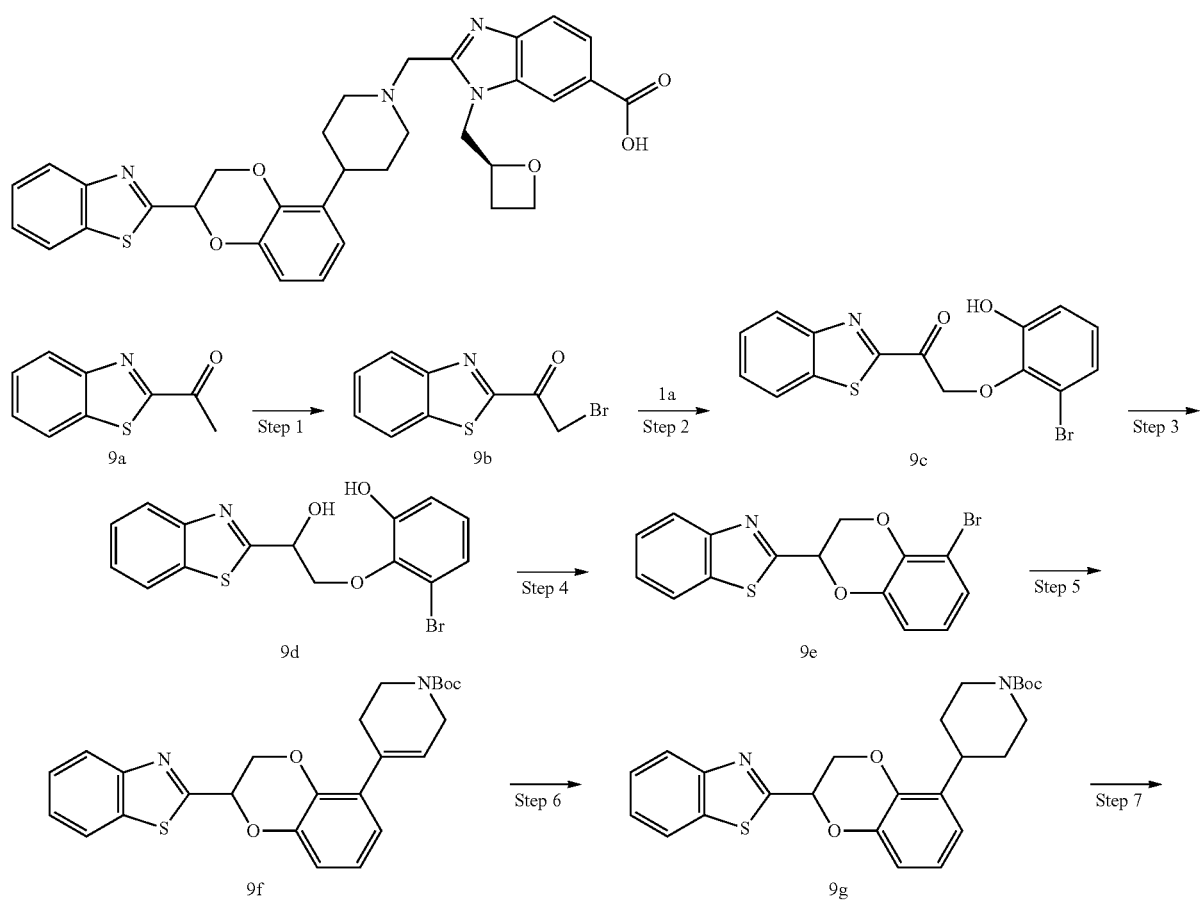

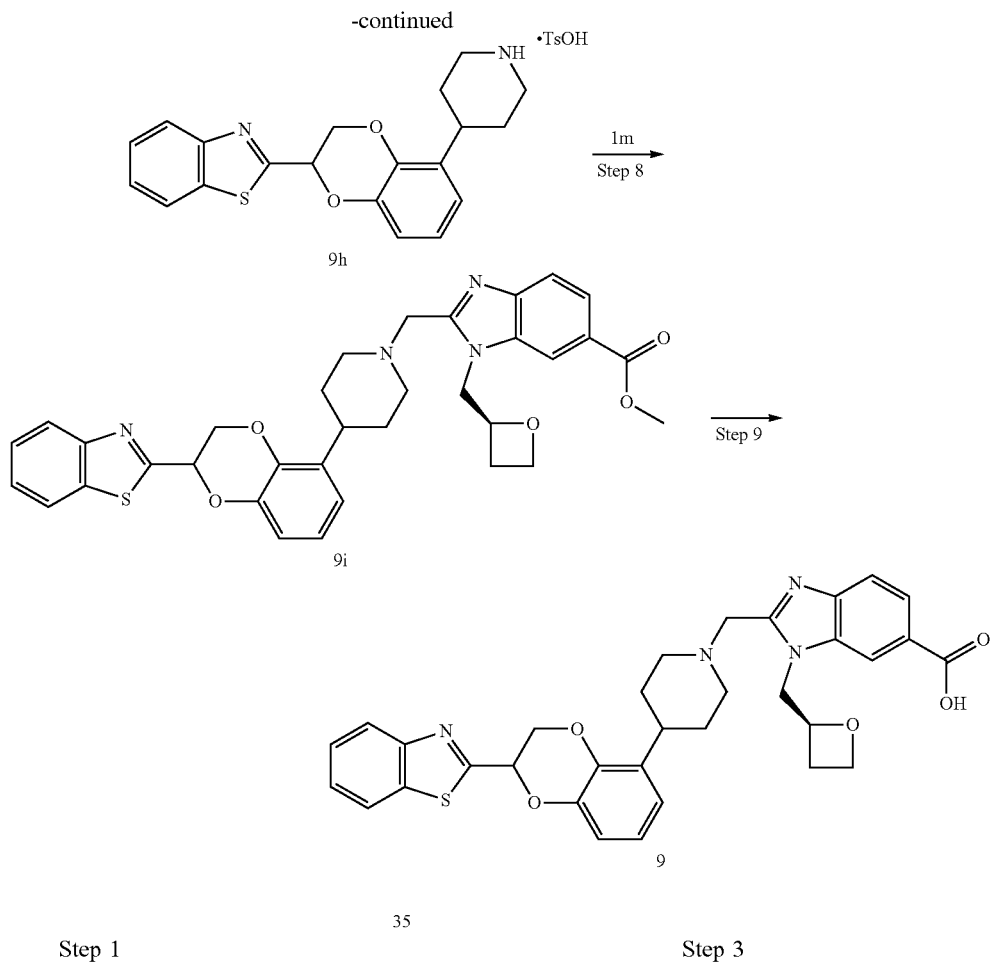

Step 1

1-(Benzo[d]thiazol-2-yl)-2-bromoethan-1-one 9b 1-(Benzo[d]thiazol-2-yl)ethan-1-one 9a (1.77 g, 9.98 mmol, Bide Pharmatech Ltd.) was added to tetrahydrofuran (60 mL). A solution of pyridinium tribromide (1.77 g, 9.98 mmol, Accela ChemBio (Shanghai) Inc.) in 10 mL of tetrahydrofuran was added under ice bath conditions. The mixture was reacted at room temperature for 2 h, filtered and concentrated under reduced pressure to remove the solvent. The residue was triturated with 15 mL of a mixed solution of n-hexane and ethyl acetate (V/V=10:1). The mixture was filtered. The filter cake was dried under reduced pressure to give the title product 9b (1.8 g, yield: 70.36%).

Step 2

1-(Benzo[d]thiazol-2-yl)-2-(2-bromo-6-hydroxyphenoxy)ethan-1-one 9c

Compound 9b (0.8 g, 3.12 mmol) was dissolved in acetone (35 mL). Sodium bicarbonate (839 g, 9.99 mmol) was added. A solution of compound 1a (591 mg, 3.12 mmol) in 5 mL of acetone was added dropwise under ice bath conditions. The mixture was reacted at room temperature for 48 h, filtered, concentrated under reduced pressure to remove the solvent and purified by silica gel column chromatography with eluent system B to give the title product 9c (400 mg, yield: 35.16%).

MS m/z (ESI): 365.9 [M+1].

Step 3

2-(2-(Benzo[d]thiazol-2-yl)-2-hydroxyphenoxy)-3-bromophenol 9d

Compound 9c (400 mg, 1.09 mmol) was dissolved in 20 mL of methanol. Sodium borohydride (62.3 mg, 1.64 mmol, Accela ChemBio (Shanghai) Inc.) was added under ice bath conditions. The mixture was stirred for 1 h. Water (20 mL) was added, and the mixture was stirred, extracted with ethyl acetate (20 mL×3), washed with saturated brine (20 mL), dried over anhydrous sodium sulfate and concentrated under reduced pressure to remove the solvent to give the title compound 9d (400 mg, yield: 99.44%).

MS m/z (ESI): 367.9[M+1].

Step 4

2-(5-Bromo-2,3-dihydrobenzo[b][1,4]dioxan-2-yl)benzo[d]thiazole 9e

Compound 9d (400 mg, 1.09 mmol) was dissolved in 20 mL of tetrahydrofuran. Triphenylphosphine (429 mg, 1.63 mmol, Sinopharm Chemical Reagent Co., Ltd.) was added. Diisopropyl azodicarboxylate (331 mg, 1.63 mmol, Accela ChemBio (Shanghai) Inc.) was added dropwise under ice bath conditions. The reaction continued for 1 h. The reaction mixture was concentrated under reduced pressure. The resulting residue was purified by silica gel column chromatography with eluent system B to give the title compound 9e (300 mg, yield: 78.88%).

MS m/z (ESI): 349.9 [M+1].

Step 5 tert-Butyl 4-(2-(benzo[d]thiazol-2-yl)-2,3-dihydrobenzo[b][1,4]dioxan-5-yl)-3,6-dihydropiperidine-1(2H)-carboxylate 9f Compound 9e (230 mg, 0.66 mmol) was dissolved in 1,4-dioxane (20 mL). Compound 1i (245 mg, 0.79 mmol), sodium carbonate (140 mg, 1.32 mmol), tetrakis(triphenylphosphine)palladium (45.8 mg, 39 μmol) and water (4 mL) were added. The mixture was heated to 90° C. and stirred for 4 h under nitrogen, cooled to room temperature, concentrated and then purified by silica gel column chromatography with eluent system B to give the title compound 9f (260 mg, yield: 87.36%).

MS m/z (ESI): 451.1 [M+1].

Step 6 tert-Butyl 4-(2-(benzo[d]thiazol-2-yl)-2,3-dihydrobenzo[b][1,4]dioxan-5-yl)piperidine-1-carboxylate 9g Compound 9f (230 mg, 0.51 mmol) was dissolved in ethyl acetate (20 mL). 10% palladium on carbon (80 mg, 0.51 mmol) was added. Hydrogenation was performed at room temperature for 3 h under one atmosphere of hydrogen. The mixture was filtered. The filtrate was concentrated to give the crude title compound 9g (230 mg). The product was directly used in the next step without being purified.

MS m/z (ESI): 453.0 [M+1].

Step 7

2-(5-(Piperidin-4-yl)-2,3-dihydrobenzo[b][1,4]dioxan-2-yl)benzo[d]thiazole 4-methylbenzenesulfonate 9h Compound 9g (210 mg, 0.46 mmol) was dissolved in ethyl acetate (5 mL). p-Toluenesulfonic acid (176 mg, 0.92 mmol) was added. The mixture was stirred at room temperature for 12 h and concentrated under reduced pressure to give the crude title compound 9h (160 mg). The product was directly used in the next step without being purified.

MS m/z (ESI): 353.1 [M+1].

Step 8

Methyl 2-((4-(2-(benzo[d]thiazol-2-yl)-2,3-dihydrobenzo[b][1,4]dioxan-5-yl)piperidin-1-yl)methyl)-1-(((S)-oxetan-2-yl)methyl)-1H-benzo[d]imidazole-6-carboxylate (A Mixture of Diastereomers) 9i Compound 9h (160 mg, 0.45 mmol) was dissolved in 15 mL of acetonitrile. Compound 1m (133 mg, 0.45 mmol, prepared using the method for intermediate 23 disclosed on page 69 of the specification in patent application WO2018109607A1) was added. Potassium carbonate (670 mg, 4.8 mmol) was added. The mixture was heated to 50° C. and stirred for 5 h. The reaction mixture was cooled to room temperature and concentrated under reduced pressure. The resulting residue was purified by silica gel column chromatography with eluent system B to give the title mixture of diastereomers 9i (220 mg, yield: 79.35%).

MS m/z (ESI): 611.2 [M+1].

Step 9

2-((4-(2-(Benzo[d]thiazol-2-yl)-2,3-dihydrobenzo[b][1,4]dioxan-5-yl)piperidin-1-yl)methyl)-1-(((S)-oxetan-2-yl)methyl)-1H-benzo[d]imidazole-6-carboxylic acid (A Mixture of Diastereomers) 9

Compound 9i (10 mg, 0.016 mmol) was dissolved in 3 mL of acetonitrile. Lithium hydroxide monohydrate (5.5 mg, 0.13 mmol) and 0.6 mL of water were added at room temperature. The mixture was reacted at 40° C. for 16 h, cooled to room temperature, adjusted to pH 6-7 with 5% aqueous citric acid solution and extracted with ethyl acetate (20 mL×2). The organic layers were combined, concentrated and purified by silica gel column chromatography with eluent system A to give the title mixture of diastereomers 9 (6.5 mg, yield: 66.52%).

MS m/z (ESI): 597.2 [M+1].

$^1$H NMR (500 MHz, DMSO-$d_6$) δ 12.74 (s, 1H), 8.28 (d, 1H), 8.18 (d, 1H), 8.06 (d, 1H), 7.81 (d, 1H), 7.61-7.65 (m, 1H), 7.46-7.53 (m, 2H), 6.84-7.04 (m, 3H), 5.08-5.14 (m, 2H), 4.64-4.72 (m, 2H), 4.46-4.62 (m, 3H), 3.96-3.98 (m, 1H), 3.80-3.83 (m, 1H), 2.83-2.99 (m, 4H), 2.68-2.70 (m, 1H), 2.40-2.49 (m, 1H), 2.20-2.45 (m, 4H), 1.65-1.80 (m, 2H).

Example 10

2-((4-((R)-2-(Benzo[d]thiazol-2-yl)-2,3-dihydrobenzo[b][1,4]dioxan-5-yl)piperidin-1-yl)methyl)-1-(((S)-oxetan-2-yl)methyl)-1H-benzo[d]imidazole-6-carboxylic acid 10

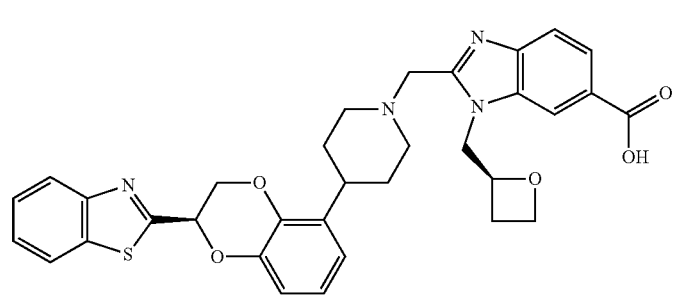

-continued
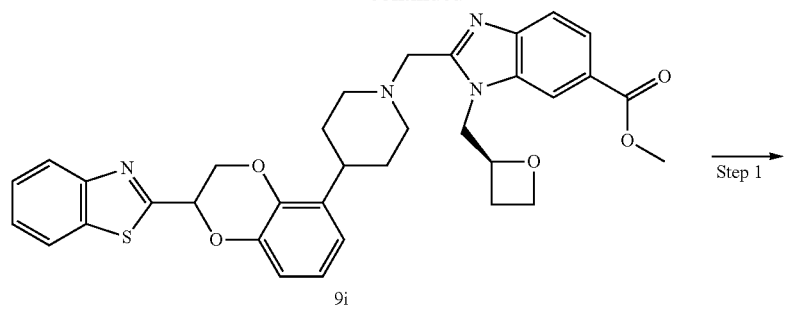
9i
Step 1
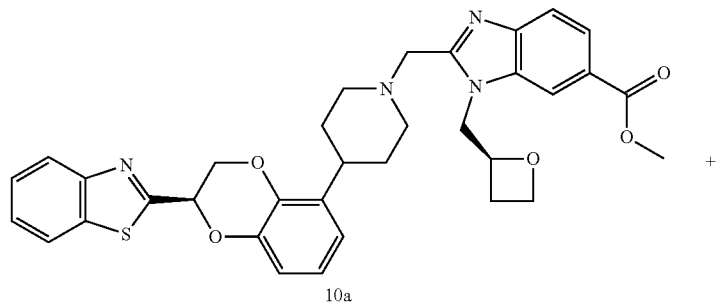
10a
+
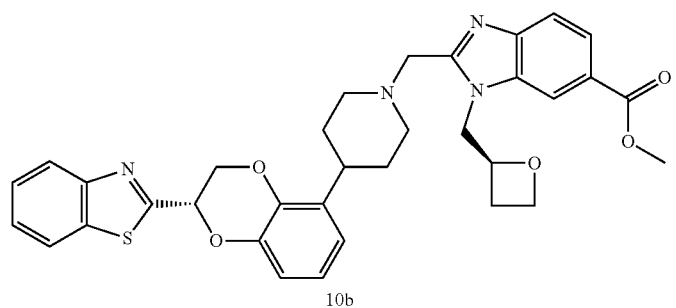
10b
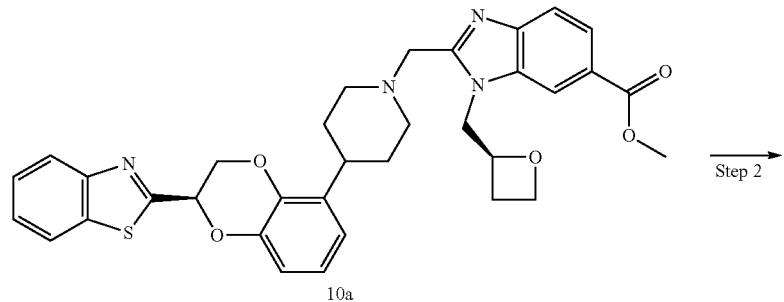
10a
Step 2
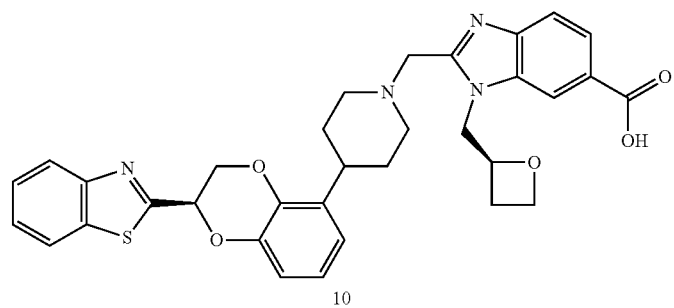
10

Step 1

Methyl 2-((4-((R)-2-(benzo[d]thiazol-2-yl)-2,3-dihydrobenzo[b][1,4]dioxan-5-yl)piperidin-1-yl)methyl)-1-(((S)-oxetan-2-yl)methyl)-1H-benzo[d]imidazole-6-carboxylate 10a Methyl 2-((4-((S)-2-(benzo[d]thiazol-2-yl)-2,3-dihydrobenzo[b][1,4]dioxan-5-yl)piperidin-1-yl)methyl)-1-(((S)-oxetan-2-yl)methyl)-1H-benzo[d]imidazole-6-carboxylate 10b Compound 9i (220 mg, 0.36 mmol) was resolved by preparative chiral chromatography. The corresponding fractions were collected and concentrated under reduced pressure to give the title products 10a (75 mg, 0.122 mmol) and 10b (75 mg, 0.122 mmol).

Single-configuration compound 10a:

Chiral HPLC analysis: retention time 8.674 min, chiral purity: 99%, (column: CHIRALPAK IE 150×4.6 mm, 5 μm (with column protection); mobile phase: hexane/EtOH (0.1% DEA)=20/80 (V/V), flow rate: 1.0 mL/min)

MS m/z (ESI): 611.2 [M+1].

Single-configuration compound 10b:

Chiral HPLC analysis: retention time 11.188 min, chiral purity: 99%, (column: CHIRALPAK IE 150×4.6 mm, 5 μm (with column protection); mobile phase: hexane/EtOH (0.1% DEA)=20/80 (V/V), flow rate: 1.0 mL/min)

MS m/z (ESI): 611.2 [M+1].

Step 2

2-((4-((R)-2-(Benzo[d]thiazol-2-yl)-2,3-dihydrobenzo[b][1,4]dioxan-5-yl)piperidin-1-yl)methyl)-1-(((S)-oxetan-2-yl)methyl)-1H-benzo[d]imidazole-6-carboxylic acid 10

Compound 10a (75 mg, 0.122 mmol) was dissolved in 8 mL of acetonitrile. Lithium hydroxide monohydrate (5.5 mg, 0.13 mmol) and 1.6 mL of water were added at room temperature. The mixture was reacted at 40° C. for 16 h, cooled to room temperature, adjusted to pH 6-7 with 5% aqueous citric acid solution and extracted with ethyl acetate (20 mL×2). The organic layers were combined, concentrated and purified by silica gel column chromatography with eluent system A to give the title product 10 (65 mg, yield: 88.70%).

MS m/z (ESI): 595.2 [M−1].

$^1$H NMR (500 MHz, DMSO-$d_6$) δ 12.75 (s, 1H), 8.28 (d, 1H), 8.18 (d, 1H), 8.07 (d, 1H), 7.81 (d, 1H), 7.61-7.65 (m, 2H), 7.44-7.53 (m, 1H), 7.04 (d, 1H), 6.80-6.98 (m, 2H), 5.08-5.12 (m, 2H), 4.63-4.72 (m, 2H), 4.48-4.62 (m, 1H), 4.34-4.47 (m, 2H), 3.96-3.98 (m, 1H), 3.80-3.82 (m, 1H), 2.82-3.06 (m, 4H), 2.68-2.74 (m, 1H), 2.40-2.49 (m, 1H), 2.23-2.32 (m, 3H), 2.20-2.22 (m, 1H), 1.65-1.80 (m, 2H).

Example 11

2-((4-((S)-2-(Benzo[d]thiazol-2-yl)-2,3-dihydrobenzo[b][1,4]dioxan-5-yl)piperidin-1-yl)methyl)-1-(((S)-oxetan-2-yl)methyl)-1H-benzo[d]imidazole-6-carboxylic acid 11

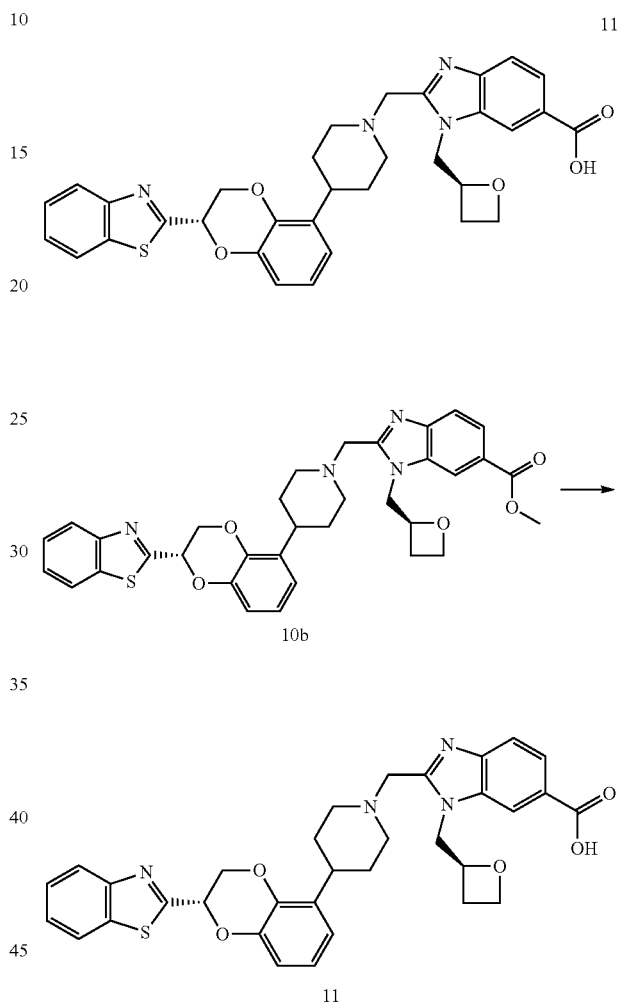

Compound 10b (75 mg, 0.122 mmol) was dissolved in 8 mL of acetonitrile. Lithium hydroxide monohydrate (5.5 mg, 0.13 mmol) and 1.6 mL of water were added at room temperature. The mixture was reacted at 40° C. for 16 h, cooled to room temperature, adjusted to pH 6-7 with 5% aqueous citric acid solution and extracted with ethyl acetate (20 mL×2). The organic layers were combined, concentrated and purified by silica gel column chromatography with eluent system A to give the title product 11 (65.3 mg, yield: 89.55%).

MS m/z (ESI): 595.2[M−1].

$^1$H NMR (500 MHz, DMSO-$d_6$) δ 12.75 (s, 1H), 8.28 (d, 1H), 8.18 (d, 1H), 8.07 (d, 1H), 7.81 (d, 1H), 7.61-7.65 (m, 2H), 7.44-7.53 (m, 1H), 7.04 (d, 1H), 6.80-6.98 (m, 2H), 5.08-5.12 (m, 2H), 4.63-4.72 (m, 2H), 4.49-4.62 (m, 1H), 4.32-4.48 (m, 2H), 3.96-3.98 (m, 1H), 3.80-3.82 (m, 1H), 2.83-3.08 (m, 4H), 2.68-2.72 (m, 1H), 2.40-2.49 (m, 1H), 2.23-2.32 (m, 3H), 2.20-2.22 (m, 1H), 1.65-1.80 (m, 2H).

Example 12

2-((4-(3-(4-Chloro-2-fluorophenyl)-2,3-dihydrobenzo[b][1,4]dioxan-5-yl)piperidin-1-yl)methyl)-3-((S)-oxetan-2-ylmethyl)-3H-imidazo[4,5-b]pyridine-5-carboxylic acid (A Mixture of Diastereomers) 12

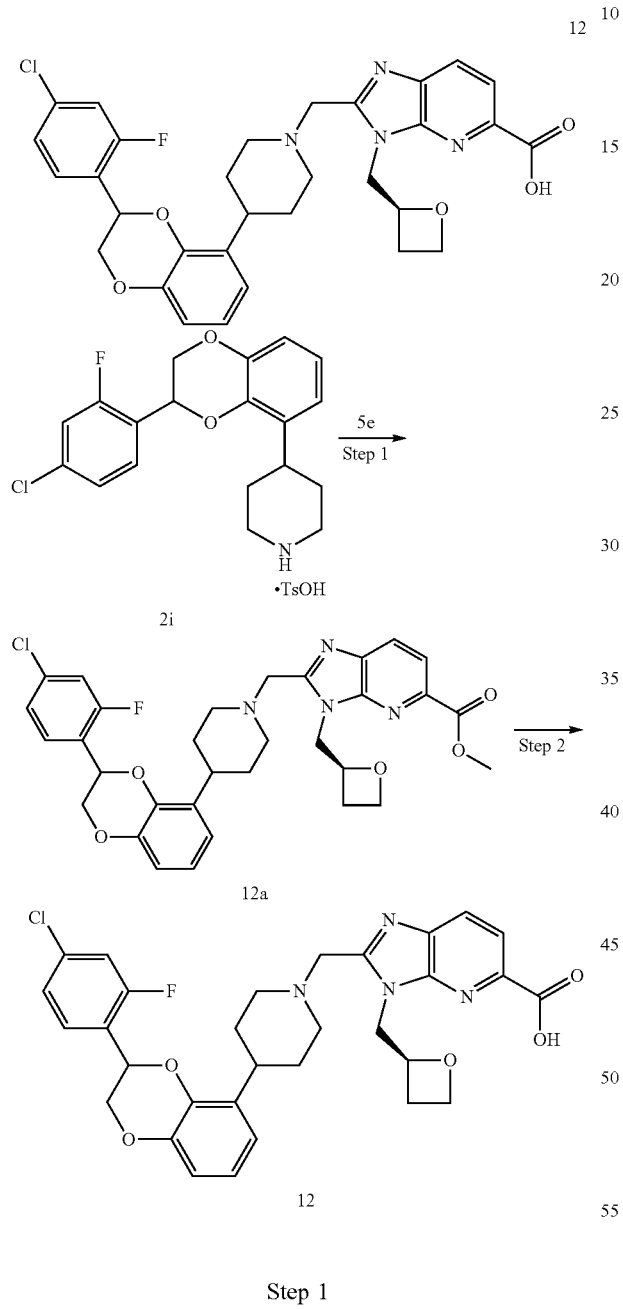

Step 1

Methyl 2-((4-(3-(4-chloro-2-fluorophenyl)-2,3-dihydrobenzo[b][1,4]dioxan-5-yl)piperidin-1-yl)methyl)-3-((S)-oxetan-2-ylmethyl)-3H-imidazo[4,5-b]pyridine-5-carboxylate (A Mixture of Diastereomers) 12a Compound 5e (50 mg, 0.17 mmol) and compound 2i (89 mg, 0.17 mmol) were dissolved in acetonitrile (5 mL). Potassium carbonate (118 mg, 0.85 mmol) was added. The mixture was stirred at 60° C. for 2 h, filtered and concentrated under reduced pressure to remove the solvent. The resulting residue was purified by silica gel column chromatography with eluent system B to give the title mixture of diastereomers 12a (59 mg, yield: 56.8%).

MS m/z (ESI): 607.2 [M+1].

Step 2

2-((4-(3-(4-Chloro-2-fluorophenyl)-2,3-dihydrobenzo[b][1,4]dioxan-5-yl)piperidin-1-yl)methyl)-3-((S)-oxetan-2-ylmethyl)-3H-imidazo[4,5-b]pyridine-5-carboxylic acid (A Mixture of Diastereomers) 12

Compound 12a (59 mg, 0.10 mmol) was dissolved in 12 mL of a mixed solution of acetonitrile and water (V/V=5:1). Lithium hydroxide monohydrate (20 mg, 0.48 mmol) was added. The mixture was stirred at 40° C. for 18 h, cooled to room temperature, adjusted to pH 5-6 with aqueous citric acid solution (1 M), extracted with ethyl acetate (30 mL×3), dried over anhydrous sodium sulfate and concentrated under reduced pressure. The resulting residue was purified by preparative high performance liquid chromatography (column: SHarpsil-T 150×30 mm, 5 μm; mobile phase 1: water (containing 10 mmol/L ammonium bicarbonate); mobile phase 2: acetonitrile; 15 min of gradient elution: 35% to 45%, flow rate: 30 mL/min) to give the title mixture of diastereomers 12 (23 mg, yield: 39.9%).

MS m/z (ESI): 593.1 [M+1].

$^1$H NMR (500 MHz, DMSO-$d_6$) δ 12.64-13.04 (brs, 1H), 8.10 (d, 1H), 7.97 (d, 1H), 7.56 (dd, 1H), 7.52 (t, 1H), 7.42 (dd, 1H), 6.75-6.88 (m, 3H), 5.46 (dd, 1H), 5.07-5.21 (m, 1H), 4.77-4.88 (m, 1H), 4.66-4.76 (m, 1H), 4.42-4.53 (m, 2H), 4.31-4.40 (m, 1H), 4.04-4.15 (m, 1H), 3.85-4.01 (m, 2H), 2.80-3.01 (m, 3H), 2.62-2.73 (m, 1H), 2.38-2.48 (m, 1H), 2.12-2.29 (m, 2H), 1.58-1.84 (m, 4H).

Example 13

2-((4-(3-(5-Chloropyridin-2-yl)-2,3-dihydrobenzo[b][1,4]dioxan-5-yl)piperidin-1-yl)methyl)-1-(((S)-oxetan-2-yl)methyl)-1H-benzo[d]imidazole-6-carboxylic acid (A Mixture of Diastereomers) 13

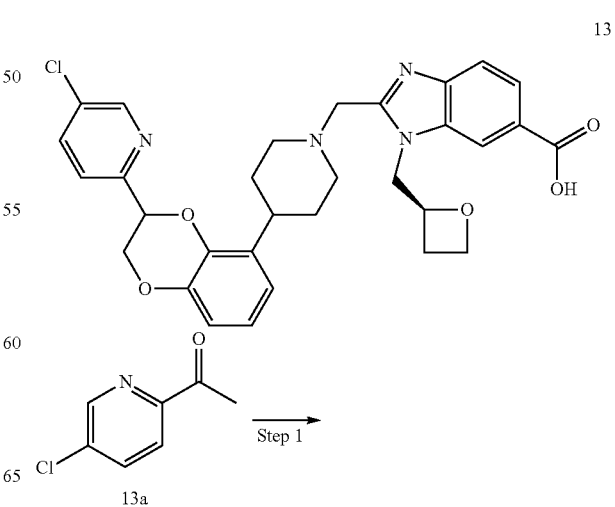

167
-continued

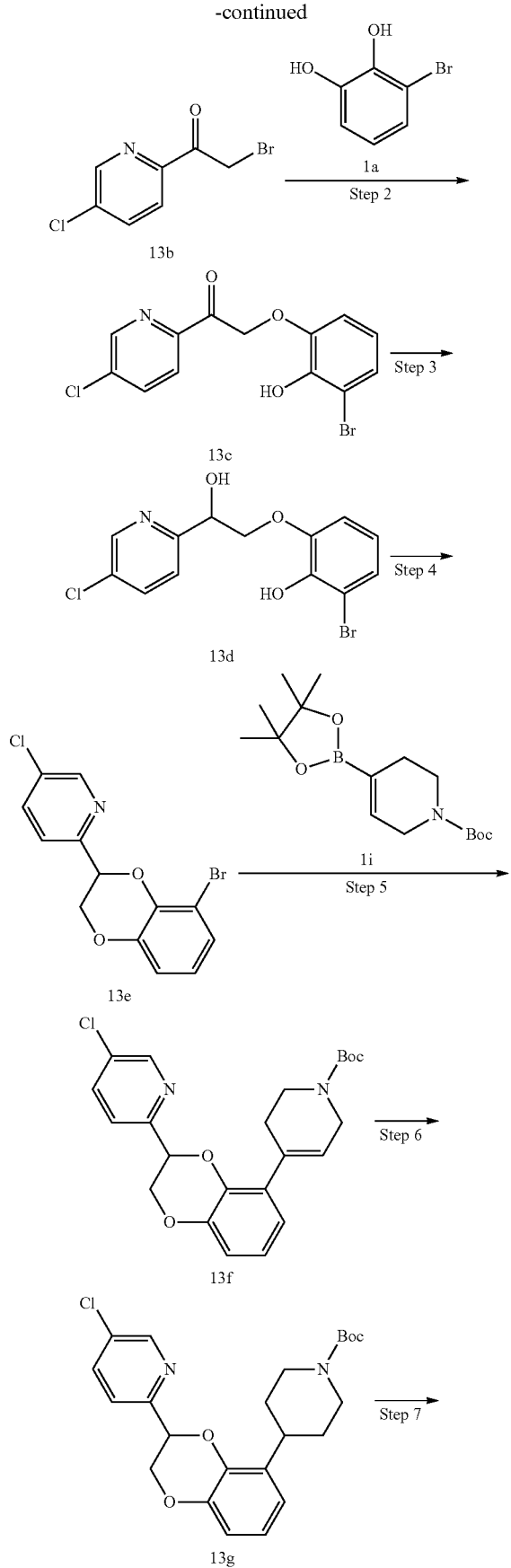

168
-continued

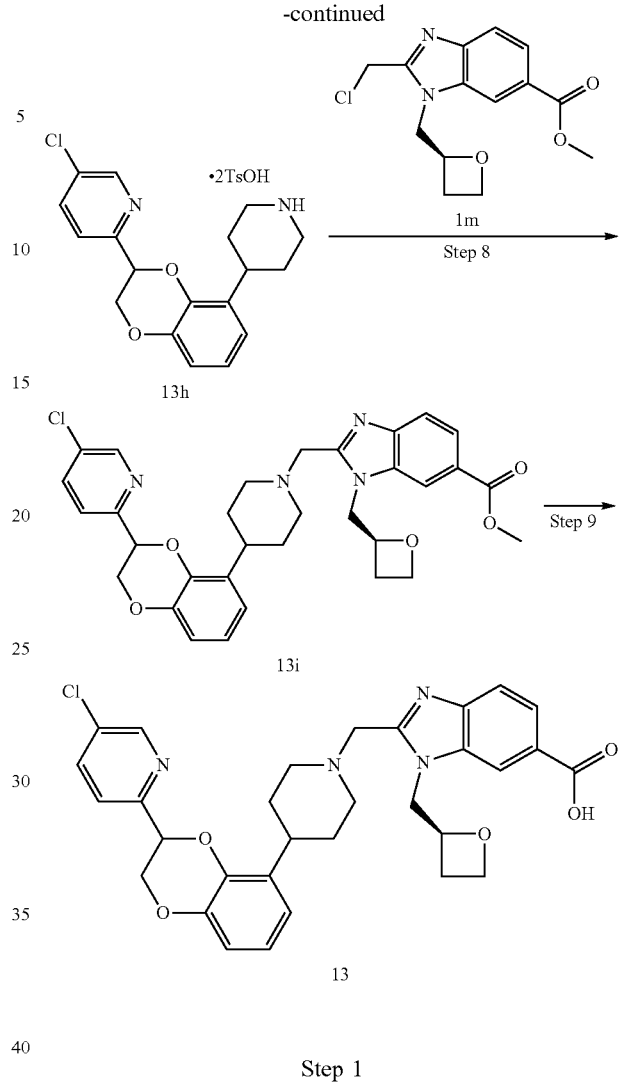

Step 1

2-Bromo-1-(5-chloropyridin-2-yl)ethyl-1-one 13b 1-(5-Chloropyridin-2-yl)ethyl-1-one (13a, 2.00 g, 12.86 mmol, Bide Pharmatech Ltd.) was added to tetrahydrofuran (15 mL) and chloroform (30 mL). Pyridinium tribromide (4.30 g, 13.45 mmol, Accela ChemBio (Shanghai) Inc.) was added. The mixture was heated to 50° C. and stirred for 3 h, cooled to room temperature, washed successively with 1 M hydrochloric acid (30 mL×2), water (30 mL×2) and saturated brine (30 mL×2), dried over anhydrous magnesium sulfate, filtered and concentrated under reduced pressure to remove the solvent to give residue 13b (3.01 g), which was directly used in the next step without being purified.

Step 2

2-(3-Bromo-2-hydroxyphenoxy)-1-(5-chloropyridin-2-yl)ethyl-1-one 13c

Compound 1a (1.60 g, 8.47 mmol) was dissolved in acetonitrile (30 mL). The solution was cooled to 0° C. Potassium carbonate (1.60 g, 11.58 mmol) and compound 13b (1.80 g, 7.68 mmol) were added. The mixture was stirred at 0° C. for 2 h, diluted with ethyl acetate (50 mL), washed with saturated brine (30 mL×2), dried over anhydrous magnesium sulfate, filtered and concentrated under reduced pressure to remove the solvent to give residue 13c (2.0 g), which was directly used in the next step without being purified.

MS m/z (ESI): 343.9 [M+1].

Step 3

2-Bromo-6-(2-(5-chloropyridin-2-yl)-2-hydroxyethoxy)phenol 13d

Compound 13c (2.00 g, 5.84 mmol) was dissolved in methanol (20 mL). Sodium borohydride (0.11 g, 2.91 mmol) was added. The mixture was stirred at room temperature for 1 h and concentrated. The resulting residue was purified by silica gel column chromatography with eluent system B to give the title compound 13d (970 mg, yield: 48.2%).

MS m/z (ESI): 346.0 [M+1].

Step 4

2-(8-Bromo-2,3-dihydrobenzo[b][1,4]dioxan-2-yl)-5-chloropyridine 13e

Compound 13d (970 mg, 2.80 mmol) was dissolved in tetrahydrofuran (20 mL). The solution was cooled to 0° C. Triphenylphosphine (1.10 g, 4.19 mmol) and diisopropyl azodicarboxylate (850 mg, 4.20 mmol) were added under nitrogen atmosphere. The mixture was stirred at 0° C. for half an hour, diluted with ethyl acetate (50 mL), washed with water (30 mL×2), washed with saturated brine (30 mL×2), dried over anhydrous sodium sulfate, filtered and concentrated under reduced pressure to remove the solvent. The resulting residue was purified by silica gel column chromatography with eluent system B to give the title compound 13e (880 mg, yield: 95.7%).

MS m/z (ESI): 327.9 [M+1].

Step 5 tert-Butyl 4-(3-(5-chloropyridin-2-yl)-2,3-dihydrobenzo[b][1,4]dioxan-5-yl)-3,6-dihydropyridine-1(2H)-carboxylate 13f Compound 13e (860 mg, 2.63 mmol) and compound 1i (900 mg, 2.91 mmol, Accela ChemBio (Shanghai) Inc.) were dissolved in 1,4-dioxane (30 mL) and water (6 mL). Sodium carbonate (560 mg, 5.28 mmol) and tetrakis(triphenylphosphine)palladium (300 mg, 0.26 mmol) were added. The mixture was stirred at 90° C. for 4 h under nitrogen atmosphere, cooled to room temperature, filtered and concentrated under reduced pressure to remove the solvent. The resulting residue was purified by silica gel column chromatography with eluent system B to give the title compound 13f (610 mg, yield: 54.0%).

MS m/z (ESI): 373.1 [M−55].

Step 6 tert-Butyl 4-(3-(5-chloropyridin-2-yl)-2,3-dihydrobenzo[b][1,4]dioxan-5-yl)piperidine-1-carboxylate 13g In an autoclave, compound 13f (290 mg, 0.68 mmol) was dissolved in methanol (50 mL). Tris(triphenylphosphine) rhodium chloride (65 mg, 0.07 mmol) was added. The system was purged with three atmospheres of hydrogen. The mixture was heated to 60° C., stirred for 14 h, cooled to room temperature and concentrated under reduced pressure to remove the solvent. The resulting residue was purified by silica gel column chromatography with eluent system B to give the title compound 13g (216 mg, yield: 74.1%).

MS m/z (ESI): 375.1 [M−55].

Step 7

5-Chloro-2-(8-(piperidin-4-yl)-2,3-dihydrobenzo[b][1,4]dioxan-2-yl)pyridine 2 4-methylbenzenesulfonate 13h Compound 13g (200 mg, 0.46 mmol) was dissolved in ethyl acetate (5 mL). p-Toluenesulfonic acid monohydrate (180 mg, 0.95 mmol) was added. The mixture was stirred at room temperature for 16 h and concentrated under reduced pressure to give the crude title product 13h (313 mg), which was directly used in the next step without being purified.

MS m/z (ESI): 331.1 [M+1].

Step 8

Methyl 2-((4-(3-(5-chloropyridin-2-yl)-2,3-dihydrobenzo[b][1,4]dioxan-5-yl)piperidin-1-yl)methyl)-1-(((S)-oxetan-2-yl)methyl)-1H-benzo[d]imidazole-6-carboxylate (A Mixture of Diastereomers) 13i Compound 13h (313 mg, 0.46 mmol) and compound 1m (140 mg, 0.48 mmol) were dissolved in acetonitrile (20 mL). Potassium carbonate (320 mg, 2.32 mmol) was added. The mixture was heated to 50° C., stirred for 5 h and concentrated under reduced pressure to remove the solvent. The resulting residue was purified by silica gel column chromatography with eluent system B to give the title mixture of diastereomers 13i (273 mg, yield: 99.9%).

MS m/z (ESI): 589.2 [M+1].

Step 9

2-((4-(3-(5-Chloropyridin-2-yl)-2,3-dihydrobenzo[b][1,4]dioxan-5-yl)piperidin-1-yl)methyl)-1-(((S)-oxetan-2-yl)methyl)-1H-benzo[d]imidazole-6-carboxylic acid (A Mixture of Diastereomers) 13

Compound 13i (273 mg, 0.46 mmol) was dissolved in acetonitrile (10 mL) and water (2 mL). Lithium hydroxide monohydrate (25 mg, 0.60 mmol) was added. The mixture was stirred at 40° C. for 16 h, cooled to room temperature, adjusted to pH 5-6 with 5% aqueous citric acid solution, extracted with ethyl acetate (30 mL×3), dried over anhydrous sodium sulfate and concentrated under reduced pressure. The resulting residue was purified by preparative high performance liquid chromatography (column: Sharpsil-T Prep C18 30×150 mm, 5 μm; mobile phase: water (containing 10 mmol/L ammonium bicarbonate); mobile phase: acetonitrile; 20 min of gradient elution: 35% to 55%, flow rate: 30 mL/min) to give the title mixture of diastereomers 13 (190 mg, yield: 71.3%).

MS m/z (ESI): 575.2 [M+1].
$^1$H NMR (500 MHz, DMSO-d$_6$) δ 8.68 (d, 1H), 8.26 (d, 1H), 8.01 (dd, 1H), 7.80 (dd, 1H), 7.62 (d, 1H), 7.55 (d, 1H), 6.90-6.73 (m, 3H), 5.35 (dd, 1H), 5.14-5.05 (m, 1H), 4.79 (dd, 1H), 4.65 (dd, 1H), 4.56 (dd, 1H), 4.53-4.46 (m, 1H), 4.38 (dtd, 1H), 4.29 (dd, 1H), 3.93 (dd, 1H), 3.78 (dd, 1H), 2.98 (dt, 1H), 2.84 (qd, 2H), 2.71 (ddtd, 1H), 2.43 (ddtd, 1H), 2.2-2.11 (m, 2H), 1.76-1.52 (m, 4H).

Example 14

2-((4-((S)-3-(4-Chloro-2-fluorophenyl)-2,3-dihydrobenzo[b][1,4]dioxan-5-yl)piperazin-1-yl)methyl)-1-(((S)-oxetan-2-yl)methyl)-1H-benzo[d]imidazole-6-carboxylic acid 14

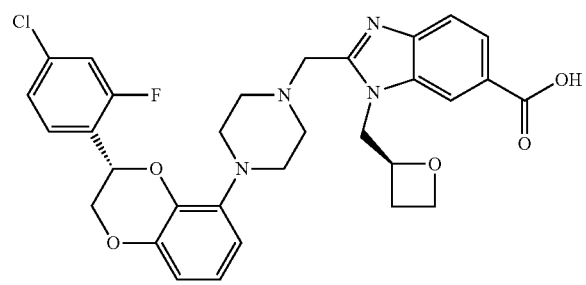

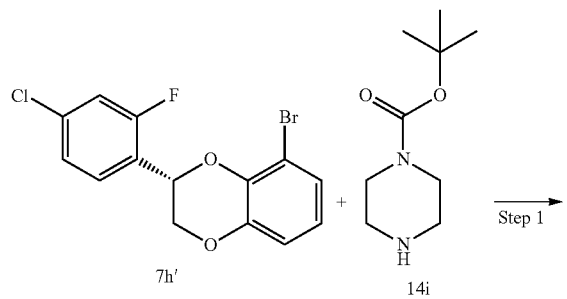

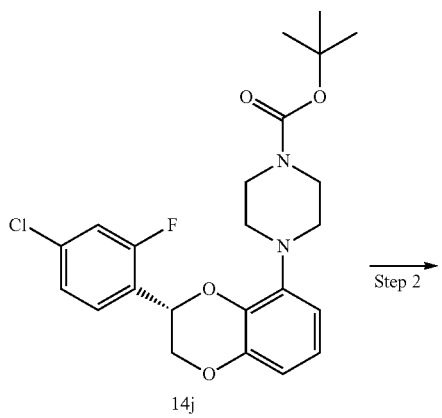

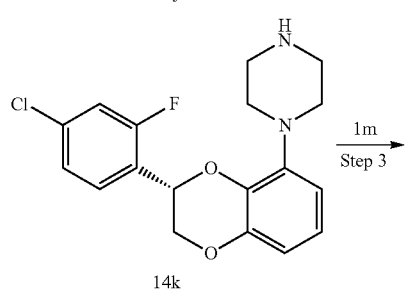

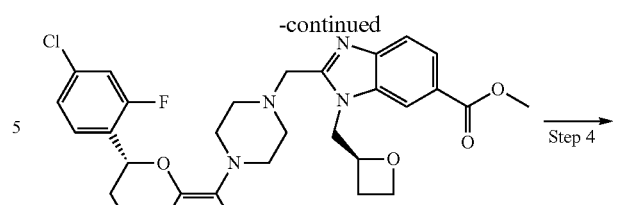

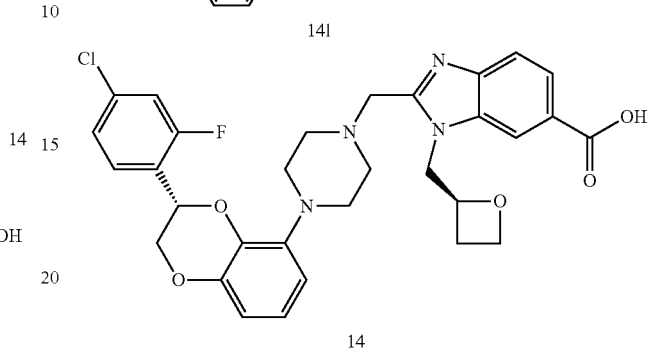

Step 1 tert-Butyl (S)-4-(3-(4-chloro-2-fluorophenyl)-2,3-dihydrobenzo[b][1,4]dioxan-5-yl)piperazine-1-carboxylate 14j Compound 7h' (206 mg, 0.60 mmol) and tert-butyl piperazine-1-carboxylate 14i (120 mg, 0.61 mmol, Bide Pharmatech Ltd.) were dissolved in 10 mL of 1,4-dioxane. Methanesulfonato(2-dicyclohexylphosphino-2'',6''-diisopropoxy-1,1''-biphenyl)(2''-amino-1,1''-biphenyl-2-yl)palladium(II) (103 mg, 0.12 mmol, Bide Pharmatech Ltd.) and cesium carbonate (391 mg, 1.204 mmol, Accela ChemBio Inc.) were added. The mixture was heated to 110° C. and stirred for 10 h under nitrogen atmosphere. The reaction mixture was cooled to room temperature, filtered and concentrated under reduced pressure. The resulting residue was purified by silica gel column chromatography with eluent system B to give the title product 14j (90 mg, yield: 33.4%).

MS m/z (ESI): 449.1 [M+1].

Step 2

(S)-1-(3-(4-Chloro-2-fluorophenyl)-2,3-dihydrobenzo[b][1,4]dioxan-5-yl)piperazine 14k Compound 14j (90 mg, 0.12 mmol) was dissolved in 15 mL of dichloromethane. 1 mL of trifluoroacetic acid was added at 0° C. The mixture was stirred at that temperature for another 2 h, slowly warmed to room temperature and concentrated under reduced pressure to give the title product 14k (40 mg, yield: 95.3%).

MS m/z (ESI): 349.1 [M+1].

Step 3

Methyl 2-((4-((S)-3-(4-chloro-2-fluorophenyl)-2,3-dihydrobenzo[b][1,4]dioxan-5-yl)piperazin-1-yl)methyl)-1-(((S)-oxetan-2-yl)methyl)-1H-benzo[d]imidazole-6-carboxylate 14l Compound 14k (40 mg, 0.12 mmol) and compound 1m (35 mg, 0.12 mmol) were dissolved in 10 mL of acetonitrile.

Potassium carbonate (80 mg, 0.58 mmol, Accela ChemBio Inc.) was added at room temperature. The mixture was heated to 60° C. and reacted for 1 h. The reaction mixture was cooled to room temperature and concentrated under reduced pressure. The resulting residue was purified by silica gel column chromatography with eluent system B to give the title product 14l (56 mg, yield: 80.4%).

MS m/z (ESI): 607.1 [M+1].

Step 4

2-((4-((S)-3-(4-Chloro-2-fluorophenyl)-2,3-dihydrobenzo[b][1,4]dioxan-5-yl)piperazin-1-yl)methyl)-1-(((S)-oxetan-2-yl)methyl)-1H-benzo[d]imidazole-6-carboxylic acid 14

Compound 14l (56 mg, 0.1 mmol) was dissolved in 10 mL of acetonitrile. 2 mL of water and lithium hydroxide monohydrate (25 mg, 0.6 mmol, Accela ChemBio Inc.) were added. The mixture was heated to 40° C. and reacted for 16 h. The reaction mixture was cooled, then adjusted to pH 5-6 with citric acid (2.5 M), concentrated under reduced pressure and purified by high performance liquid chromatography (column: SharpSil-T Prep C18 50×30 mm, 5 μm; mobile phase: water (containing 10 mmol/L ammonium bicarbonate), mobile phase: acetonitrile; 17 min of gradient elution: 30% to 47%) to give the title product 14 (15 mg, yield: 19.2%).

MS m/z (ESI): 595.2 [M+1].
$^1$H NMR (500 MHz, DMSO-$d_6$) δ 8.19 (s, 1H), 7.78-7.80 (dd, 1H), 7.55-7.57 (dd, 1H), 7.42-7.45 (t, 1H), 6.76-6.90 (m, 5H), 5.41-5.43 (m, 2H), 4.67-4.77 (d, 1H), 4.44-4.49 (d, 1H), 4.32-4.35 (m, 1H), 4.25-4.29 (m, 2H), 4.07-4.11 (dd, 1H), 3.75-3.79 (m, 3H), 3.22-3.24 (sbr, 4H), 3.62-3.65 (sbr, 4H), 1.98-2.02 (m, 2H).

Example 15

2-(((S)-4-((S)-3-(4-Chloro-2-fluorophenyl)-2,3-dihydrobenzo[b][1,4]dioxan-5-yl)-2-methylpiperazin-1-yl)methyl)-1-((S)-oxetan-2-ylmethyl)-3a,6a-dihydro-1H-thieno[2,3-d]imidazole-5-carboxylic acid 15

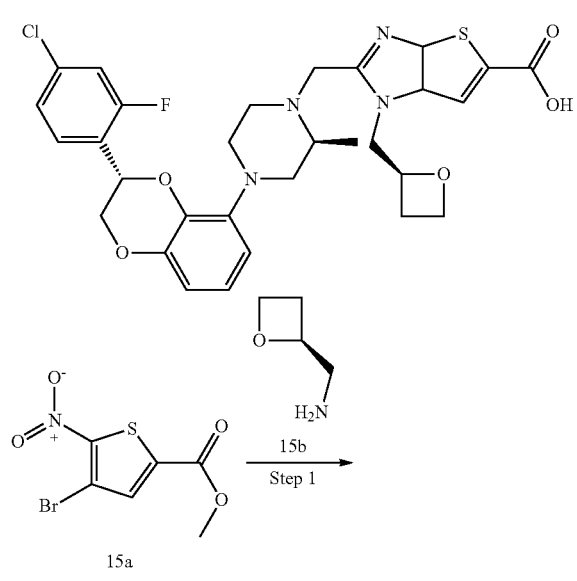

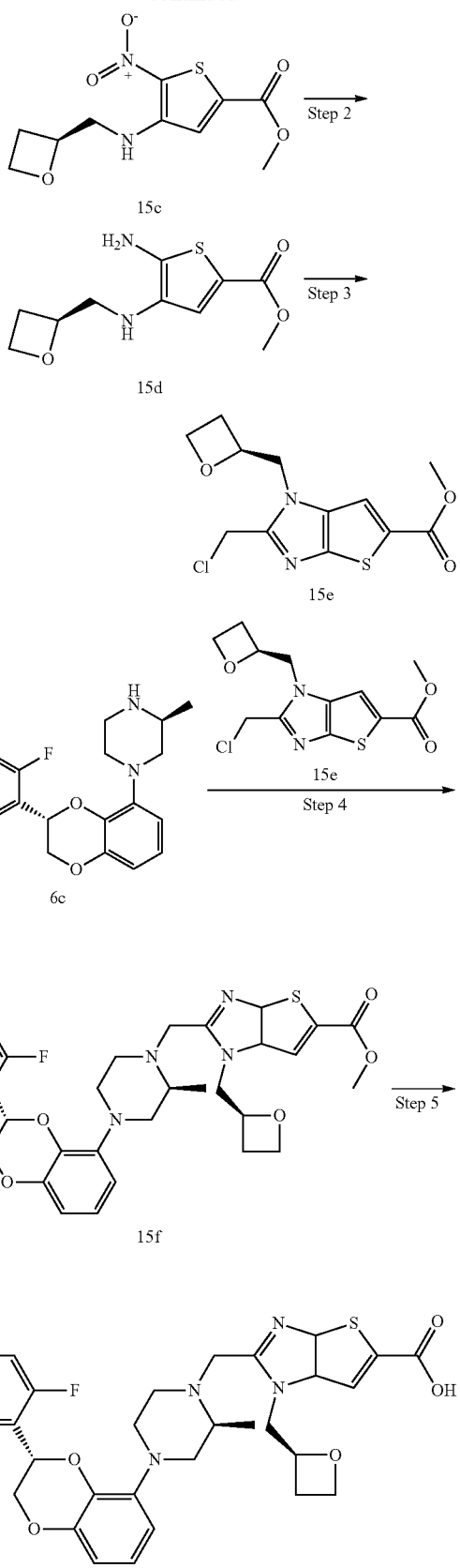

Step 1

Methyl (S)-5-nitro-4-((oxetan-2-ylmethyl)amino)thiophene-2-carboxylate 15c

The compound methyl 4-bromo-5-nitrothiophene-2-carboxylate 15a (305 mg, 1.15 mmol, prepared using the method for intermediate C disclosed in Example 114 on page 124 of the specification in patent application WO2003099805A1), the compound (S)-oxetan-2-ylmethylamine 15b (100 mg, 1.15 mmol, PharmaBlock Sciences (Nanjing), Inc.) and triethylamine (580 mg, 5.73 mmol) were dissolved in tetrahydrofuran (10 mL). The mixture was stirred at 80° C. for 16 h, cooled to room temperature, concentrated under reduced pressure and then purified by silica gel column chromatography with eluent system B to give the title compound 15c (310 mg, yield: 90.1%).
MS m/z (ESI): 273.1 [M+1].

Step 2

Methyl (S)-5-amino-4-((oxetan-2-ylmethyl)amino)thiophene-2-carboxylate 15d

Compound 15c (310 mg, 1.14 mmol) was dissolved in 20 mL of tetrahydrofuran. Palladium on carbon (300 mg, 10%) was added. The mixture was stirred at room temperature for 2 h under hydrogen, filtered through celite and concentrated to give the crude title product 15d (253 mg). The product was directly used in the next step without being purified.
MS m/z (ESI): 243.0 [M+1].

Step 3

Methyl (S)-2-(chloromethyl)-1-(oxetan-2-ylmethyl)-1H-thieno[2,3-d]imidazole-5-carboxylate 15e The crude compound 15d (253 mg, 0.69 mmol) was dissolved in 10 mL of acetonitrile. 2-Chloro-1,1,1-trimethoxy-ethane (152 mg, 1.05 mmol, Accela ChemBio (Shanghai) Inc.) and p-toluenesulfonic acid monohydrate (20 mg, 0.1 mmol, Sinopharm Chemical Reagent Co., Ltd.) were added and stirred at 60° C. for 1 h. The mixture was cooled to room temperature, concentrated under reduced pressure and purified by silica gel column chromatography with eluent system A to give crude title product 15e (71 mg). The product was directly used in the next step without being purified.
MS m/z (ESI): 300.9 [M+1].

Step 4

Methyl 2-(((S)-4-((S)-3-(4-chloro-2-fluorophenyl)-2,3-dihydrobenzo[b][1,4]dioxan-5-yl)-2-methylpiperazin-1-yl)methyl)-1-((S)-oxetan-2-ylmethyl)-3a,6a-dihydro-1H-thieno[2,3-d]imidazole-5-carboxylate 15f Compound 6c (70 mg, 0.19 mmol, TFA) and compound 15e (64 mg, 0.21 mmol) were dissolved in 5 mL acetonitrile. Potassium carbonate (134 mg, 0.97 mmol, Accela ChemBio (Shanghai) Inc.) was added at room temperature. The mixture was heated to 50° C. and reacted for 16 h. The reaction mixture was cooled to room temperature and concentrated under reduced pressure. The resulting residue was purified by silica gel column chromatography with eluent system A to give the title product 15f (117 mg, yield: 96.7%).
MS m/z (ESI): 627.1 [M+1].

Step 5

2-(((S)-4-((S)-3-(4-Chloro-2-fluorophenyl)-2,3-dihydrobenzo[b][1,4]dioxan-5-yl)-2-methylpiperazin-1-yl)methyl)-1-((S)-oxetan-2-ylmethyl)-3a,6a-dihydro-1H-thieno[2,3-d]imidazole-5-carboxylic acid 15

Compound 15f (117 mg, 0.186 mmol) was dissolved in 5 mL of acetonitrile. 1 mL of water and lithium hydroxide monohydrate (40 mg, 0.953 mmol, Accela ChemBio (Shanghai) Inc.) were added. The mixture was heated to 40° C. and reacted for 16 h. The reaction mixture was cooled, then adjusted to pH 5-6 with citric acid (0.5 M), concentrated under reduced pressure and purified by high performance liquid chromatography (column: SharpSil-T Prep C18 50×30 mm, 5 μm; mobile phase: water (containing 10 mmol/L ammonium bicarbonate), mobile phase: acetonitrile; 20 min of gradient elution: 30% to 50%) to give the title product 15 (72 mg, yield: 62.9%).
MS m/z (ESI): 613.1 [M+1].
$^1$H NMR (500 MHz, DMSO-d$_6$) δ 7.74 (s, 1H), 7.63-7.54 (m, 2H), 7.44 (dd, 1H), 6.78 (t, 1H), 6.62-6.56 (m, 1H), 6.49 (d, 1H), 5.42 (dd, 1H), 5.12 (dd, 1H), 4.64-4.52 (m, 2H), 4.49-4.43 (m, 2H), 4.30-4.20 (m, 2H), 4.08 (dd, 1H), 3.48 (d, 1H), 3.31 (d, 1H), 3.02 (d, 1H), 2.78 (d, 1H), 2.68-2.60 (m, 3H), 2.52-2.56 (m, 1H), 2.38-2.30 (m, 2H), 1.08 (d, 3H).

Example 16

2-((4-(3-(4-Cyano-2-fluorophenyl)-2,3-dihydrobenzo[b][1,4]dioxan-5-yl)piperidin-1-yl)methyl)-1-((S)-oxetan-2-ylmethyl)-1H-benzo[d]imidazole-6-carboxylic acid (A Mixture of Diastereomers) 16

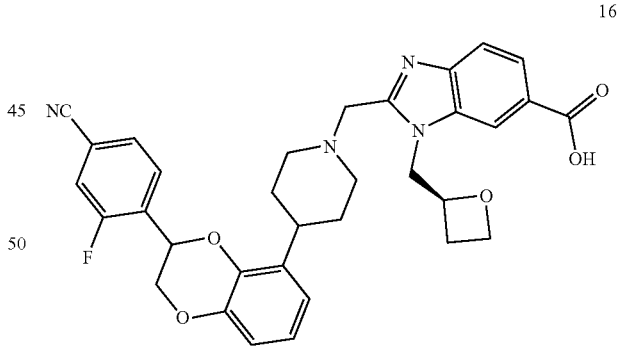

The title mixture of diastereomers 16 (16 mg, yield: 40.96%) was prepared by using the synthesis scheme of Example 2 and replacing 4-chloro-2-fluorobenzaldehyde 2a, the starting material of step 1, with 4-cyano-2-fluorobenzaldehyde.
MS m/z (ESI): 583.2 [M−1].
$^1$H NMR (500 MHz, DMSO-d$_6$) δ 12.42-12.97 (brs, 1H), 8.26 (s, 1H), 8.00 (d, 1H), 7.74-7.82 (m, 2H), 7.63-7.68 (m, 2H), 6.70-6.82 (m, 3H), 5.55-5.60 (m, 1H), 5.01-5.08 (m, 1H), 4.79-4.84 (m, 1H), 4.59-4.65 (m, 1H), 4.39-4.48 (m, 2H), 4.31-4.36 (m, 1H), 4.04-4.12 (m, 1H), 3.86-3.93 (m, 1H), 3.71-3.78 (m, 1H), 2.91-2.99 (m, 1H), 2.77-2.86 (m, 2H), 2.61-2.69 (m, 1H), 2.33-2.41 (m, 1H), 2.07-2.19 (m, 2H), 1.73-1.81 (m, 1H), 1.63-1.69 (m, 2H), 1.54-1.63 (m, 1H).

Example 17

2-((4-(3-(4-Chloro-2-fluorophenyl)-2,3-dihydrobenzo[b][1,4]dioxan-5-yl)-3,6-dihydropyridin-1(2H)-yl)methyl)-1-(((S)-oxacyclohexan-2-yl)methyl)-1H-benzo[d]imidazole-6-carboxylic acid (A Mixture of Diastereomers) 17

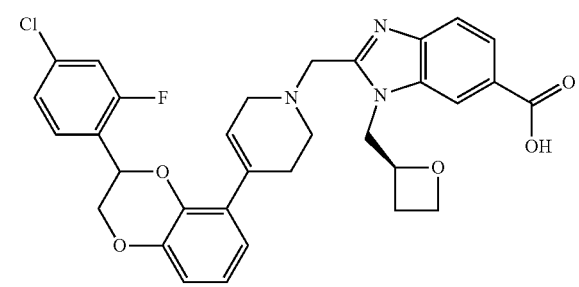

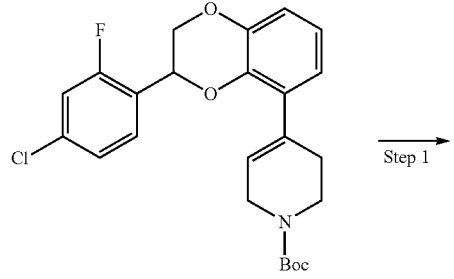

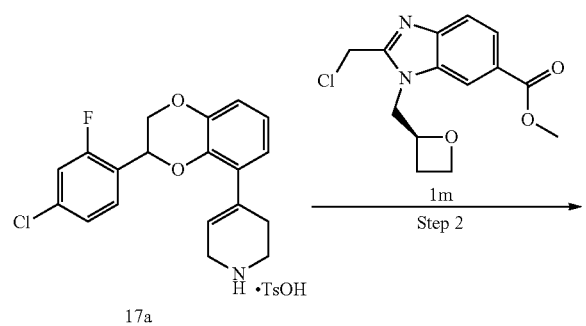

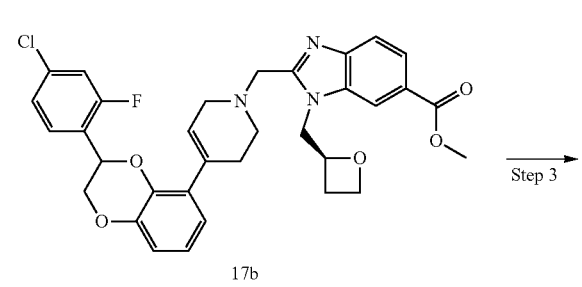

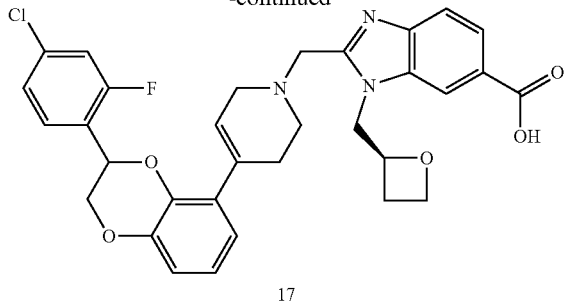

Step 1

4-(3-(4-Chloro-2-fluorophenyl)-2,3-dihydrobenzo[b][1,4]dioxan-5-yl)-1,2,3,6-tetrahydropyridine 4-methylbenzenesulfonate 17a Compound 2g (202 mg, 0.45 mmol) was dissolved in ethyl acetate (5 mL). p-Toluenesulfonic acid monohydrate (140 mg, 0.74 mmol) was added. The mixture was stirred at 60° C. for 2 h, cooled to room temperature and concentrated under reduced pressure to give the crude title product 17a (234 mg). The product was directly used in the next step without being purified.

MS m/z (ESI): 346.1 [M+1].

Step 2

Methyl 2-((4-(3-(4-chloro-2-fluorophenyl)-2,3-dihydrobenzo[b][1,4]dioxan-5-yl)-3,6-dihydropyridin-1(2H)-yl)methyl)-1-(((S)-oxetan-2-yl)methyl)-1H-benzo[d]imidazole-6-carboxylate (A Mixture of Diastereomers) 17b Compound 1m (133 mg, 0.45 mmol) and 17a (234 mg, 0.45 mmol) were dissolved in acetonitrile (10 mL). Potassium carbonate (312 mg, 2.26 mmol) was added. The mixture was stirred at 50° C. for 18 h, filtered and concentrated under reduced pressure to remove the solvent. The resulting residue was purified by silica gel column chromatography with eluent system B to give the title mixture of diastereomers 17b (213 mg, yield: 78.1%).

MS m/z (ESI): 604.2 [M+1].

Step 3

2-((4-(3-(4-Chloro-2-fluorophenyl)-2,3-dihydrobenzo[b][1,4]dioxan-5-yl)-3,6-dihydropyridin-1(2H)-yl)methyl)-1-(((S)-oxacyclohexan-2-yl)methyl)-1H-benzo[d]imidazole-6-carboxylic acid (A Mixture of Diastereomers) 17

Compound 17b (46 mg, 0.08 mmol) was dissolved in 12 mL of a mixed solution of acetonitrile and water (V/V=5:1). Lithium hydroxide monohydrate (16 mg, 0.38 mmol) was added. The mixture was stirred at 40° C. for 18 h, cooled to room temperature, adjusted to pH 5-6 with aqueous citric acid solution (1 M), extracted with ethyl acetate (30 mL×3), dried over anhydrous sodium sulfate and concentrated under reduced pressure. The resulting residue was purified by preparative high performance liquid chromatography (column: SHarpsil-T 150×30 mm, 5 μm; mobile phase: water (containing 10 mmol/L ammonium bicarbonate); mobile phase: acetonitrile; 15 min of gradient elution: 35% to 45%, flow rate: 30 mL/min) to give the title mixture of diastereomers 17 (17 mg, yield: 37.8%).

MS m/z (ESI): 590.1 [M+1].

$^1$H NMR (500 MHz, DMSO-$d_6$) δ 12.58-12.99 (brs, 1H), 8.24 (d, 1H), 7.79 (d, 1H), 7.63 (d, 1H), 7.53-7.58 (m, 1H), 7.51 (t, 1H), 7.36-7.42 (m, 1H), 6.80-6.87 (m, 2H), 6.74-7.79 (m, 1H), 5.77-5.86 (m, 1H), 5.44 (dd, 1H), 4.96-5.07 (m, 1H), 4.68-4.78 (m, 1H), 4.55-4.64 (m, 1H), 4.41-4.47 (m, 1H), 4.35-4.40 (m, 1H), 4.27-4.33 (m, 1H), 4.08-4.16 (m, 1H), 3.96-4.04 (m, 1H), 3.82-2.89 (m, 1H), 3.03-3.21 (m, 2H), 2.61-2.75 (m, 2H), 2.50-2.60 (m, 2H), 2.25-2.41 (m, 2H).

Example 18

2-((4-(2-(4-Chloro-2-fluorophenyl)-2-methyl-2,3-dihydrobenzo[b][1,4]dioxan-5-yl)piperidin-1-yl)methyl)-1-(((S)-oxetan-2-yl)methyl)-1H-benzo[d]imidazole-6-carboxylic acid (A Mixture of Diastereomers) 18

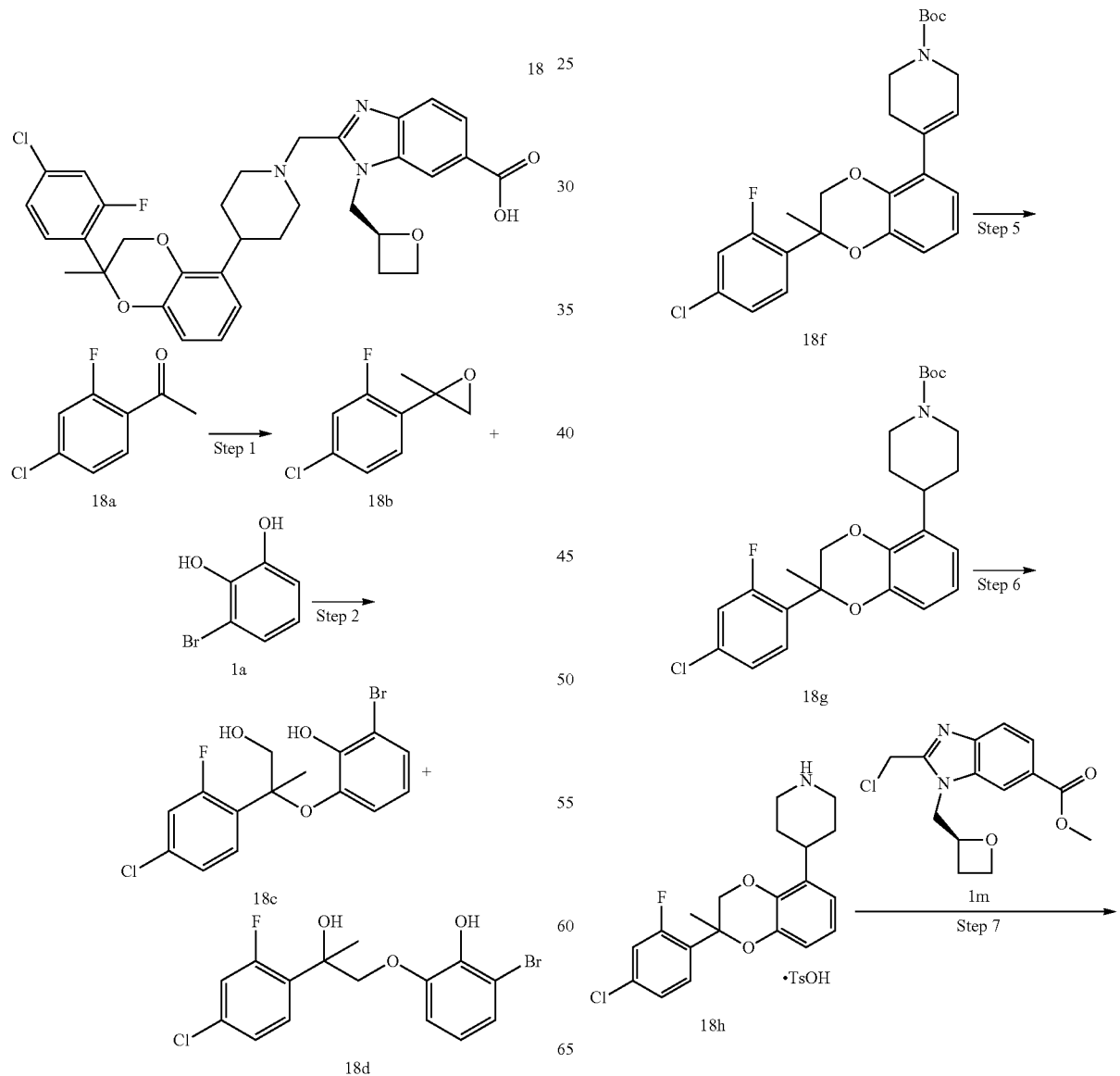

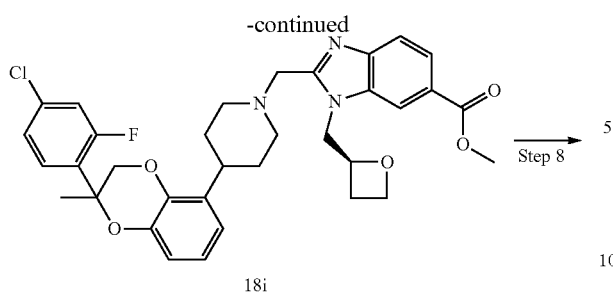

18i

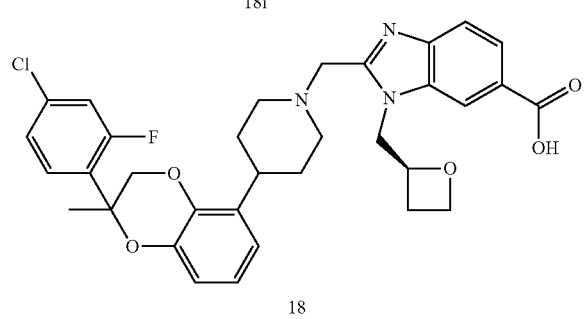

18

Step 1

2-(4-Chloro-2-fluorophenyl)-2-methyloxirane 18b

Potassium tert-butoxide (7.73 g, 67.88 mmol, Accela ChemBio (Shanghai) Inc.) was added to tetrahydrofuran (200 mL). Trimethylsulfonium iodide (14.20 g, 69.58 mmol, Adamas Reagent Co., Ltd.) was added under ice bath conditions. The mixture was stirred for 5 min. 1-(4-Chloro-2-fluorophenyl)ethyl-1-one 18a (10.0 g, 57.94 mmol, Accela ChemBio (Shanghai) Inc.) was added. The mixture was stirred at room temperature for 16 h, filtered, diluted with ethyl acetate (80 mL), washed successively with saturated aqueous ammonium chloride solution (50 mL×2) and saturated brine (30 mL×2), dried over anhydrous sodium sulfate and concentrated under reduced pressure to remove the solvent to give the title compound 18b (10.0 g, yield: 92.4%).

$^1$H NMR (500 MHz, CDCl$_3$) δ7.36 (t, 1H), 7.13 (dd, 1H), 7.08 (dd, 1H), 2.97 (d, 1H), 2.79 (d, 1H), 1.60 (s, 3H).

Step 2

2-Bromo-6-((2-(4-chloro-2-fluorophenyl)-1-hydroxypropan-2-yl)oxy)phenol 18c

2-Bromo-6-((2-(4-chloro-2-fluorophenyl)-2-hydroxypropoxy)phenol 18d

After compound 18b (1.0 g, 5.35 mmol) and 1a (1.0 g, 5.29 mmol, Shanghai Haohong Biomedical Technology Co., Ltd.) were mixed, sodium methoxide (30 mg, 0.555 mmol, Adamas Reagent Co., Ltd.) was added. The mixture was stirred at 120° C. for 2 h. After cooling, the resulting residue was purified by silica gel column chromatography with eluent system B to give the title compound 18c (300 mg, yield: 14.9%) and compound 18d (240 mg, yield: 11.9%).

18c MS m/z (ESI): 375.2 [M−1];
18d MS m/z (ESI): 375.2 [M−1].

Step 3

5-Bromo-2-(4-chloro-2-fluorophenyl)-2-methyl-2,3-dihydrobenzo[b][1,4]dioxane 18e Compound 18c (300 mg, 0.798 mmol) was dissolved in dry tetrahydrofuran (15 mL). Triphenylphosphine (315 mg, 1.20 mmol, Accela ChemBio (Shanghai) Inc.) was added. Diisopropyl azodicarboxylate (243 mg, 1.20 mmol, Sinopharm Chemical Reagent Co., Ltd.) was added dropwise at 0° C. under nitrogen atmosphere. The mixture was stirred at 0° C. for half an hour. The reaction mixture was quenched with 10 mL of water, extracted with ethyl acetate (20 mL×2) and concentrated under reduced pressure to remove the solvent. The resulting residue was purified by silica gel column chromatography with eluent system B to give the title compound 18e (240 mg, yield: 84.0%).

$^1$H NMR (500 MHz, CDCl$_3$) δ7.37-7.32 (m, 3H), 7.14-7.11 (m, 2H), 6.83-6.79 (m, 1H), 4.57 (dd, 1H), 4.25 (ddd, 1H), 1.71 (dd, 3H).

Step 4 tert-Butyl 4-(2-(4-chloro-2-fluorophenyl)-2-methyl-2,3-dihydrobenzo[b][1,4]dioxan-5-yl)-3,6-dihydropyridine-1(2H)-carboxylate 18f Compound 18e (230 mg, 0.643 mmol) and compound 1i (198 mg, 0.640 mmol, Accela ChemBio (Shanghai) Inc.) were dissolved in 12 mL of a mixed solution of 1,4-dioxane and water (V/V=5:1). Sodium carbonate (136 mg, 1.28 mmol), tetrakis(triphenylphosphine)palladium (75 mg, 0.065 mmol) were added. The mixture was stirred at 90° C. for 4 h under nitrogen, cooled to room temperature, filtered and concentrated under reduced pressure to remove the solvent. The resulting residue was purified by silica gel column chromatography with eluent system B to give the title compound 18f (205 mg, yield: 69.3%).

MS m/z (ESI): 404.0 [M−55].

$^1$H NMR (500 MHz, CDCl$_3$) δ7.45 (t, 0.5H), 7.31 (t, 0.5H), 7.14-7.07 (m, 2H), 6.96 (dd, 0.5H), 6.88 (t, 0.5H), 6.82-6.75 (m, 2H), 5.86 (d, 1H), 4.48 (dd, 1H), 4.18 (dd, 1H), 4.11 (brs, 1H), 4.03 (brs, 1H), 3.65 (brs, 1H), 3.57 (brs, 1H), 2.55-2.35 (m, 2H), 1.68 (d, 3H), 1.51 (d, 9H).

Step 5 tert-Butyl 4-(2-(4-chloro-2-fluorophenyl)-2-methyl-2,3-dihydrobenzo[b][1,4]dioxan-5-yl)piperidine-1-carboxylate 18g Compound 18f (200 mg, 0.434 mmol) was dissolved in ethyl acetate (10 mL) and 1,2-dichlorobenzene (1 mL, TCI (Shanghai) Co., Ltd.). 10% palladium on carbon (50 mg, 0.087 mmol) was added. Hydrogenation was performed at room temperature for 1 h under one atmosphere of hydrogen. The mixture was filtered and concentrated under reduced pressure to remove the solvent. The resulting residue was purified by silica gel column chromatography with eluent system B to give the title compound 18g (200 mg, yield: 99.5%).

MS m/z (ESI): 406.0[M−55].

Step 6

4-(2-(4-Chloro-2-fluorophenyl)-2-methyl-2,3-dihydrobenzo[b][1,4]dioxan-5-yl)piperidine TFA 18h Compound 18g (80 mg, 0.173 mmol) was dissolved in dichloromethane (2 mL). Trifluoroacetic acid (0.1 mL) was added at 0° C. The mixture was stirred at 0° C. for 2 h and concentrated under reduced pressure to give the crude title product 18h (62 mg). The product was directly used in the next step without being purified.

MS m/z (ESI): 362.0 [M+1].

Step 7

Methyl 2-((4-(2-(4-chloro-2-fluorophenyl)-2-methyl-2,3-dihydrobenzo[b][1,4]dioxan-5-yl)piperidin-1-yl)methyl)-1-(((S)-oxetan-2-yl)methyl)-1H-benzo[d]imidazole-6-carboxylate (A Mixture of Diastereomers) 18i Compound 1m (50 mg, 0.169 mmol) and 18h (62 mg, 0.171 mmol) were dissolved in acetonitrile (5 mL). Potassium carbonate (117 mg, 0.846 mmol) was added. The mixture was stirred at 70° C. for 2 h, filtered and concentrated under reduced pressure to remove the solvent. The resulting residue was purified by silica gel column chromatography with eluent system B to give the title mixture of diastereomers 18i (94 mg, yield: 89.3%).

MS m/z (ESI): 620.1 [M+1].

Step 8

2-((4-(2-(4-Chloro-2-fluorophenyl)-2-methyl-2,3-dihydrobenzo[b][1,4]dioxan-5-yl)piperidin-1-yl)methyl)-1-(((S)-oxetan-2-yl)methyl)-1H-benzo[d]imidazole-6-carboxylic acid (A Mixture of Diastereomers) 18

Compound 18i (94 mg, 0.151 mmol) was dissolved in 6 mL of a mixed solution of acetonitrile and water (V/V=5:1). Lithium hydroxide monohydrate (20 mg, 0.50 mmol) was added. The mixture was stirred at 40° C. for 18 h, cooled to room temperature, adjusted to pH 5-6 with aqueous citric acid solution (1 M), extracted with ethyl acetate (30 mL×3), dried over anhydrous sodium sulfate, concentrated under reduced pressure and purified by silica gel column chromatography with eluent system B to give the title mixture of diastereomers 18 (50 mg, yield: 54.4%).

MS m/z (ESI): 606.1 [M+1].

$^1$H NMR (500 MHz, DMSO-$d_6$) δ 12.75 (s, 1H), 8.27 (d, 1H), 7.80 (dd, 1H), 7.64 (d, 1H), 7.48 (dt, 1H), 7.42 (t, 1H), 7.27 (dt, 1H), 6.91-6.82 (m, 2H), 6.75 (dd, 1H), 5.11-5.06 (m, 1H), 4.78 (dd, 1H), 4.67-4.61 (m, 2H), 4.54-4.46 (m, 1H), 4.40-4.35 (m, 1H), 4.16 (d, 1H), 3.92 (d, 1H), 3.76 (d, 1H), 2.96 (t, 1H), 2.81 (t, 1H), 2.76-2.67 (m, 2H), 2.48-2.38 (m, 2H), 2.23-2.12 (m, 1H), 1.68 (t, 1H), 1.57-1.49 (m, 6H).

Example 19

2-(((2S)-4-(3-(4-Chloro-2-fluorophenyl)-2,3-dihydrobenzo[b][1,4]dioxan-5-yl)-2-methylpiperazin-1-yl)methyl)-1-(((S)-oxetan-2-yl)methyl)-1H-benzo[d]imidazole-6-carboxylic acid (A Mixture of Diastereomers) 19

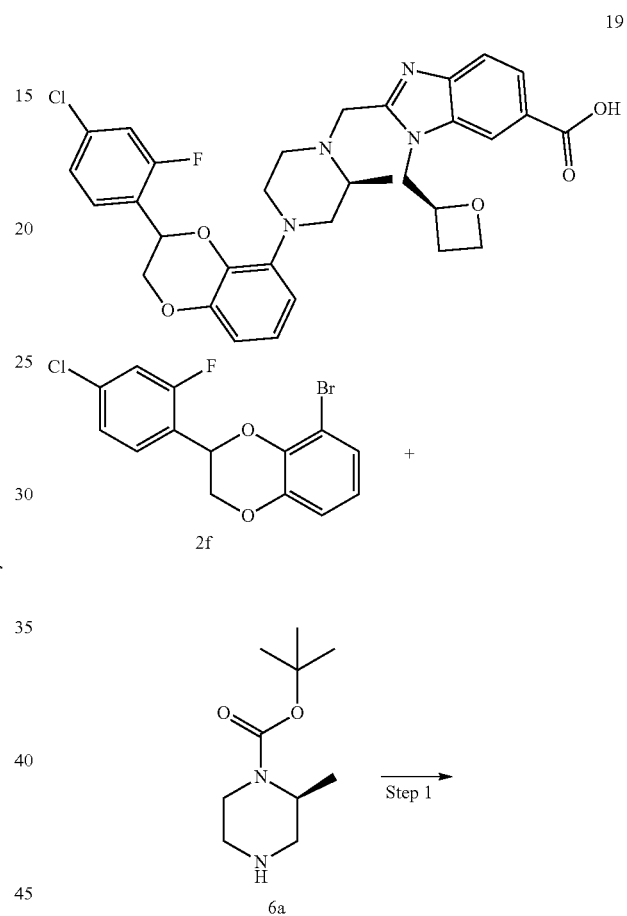

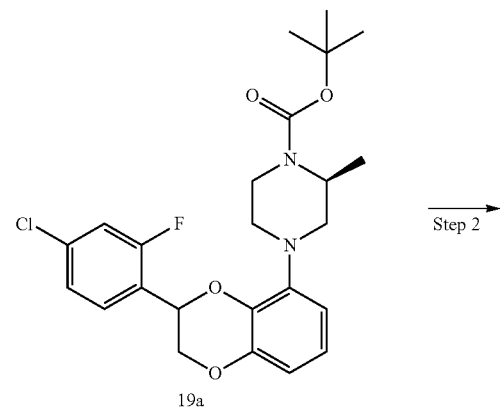

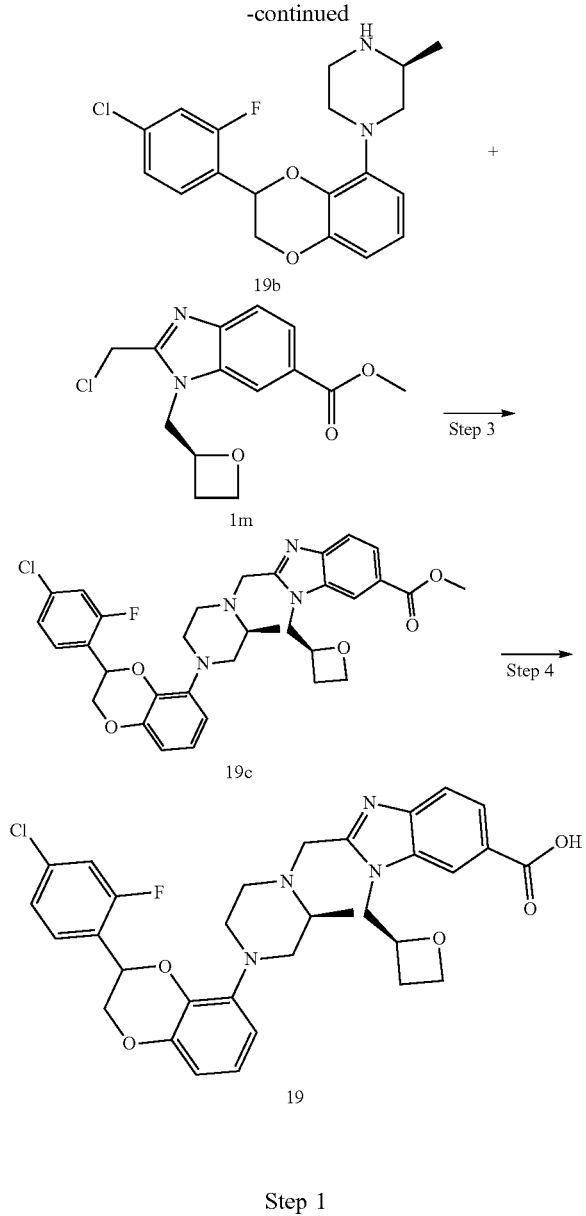

Step 1 tert-Butyl (2S)-4-(3-(4-chloro-2-fluorophenyl)-2,3-dihydrobenzo[b][1,4]dioxan-5-yl)-2-methylpiperazine-1-carboxylate 19a Compound 2f (145 mg, 0.42 mmol) and compound 6a (85 mg, 0.42 mmol, Accela ChemBio Inc.) were dissolved in 10 mL of 1,4-dioxane. Methanesulfonato(2-dicyclohexylphosphino-2",6"-diisopropoxy-1,1"-biphenyl)(2"-amino-1,1"-biphenyl-2-yl)palladium(II) (71 mg, 0.08 mmol, Bide Pharmatech Ltd.) and cesium carbonate (275 mg, 0.84 mmol, Accela ChemBio Inc.) were added. The mixture was heated to 90° C. and stirred for 10 h under nitrogen atmosphere. The reaction mixture was cooled to room temperature, filtered and concentrated under reduced pressure. The resulting residue was purified by silica gel column chromatography with eluent system B to give the title product 19a (40 mg, yield: 20.47%).

MS m/z (ESI): 463.3 [M+1].

Step 2

(3S)-1-(3-(4-Chloro-2-fluorophenyl)-2,3-dihydrobenzo[b][1,4]dioxan-5-yl)-3-methylpiperazine 19b Compound 19a (40 mg, 0.086 mmol) was dissolved in 10 mL of dichloromethane. 0.5 mL of trifluoroacetic acid was added at 0° C. The mixture was stirred at that temperature for another 2 h. The reaction mixture was warmed to room temperature and concentrated under reduced pressure to give the title product 19b (30 mg, yield: 95.7%).

MS m/z (ESI): 363.3 [M+1].

Step 3

Methyl 2-(((2S)-4-(3-(4-chloro-2-fluorophenyl)-2,3-dihydrobenzo[b][1,4]dioxan-5-yl)-2-methylpiperazin-1-yl)methyl)-1-(((S)-oxetan-2-yl)methyl)-1H-benzo[d]imidazole-6-carboxylate (A Mixture of Diastereomers) 19c Compound 19b (30 mg, 0.08 mmol) and compound 1m (24 mg, 0.08 mmol) were dissolved in 10 mL of acetonitrile. Potassium carbonate (57 mg, 0.4 mmol, Accela ChemBio Inc.) was added at room temperature. The mixture was heated to 60° C. and reacted for 1 h. The reaction mixture was cooled to room temperature and concentrated under reduced pressure. The resulting residue was purified by silica gel column chromatography with eluent system B to give the title mixture of diastereomers 19c (30 mg, yield: 58.4%).

MS m/z (ESI): 621.2 [M+1].

Step 4

2-(((2S)-4-(3-(4-Chloro-2-fluorophenyl)-2,3-dihydrobenzo[b][1,4]dioxan-5-yl)-2-methylpiperazin-1-yl)methyl)-1-(((S)-oxetan-2-yl)methyl)-1H-benzo[d]imidazole-6-carboxylic acid 19

Compound 19c (30 mg, 0.05 mmol) was dissolved in 10 mL of acetonitrile. 2 mL of water and lithium hydroxide monohydrate (10 mg, 0.24 mmol, Accela ChemBio Inc.) were added. The mixture was heated to 40° C. and reacted for 16 h. The reaction mixture was cooled, then adjusted to pH 5-6 with citric acid (2.5 M), concentrated under reduced pressure and purified by high performance liquid chromatography (column: SharpSil-T Prep C18 50×30 mm, 5 μm; mobile phase: water (containing 10 mmol/L ammonium bicarbonate), mobile phase: acetonitrile; 17 min of gradient elution: 30% to 47%, flow rate: 30 mL/min) to give the title mixture of diastereomers 19 (3 mg, yield: 10.23%).

MS m/z (ESI): 607.1 [M+1].

$^1$H NMR (500 MHz, DMSO-$d_6$) δ 8.25 (s, 1H), 7.78-7.80 (dd, 1H), 7.62-7.65 (m, 1H), 7.55-7.60 (m, 1H), 7.42-7.45 (dd, 1H), 6.76-6.80 (m, 1H), 6.58-6.60 (dd, 1H), 6.48-6.5 m (dd, 1H), 6.66 (sbr, 1H), 5.41-5.43 (dd, 1H), 5.13-5.18 (m, 1H), 4.67-4.77 (m, 2H), 4.44-4.49 (m, 2H), 4.32-4.35 (d, 1H), 4.25-4.29 (m, 1H), 4.07-4.11 (dd, 1H), 3.59-3.62 (d, 1H), 3.32-3.34 (d, 1H), 3.02-3.05 (d, 1H), 2.78-2.82 (m, 1H), 2.64-2.69 (m, 3H), 2.35-2.41 (m, 3H), 1.09-1.10 (d, 3H).

Example 20

2-((4-(3-(4-Chloro-2-fluorophenyl)-3-methyl-2,3-dihydrobenzo[b][1,4]dioxan-5-yl)piperidin-1-yl)methyl)-1-(((S)-oxetan-2-yl)methyl)-1H-benzo[d]imidazole-6-carboxylic acid (A Mixture of Diastereomers) 20

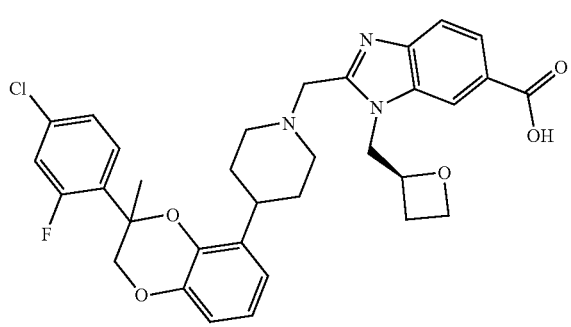

The title mixture of diastereomers 20 (46 mg, yield: 56.83%) was prepared by using the synthesis scheme of Example 2 and replacing 2a, the starting material of step 1, with 2-fluoro-4-chloroacetophenone (Accela ChemBio (Shanghai) Inc.).

MS m/z (ESI): 606.3 [M+1].

$^1$H NMR (500 MHz, DMSO-$d_6$) δ 12.77 (brs, 1H), 8.28 (s, 1H), 7.81 (d, 1H), 7.65 (d, 1H), 7.50 (dt, 1H), 7.38 (t, 1H), 7.30 (d, 1H), 6.83 (d, 1H), 6.78 (t, 1H), 6.68 (d, 1H), 5.06-5.11 (m, 1H), 4.82 (d, 1H), 4.68 (d, 1H), 4.45-4.57 (m, 2H), 4.35-4.42 (m, 1H), 4.16 (d, 1H), 3.98 (d, 1H), 3.82 (d, 1H), 2.95-3.08 (m, 2H), 2.84-2.94 (m, 1H), 2.66-2.76 (m, 1H), 2.40-2.47 (m, 1H), 2.18-2.32 (m, 2H), 1.73-1.86 (m, 2H), 1.64-1.70 (m, 2H), 1.63 (s, 3H).

BIOLOGICAL EVALUATION

Test Example 1: Evaluation of Agonist Activity Against GLP-1 Receptor

I. Purpose

This experiment was intended to test the agonist activity of the compound molecules against the GLP-1 receptor and evaluate the in vitro activity of the molecules according to $EC_{50}$. The experiment adopted a ONE-Glo™ Luciferase Assay System (Promega, E6110). Under the action of compound molecules, GLP-1R downstream signaling pathways were activated to cause elevated cAMP level. The combination of cAMP and CRE could start the transcription expression of CRE downstream luciferase genes, the luciferase could emit fluorescence when reacting with substrates thereof, and the activity of the compound for agonizing GLP-1 receptors was reflected by measuring fluorescence signals through a ONE-Glo™ reagent.

II. Method

Stably-expressed CHO-K1/CRE-luc/GLP-1 receptor cell strains (self-construction of GLP-1 receptor plasmid; CRE-luc plasmid Promega E8471) were constructed. CHO-K1/CRE-luc/GLP-1 receptor cells were digested, and resuspended after centrifugation. Single cell suspension was uniformly mixed, and adjusted to a viable cell density of $2.5\times10^5$ cells/mL with a cell culture medium (DME/F-12+10% FBS), and the resulting solution was added to a 96-well cell culture plate at 90 µL/well (Corning, #3903). The plate was incubated in an incubator for 16 h (37° C., 5% $CO_2$).

The compound was dissolved in DMSO to prepare a stock solution with an initial concentration of 20 mM. The starting concentration of the small molecule compound was 0.2 mM, and the compound underwent 3-fold serial dilution for a total of 10 concentration points, with DMSO at the 11$^{th}$ point. To another 96-well plate was added 95 µL of cell culture medium (DME/F-12+10% FBS), 5 µL of test samples with different concentrations were added to each well, followed by uniform mixing, and then 10 µL of test samples with different concentrations were added to each well, with two duplicate wells set for each sample. The plate was incubated in an incubator for 6 h (37° C., 5% $CO_2$). The 96-well cell culture plate was taken out, and 100 µL of ONE-Glo™ reagent was added to each well, followed by incubation at room temperature for 10 min. The plate was placed in a microplate reader (EnVision 2105, PE) for determination of chemiluminescence.

III. Data Analysis

Data were processed and analyzed using Microsoft Excel and Graphpad Prism 5. $EC_{50}$ values of the compounds were obtained, and the results are shown in Table 1 below.

TABLE 1

$EC_{50}$ of compounds of the present disclosure for agonist activity against GLP-1 receptor

| Example No. | $EC_{50}$(nM) | Emax % |
|---|---|---|
| 1 | 0.56 | 109 |
| 2 | 0.42 | 108 |
| 4 | 0.74 | 103 |
| 5 | 0.12 | 107 |
| 6 | 0.34 | 102 |
| 7 | 0.09 | 105 |
| 8 | 0.29 | 112 |
| 9 | 2.05 | 104 |
| 10 | 1.19 | 103 |
| 11 | 1.68 | 104 |
| 12 | 1.72 | 114 |
| 13 | 1.76 | 108 |
| 14 | 1.79 | 104 |
| 15 | 2.04 | 102 |
| 16 | 1.42 | 116 |
| 17 | 9.9 | 112 |
| 18 | 18.4 | 103 |
| 19 | 1.25 | 109 |
| 20 | 51 | 90 |

Conclusion: the compounds of the present disclosure have high agonist activity against the GLP-1 receptor.

Test Example 2: Effect of Compounds of the Present Disclosure on hERG Potassium Ion Channel I. Purpose This example is intended to assess the blocking effect of the compounds of the present disclosure and positive compound 1 (see the compound of Example 7 on page 125 of WO2019239319A1) on hERG potassium currents in a stable cell strain transfected with an hERG potassium channel by a manual patch-clamp assay. The structure of positive compound 1 is shown below:

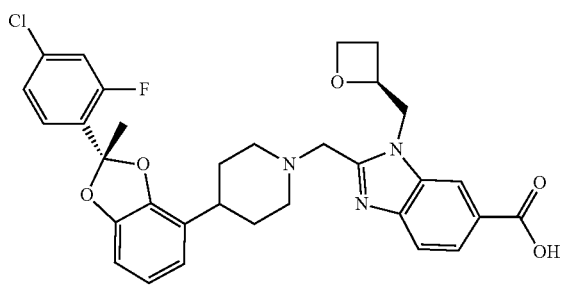 [SMILES: C[C@]1(c2ccc(Cl)cc2F)Oc2cccc(C3CCN(Cc4nc5ccc(C(=O)O)cc5n4C[C@@H]4CCO4)CC3)c2O1]

II. Method

1. Cell Culture

The cells used in this experiment were from a CHO cell line (provided by Sophion Bioscience, Denmark) transfected with hERG cDNA and stably expressing hERG channel at cell passage number of P5. Cells were cultured in a medium containing the following components (all from Invitrogen): Ham's F12 medium, 10% (v/v) inactivated fetal bovine serum, 100 µg/mL hygromycin B, and 100 µg/mL geneticin.

CHO hERG cells were grown in a culture dish containing the above culture medium and cultured in an incubator at 37° C. with 5% $CO_2$. 24-48 h before the electrophysiological experiment, CHO hERG cells were transferred to round slides placed in the culture dish and grown in the same culture medium and culture conditions as above. The density of CHO hERG cells on each round slide was required to achieve the requirement that most cells were independent and individual.

2. Experimental Solutions

TABLE 2

Compositions of intracellular and extracellular fluids

| Reagent | Extracellular fluid (mM) (EC 0.0.0 NaCl-Ringer's solution) | Intracellular fluid (mM) (IC 0.0.0 KCl-Ringer's solution) |
| --- | --- | --- |
| $CaCl_2$ | 2 | 5.4 |
| $MgCl_2$ | 1 | 1.8 |
| KCl | 4 | 120 |
| NaCl | 145 | — |
| Glucose | 10 | — |
| HEPES | 10 | 10 |
| EGTA | — | 5 |
| Na-ATP | — | 4 |
| pH | 7.4 (adjusted with NaOH) | 7.25 (adjusted with NaOH) |
| Osmotic pressure | Osmotic pressure of about 305 mOsm | Osmotic pressure of about 295 mOsm |

TABLE 3

Reagent details

| Reagent | Cat. No. | Batch No. | Molecular weight | Supplier |
| --- | --- | --- | --- | --- |
| NaCl | S1679-1KG | WXBC1368V | 58.44 | Sigma |
| KCl | 31248-100G | WXBC2571V | 74.55 | Sigma |
| $CaCl_2$ | 21114-1L | BCBM6063V | 110.98 | Sigma |
| $MgCl_2·H_2O$ | M7304-100G | V900020-500G | 203.30 | Sigma |
| HEPES | H3375-1KG | SLBP2246V | 238.30 | Sigma |
| Glucose | G8270-1KG | WXBC2393V | 180.16 | Sigma |

TABLE 3-continued

Reagent details

| Reagent | Cat. No. | Batch No. | Molecular weight | Supplier |
| --- | --- | --- | --- | --- |
| EGTA | 03777-50G | SLBP2807V | 380.15 | Sigma |
| $Na_2$-ATP | A-7699-5G | SLBJ8915V | 551.14 | Sigma |
| NaOH | 35254-1L | BCBG6297V | 40.00 | Sigma |
| KOH | 232041-50G | SLBK9251V | 56.00 | Sigma |

3. Electrophysiological Recording System

In this experiment, a manual patch-clamp system (HEKA EPC-10 signal amplifier and digital conversion system, purchased from HEKA Electronics, Germany) was used for whole cell current recording. Round slides with CHO hERG cells grown on the surface were placed in an electrophysiological recording chamber under an inverted microscope. The chamber was continuously perfused with extracellular fluid (approximately 1 mL/min). The experimental procedures were performed by conventional whole-cell patch-clamp current recording technology. Unless otherwise stated, the experiment was performed at room temperature (~25° C.). The cells were clamped at a voltage of −80 mV. The cell clamp voltage was depolarized to +20 mV to activate the hERG potassium channel, and then clamped to −50 mV 5 s later to eliminate inactivation and generate tail currents. The tail current peak was used as a value for the numeral value of the hERG current. After the hERG potassium currents recorded in the above step were stable under the continuous extracellular fluid perfusion in the recording chamber, the drug to be tested could be added for perfusion until the inhibitory effect of the drug on the hERG current reached a stable state. Generally, the last superposition of 3 consecutive current recording lines is used as a criterion for determining whether a stable state is reached. After reaching a stable state, the chamber was flushed by perfusion with extracellular fluid until the hERG currents returned to the level before dosing. One or more drugs, or multiple concentrations of the same drug, can be tested on one cell, but extracellular fluid flushes are required between different drugs. Cisapride (purchased from Sigma) was used as a positive control in the experiment to ensure that the cells used were of normal quality.

4. Procedures

To obtain $IC_{50}$ of the compounds, the following concentrations (30 µM, 10 µM, 3 µM, 1 µM, 0.3 µM and 0.1 µM) were selected for testing. Prior to the test, the compound was formulated into a 10 mM DMSO stock solution with DMSO (Sigma), which was diluted in a gradient to obtain stock solutions at 3 mM, 1 mM, 0.3 mM and 0.1 mM. The stock solutions were then diluted with extracellular fluid to the final µM test concentrations.

The final concentration of DMSO was 0.1% in each concentration of compound solution except for the 30 µM compound test solution in which the final concentration of DMSO was about 0.3%. The test concentration of the control cisapride was 0.1 µM. All compound solutions were routinely sonicated and shaken for 5 to 10 min to ensure complete dissolution of the compounds.

The experimental data were analyzed by data analysis software supplied by HEKA Patchmaster(V2x73.2), Microsoft Excel, and Graphpad Prism 5.0.

5. Test Results

The blocking effect of the compounds of the present disclosure on hERG potassium currents was tested by the above experiment. The $IC_{50}$ values obtained are shown in Table 4.

TABLE 4

IC$_{50}$ for the blocking effect of the compounds of the present disclosure on the hERG potassium ion channel

| Example No. | IC$_{50}$(μM) |
|---|---|
| 4 | 10.1 |
| 5 | 25.9 |
| 6 | >30 |
| 12 | 26.1 |
| Positive compound 1 | 4.6 |

Conclusion: the compounds of the present disclosure have a weak inhibitory effect on hERG and can reduce side effects caused by the hERG pathway; the compounds of the present disclosure have a weaker inhibitory effect on hERG than positive compound 1.

Test Example 3: Inhibitory Effect of Compounds of the Present Disclosure on Human Liver Microsome CYP450 Enzyme This test example was mainly intended to evaluate the inhibitory effects of the compounds of the present disclosure and positive compound 1 (see Test Example 2 for its specific structure) on human liver microsome CYP450 enzyme, and specifically, determination was carried out using the experimental method described below.

I. Materials and Instruments
1. Phosphate buffered saline (20×PBS, purchased from Sangon);
2. NADPH (ACROS, A2646-71-1);
3. Human liver microsome (Corning Gentest, Cat No. 452161, Lot No. 905002, Donor35);
4. ABI QTrap 4000 LC-MS System (AB Sciex);
5. ZORBAX Extend-C18, 3×50 mm, 3.5 μm (Agilent, USA);
6. CYP probe substrate.

II. Procedures
1. Preparation of Solutions
1) Preparation of 100 mM Phosphate Buffered Saline (PBS)
50 mL of PBS solution at the concentration of 2000 mM was diluted to 1000 mL with 950 mL of ultrapure water, mixed uniformly and adjusted to pH 7.4 by a pH meter to obtain the PBS solution of pH 7.4, which was stored in a refrigerator at 4° C. (for a period up to 6 months).
2) Preparation of NADPH Solution
An appropriate amount of NADPH powder was precisely weighed, and dissolved in a PBS buffer solution to prepare a solution at the concentration of 5 mM for later use (prepared right before use).
3) Preparation of Liver Microsome Solution
An appropriate amount of human liver microsome stock solution (20 mg/mL) was diluted to obtain a 0.25 mg/mL microsome solution with 7.5 mM MgCl$_2$ solution for later use (prepared right before use).
4) Preparation of MgCl$_2$ Solution
An appropriate amount of MgCl$_2$ powder was weighed out and prepared into a 300 mM stock solution with a PBS solution, which was stored in a refrigerator at 4° C. for later use. The solution was precisely measured, and diluted to obtain a 7.5 mM working solution with 100 mM PBS solution (prepared right before use).
5) Preparation of Test Compound Solutions
a. An appropriate amount of test compound standard was precisely weighed out and prepared into a stock solution at the concentration of 30 mM with DMSO, which was stored in a refrigerator at 4° C.
b. An appropriate amount of the stock solution was precisely pipetted, and diluted into series solution I at the concentrations of 10 mM, 3 mM, 1 mM, 0.3 mM, 0.03 mM and 0.003 mM with an appropriate amount of DMSO solution. An appropriate amount of the above series solution I was precisely pipetted, and diluted to obtain series solution II at the concentrations of 3 mM, 1 mM, 0.3 mM, 0.1 mM, 0.03 mM, 0.003 mM and 0.0003 mM with an appropriate amount of acetonitrile. An appropriate amount of the above series solution II was precisely pipetted, and diluted with PBS to obtain a working solution at the concentrations of 150 μM, 50 μM, 15 μM, 5 μM, 1.5 μM, 0.15 μM and 0.015 μM for later use.

6) Selection of CYP Probe Substrates and Selective Inhibitors
a. Preparation of a probe substrate stock solution: an appropriate amount of each probe substrate was weighed out and prepared into a stock solution with DMSO, with the concentrations shown in Table 5 below.
b. Preparation of a probe substrate working solution: an appropriate amount of probe substrate stock solution was precisely pipetted, and subjected to a 200-fold dilution with a PBS solution to obtain the probe substrate working solution, with the concentration shown in Table 5 below.

TABLE 5

| CYP | Probe substrate | Stock solution concentration (mM) | Working solution concentration (μM) |
|---|---|---|---|
| 1A2 | Phenacetin | 12 | 60 |
| 2C19 | (S)-Mephenytoin | 20 | 100 |
| 3A4M | Midazolam | 3 | 15 |

2. Liver Microsome Incubation and Sample Preparation
The concentrations of the proteins, substrates and inhibitors in the reaction system are shown in Table 6 below.

TABLE 6

| CYP | Probe substrate | Substrate concentration (μM) | Protein concentration (mg/mL) | Test compounds (μM) |
|---|---|---|---|---|
| 1A2 | Phenacetin | 12 | 0.1 | 30, 10, 3, 1, 0.3, 0.03, 0.003, 0 |
| 2C19 | (S)-Mephenytoin | 20 | | |
| 3A4M | Midazolam | 3 | | |

3. Procedures
1) 40 μL of human liver microsome solution (0.25 mg/mL), 20 μL of probe substrate solution and 20 μL of test compound solution were precisely pipetted into a 96-well plate and pre-incubated for 5 min under a water bath at 37° C.
2) After 5 min of pre-incubation, the mixture was taken out, 20 μL of 5 mM NADPH solution was added to initiate the reaction, and the resulting mixture was incubated for 30 min under a water bath at 37° C. Each sample was run in duplicate.
3) After the incubation was completed, 250 μL of acetonitrile solution containing an internal standard was added to terminate the reaction, and the mixture was shaken at 800 rpm for 10 min and centrifuged at 3700 rpm for 10 min. 100 μL of supernatant was precisely pipetted, diluted with 80 μL of distilled water, and shaken at 800 rpm for 10 min. The supernatant was pipetted for LC-MS/MS analysis.

The values were calculated by Graphpad Prism to obtain the $IC_{50}$ values for the inhibition of drugs on CYP1A2 phenacetin, CYP2C19 (S)-mephenytoin and CYP3A4M midazolam sites of metabolism in human liver microsomes, as shown in Table 7.

TABLE 7

$IC_{50}$ values of the compounds of the present disclosure for CYP1A2 phenacetin, CYP2C19 (S)-mephenytoin and CYP3A4M midazolam sites of metabolism

| Example No. | $IC_{50}(\mu M)$-CYP1A2 | $IC_{50}(\mu M)$-CYP2C19 | $IC_{50}(\mu M)$-CYP3A4M |
|---|---|---|---|
| 4 | >30 | >30 | >30 |
| 5 | >30 | >30 | >30 |
| 6 | >30 | >30 | >30 |
| Positive compound 1 | 12.5 | 7.4 | 25.5 |

Conclusion: metabolic drug interactions based on CYP1A2 phenacetin, CYP2C19 (S)-mephenytoin and CYP3A4M midazolam sites of metabolism do not occur over the 30 µM concentration range of the compounds of the present disclosure, and these compounds exhibit better safety than positive compound 1.

Test Example 4: Time-Dependent Inhibition (TDI) of Enzyme of CYP2C19 (S)-Mephenytoin Site of Metabolism in Human Liver Microsomes by Compounds of the Present Disclosure This test example was mainly intended to evaluate the time-dependent inhibition (TDI) of the enzyme of the CYP2C19 (S)-mephenytoin site of metabolism in human liver microsomes by the compounds of the present disclosure and positive compound 1 (see Test Example 2 for its specific structure), and specifically, determination was carried out using the experimental method described below.

I. Materials and Instruments
1. Phosphate buffered saline (20×PBS, purchased from Sangon);
2. NADPH (ACROS, A2646-71-1);
3. Human liver microsome (Corning Gentest, Cat No. 452161, Lot No. 905002, Donor36);
4. ABI QTrap 4000 LC-MS System (AB Sciex);
5. ZORBAX Extend-C18, 3×50 mm, 3.5 µm (Agilent, USA);
6. CYP probe substrate ((S)-mephenytoin/20 µM, powder purchased from J&K Scientific Ltd., Cat No. 303768) and positive control inhibitor (ticlopidine, powder purchased from SIGMA, Cat No. T6654-1G).

II. Procedures
A 100 mM PBS buffer was prepared. A 15 mM $MgCl_2$ solution and a 10 mM NADPH solution were prepared using the buffer. A 0.5 mg/mL microsome solution was prepared using the 15 mM $MgCl_2$ solution. A 30 mM stock solution was diluted with DMSO to a series of solutions I with concentrations of 30 mM, 10 mM, 3 mM, 1 mM, 0.3 mM, 0.1 mM, 0.03 mM and 0 mM, which were then 10-fold diluted with acetonitrile (ACN) and finally 50-fold diluted with phosphate-buffered solution (PBS) to obtain a series of test working solutions II (60 µM, 20 µM, 6 µM, 2 µM, 0.6 µM, 0.2 µM, 0.06 µM and 0 µM). A 20 µM working solution of (S)-mephenytoin was prepared by dilution with PBS.

The above prepared series of working solutions were well shaken and divided into 50 µL aliquots in corresponding reaction plates (+NADPH group and –NADPH group were set) in triplicate. 20 µL of the liver microsome working solution was added to each 96-well plate. 10 µL of NADPH was added to +NADPH group. The plates were incubated in a water bath at 37° C., and a timer was set on the incubation. After 30 min of incubation, the plates were taken out, and +NADPH group was supplemented with 20 µL of corresponding substrate solutions and –NADPH group with 20 µL of corresponding substrate solutions and 10 µL of NADPH. The plates were incubated in a water bath at 37° C., and a timer was set on the incubation. After 30 min of incubation, the plates were taken out, and the reactions were terminated with 250 µL of an ACN solution containing an internal standard. The plates were shaken on a shaker at 800 rpm for 10 min and centrifuged on a centrifuge at 4000 rpm for 15 min. 100 µL of supernatant and 80 µL of ultrapure water were well mixed and subjected to LC-MS/MS analysis.

After calculation using Graphpad Prism, the $IC_{50}$ values and $IC_{50}$ shift fold values of the drugs for the CYP2C19 (S)-mephenytoin site were obtained and are shown in Table 8.

TABLE 8

IC50 values and $IC_{50}$ shift fold values of the compounds of the present disclosure for the CYP2C19 (S)-mephenytoin site of metabolism in human liver microsomes

| Example No. | (+)NADPH $IC_{50}(\mu M)$ | (−)NADPH $IC_{50}(\mu M)$ | $IC_{50}$ shift fold |
|---|---|---|---|
| 4 | >30 | >30 | TDI not found |
| Positive compound 1 | 2.6 | 6.4 | 2.5 |

Conclusion: compared with positive compound 1, the compounds of the present disclosure showed no inhibitory effect and no TDI effect on the CYP2C19 (S)-mephenytoin site of metabolism in human liver microsomes—that is, the compounds will not interact with CYP2C19-based metabolic drugs, showing better safety.

Test Example 5. Pharmacokinetic Evaluation of Compounds of the Present Disclosure in Mice 1. Abstract
The drug concentrations in the plasma of the test animals (mice) at different time points after intragastric (ig) administration/intravenous (iv) injection of the compounds of the present disclosure were determined by an LC/MS/MS method. The pharmacokinetic behavior of the compound of the present disclosure in mice was studied and its pharmacokinetic profile was evaluated.

2. Methodology
2.1. Test Compounds
The compound of Example 4 and the compound of Example 5.

2.2. Test Animals
Thirty-six C57 mice, female, evenly divided into 4 groups, purchased from Beijing Vital River Laboratory Animal Technology Co., Ltd., with animal production license number: SCXK (Shanghai) 2017-0005.

2.3. Drug Preparation
An amount of the compound of Example 4 and the compound of Example 5 was weighed out, dissolved with 5% by volume of DMSO and 5% tween 80 (Shanghai Titan Scientific Co., Ltd.), and then prepared into 0.1 mg/mL clear solutions with 90% normal saline.

2.4. Administration

Intragastric administration: the drugs were intragastrically administered to mice at a dose of 2.0 mg/kg and a volume of 20.0 mL/kg.

Intravenous injection administration: the drugs were administered to mice by intravenous injection at a dose of 1.0 mg/kg and a volume of 10.0 mL/kg.

3. Procedures

The compound of Example 4 and the compound of Example 5 were administered intragastrically to mice, and 0.1 mL of blood was collected from the orbit before administration and 0.25 h, 0.5 h, 1.0 h, 2.0 h, 4.0 h, 6.0 h, 8.0 h, 11.0 h and 24.0 h after administration. The blood was placed in an EDTA-K2 anticoagulation tube and centrifuged at 10,000 rpm for 1 min (4° C.), and plasma was separated out within 1 h and then stored at −80° C. before being tested. The process from blood collection to centrifugation was performed under an ice bath.

The compound of Example 4 and the compound of Example 5 were administered to mice by intravenous injection, and 0.1 mL of blood was collected before administration and 5 min, 0.25 h, 0.5 h, 1.0 h, 2.0 h, 4.0 h, 8.0 h, 11.0 h and 24 h after administration, and treated in the same way as the blood of the intragastrical group.

The content of the test compounds at different concentrations in plasma of mice after the administration was determined: 25 μL of plasma of mice at each time point after the administration was mixed with 200 μL of acetonitrile (containing 50 μL of a solution of internal standard camptothecin (100 ng/mL)); the mixture was vortexed for 1 min, and centrifuged for 10 min (4000 r/min), and 0.5 μL of supernatant was taken for LC/MS/MS analysis.

4. Pharmacokinetic Parameters

2. Methodology 2.1. Test Compounds

The compound of Example 4 and the compound of Example 5.

2.2. Test Animals

Twelve beagle dogs, males, evenly divided into 4 groups, provided by the animal reserve bank (999M-004) of Shanghai Medicilon Inc. All animals were beagle dogs qualified for physical examination and healthy without abnormalities.

2.3. Drug Preparation

Intragastric administration group: an amount of the compound of Example 4 and the compound of Example 5 was weighed out, dissolved with 5% by volume of DMSO and 20% PEG400, and then prepared into 0.4 mg/mL clear solutions with 55% normal saline. Intravenous injection administration group: an amount of the compound of Example 4 and the compound of Example 5 was weighed out, dissolved with 5% by volume of DMSO and 20% PEG400, and then prepared into 0.25 mg/mL clear solutions with 55% normal saline.

2.4. Administration

Intragastric administration: the dose was 2 mg/kg and the volume was 50.0 mL/kg.

Intravenous injection administration: the dose was 0.5 mg/kg and the volume was 20.0 mL/kg.

3. Procedures

The compound of Example 4 and the compound of Example 5 were administered intragastrically to beagle dogs, and 1.0 mL of blood was collected from the forelimb vein before administration and 0.25 h, 0.5 h, 1.0 h, 2.0 h, 4.0 h, 6.0 h, 8.0 h, 12.0 h and 24.0 h after administration. The blood was placed in an EDTA-K2 anticoagulation tube and centrifuged at 10,000 rpm for 5 min (4° C.), and plasma was

TABLE 9

Pharmacokinetic parameters of the compounds of the present disclosure

| Route of administration | No. | Dose of administration (mg/kg) | Plasma concentration $C_{max}$ (ng/mL) | Area under curve $AUC_{0-t}$ (ng/mL*h) | Half-life $T^{1/2}$ (h) | Clearance CLz/F (ml/min/kg) | Apparent distribution volume Vz/F (ml/kg) |
|---|---|---|---|---|---|---|---|
| Intragastric administration | Compound of Example 4 | 2 | 797 | 2247 | 3.1 | 14.8 | 4013 |
| | Compound of Example 5 | 2 | 359 | 1440 | 2.9 | 23.1 | 5764 |
| Intravenous injection | Compound of Example 4 | 1 | — | 1869 | 1.3 | 8.9 | 1014 |
| | Compound of Example 5 | 1 | — | 2193 | 1.5 | 7.55 | 981 |

Conclusion: both the compounds of the present disclosure have good pharmacokinetic absorption activity in mice, and have pharmacokinetic advantages.

Test Example 6: Pharmacokinetic Evaluation of Compound of the Present Disclosure in Dogs 1. Abstract Dogs are the test animals. The drug concentrations in the plasma of dogs at different time points after intragastric (ig) administration/intravenous (iv) injection of the compounds of the present disclosure were determined by an LC/MS/MS method. The pharmacokinetic performance in beagles of the compounds of the present disclosure was studied and the pharmacokinetic profile thereof was evaluated.

separated out within 1 h and then stored at −80° C. before being tested. Food intake was resumed 3 h after administration.

The compound of Example 4 and the compound of Example 5 were administered to beagle dogs by intravenous injection, and 0.1 mL of blood was collected before administration and 5 min, 15 min, 0.5 h, 1.0 h, 2.0 h, 4.0 h, 8.0 h, 12.0 h and 24 h after administration and treated in the same way as the blood of the intragastrical group. The process from blood collection to centrifugation was performed under an ice bath.

The content of the test compounds at different concentrations in plasma of beagle dogs after the administration was determined: 10 μL of plasma of beagle dogs at each time point after the administration was mixed with 200 μL of acetonitrile (containing a solution of internal standard camptothecin (100 ng/mL)); the mixture was vortexed for 1 min, and centrifuged for 7 min (18,000 r/min), and 6 μL of supernatant was taken for LC/MS/MS analysis.

4. Pharmacokinetic Parameters

TABLE 10

Pharmacokinetic parameters of the compounds of the present disclosure

| Route of administration | No. | Dose of administration (mg/kg) | Plasma concentration $C_{max}$ (ng/mL) | Area under curve $AUC_{0-t}$ (ng/mL*h) | Half-life $T\frac{1}{2}$ (h) | Clearance CLz/F (ml/min/kg) | Apparent distribution volume Vz/F (ml/kg) |
|---|---|---|---|---|---|---|---|
| Intragastric administration | Compound of Example 4 | 2 | 4044 | 21382 | 5.3 | 1.6 | 713 |
| | Compound of Example 5 | 2 | 4428 | 22119 | 4.9 | 1.7 | 636 |
| Intravenous injection | Compound of Example 4 | 0.5 | 1225 | 4008 | 5.4 | 1.9 | 908 |
| | Compound of Example 5 | 0.5 | 1742 | 4829 | 3.0 | 1.8 | 448 |

Conclusion: both the compounds of the present disclosure have good pharmacokinetic absorption activity in dogs, and have pharmacokinetic advantages.

The invention claimed is:

1. A compound of general formula (IM) or a tautomer, racemate, enantiomer or diastereomer thereof or a mixture thereof, or a pharmaceutically acceptable salt thereof:

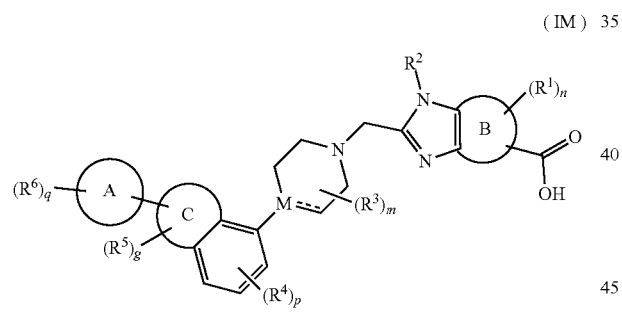

(IM)

wherein:
ring B is phenyl or 5- or 6-membered heteroaryl;
M is a N atom or a C atom;
═══ is a single bond or double bond; when M is a N atom, ═══ is a single bond, and when M is a C atom, ═══ is a single bond or double bond;
ring C is 6- to 7-membered heterocyclyl, and the 6- to 7-membered heterocyclyl contains 2 heteroatoms selected from the group consisting of an O atom and an S atom;
ring A is aryl or heteroaryl;
each $R^1$ is identical or different and each is independently selected from the group consisting of a hydrogen atom, halogen, alkyl, alkenyl, alkynyl, alkoxy, haloalkyl, haloalkoxy, hydroxyalkyl, cyano, amino, nitro, hydroxy, and cycloalkyl;
$R^2$ is selected from the group consisting of a hydrogen atom, alkyl, heterocyclylalkyl, cycloalkylalkyl, alkenyl, alkynyl, haloalkyl, hydroxyalkyl, cycloalkyl, heterocyclyl, aryl and heteroaryl, wherein the alkyl, heterocyclylalkyl, cycloalkylalkyl, alkenyl, alkynyl, cycloalkyl, heterocyclyl, aryl and heteroaryl are each independently optionally substituted with one or more substituents selected from the group consisting of halogen, alkyl, alkenyl, alkynyl, alkoxy, haloalkyl, haloalkoxy, cyano, amino, nitro, hydroxy, hydroxyalkyl, cycloalkyl, heterocyclyl, aryl and heteroaryl;

each $R^3$ is identical or different and each is independently selected from the group consisting of a hydrogen atom, halogen, alkyl, oxo, alkenyl, alkynyl, alkoxy, haloalkyl, haloalkoxy, hydroxyalkyl, cyano, amino, nitro, hydroxy, and cycloalkyl;

each $R^4$ is identical or different and each is independently selected from the group consisting of a hydrogen atom, halogen, alkyl, alkenyl, alkynyl, alkoxy, haloalkyl, haloalkoxy, cyano, amino, nitro, hydroxy, hydroxyalkyl, and cycloalkyl;

each $R^5$ is identical or different and each is independently selected from the group consisting of a hydrogen atom, halogen, alkyl, alkenyl, alkynyl, alkoxy, haloalkyl, haloalkoxy, hydroxyalkyl, cyano, amino, nitro, hydroxy, and cycloalkyl;

each $R^6$ is identical or different and is each independently selected from the group consisting of a hydrogen atom, halogen, alkyl, alkoxy, cyano, heterocyclylalkyl, cycloalkylalkyl, alkenyl, alkynyl, haloalkyl, haloalkoxy, hydroxyalkyl, and cycloalkyl, wherein the alkyl, heterocyclylalkyl, cycloalkylalkyl, alkenyl, alkynyl, and cycloalkyl are each independently optionally substituted with one or more substituents selected from the group consisting of halogen, alkyl, alkenyl, alkynyl, alkoxy, haloalkyl, haloalkoxy, cyano, amino, nitro, hydroxy, hydroxyalkyl, and cycloalkyl;

n is 0, 1, 2 or 3;
m is 0, 1, 2, 3 or 4;
p is 0, 1, 2 or 3;
g is 0, 1, 2, 3, 4 or 5; and
q is 0, 1, 2, 3 or 4;

provided that the compound is not:
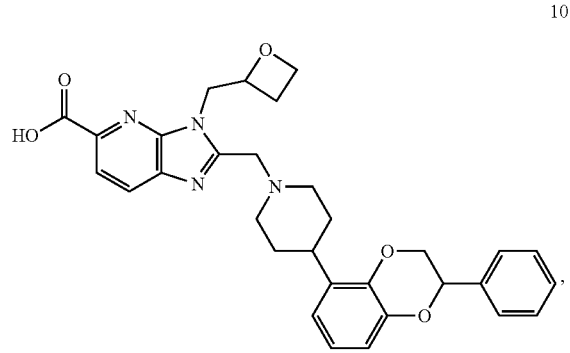
101
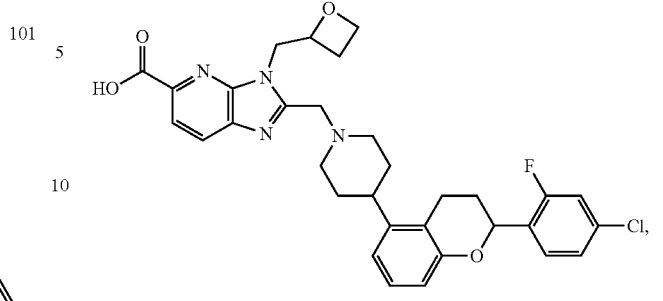
105
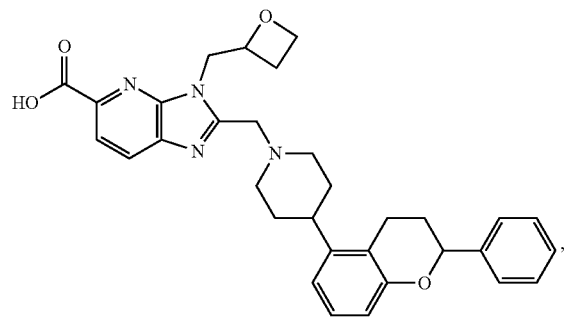
102
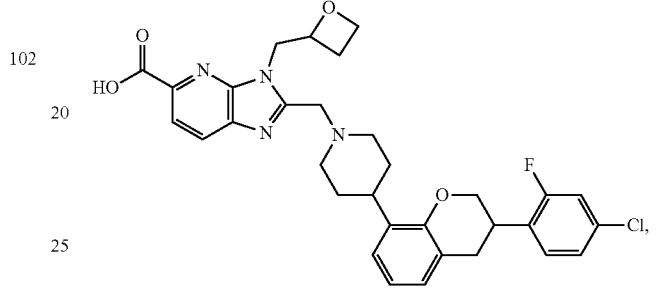
106
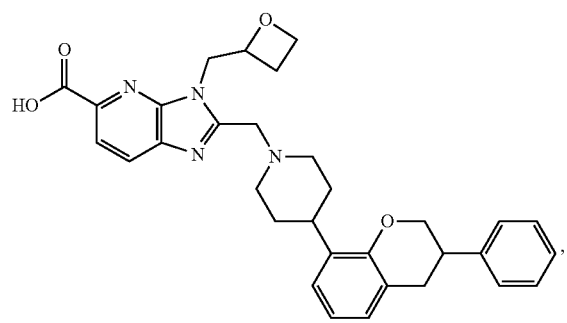
103
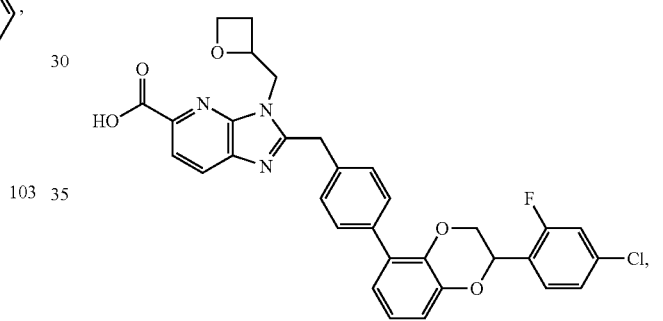
107
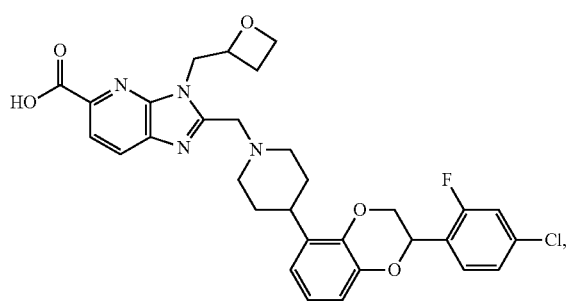
104
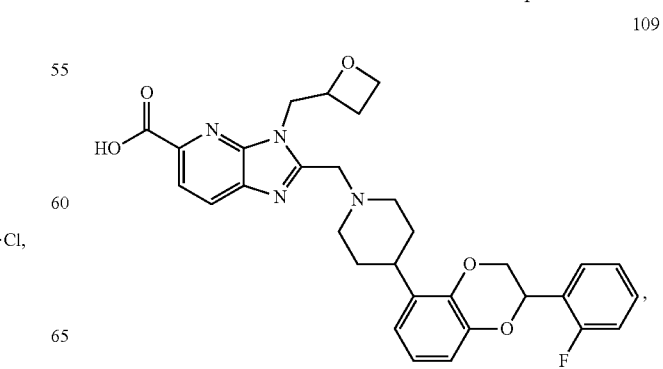
108, 109

110
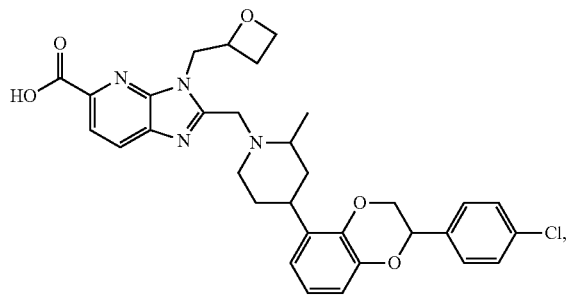
111
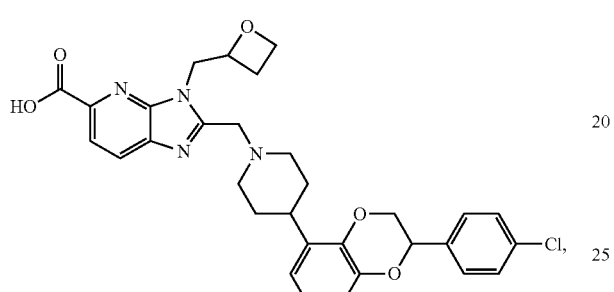
112
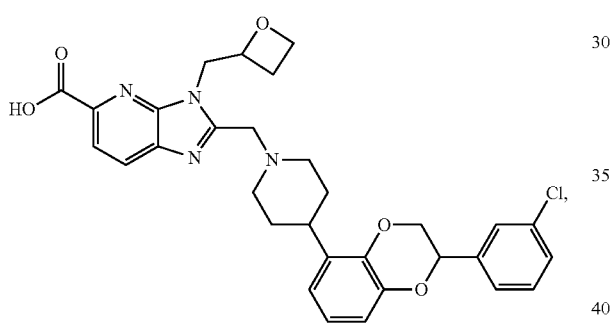
113
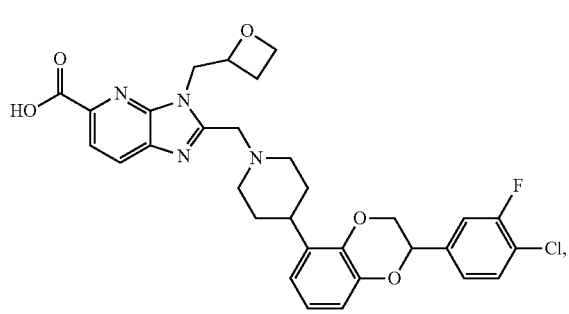
114
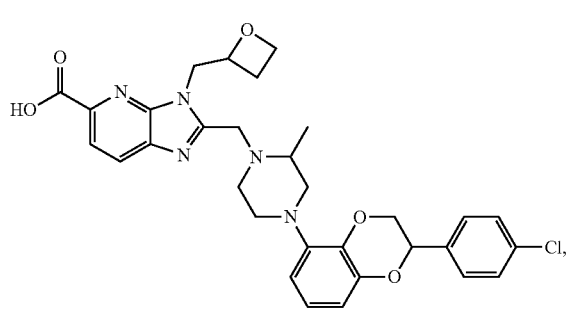
115
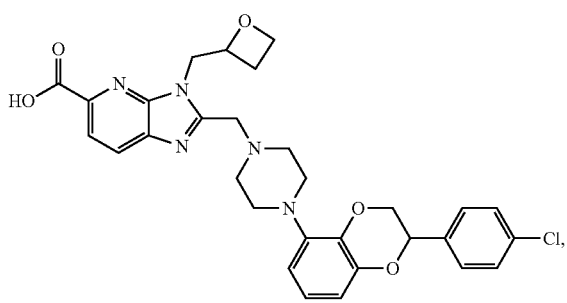
116
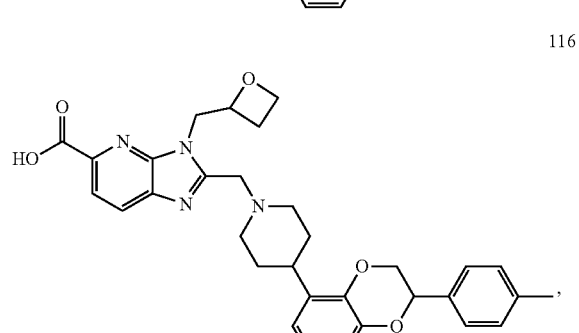
117
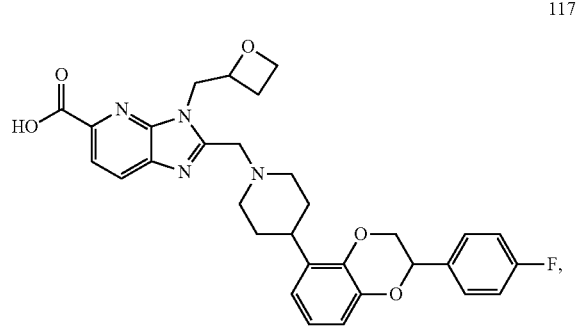
118
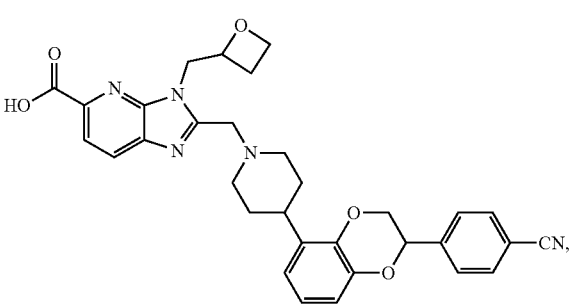
119
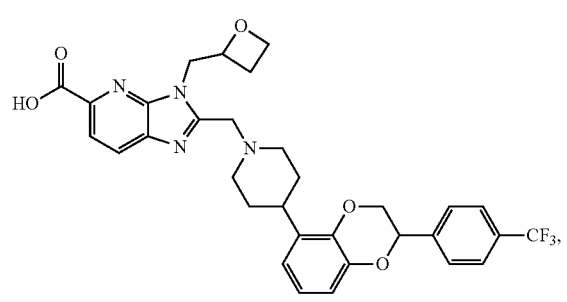

120
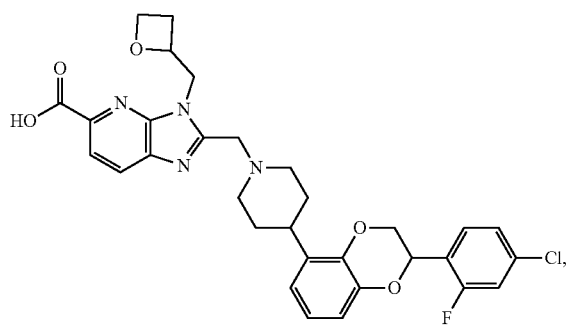
121
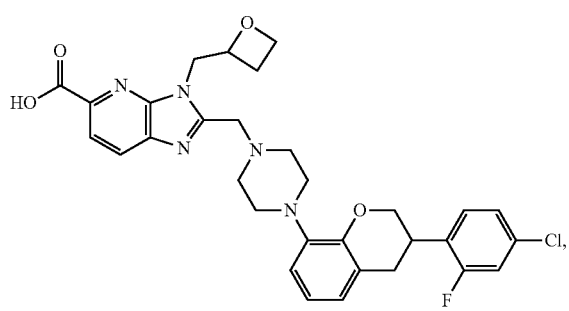
122
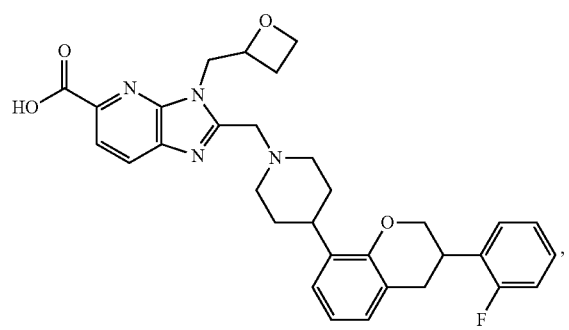
123
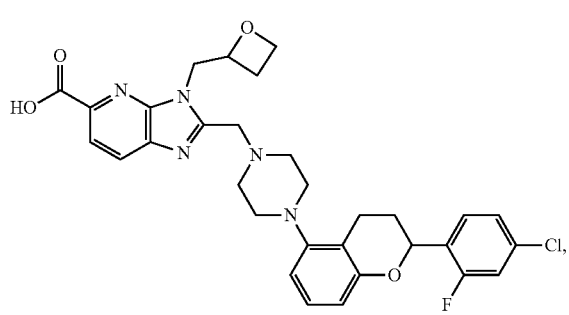
124
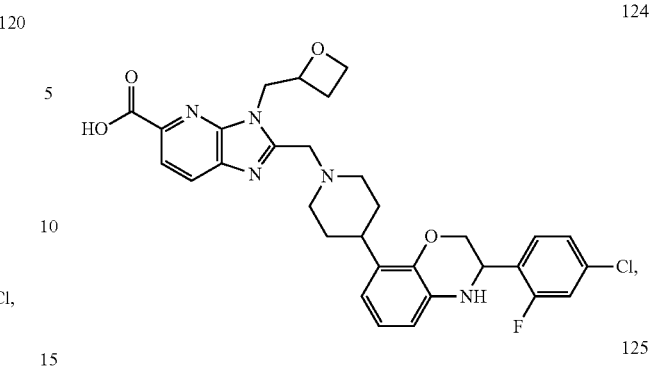
125
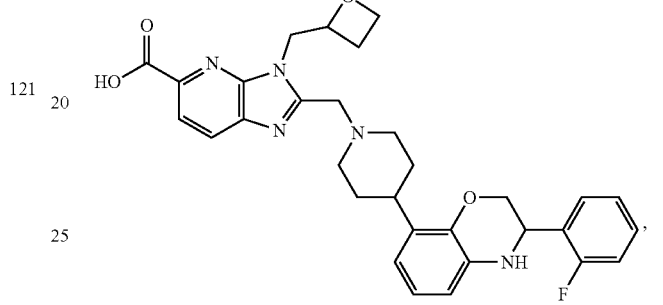
127
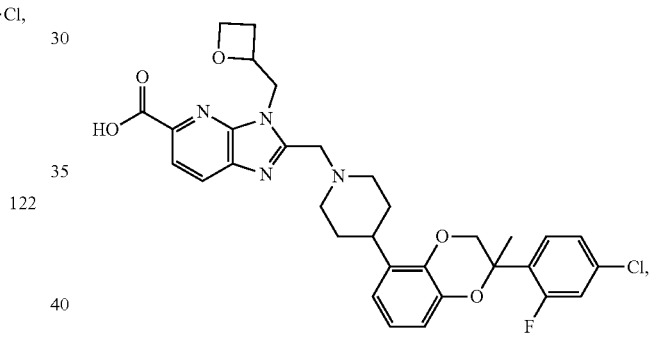
128
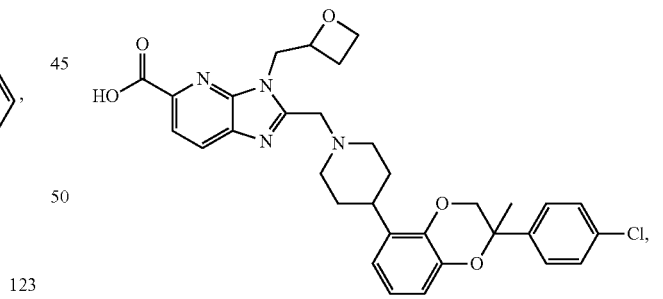
129
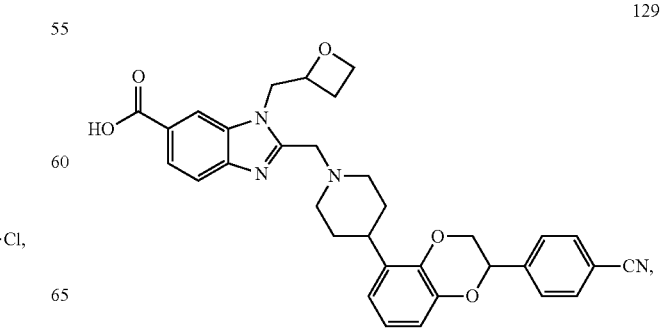

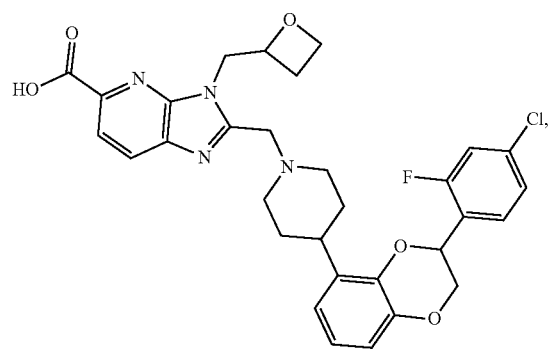
130
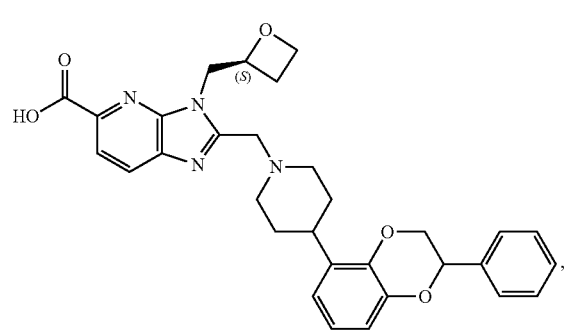
101a
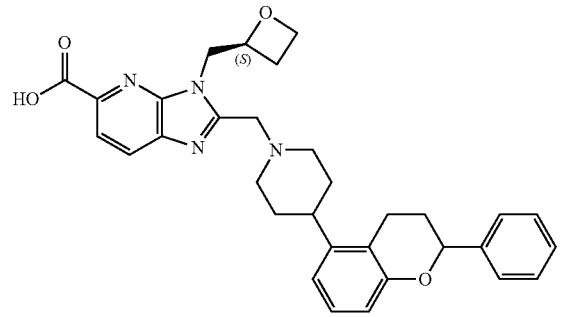
102a
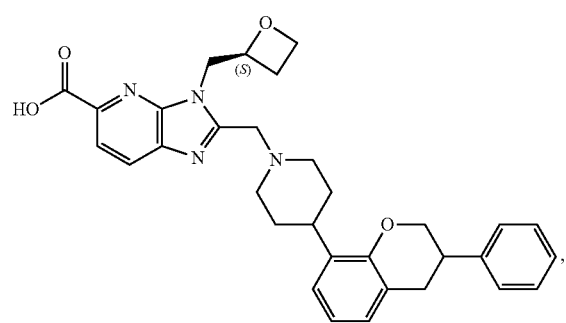
103a
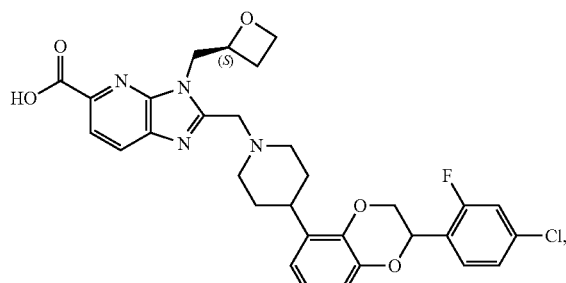
104a
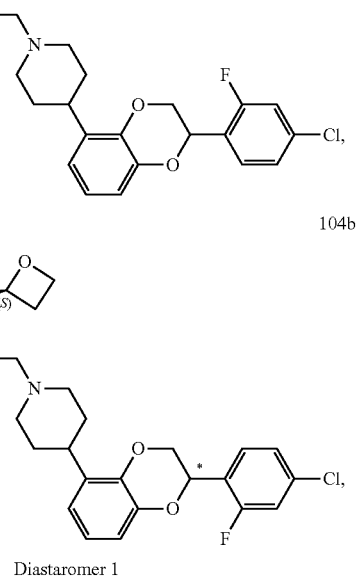
104b
Diastaromer 1
104c
Diastaromer 2
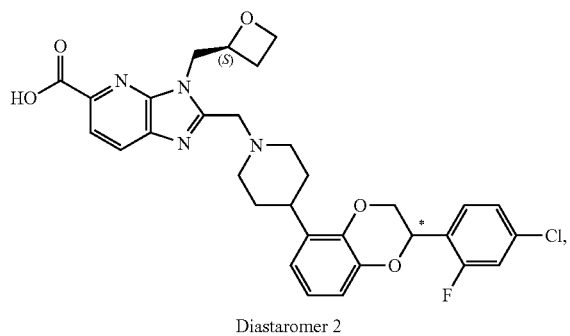
105a
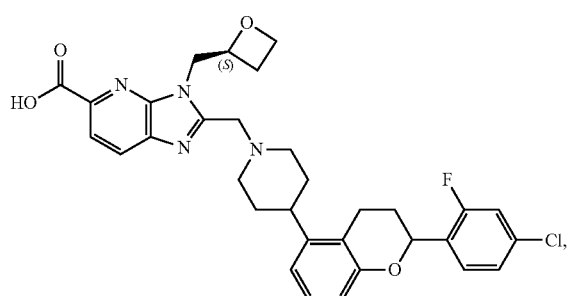

207
-continued
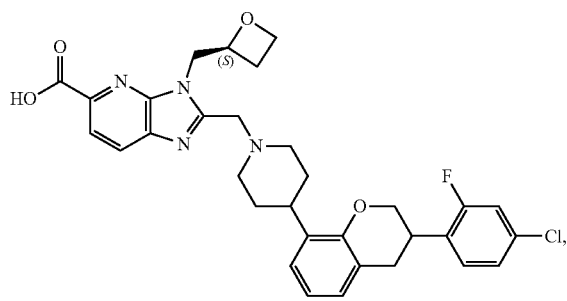
106a
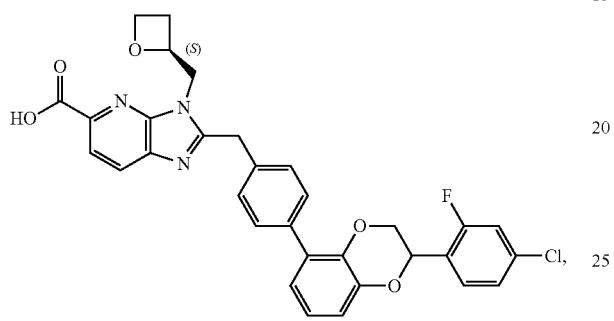
107a
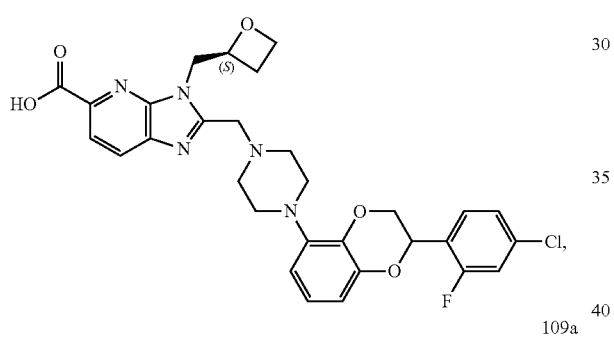
108a
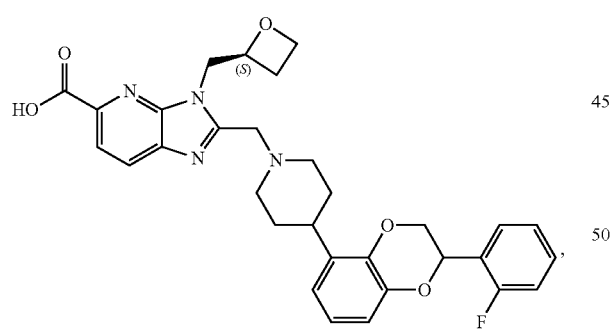
109a
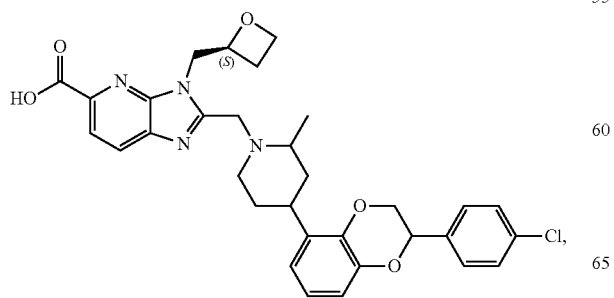
208
-continued
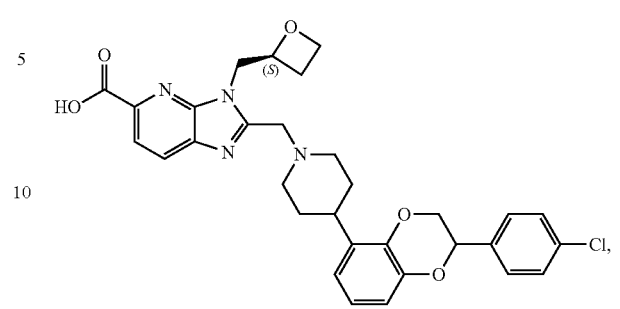
111a
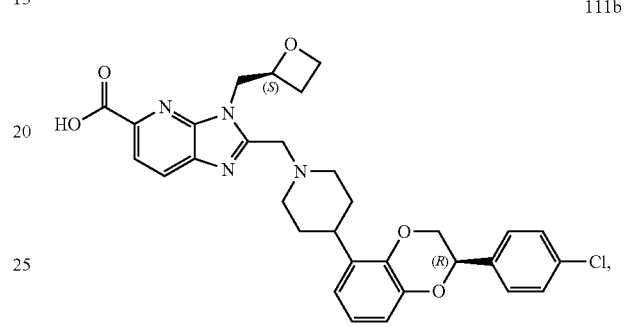
111b
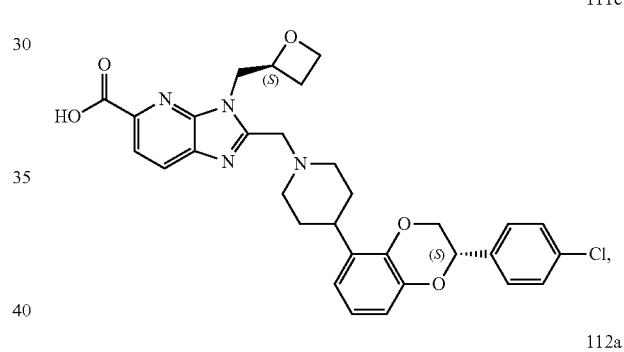
111c
112a
113a

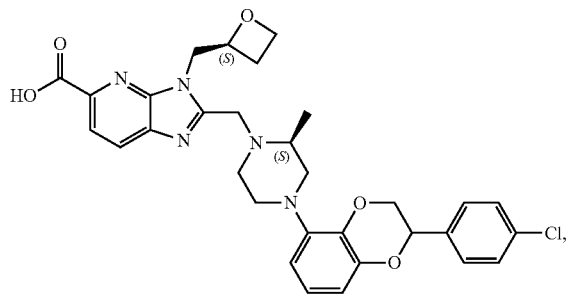
114a
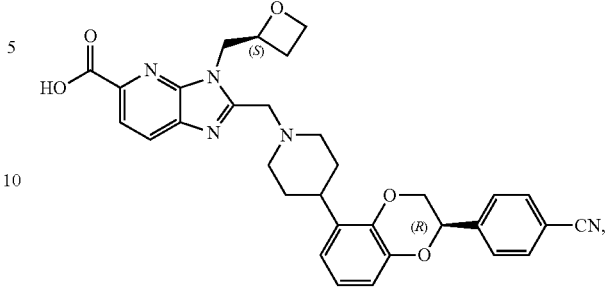
118b
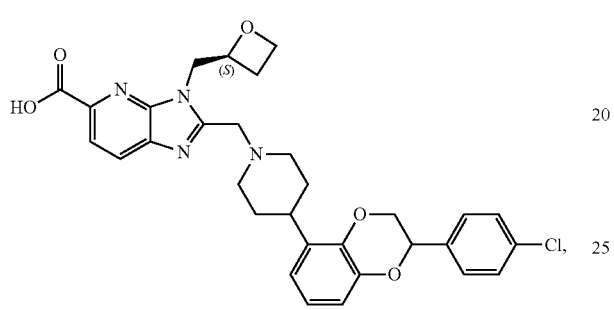
115a
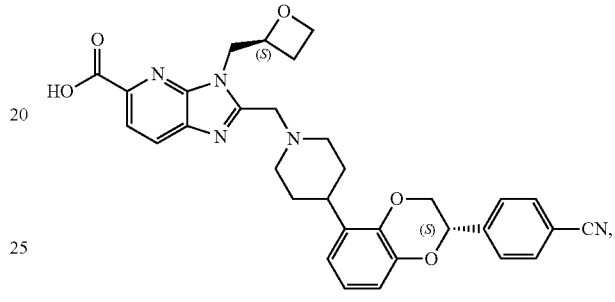
118c
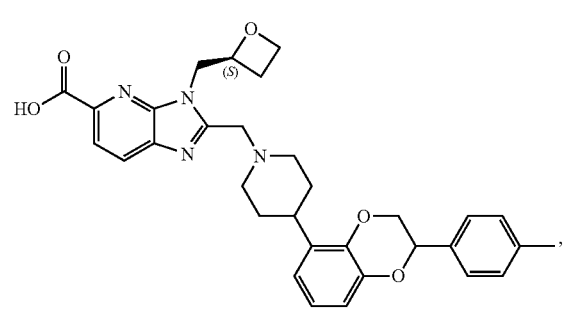
116a
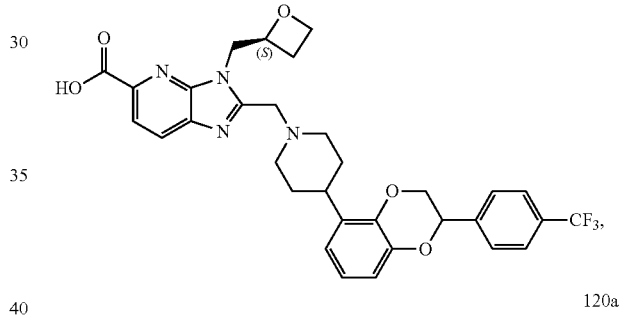
119a
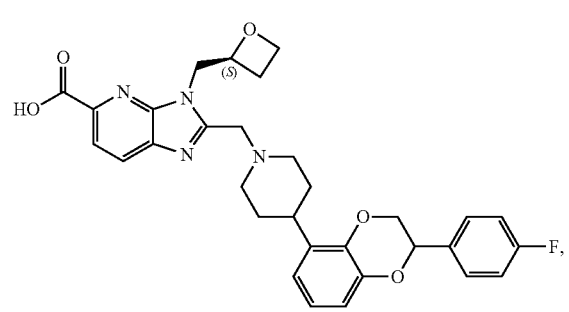
117a
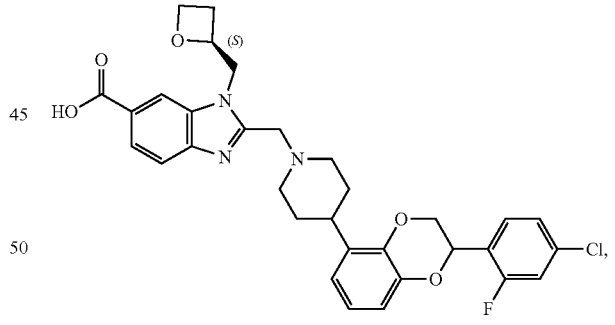
120a
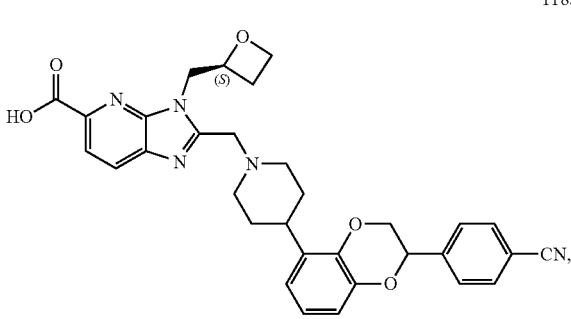
118a
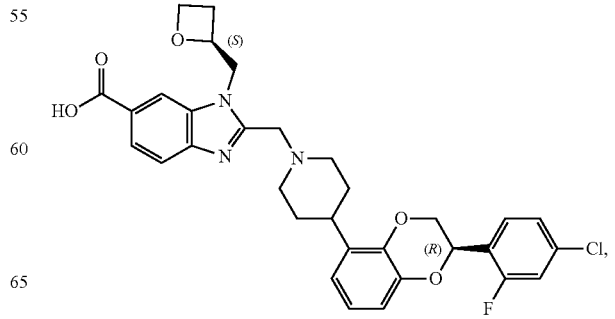
120b -continued
120c
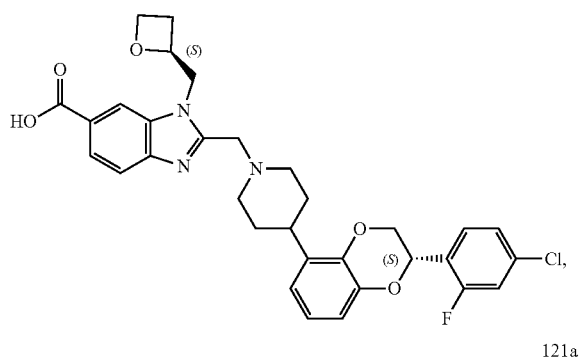
121a
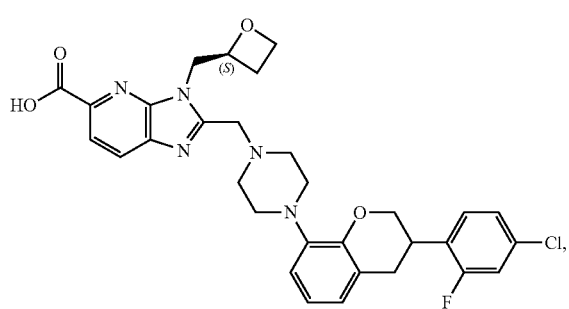
122a
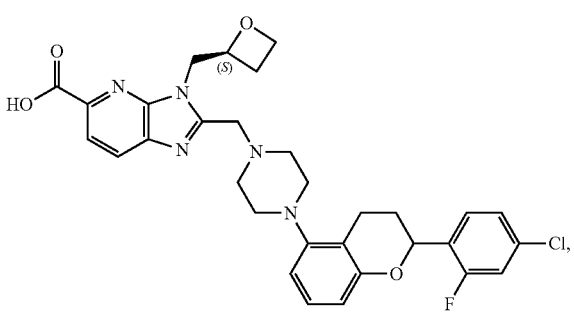
123a
124a
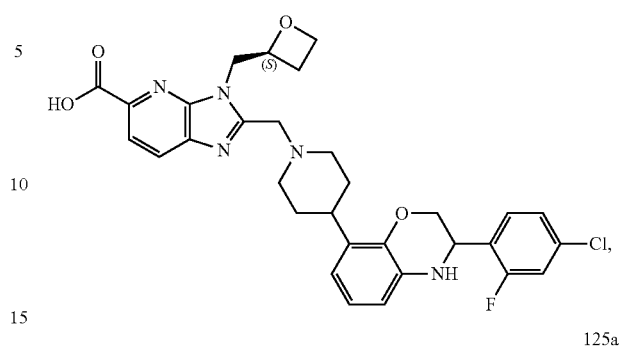
125a
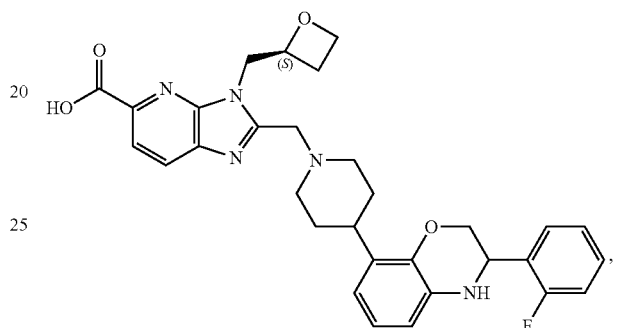
127a
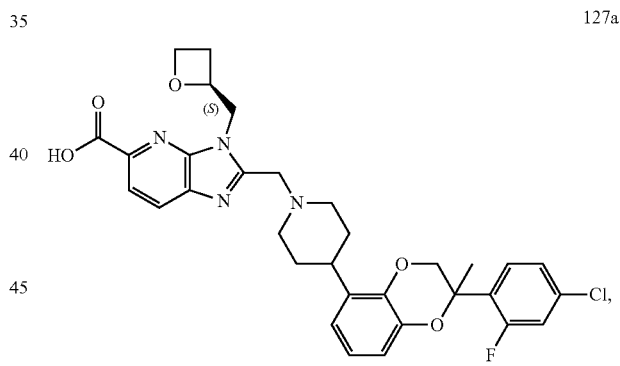
128a
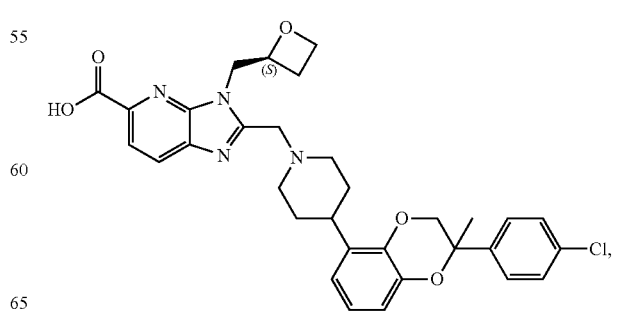

213

-continued

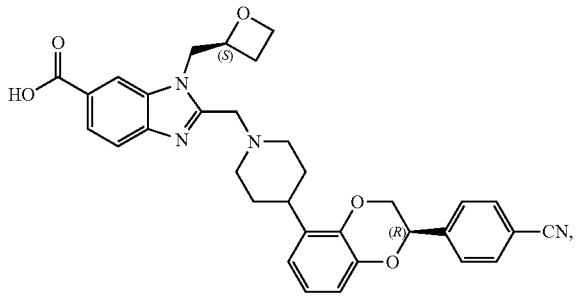

129a

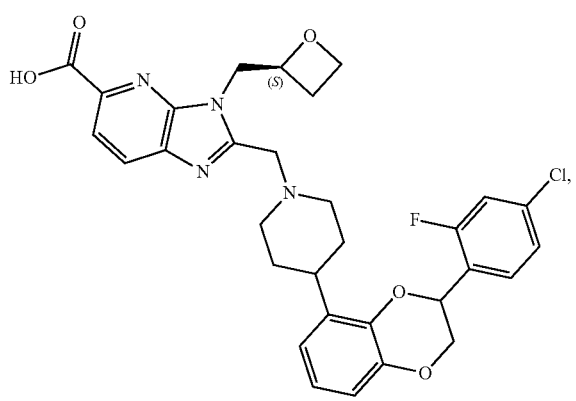

130a

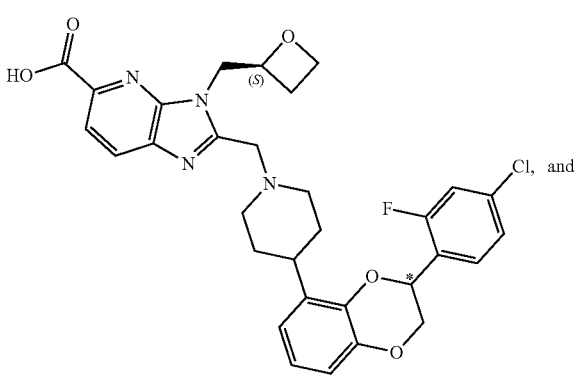

130b

Diastereomer 1

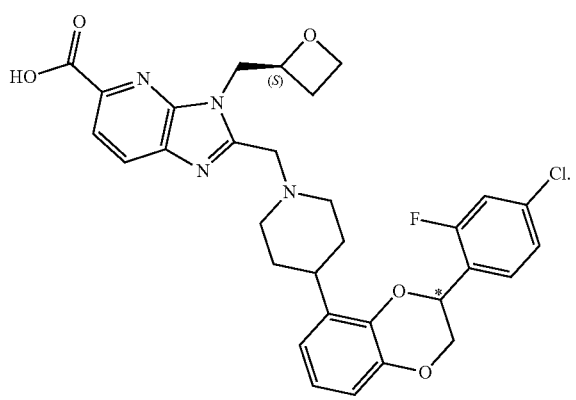

130c

Diastereomer 2

2. The compound of general formula (IM) or the tautomer, racemate, enantiomer or diastereomer thereof or the mixture thereof, or the pharmaceutically acceptable salt thereof according to claim 1, wherein the compound is represented by general formula (IN) or a tautomer, racemate, enantiomer or diastereomer thereof or a mixture thereof, or a pharmaceutically acceptable salt thereof:

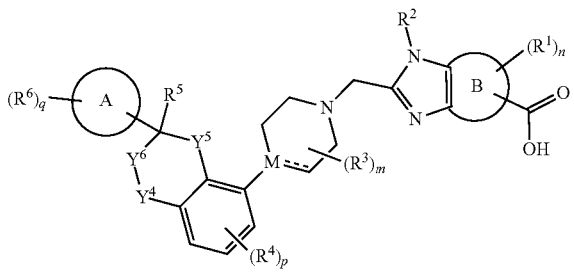

(IN)

wherein:

Y$^5$ is an O atom or a S atom;

Y$^4$ and Y$^6$ are identical or different and are each independently selected from the group consisting of an O atom, a S atom and —(CR$^m$R$^n$)$_{k-}$, provided that Y$^4$ and Y$^6$ are not both heteroatoms;

R$^m$ and R$^n$ are identical or different and are each independently selected from the group consisting of a hydrogen atom, halogen, alkyl, alkenyl, alkynyl, alkoxy, haloalkyl, haloalkoxy, hydroxyalkyl, cyano, amino, nitro, hydroxy, and cycloalkyl;

k is 1 or 2;

ring B, M, , ring A, R$^1$ to R$^6$, n, m, p and q are as defined in claim 1.

3. The compound of general formula (IM) or the tautomer, racemate, enantiomer or diastereomer thereof or the mixture thereof, or the pharmaceutically acceptable salt thereof according to claim 1, wherein ring B is selected from the group consisting of phenyl, pyridinyl and thienyl, ring A is selected from the group consisting of phenyl, 5- or 6-membered heteroaryl and

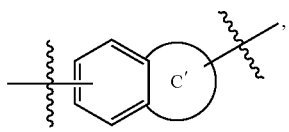

and ring C' is 5- or 6-membered heteroaryl.

4. The compound of general formula (IM) or the tautomer, racemate, enantiomer or diastereomer thereof or the mixture thereof, or the pharmaceutically acceptable salt thereof according to claim 1, wherein the compound is represented by general formula (IIG) or a tautomer, racemate, enantiomer or diastereomer thereof or a mixture thereof, or a pharmaceutically acceptable salt thereof:

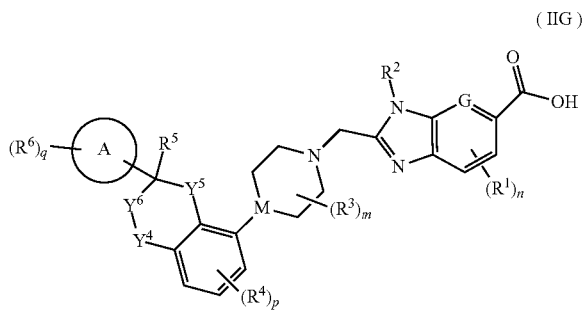

(IIG)

wherein:
G is a C atom or a N atom;
$Y^5$ is an O atom or a S atom;
$Y^4$ and $Y^6$ are identical or different and are each independently selected from the group consisting of an O atom, a S atom and —$(CR'''R'')_{k-}$, provided that $Y^4$ and $Y^6$ are not both heteroatoms;
$R'''$ and $R''$ are identical or different and are each independently selected from the group consisting of a hydrogen atom, halogen, alkyl, alkenyl, alkynyl, alkoxy, haloalkyl, haloalkoxy, hydroxyalkyl, cyano, amino, nitro, hydroxy, and cycloalkyl;
k is 1 or 2;
M, ring A, $R^1$ to $R^6$, n, m, p and q are as defined in claim 1.

5. The compound of general formula (IM) or the tautomer, racemate, enantiomer or diastereomer thereof or the mixture thereof, or the pharmaceutically acceptable salt thereof according to claim 4, wherein the compound is represented by general formula (IIGa) or a tautomer, racemate, enantiomer or diastereomer thereof or a mixture thereof, or a pharmaceutically acceptable salt thereof:

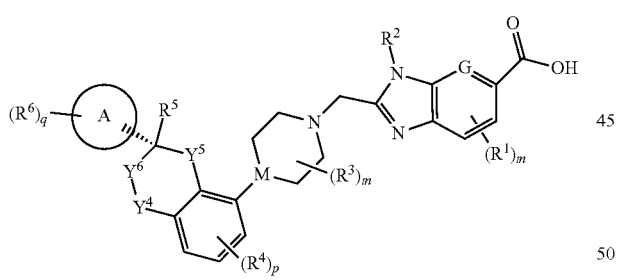

(IIGa)

wherein:
G is a C atom or a N atom;
$Y^5$ is an O atom or a S atom;
$Y^4$ and $Y^6$ are identical or different and are each independently selected from the group consisting of an O atom, a S atom and —$(CR'''R'')_{k-}$, provided that $Y^4$ and $Y^6$ are not both heteroatoms;
$R'''$ and $R''$ are identical or different and are each independently selected from the group consisting of a hydrogen atom, halogen, alkyl, alkenyl, alkynyl, alkoxy, haloalkyl, haloalkoxy, hydroxyalkyl, cyano, amino, nitro, hydroxy, and cycloalkyl;
k is 1 or 2;
M, ring A, $R^1$ to $R^6$, n, m, p and q are as defined in claim 4.

6. The compound of general formula (IM) or the tautomer, racemate, enantiomer or diastereomer thereof or the mixture thereof, or the pharmaceutically acceptable salt thereof according to claim 4, wherein $Y^4$ and $Y^5$ are O atoms, and $Y^6$ is —$(CR'''R'')_{k-}$; or, $Y^5$ and $Y^6$ are O atoms, and $Y^4$ is —$(CR'''R'')_{k-}$; k is 1 or 2; $R'''$ and $R''$ are identical or different and are each independently selected from the group consisting of a hydrogen atom, halogen, $C_{1-6}$ alkyl, $C_{2-6}$ alkenyl, $C_{2-6}$ alkynyl, $C_{1-6}$ alkoxy, $C_{1-6}$ haloalkyl, $C_{1-6}$ haloalkoxy, hydroxy $C_{1-6}$ alkyl, cyano, amino, nitro, hydroxy, and 3- to 8-membered cycloalkyl.

7. The compound of general formula (IM) or the tautomer, racemate, enantiomer or diastereomer thereof or the mixture thereof, or the pharmaceutically acceptable salt thereof according to claim 1, wherein the compound is represented by general formula (IIIN-1) or general formula (IIIN-2) or a tautomer, racemate, enantiomer or diastereomer thereof or a mixture thereof, or a pharmaceutically acceptable salt thereof:

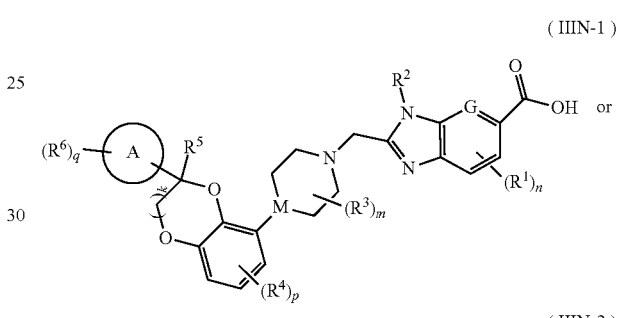

(IIIN-1) or

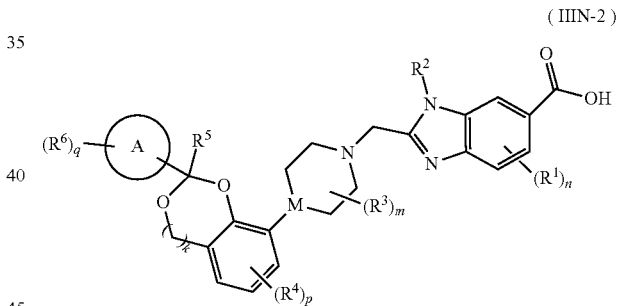

(IIIN-2)

wherein:
k is 1 or 2;
M, ring A, $R^1$ to $R^6$, n, m, p and q are as defined in claim 1.

8. The compound of general formula (IM) or the tautomer, racemate, enantiomer or diastereomer thereof or the mixture thereof, or the pharmaceutically acceptable salt thereof according to claim 1, wherein

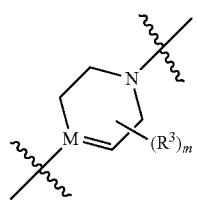

is selected from the group consisting of

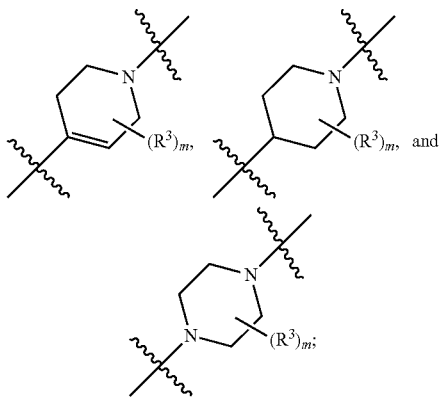

R³ and m are as defined in claim 1.

9. The compound of general formula (IM) or the tautomer, racemate, enantiomer or diastereomer thereof or the mixture thereof, or the pharmaceutically acceptable salt thereof according to claim 7, wherein ring A is 6- to 10-membered aryl or 5- to 10-membered heteroaryl; M is CH.

10. The compound of general formula (IM) or the tautomer, racemate, enantiomer or diastereomer thereof or the mixture thereof, or the pharmaceutically acceptable salt thereof according to claim 1, wherein

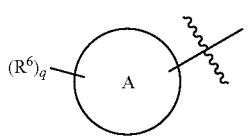

is selected from the group consisting of

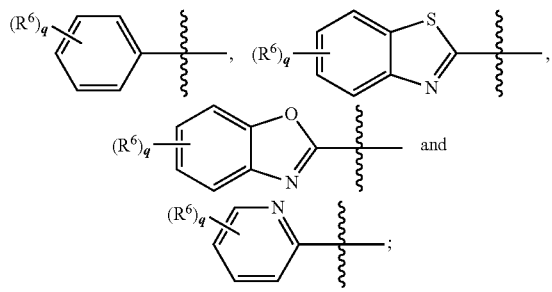

R⁶ and q are as defined in claim 1.

11. The compound of general formula (IM) or the tautomer, racemate, enantiomer or diastereomer thereof or the mixture thereof, or the pharmaceutically acceptable salt thereof according to claim 1, wherein each R¹ is identical or different and each is independently selected from the group consisting of a hydrogen atom, halogen and $C_{1-6}$ alkyl; each R³ is identical or different and each is independently selected from the group consisting of a hydrogen atom, halogen, oxo and $C_{1-6}$ alkyl; each R⁴ is identical or different and each is independently selected from the group consisting of a hydrogen atom, halogen and $C_{1-6}$ alkyl; each R⁵ is identical or different and each is independently a hydrogen atom or $C_{1-6}$ alkyl.

12. The compound of general formula (IM) or the tautomer, racemate, enantiomer or diastereomer thereof or the mixture thereof, or the pharmaceutically acceptable salt thereof according to claim 1, wherein R² is $C_{1-6}$ alkyl, wherein the $C_{1-6}$ alkyl is optionally substituted with one or more substituents selected from the group consisting of halogen, hydroxy, $C_{1-6}$ alkoxy, 3- to 6-membered cycloalkyl and 3- to 6-membered heterocyclyl; R⁶ are identical or different and are each independently selected from the group consisting of a hydrogen atom, halogen, $C_{1-6}$ alkyl, $C_{1-6}$ alkoxy, cyano and $C_{1-6}$ haloalkyl.

13. A compound selected from the group consisting of the following compounds:

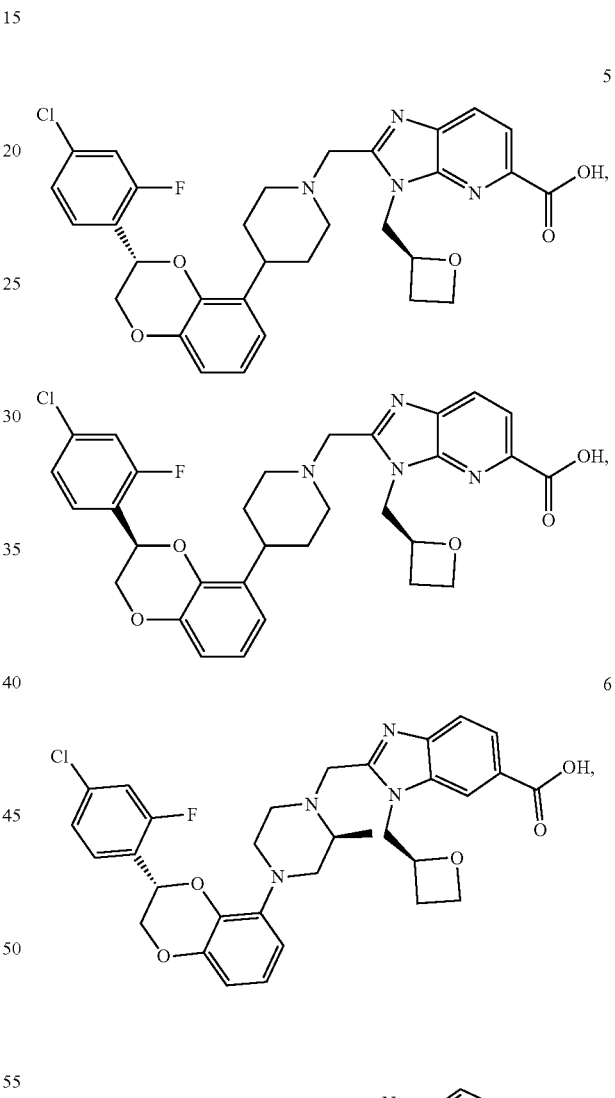

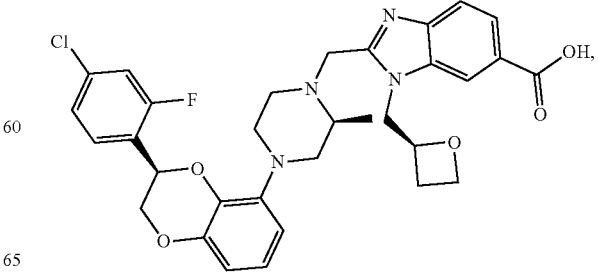

7
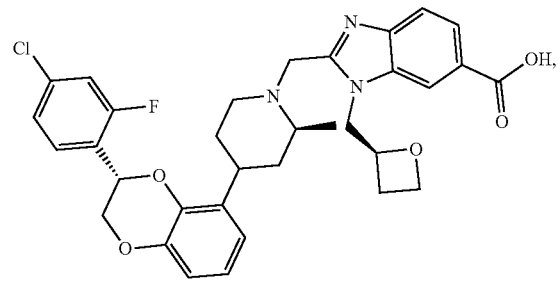
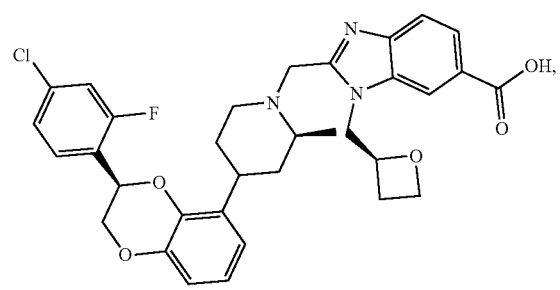
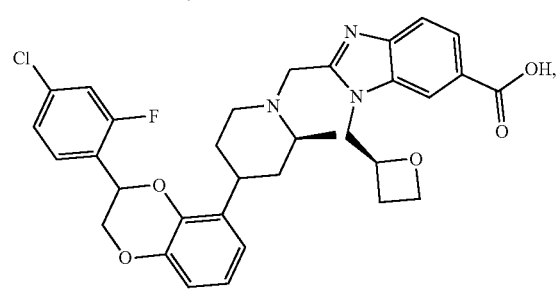
8
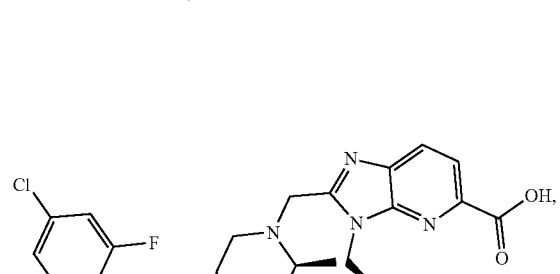
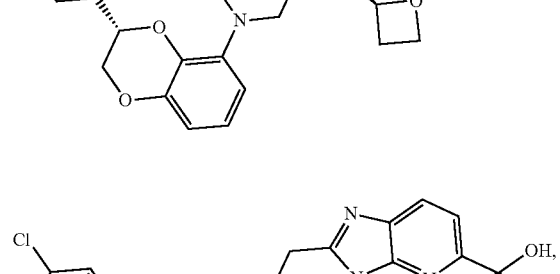
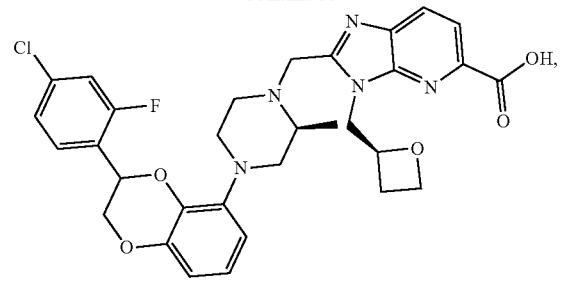
9
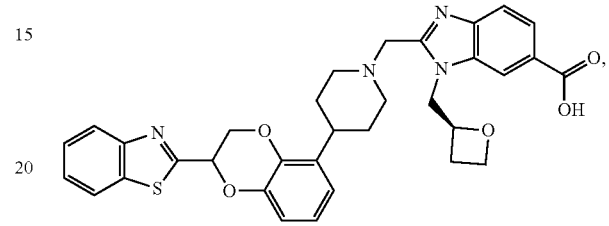
10
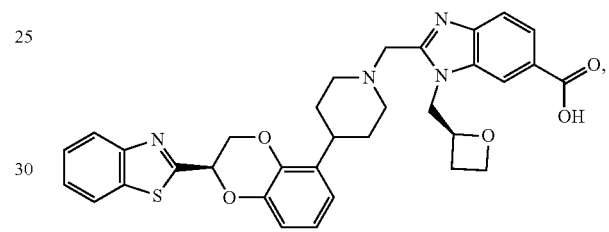
11
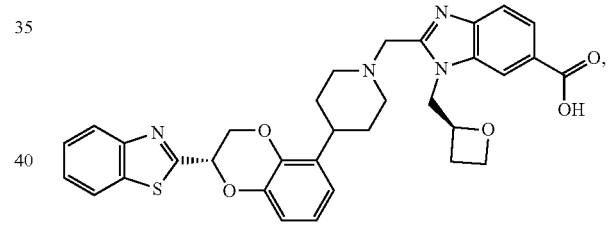
12
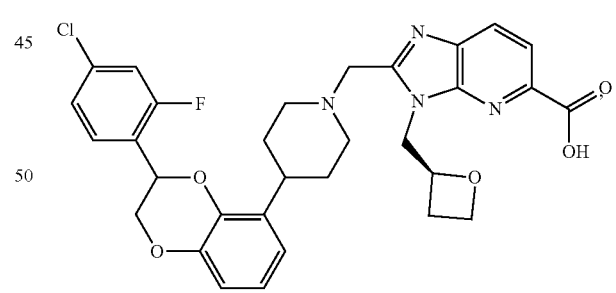
13
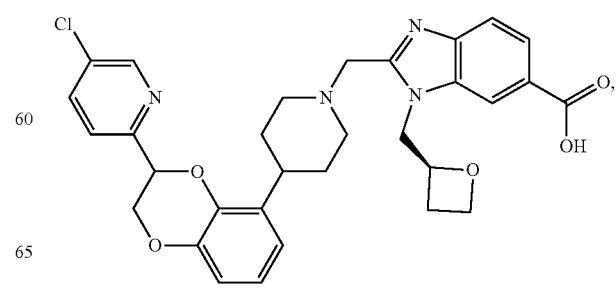

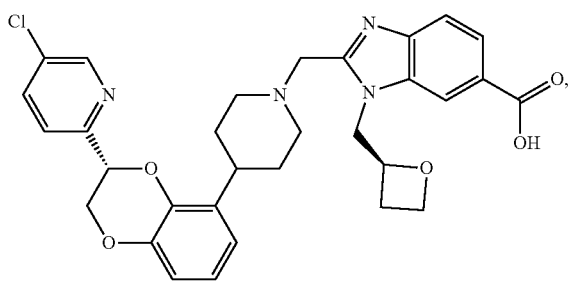
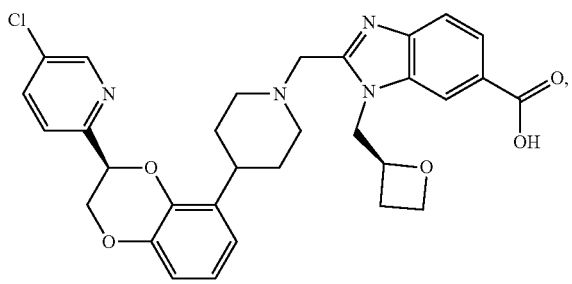
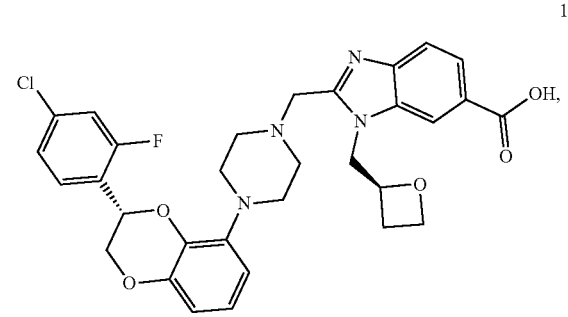
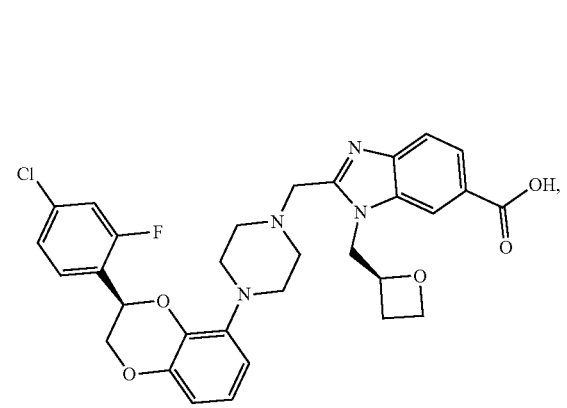
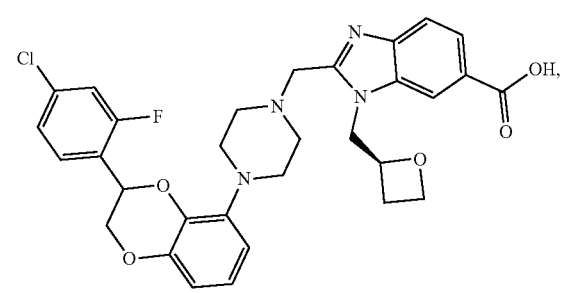
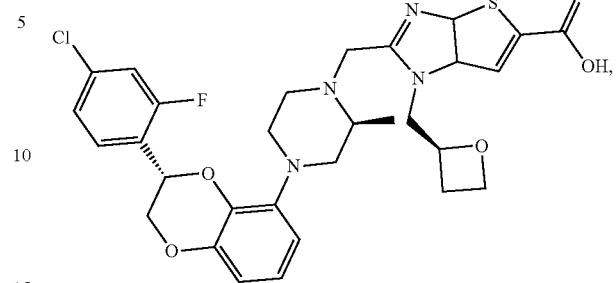
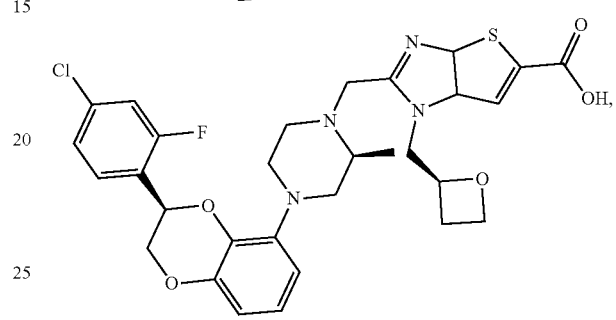
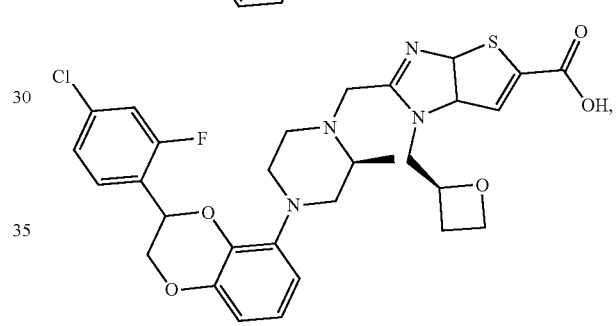
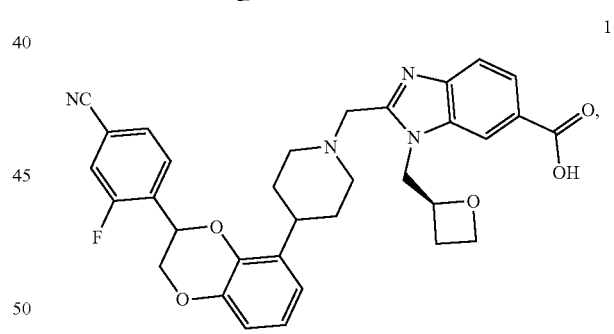
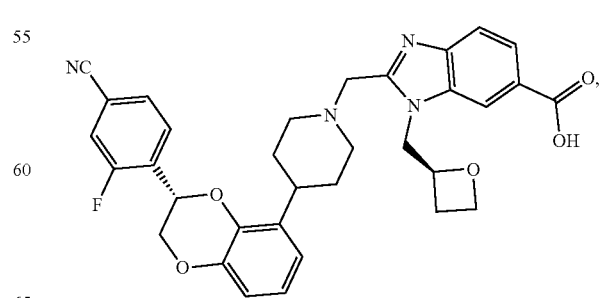

223
-continued

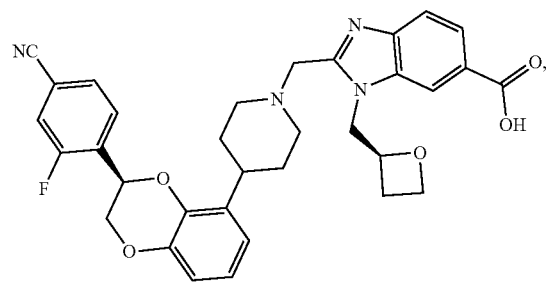

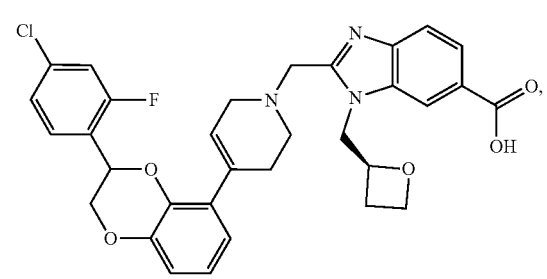

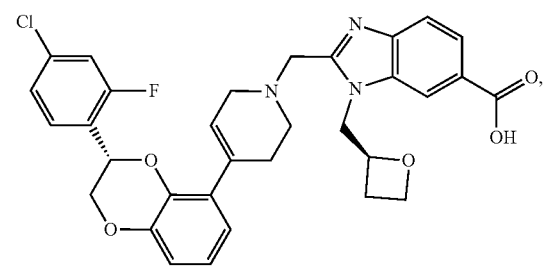

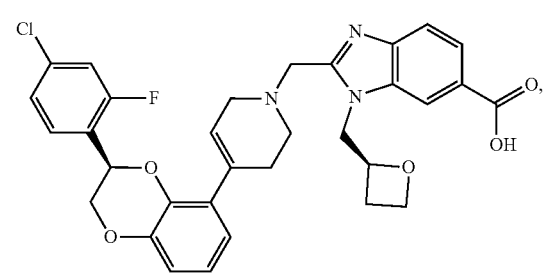

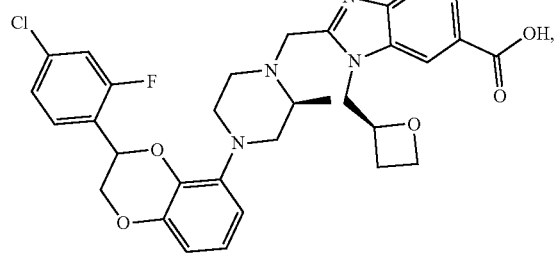

224
-continued

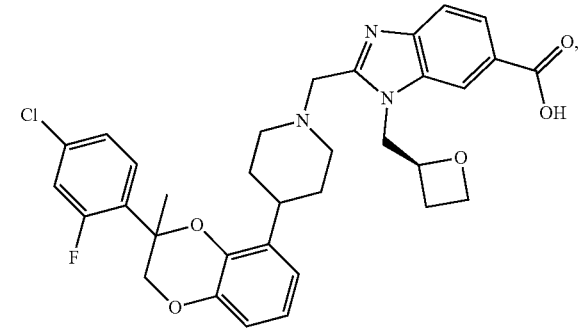

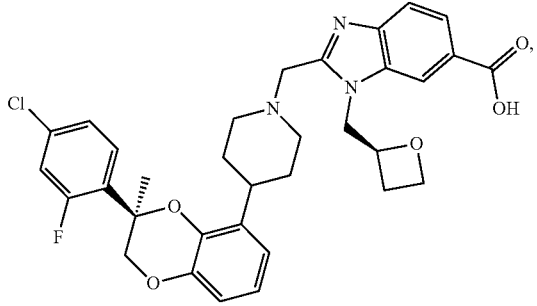 [SMILES: C[C@@]1(c2ccc(Cl)cc2F)COc2cccc(C3CCN(Cc4nc5ccc(C(=O)O)cc5n4C[C@@H]4CCO4)CC3)c2O1]

or a tautomer, racemate, enantiomer or diastereomer thereof or a mixture thereof, or a pharmaceutically acceptable salt thereof.

14. A compound of general formula (IMA) or a tautomer, racemate, enantiomer or diastereomer thereof or a mixture thereof, or a pharmaceutically acceptable salt thereof,

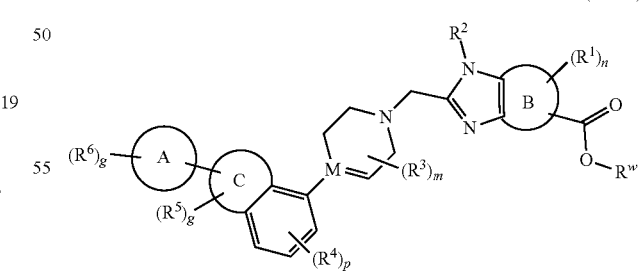

(IMA)

wherein:
$R^w$ is $C_{1-6}$ alkyl;
ring B is phenyl or 5- or 6-membered heteroaryl;
M is a N atom or a C atom;
═══ is a single bond or double bond; when M is a N atom, ═══ is a single bond, and when M is a C atom, ═══ is a single bond or double bond;

ring C is 6- to 7-membered heterocyclyl, and the 6- to 7-membered heterocyclyl contains 2 heteroatoms selected from the group consisting of an O atom and a S atom;

ring A is aryl or heteroaryl;

each $R^1$ is identical or different and each is independently selected from the group consisting of a hydrogen atom, halogen, alkyl, alkenyl, alkynyl, alkoxy, haloalkyl, haloalkoxy, hydroxyalkyl, cyano, amino, nitro, hydroxy, and cycloalkyl;

$R^2$ is selected from the group consisting of a hydrogen atom, alkyl, heterocyclylalkyl, cycloalkylalkyl, alkenyl, alkynyl, haloalkyl, hydroxyalkyl, cycloalkyl, heterocyclyl, aryl and heteroaryl, wherein the alkyl, heterocyclylalkyl, cycloalkylalkyl, alkenyl, alkynyl, cycloalkyl, heterocyclyl, aryl and heteroaryl are each independently optionally substituted with one or more substituents selected from the group consisting of halogen, alkyl, alkenyl, alkynyl, alkoxy, haloalkyl, haloalkoxy, cyano, amino, nitro, hydroxy, hydroxyalkyl, cycloalkyl, heterocyclyl, aryl and heteroaryl;

each $R^3$ is identical or different and each is independently selected from the group consisting of a hydrogen atom, halogen, alkyl, oxo, alkenyl, alkynyl, alkoxy, haloalkyl, haloalkoxy, hydroxyalkyl, cyano, amino, nitro, hydroxy, and cycloalkyl;

each $R^4$ is identical or different and each is independently selected from the group consisting of a hydrogen atom, halogen, alkyl, alkenyl, alkynyl, alkoxy, haloalkyl, haloalkoxy, cyano, amino, nitro, hydroxy, hydroxyalkyl, and cycloalkyl;

each $R^5$ is identical or different and each is independently selected from the group consisting of a hydrogen atom, halogen, alkyl, alkenyl, alkynyl, alkoxy, haloalkyl, haloalkoxy, hydroxyalkyl, cyano, amino, nitro, hydroxy, and cycloalkyl;

each $R^6$ is identical or different and is independently selected from the group consisting of a hydrogen atom, halogen, alkyl, alkoxy, cyano, heterocyclylalkyl, cycloalkylalkyl, alkenyl, alkynyl, haloalkyl, haloalkoxy, hydroxyalkyl, and cycloalkyl, wherein the alkyl, heterocyclylalkyl, cycloalkylalkyl, alkenyl, alkynyl, and cycloalkyl are each independently optionally substituted with one or more substituents selected from the group consisting of halogen, alkyl, alkenyl, alkynyl, alkoxy, haloalkyl, haloalkoxy, cyano, amino, nitro, hydroxy, hydroxyalkyl, and cycloalkyl;

n is 0, 1, 2 or 3;
m is 0, 1, 2, 3 or 4;
p is 0, 1, 2 or 3;
g is 0, 1, 2, 3, 4 or 5; and
q is 0, 1, 2, 3 or 4;

provided that the compound is not:

10

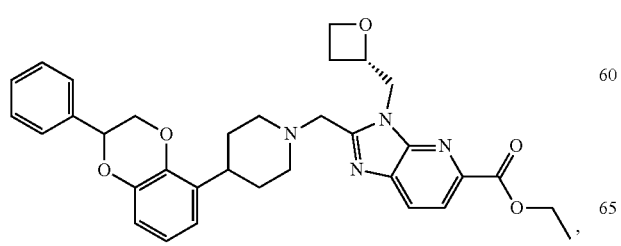

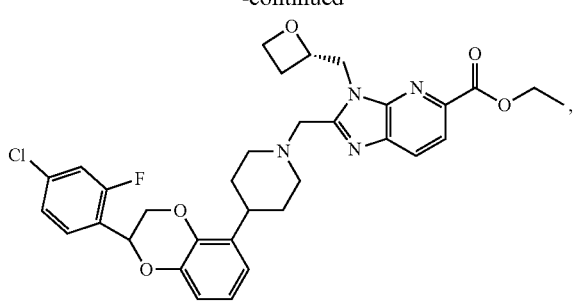

7

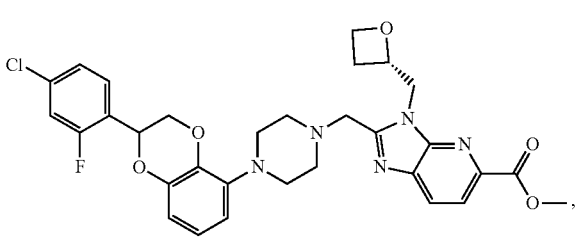

9

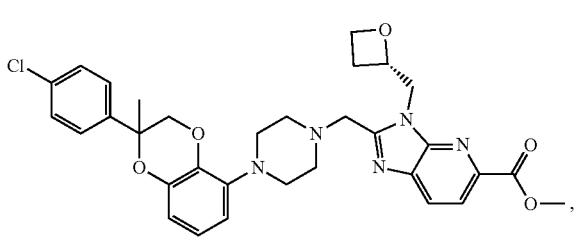

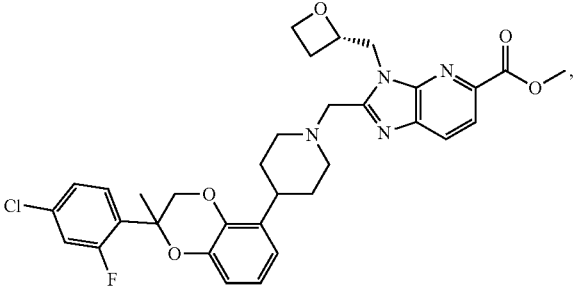

10

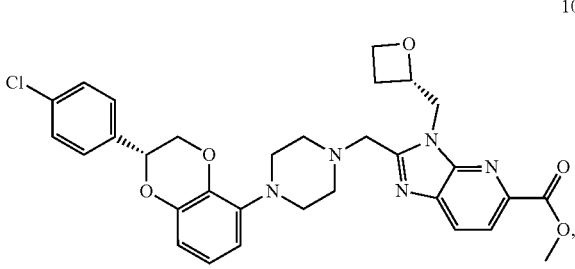

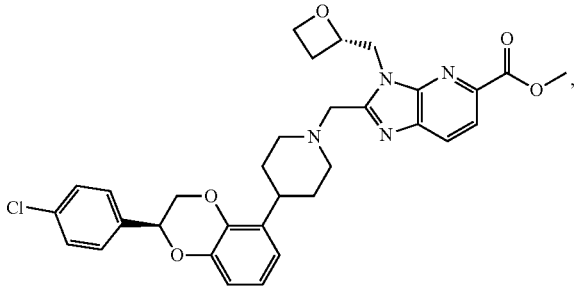

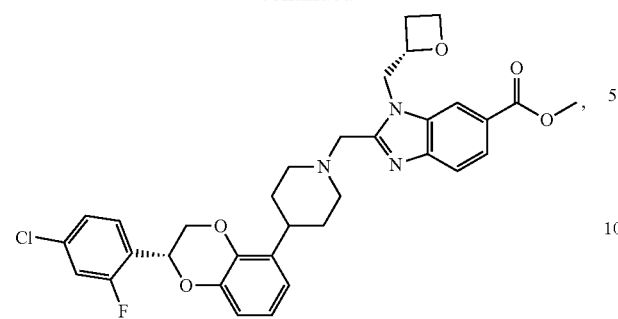
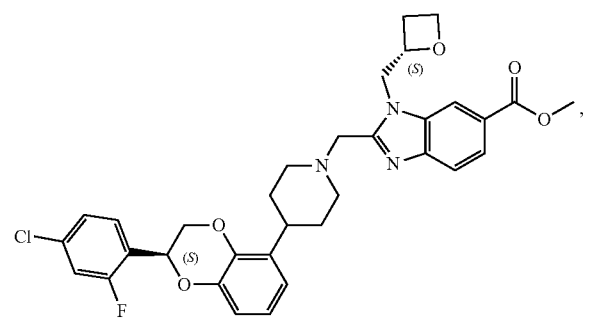
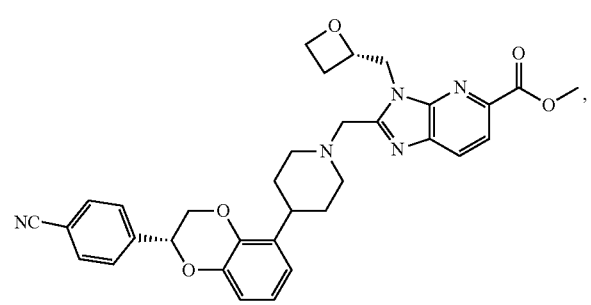
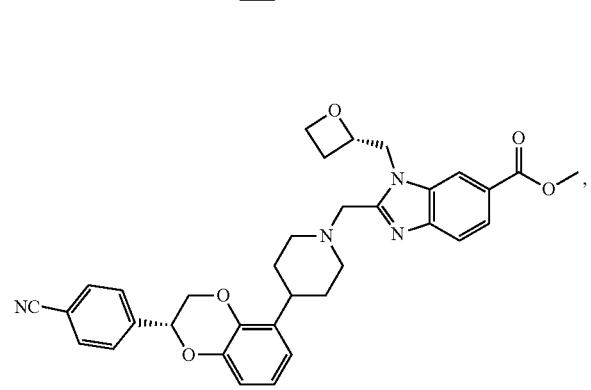
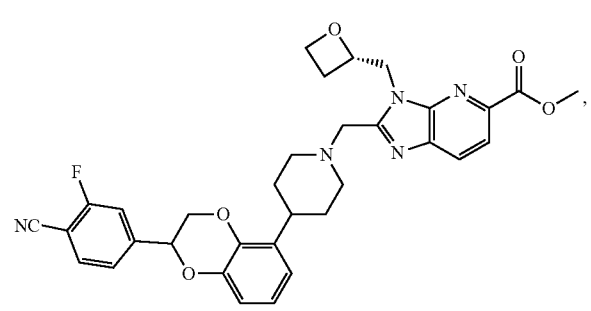
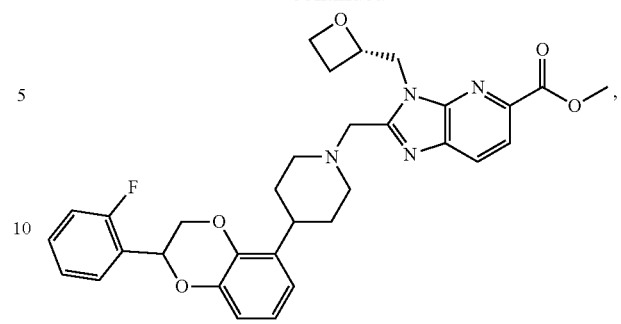
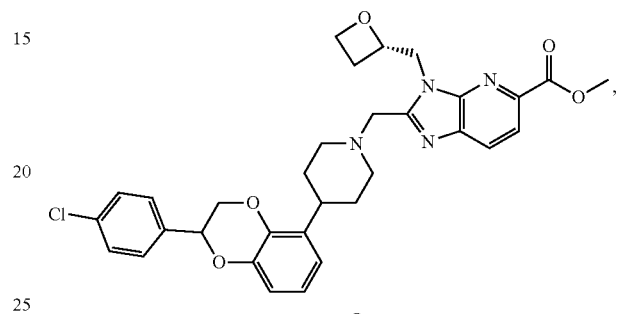
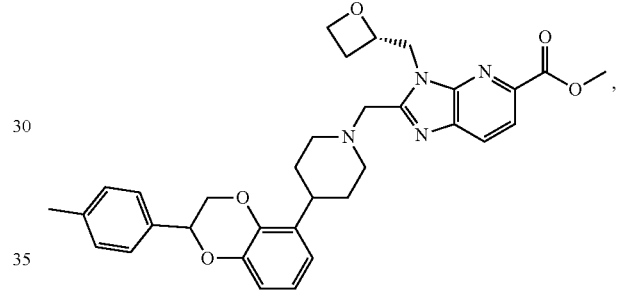
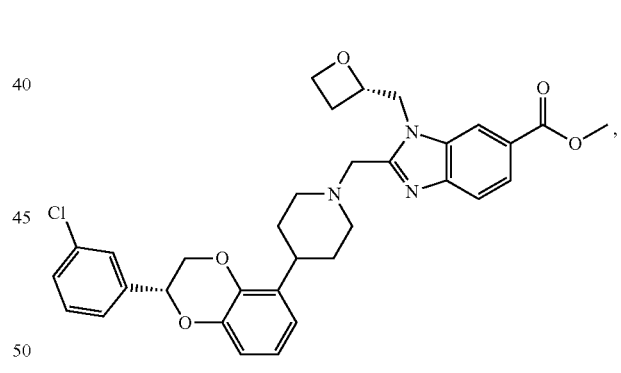
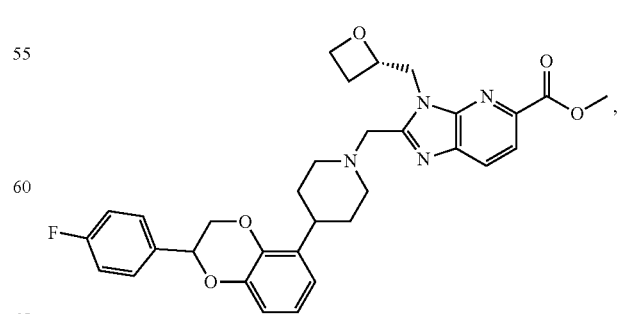

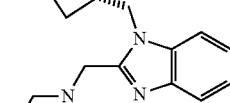
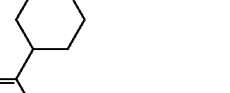

231
-continued
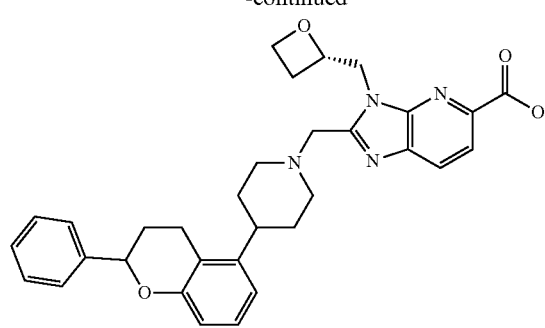
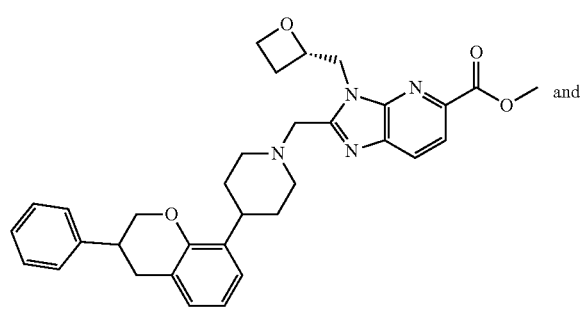
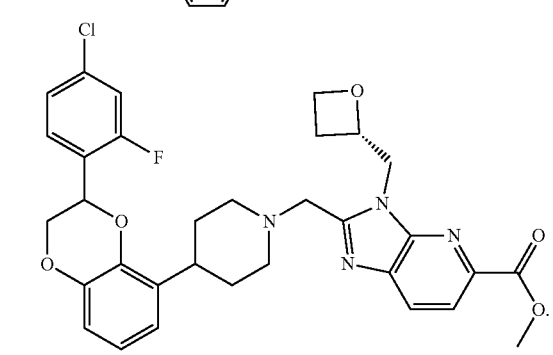
15. The compound of general formula (IMA) or the tautomer, racemate, enantiomer or diastereomer thereof or the mixture thereof, or the pharmaceutically acceptable salt thereof according to claim 14, being selected from the group consisting of the following compounds:
1n
232
-continued
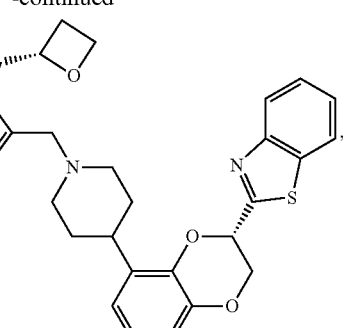
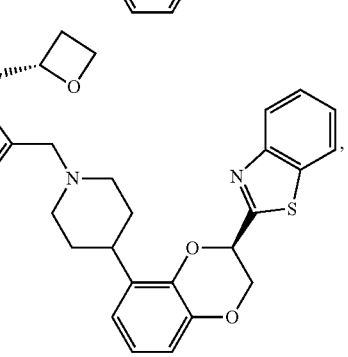
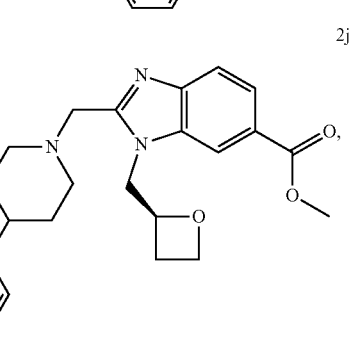
2j
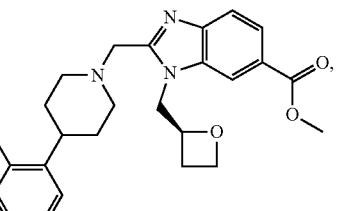
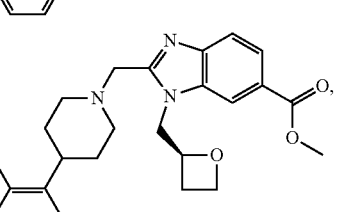
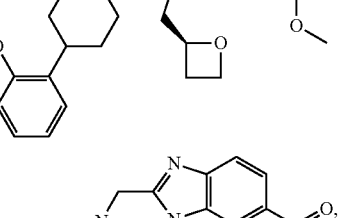

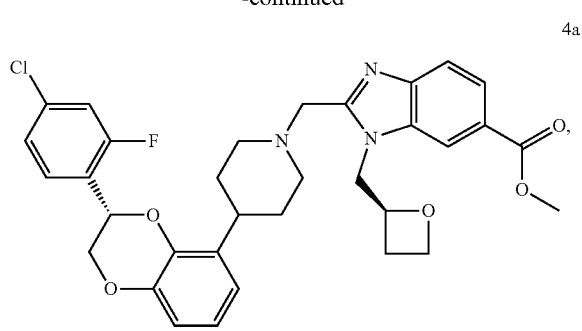
4a
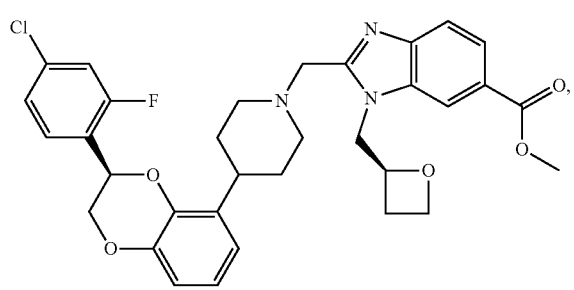
4b
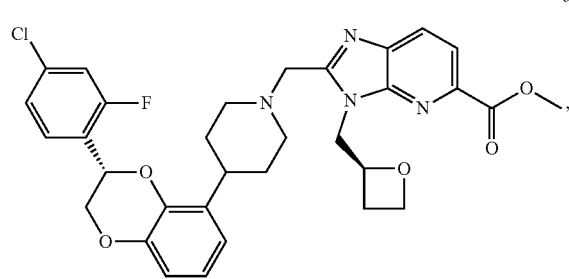
5f
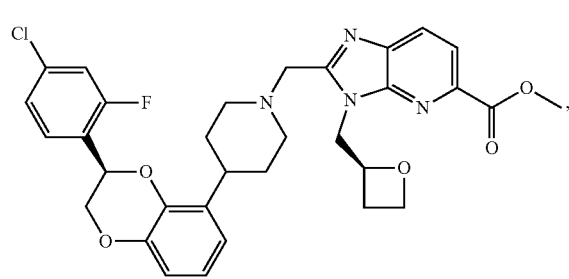
6d
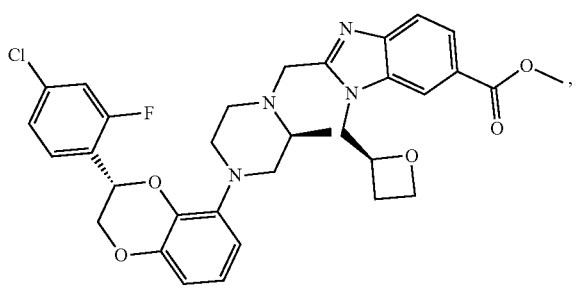
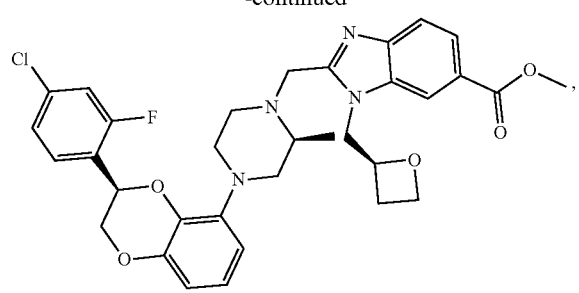
7g 235
-continued
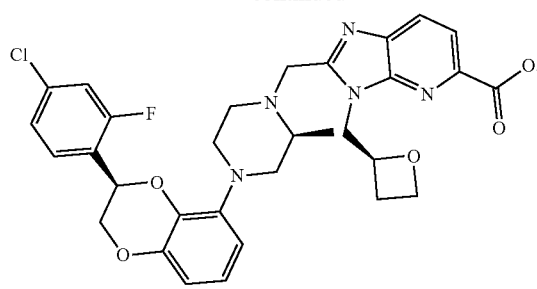
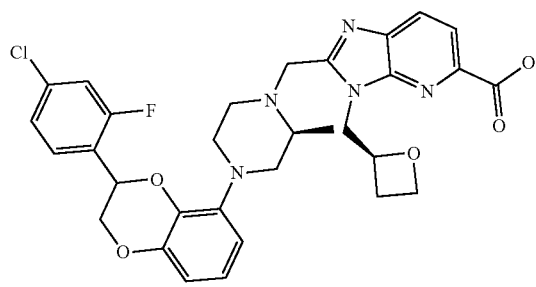
9i
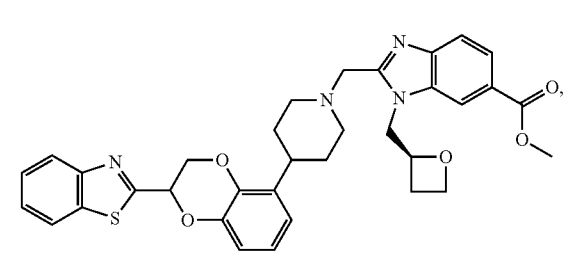
10a
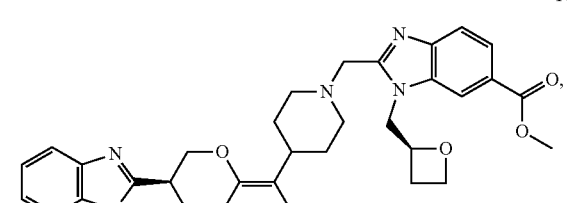
10b
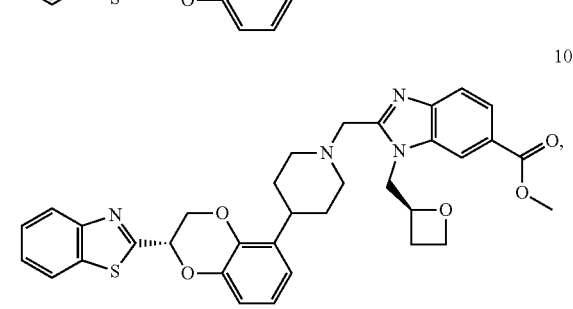
12a
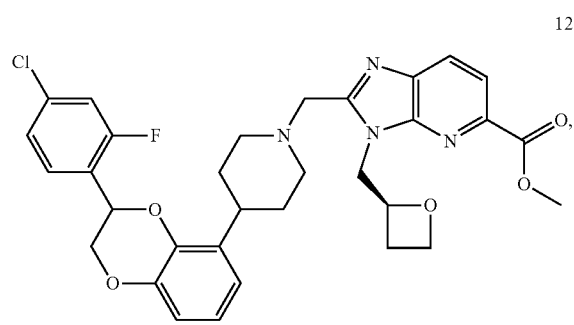
236
-continued
13i
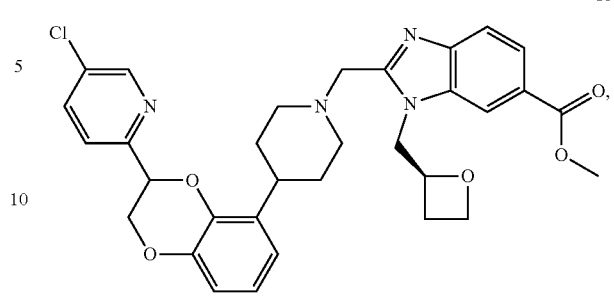
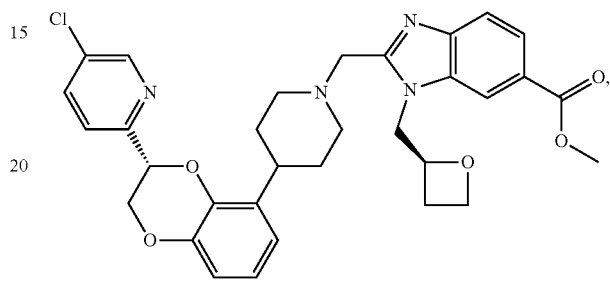
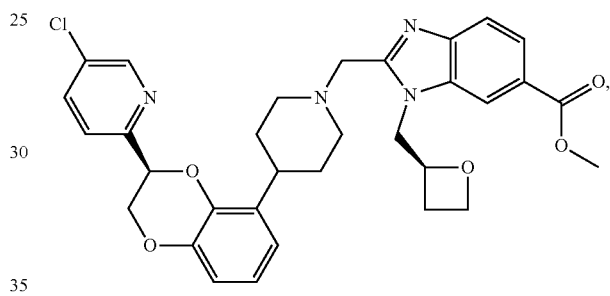
14l
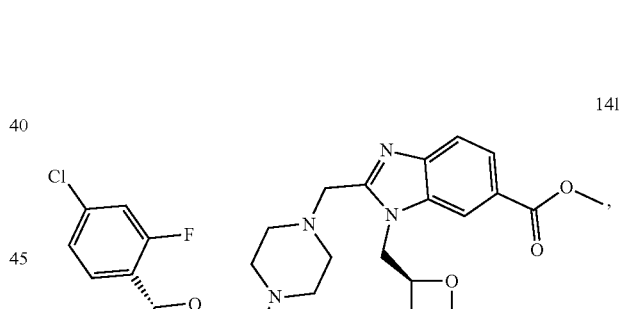
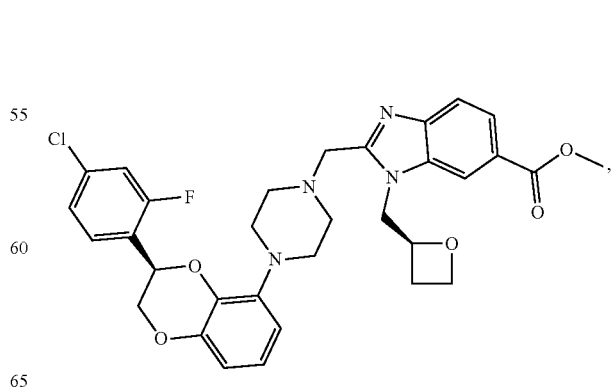

237 -continued
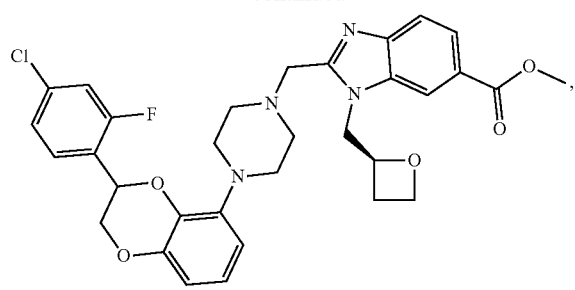
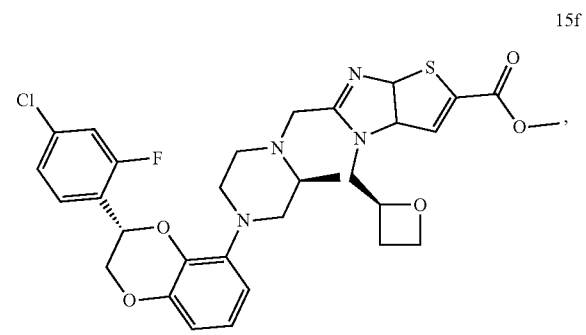
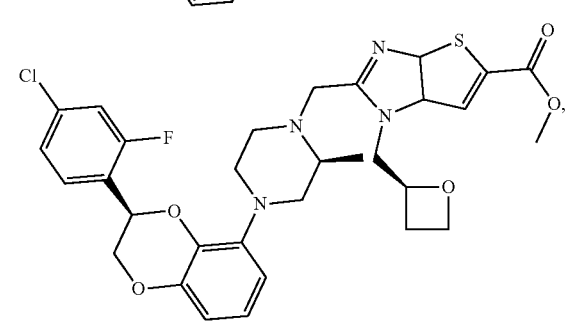
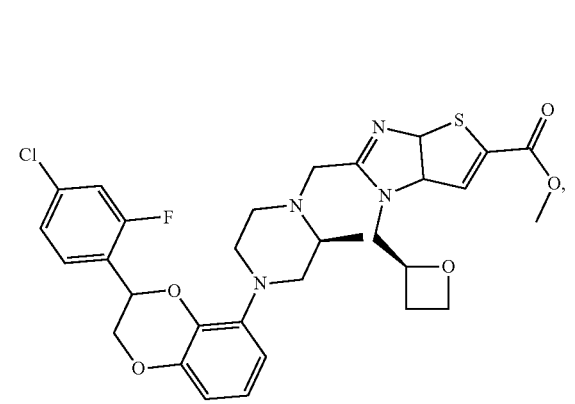
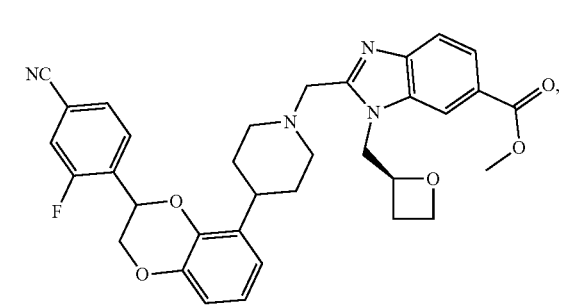
238 -continued
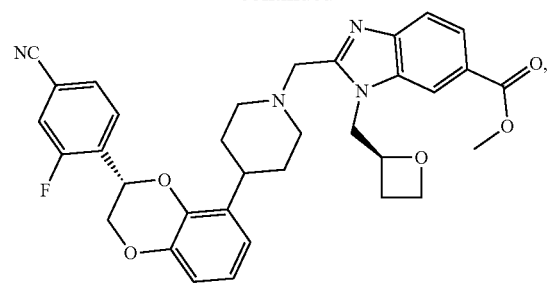
15f
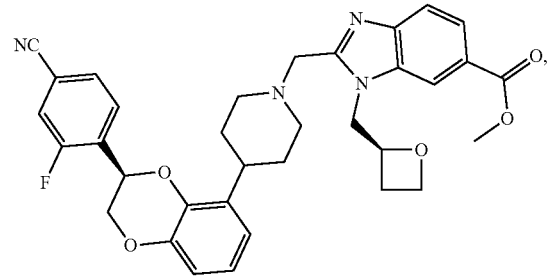
17b
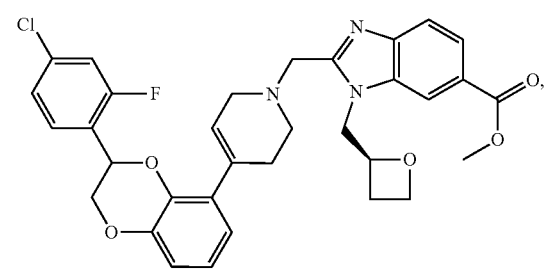
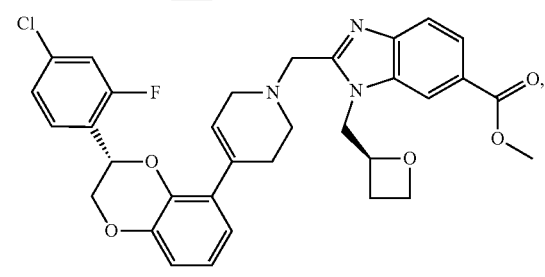
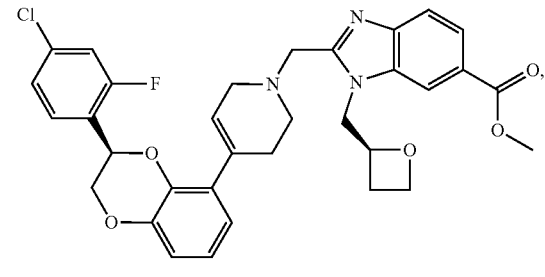
18i
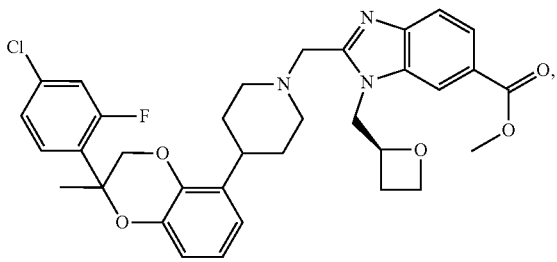

239
-continued

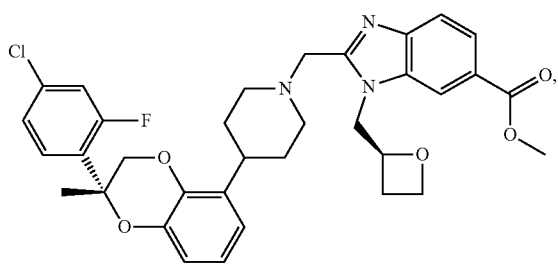

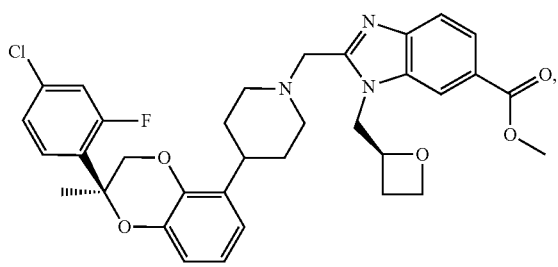

19c

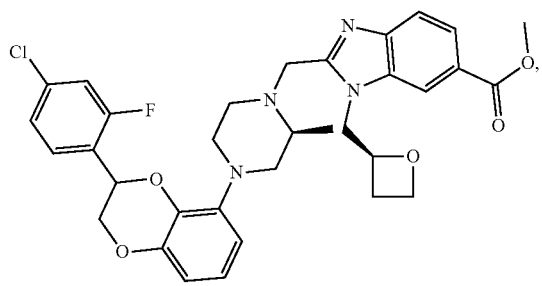

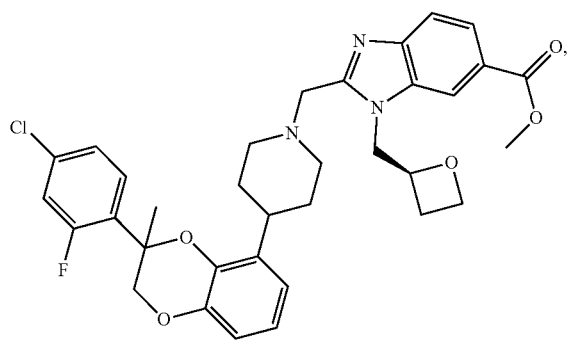

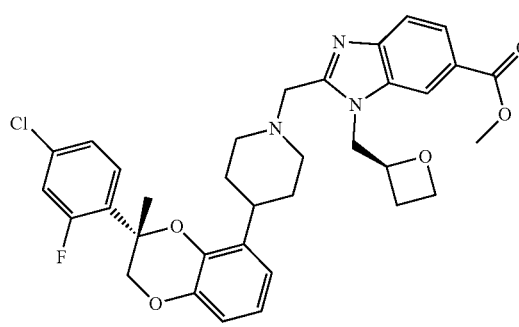

and

240
-continued

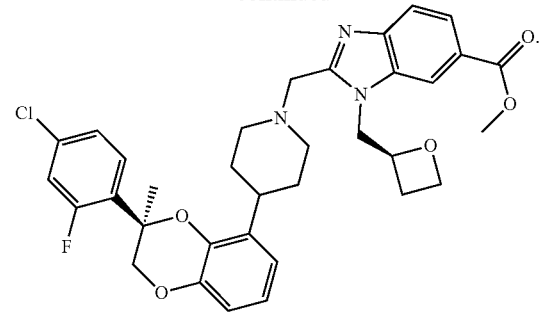 [SMILES: COC(=O)c1ccc2nc(CN3CCC(c4cccc5c4O[C@](C)(c4ccc(Cl)cc4F)CO5)CC3)n(C[C@@H]3CCO3)c2c1]

16. A pharmaceutical composition, comprising the compound of general formula (IM) or the tautomer, racemate, enantiomer or diastereomer thereof or the mixture thereof, or the pharmaceutically acceptable salt thereof according to claim 1, and one or more pharmaceutically acceptable carriers, diluents or excipients.

17. The compound of general formula (IM) or the tautomer, racemate, enantiomer or diastereomer thereof or the mixture thereof, or the pharmaceutically acceptable salt thereof according to claim 1, wherein each $R^6$ is identical or different and each is independently selected from the group consisting of a hydrogen atom, halogen, alkyl, alkoxy, heterocyclylalkyl, cycloalkylalkyl, alkenyl, alkynyl, haloalkyl, haloalkoxy, hydroxyalkyl, and cycloalkyl, wherein the alkyl, heterocyclylalkyl, cycloalkylalkyl, alkenyl, alkynyl, and cycloalkyl are each independently optionally substituted with one or more substituents selected from the group consisting of halogen, alkyl, alkenyl, alkynyl, alkoxy, haloalkyl, haloalkoxy, cyano, amino, nitro, hydroxy, hydroxyalkyl, and cycloalkyl.

18. The compound of general formula (IM) or the tautomer, racemate, enantiomer or diastereomer thereof or the mixture thereof, or the pharmaceutically acceptable salt thereof according to claim 1, wherein the compound is represented by general formula (IIN) or a tautomer, racemate, enantiomer or diastereomer thereof or a mixture thereof, or a pharmaceutically acceptable salt thereof:

(IIN)

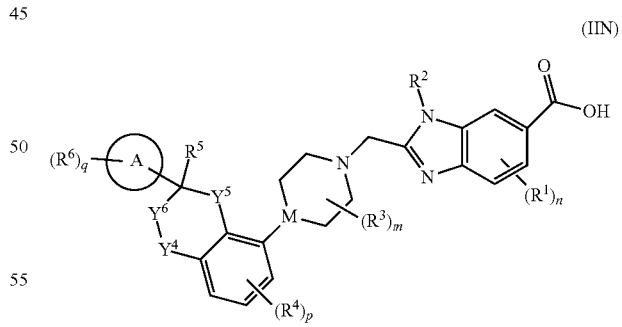

wherein:
Y$^5$ is an O atom or a S atom;
Y$^4$ and Y$^6$ are identical or different and are each independently selected from the group consisting of an O atom, a S atom and —(CR$^m$R$^n$)$_{k-}$, provided that Y$^4$ and Y$^6$ are not both heteroatoms;
R$^m$ and R$^n$ are identical or different and are each independently selected from the group consisting of a hydrogen atom, halogen, alkyl, alkenyl, alkynyl, alkoxy, haloalkyl, haloalkoxy, hydroxyalkyl, cyano, amino, nitro, hydroxy, and cycloalkyl;

k is 1 or 2;

M, ring A, $R^1$ to $R^6$, n, m, p and q are as defined in claim 1.

* * * * *